(12) United States Patent
Spriggs et al.

(10) Patent No.: US 9,790,283 B2
(45) Date of Patent: Oct. 17, 2017

(54) ANTIBODIES TO MUC16 AND METHODS OF USE THEREOF

(71) Applicant: Memorial Sloan Kettering Cancer Center, New York, NY (US)

(72) Inventors: David Spriggs, New York, NY (US); Dharmarao Thapi, Bayside Hills, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 14/850,675

(22) Filed: Sep. 10, 2015

(65) Prior Publication Data

US 2016/0168262 A1    Jun. 16, 2016

Related U.S. Application Data

(62) Division of application No. 13/635,090, filed as application No. PCT/US2011/030025 on Mar. 25, 2011, now Pat. No. 9,169,328.

(60) Provisional application No. 61/317,964, filed on Mar. 26, 2010.

(51) Int. Cl.
  *A61K 39/395*    (2006.01)
  *C07K 16/30*     (2006.01)
  *G01N 33/574*    (2006.01)
  *A61K 39/00*     (2006.01)

(52) U.S. Cl.
  CPC ... *C07K 16/3092* (2013.01); *G01N 33/57488* (2013.01); *A61K 2039/505* (2013.01); *A61K 2039/5156* (2013.01); *C07K 2317/24* (2013.01); *C07K 2317/33* (2013.01); *C07K 2317/34* (2013.01); *C07K 2317/622* (2013.01); *C07K 2317/77* (2013.01); *C07K 2317/92* (2013.01); *C07K 2319/02* (2013.01); *C07K 2319/03* (2013.01); *G01N 2333/705* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,946,778 A | 8/1990 | Ladner et al. |
| 4,975,369 A | 12/1990 | Beavers et al. |
| 4,978,745 A | 12/1990 | Schoemaker et al. |
| 5,057,313 A | 10/1991 | Shih et al. |
| 5,225,539 A | 7/1993 | Winter |
| 5,475,092 A | 12/1995 | Chari et al. |
| 5,545,806 A | 8/1996 | Lonberg et al. |
| 5,569,825 A | 10/1996 | Lonberg et al. |
| 5,585,499 A | 12/1996 | Chari et al. |
| 5,625,126 A | 4/1997 | Lonberg et al. |
| 5,736,137 A | 4/1998 | Anderson et al. |
| 5,846,545 A | 12/1998 | Chari et al. |
| 5,976,818 A | 11/1999 | O'Brien |
| 6,333,410 B1 | 12/2001 | Chari et al. |
| 6,340,701 B1 | 1/2002 | Chari et al. |
| 6,372,738 B2 | 4/2002 | Chari et al. |
| 6,429,295 B1 | 8/2002 | Carr Perez et al. |
| 7,202,346 B2 | 4/2007 | Payne et al. |
| 7,227,002 B1 | 6/2007 | Kufer et al. |
| 7,501,123 B2 | 3/2009 | Roschke et al. |
| 7,585,952 B2 | 9/2009 | D'Alessio et al. |
| 7,632,925 B2 | 12/2009 | Kufer et al. |
| 7,662,387 B2 | 2/2010 | Law et al. |
| 7,666,425 B1 | 2/2010 | Bander |
| 9,169,328 B2 | 10/2015 | Spriggs et al. |
| 2004/0057952 A1 | 3/2004 | Payne et al. |
| 2004/0162413 A1 | 8/2004 | Watkins et al. |
| 2006/0094069 A1 | 5/2006 | Robertson et al. |

FOREIGN PATENT DOCUMENTS

| | | |
|---|---|---|
| JP | 2006/502110 | 1/2006 |
| WO | WO 90/13678 | 11/1990 |
| WO | WO 92/22653 | 12/1992 |
| WO | WO 2004/005470 A2 | 1/2004 |
| WO | WO 2008/141044 | 11/2008 |
| WO | WO 2015/006043 A1 | 1/2015 |
| WO | WO 2016/149368 A1 | 9/2016 |

OTHER PUBLICATIONS

Badgwell and Bast, "Early detection of ovarian cancer." *Dis Markers*, 23(5-6):397-410 (2007).
Bafna et al., "MUC4, a multifunctional transmembrane glycoprotein, induces oncogenic transformation of NIH3T3 mouse fibroblast cells." *Cancer Res.*, 68(22):9231-9238 (2008).
Barber et al., "Chimeric NKG2D receptor-bearing T cells as immunotherapy for ovarian cancer." *Cancer Res.*, 67(10):5003-5008 (2007).
Barber et al., "Immunotherapy with chimeric NKG2D receptors leads to long-term tumor-free survival and development of host antitumor immunity in murine ovarian cancer." *J Immunol.*, 180(1):72-78 (2008).
Bast et al., "Reactivity of a monoclonal antibody with human ovarian carcinoma." *J Clin Invest.*, 68(5):1331-1337 (1981).
Bast et al., "A radioimmunoassay using a monoclonal antibody to monitor the course of epithelial ovarian cancer." *N Eng J Med.*, 309(15):883-887 (1983).
Bast et al., "New tumor markers: CA125 and beyond." *Int J Gynecol Cancer*, 15 Suppl 3:274-281 (2005).

(Continued)

*Primary Examiner* — Sheela J Huff
(74) *Attorney, Agent, or Firm* — Jones Day

(57) ABSTRACT

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

43 Claims, 65 Drawing Sheets

(56) References Cited

OTHER PUBLICATIONS

Bellone et al., "Generation of CA125-specific cytotoxic 1' lymphocytes in human leukocyte antigen-A2.1-positive healthy donors and patients with advanced ovarian cancer." *Am J Obstet Gynecol.*, 200(1):75 e71-10 (2009).
Berek, "Immunotherapy of ovarian cancer with antibodies: a focus on oregovomab." *Expert Opin Biol Ther.*, 4(7):1159-1165 (2004).
Bernsel and Von Heijne, "Improved membrane protein topology prediction by domain assignments." *Protein Sci.*, 14(7):1723-1728 (2005).
Borghouts et al., "Current strategies for the development of peptide-based anti-cancer therapeutics." *J Pept Sci.*, 11(11):713-726 (2005).
Brentjens et al., "Eradication of systemic B-cell tumors by genetically targeted human T lymphocytes co-stimulated by CD80 and interleukin-15." *Nat Med.*, 9(3):279-286 (2003).
Brentjens and Sadelain, "Somatic cell engineering and the immunotherapy of leukemias and lymphomas." *Adv Pharmacol*, 51:347-370 (2004).
Brentjens et al., "Genetically targeted T cells eradicate systemic acute lymphoblastic leukemia xenografts." *Clin Cancer Res.*, 13(18 Pt 1):5426-5435 (2007).
Brentjens, "A Phase I trial for the treatment of chemo-refractory chronic lymphocytic leukemia with CD19-targeted autologous T cells." *Molecular Therapy* 16:S15 (2008).
Carpenito et al., "Control of large, established tumor xenografts with genetically retargeted human T cells containing CD28 and CD137 domains " *Proc Natl Acad Sci., USA*, 106(9):3360-3365 (2009).
Chang et al., "A novel peptide enhances therapeutic efficacy of liposomal anti-cancer drugs in mice models of human lung cancer." *PLoS One*, 4(1):e4171 (2009).
Cole et al., "The EBV-hybridoma technique and its application to human lung cancer." in *Monoclonal Antibodies and Cancer Therapy* (Sell, Ed.), pp. 77-96, Alan R. Liss, Inc. (1985).
Cote et al., "Generation of human monoclonal antibodies reactive with cellular antigens." *Proc Natl Acad Sci., USA*, 80(7):2026-2030 (1983).
Curiel et al., "Specific recruitment of regulatory T cells in ovarian carcinoma fosters immune privilege and predicts reduced survival." *Nat Med.*, 10(9):942-949 (2004).
Daly et al., "Recognition of human colon cancer by T cells transduced with a chimeric receptor gene." *Cancer Gene Ther.*, 7(2):284-291 (2000).
David and Reisfeld, "Protein iodination with solid state lactoperoxidase." *Biochemistry*, 13(5):1014-1021(1974).
Doenecke et al., "Rapid amplification of cDNA ends (RACE) improves the PCR-based isolation of immunoglohulin variable region genes from murine and human lymphoma cells and cell lines." *Leukemia*, 11(10):1787-1792 (1997).
Elofsson and von Heijne, "Membrane protein structure: prediction versus reality." *Annu Rev BioChem.*, 76:125-140 (2007).
Faisal et al., "Leptasome-entrapped leptospiral antigens conferred significant higher levels of protection than those entrapped with PC-liposomes in a hamster model." *Vaccine*, 27(47):6537-6545 (2009).
Fendrick et al., "Characterization of CA 125 synthesized by the human epithelial amnion WISH cell line." *Tumour Biol.*, 14(5):310-318 (1993).
Fendrick et al., "CA125 phosphorylation is associated with its secretion from the WISH human amnion cell line." *Tumour Biol.*, 18(5):278-289 (1997).
Finney et al., "Activation of resting human primary T cells with chimeric receptors: costimulation from CD28, inducible costimulator, CD134, and CD137 in series with signals from the TCR zeta chain." *J Immunol.*, 172(1):104-113 (2004).
Fritsche and Bast, "CA 125 in ovarian cancer: advances and controversy." *Clin Chem.*, 44(7):1379-1380(1998).

Gong et al., "Cancer patient T cells genetically targeted to prostate-specific membrane antigen specifically lyse prostate cancer cells and release cytokines in response to prostate-specific membrane antigen." *Neoplasia*, 1(2):123-127 (1999).
Greenwood and Hunter, "Preparation of iodine-131 labelled human growth hormone of high specific activity." *Nature*, 194:495-496 (1962).
Habib-Agahi et al., "Co-stimulation with 4-1BB ligand allows extended T-cell proliferation, synergizes with CD80/CD86 and can reactivate anergic T cells." *Int Immunol.*, 19(12):1383-1394 (2007).
Habib-Agahi et al., "Co-stimulation with 4-1BB ligand allows extended T-cell proliferation, synergizes with CD80/CD86 and can reactivate anergic T cells." *Int Immunol.*, 19(12):1383-1394, Sup. List (2007).
Habib-Agahi et al., "Co-stimulation with 4-1BB ligand allows extended T-cell proliferation, synergizes with CD80/CD86 and can reactivate anergic T cells." *Int Immunol.*, 19(12):1383-1394, Sup. Fig. 1 (2007).
Habib-Agahi et al., "Co-stimulation with 4-1BB ligand allows extended T-cell proliferation, synergizes with CD80/CD86 and can reactivate anergic T cells." *Int Immunol* 19(12):1383-1394, Sup. Fig. 2 (2007).
Habib-Agahi et al., "4-1BBL costimulation retrieves CD28 expression in activated T cells." *Cell Immunol.*, 256(1-2):39-46 (2009).
Hamanishi et al., "Programmed cell death 1 ligand 1 and tumor-infiltrating CD8+ T lymphocytes are prognostic factors of human ovarian cancer." *Proc Natl Acad Sci., USA*, 104(9):3360-3365 (2007).
Harris et al., "A comparison of the metastatic pattern of infiltrating lobular carcinoma and infiltrating duct carcinoma of the breast." *Br J Cancer*, 50(1):23-30 (1984).
Hedvat et al., "Application of tissue microarray technology to the study of non-Hodgkin's and Hodgkin's lymphoma." *Hum Pathol.*, 33(10):968-974 (2002).
High et al., "Sec61p is adjacent to nascent type I and type II signal-anchor proteins during their membrane insertion." *J Cell Biol.*, 121(4):743-750 (1993).
Hollingsworth and Swanson, "Mucins in cancer: protection and control of the cell surface." *Nat Rev Cancer*, 4(1):45-60 (2004).
Hollyman et al., "Manufacturing validation of biologically functional T cells targeted to CD19 antigen for autologous adoptive cell therapy." *J Immuno Ther.*, 32(2):169-180 (2009).
Huang et al., "MUC1 cytoplasmic domain coactivates Wnt target gene transcription and confers transformation." *Cancer Biol. Ther.*, 2(6):702-706 (2003).
Hung et al., "Antigen-specific immunotherapy of cervical and ovarian cancer." *Immunol Rev.*, 222:43-69 (2008).
Huse et al., "Generation of a large combinatorial library of the immunoglobulin repertoire in phage lambda." *Science*, 246(4935):1275-1281 (1989).
Huwyler et al., "Tumor targeting using liposomal antineoplastic drugs." *Int J Nanomedicine*, 3(1):21-29 (2008).
Hwu et al., "In vivo antitumor activity of T cells redirected with chimeric antibody/T-cell receptor genes." *Cancer Res.*, 55(15):3369-3373 (1995).
Imai et al., "Chimeric receptors with 4-1BB signaling capacity provoke potent cytotoxicity against acute lymphoblastic leukemia." *Leukemia*, 18(4):676-684 (2004).
Jensen et al., "Engineered CD20-specific primary human cytotoxic T lymphocytes for targeting B-cell malignancy." *Cytotherapy*, 5(2):131-138 (2003).
Kaneko et al., "A binding domain on mesothelin for CA125/MUC16." *J Biol Chem*, 284(6):3739-3749 (2009).
Kershaw et al., "Dual-specific T cells combine proliferation and antitumor activity." *Nat Biotechnol.*, 20(12):1221-1227 (2002).
Kershaw et al., "A phase I study on adoptive immunotherapy using gene-modified T cells for ovarian cancer." *Clin Cancer Res.*, 12(20 Pt 1):6106-6115 (2006).
Kochenderfer et al., "Construction and preclinical evaluation of an anti-CD19 chimeric antigen receptor." *J ImmunoTher.*, 32(7):689-702 (2009).

(56) References Cited

OTHER PUBLICATIONS

Kohler and Milstein, "Continuous cultures of fused cells secreting antibody of predefined specificity." *Nature*, 256(5517):495-497 (1975).
Kononen et al., "Tissue microarrays for high-throughput molecular profiling of tumor specimens." *Nat Med.*, 4(7):844-847 (1998).
Kozbor and Roder, "Comparison of the specific IgM and IgG antibody response in humans induced by antigen (tetanus toxoid) or a polyclonal activator (EBV) in vitro." *Int Arch Allergy Appl Immunol.*, 72(3):260-266 (1983).
Krivak et al., "A Gynecologic Oncology Group Study of serum CA-125 levels in patients with stage III optimally debulked ovarian cancer treated with intraperitoneal compared to intravenous chemotherapy: an analysis of patients enrolled in GOG 172." *Gynecol Oncol.*, 115(1):81-85 (2009).
Lamers et al., "Gene-modified T cells for adoptive immunotherapy of renal cell cancer maintain transgene-specific immune functions in vivo." *Cancer Immunol ImmunoTher.*, 56(12):1875-1883 (2007).
Lamers et al., "Treatment of metastatic renal cell carcinoma with autologous T-lymphocytes genetically retargeted against carbonic anhydrase IX: first clinical experience." *J Clin Oncol.*, 24(13):e20-22 (2006).
Latouche and Sadelain, "Induction of human cytotoxic T lymphocytes by artificial antigen-presenting cells." *Nat Biotechnol.*, 18(4):405-409 (2000).
Leffers et al., "Survival of ovarian cancer patients overexpressing the tumour antigen p53 is diminished in case of MHC class I down-regulation." *Gynecol Oncol.*, 110(3):365-373 (2008).
Leffers et al., "Prognostic significance of tumor-infiltrating T-lymphocytes in primary and metastatic lesions of advanced stage ovarian cancer." *Cancer Immunol ImmunoTher.*, 58(3):449-459 (2009).
Li et al., "Interaction of human MUC1 and beta-catenin is regulated by Lck and ZAP-70 in activated Jurkat T cells." *Biochem Biophys Res Commun.*, 315(2):471-476 (2004).
Li et al., "4-1BB (CD137) ligand enhanced anti-tumor immune response against mouse forestomach carcinoma in vivo." *Cell Mol Immunol.*, 5(5):379-384 (2008).
Loskog et al., "Addition of the CD28 signaling domain to chimeric T-cell receptors enhances chimeric T-cell resistance to T regulatory cells." *Leukemia*, 20(10):1819-1828 (2006).
Maher et al., "Human T-lymphocyte cytotoxicity and proliferation directed by a single chimeric TCRzeta /CD28 receptor." *Nat Biotechnol.*, 20(1):70-75 (2002).
Markwell and Fox, "Surface-specific iodination of membrane proteins of viruses and eucaryotic cells using 1,3,4,6-tetrachloro-3alpha,6alpha-diphenylglycoluril." *Biochemistry*, 17(22):4807-4817 (1978).
Moeller et al., "A functional role for CD28 costimulation in tumor recognition by single-chain receptor-modified T cells." *Cancer Gene Ther.*, 11(5):371-379 (2004).
Moore et al., "Current stale of biomarker development for clinical application in epithelial ovarian cancer." *Gynecol Oncol.*, 116(2):240-245 (2010).
Nap et al., "Immunohistochemical characterization of 22 monoclonal antibodies against the CA125 antigen: 2nd report from the ISOBM TD-1 Workshop." *Tumour Biol.*, 17(6):325-331 (1996).
Nelson, "The impact of T-cell immunity on ovarian cancer outcomes." *Immunol Rev.*, 222:101-116 (2008).
Nustad et al., "Epitopes on CA 125 from cervical mucus and ascites fluid and characterization of six new antibodies. Third report from the ISOBM TD-1 workshop." *Tumour Biol.*, 23(5):303-314 (2002).
Nygren, "Conjugation of horseradish peroxidase to $F_{ab}$ fragments with different homobifunctional and heterobifunctional cross-linking reagents. A comparative study." *Journal of Histochemistry & Cytochemistry*, 30(5):407-412 (1982).
O'Brien et al., "More than 15 years of CA 125: what is known about the antigen, its structure and its function." *Int J Biol Markers*, 13(4):188-195 (1998).
O'Brien et al., "The CA 125 gene: an extracellular superstructure dominated by repeat sequences." *Tumour Biol.*, 22(6):348-366 (2001).
O'Brien et al., "The CA 125 gene: a newly discovered extension of the glycosylated N-terminal domain doubles the size of this extracellular superstructure." *Tumour Biol.*, 23(3):154-169 (2002).
Orlandi et al., "Cloning immunoglobulin variable domains for expression by the polymerase chain reaction." *Proc Natl Acad Sci., USA*, 86(10):3833-3837 (1989).
Pain and Surolia. "Preparation of protein A-peroxidase monoconjugate using a heterobifunctional reagent, and its use in enzyme immunoassays." *J Immunol Methods*, 40(2):219-230 (1981).
Park, "The extracellular portion of the MUC16 cytoplasmic domain is detectable in ovarian carcinoma using a novel monoclonal antibody, 4H11." *Modern pathology*, 0893-3952 (21 (suppl. 1)):217A-218A (Jan. 1, 2008).
Parker et al., "Expansion and characterization of T cells transduced with a chimeric receptor against ovarian cancer." *Hum Gene Ther.*, 11(17):2377-2387 (2000).
Ponnusamy et al., "MUC4 activates HER2 signalling and enhances the motility of human ovarian cancer cells." *Br J Cancer*, 99(3):520-526 (2008).
Pule et al., "Virus-specific T cells engineered to coexpress tumor-specific receptors: persistence and antitumor activity in individuals with neuroblastoma." *Nat Med.*, 14(11):1264-1270 (2008).
Quintas-Cardama et al., "Multifactorial optimization of gammaretroviral gene transfer into human T lymphocytes for clinical application." *Hum Gene Ther.*, 18(12):1253-1260 (2007).
Ramsauer et al., "MUC4-ErbB2 complex formation and signaling in polarized CACO-2 epithelial cells indicate that Muc4 acts as an unorthodox ligand for ErbB2."*Mol Biol Cell* 17(7):2931-2941 (2006).
Raspollini et al., "Tumour-infiltrating gamma/delta T-lymphocytes are correlated with a brief disease-free interval in advanced ovarian serous carcinoma." *Ann Oncol.*, 16(4):590-596 (2005).
Ren et al., "Human MUC1 carcinoma-associated protein confers resistance to genotoxic anticancer agents." *Cancer Cell*, 5(2):163-175 (2004).
Ren et al., "MUC1 oncoprotein is targeted to mitochondria by heregulin-induced activation of c-Src and the molecular chaperone HSP90." *Oncogene*, 25(1):20-31 (2006).
Riviere et al., "Effects of retroviral vector design on expression of human adenosine deaminase in murine hone marrow transplant recipients engrafted with genetically modified cells." *Proc Natl Acad Sci., USA*, 92(15):6733-6737 (1995).
Rosen et al., "Potential markers that complement expression of CA125 in epithelial ovarian cancer." *Gynecol Oncol.*, 99(2):267-277 (2005).
Rustin et al., "Use of CA-125 in clinical trial evaluation of new therapeutic drugs for ovarian cancer." *Clin Cancer Res.*, 10(11):3919-3926 (2004).
Sadelain et al., "Targeting tumours with genetically enhanced T lymphocytes." *Nat Rev Cancer*, 3(1):35-45 (2003).
Sadelain et al., "The promise and potential pitfalls of chimeric antigen receptors." *Curr Opin Immunol.*, 21(2):215-223 (2009).
Salih et al., "Constitutive expression of functional 4-1BB (CD137) ligand on carcinoma cells." *J Immunol.*, 165(5):2903-2910 (2000).
Santos et al., "Sensitive in vivo imaging of T cells using a membrane-bound *Gaussia princeps* luciferase." *Nat Med.*, 15(3):338-344 (2009).
Sato et al., "Intraepithelial CD8+ tumor-infiltrating lymphocytes and a high CD8+/regulatory T cell ratio are associated with favorable prognosis in ovarian cancer." *Proc Natl Acad Sci., USA*, 102(51):18538-18543 (2005).
Savoldo et al., "Epstein Barr virus specific cytotoxic T lymphocytes expressing the anti-CD3Ozeta artificial chimeric T-cell receptor for immunotherapy of Hodgkin disease." *Blood*, 110(7):2620-2630 (2007).
Singer, "The structure and insertion of integral proteins in membranes." *Annu Rev Cell Biol.*, 6:247-296, A: pp. 247-268 (1990).
Singer, "The structure and insertion of integral proteins in membranes." *Annu Rev Cell Biol.*, 6:247-296, B: pp. 269:296 (1990).

(56) References Cited

OTHER PUBLICATIONS

Singh et al., "Clinical potential of mucins in diagnosis, prognosis, and therapy of ovarian cancer." *Lancet Oncol.*, 9(11):1076-1085 (2008).
Song et al., "Peptide ligand-mediated liposome distribution and targeting to EGFR expressing tumor in vivo." *Int J Pharm.*, 363(1-2):155-161 (2008).
Soslow, "Histologic subtypes of ovarian carcinoma: an overview." *Int J Gynecol Pathol.*, 27(2):161-174 (2008).
Stephan et al., "T cell-encoded CD8O and 4-1BBL induce auto- and transcostimulation, resulting in tumor rejection." *Nat Med.*, 13(12):1440-1449 (2007).
Sun et al., "Quality of life for patients with epithelial ovarian cancer." *Nat Clin Pract Oncol*, 4(1):18-29 (2007).
Till et al., "Adoptive immunotherapy for indolent non-Hodgkin lymphoma and mantle cell lymphoma using genetically modified autologous CD20-specific T cells." *Blood*, 112(6):2261-2271 (2008).
Tomsova et al., "Prognostic significance of CD3+ tumor-infiltrating lymphocytes in ovarian carcinoma." *Gynecol Oncol.*, 108(2):415-420 (2008).
Voinea and Simionescu, "Designing of 'intelligent' liposomes for efficient delivery of drugs." *J Cell Mol Med.*, 6(4):465-474 (2002).
Wan et al., "Expression of co-stimulator 4-1BB molecule in hepatocellular carcinoma and adjacent non-tumor liver tissue, and its possible role in tumor immunity." *World J Gastroenterol.*, 10(2):195-199 (2004).
Wang et al., "A T cell-independent antitumor response in mice with bone marrow cells retrovirally transduced with an antibody/Fc-gamma chain chimeric receptor gene recognizing a human ovarian cancer antigen." *Nat Med.*, 4(2):168-172 (1998).
Wang et al., "Universal PCR amplification of mouse immunoglobulin gene variable regions: the design of degenerate primers and an assessment of the effect of DNA polymerase 3' to 5' exonuclease activity." *J Immunol Methods*, 233(1-2):167-177 (2000).
Westwood et al., "Adoptive transfer of T cells modified with a humanized chimeric receptor gene inhibits growth of Lewis-Y-expressing tumors in mice." *Proc Natl Acad Sci., USA*, 102(52):19051-19056 (2005).
Wilkie et al., "Retargeting of human T cells to tumor-associated MUC1: the evolution of a chimeric antigen receptor." *J Immunol.*, 180(7):4901-4909 (2008).
Wolf et al., "The expression of the regulatory T cell-specific forkhead box transcription factor FoxP3 is associated with poor prognosis in ovarian cancer." *Clin Cancer Res.*, 11(23):8326-8331 (2005).
Woo et al., "Regulatory CD4(+)CD25(+) T cells in tumors from patients with early-stage non-small cell lung cancer and late-stage ovarian cancer." *Cancer Res.*, 61(12):4766-4772 (2001).
Yin et al., "Ovarian cancer antigen CA125 is encoded by the MUC16 mucin gene." *Int J Cancer*, 98(5):737-740 (2002).
Yin and Lloyd, "Molecular cloning of the CA125 ovarian cancer antigen: identification as a new mucin, MUC16." *J. Biol Chem.*, 276(29):27371-27375 (2001).
Zhang et al., "Intratumoral T cells, recurrence, and survival in epithelial ovarian cancer." *N Engl J Med.*, 348(3):203-213 (2003).
ISR PCT/US2011/030025 (2011).
Davies et al., "MUC16 is produced in tracheal surface epithelium and submucosal glands and is present in secretions from normal human airway and cultured bronchial epithelial cells." *Int J Biochem Cell Biol.*, 39(10):1943-1954 (2007).
Rao et al., "Novel Monoclonal Antibodies Against the Proximal (Carboxy-Terminal) Portions of MUC16." *Applied Immunohistochemistry & Molecular Morphology*, 18(5):462-472 (2010).
Blalock et al., 2008, "Release of Membrane-Associated Mucins from Ocular Surface Epithelia", *Investigative Ophthalmology & Visual Science*, vol. 49, No. 5, pp. 1564-1871.
Blalock et al., 2007, "Functions of MUC16 in Corneal Epithelial Cells", *Investigative Ophthalmology Visual Science*, vol. 48, No. 10, pp. 4509-4518.
Strome et al., 2007, "A mechanistic perspective of monoclonal antibodies in cancer therapy beyond target-related effects.", *The Oncologist*, 12:1084-95.
Brand et al., 2006, "Prospect for anti-HER2 receptor therapy in breast cancer", *Anticancer Research*, 26:463-70.
Berek, "Immunotherapy of ovarian cancer with antibodies: a focus on oregovomab." *Expert Opinion on Biological Therapy*, 4(7):1159-1165 (2004).
Debat et al., "Overpassing an aberrant Vkappa gene to sequence an anti-idiotypic abzyme with beta-lactamase-like activity that could have a linkage with autoimmune diseases." *FASEB*, 15:815-822 (2001).
GenBank Accession No. AJ277812.1, "Mus musculus partial mRNA for immunoglobulin kappa light chain variable region (IGKV gene)." URL: http://www.ncbi.nlm.nih.gov/nuccore/7711058 (2001).
Giannakouros et al., "Transformation of NIH3T3 mouse fibroblast cells by MUC16 mucin (CA125) is driven by its cytoplasmic tail." *International Journal of Oncology*, 46(1):91-98 (2014).
Gubbels et al., "Mesothelin-MUC16 binding is a high affinity, N-glycan dependent interaction that facilitates peritoneal metastasis of ovarian tumors." *Molecular Cancer*, 5(1):50 (2006).
International Search Report for International Application No. PCT/US2016/022643, mailed Sep. 5, 2016.
Invitation to Pay Additional Fees, and, Where Applicable, Protest Fee, with Communication Relating to the Results of the Partial International Search for PCT/US2016/022643, mailed Jun. 30, 2016.
Lolli et al., "The glycopeptides CSF114(Glc) detects serum antibodies in multiple sclerosis." *Journal of Neuroimmunology*, 167(1-2):131-137 (2005).
Marcos-Silva et al., "A novel monoclonal antibody to a defined peptide epitope in MUC16." *Glycobiology*, 25(11):1172-1182 (2015).
Marcos-Silva et al., "Characterization of Binding Epitopes of CA125 Monoclonal Antibodies." *Journal of Proteome Research*, 13(7):3349-3359 (2014).
Rao et al., "Expression of the Carboxy-Terminal Portion of MUC16/CA125 Induces Transformation and Tumor Invasion." *PLoS One*, 10(5):e0126633 (2015).
Sorensen et al., "Chemoenzymatically synthesized multimeric Tn/STn MUC1 glycopeptides elicit cancer-specific anti-MUC1 antibody responses and override tolerance." *Glycobiology*, 16(2):96-107 (2006).
Written Opinion of the International Searching Authority for International Application No. PCT/US2016/022643, mailed Sep. 5, 2016.
Written Opinion of the International Searching Authority for International Application No. PCT/US2011/030025, mailed Feb. 8, 2012.

Peptide 1 near Cleavage Site:
NFSPLARRVDRVAIYEE (SEQ ID NO:01)

Peptide 2 before Transmembrane:
TLDRSSVLVDGYSPNRNE (SEQ ID NO:02)

Peptide 3 inside Transmembrane:
CGVLVTTRRRKKEGEYNVQQQ (SEQ ID NO:03)

FIGURE 1

FIG. 8A
4A5 VH (SEQ ID NO:04)
gtgaagctggaggagtcagggggaggcttcgtgaagcctggagggtccctcaaaatctcctgtgcagcctctggattcac
tttcagaaactatgccatgtcctgggttcgcctgagtcccggagatgaggctggagtgggtcgcaaccattagcagtgctg
gtggttacatcttctattctgacagtgtgcagggacgattcaccatttccagagacaatgccaagaacacctccacttg
caaatgggcagtctgaggtctggggacacggccatgtactactgtgcaaggcagggatttggtaactacggtgattacta
tgctatggactactggggccaagggaccacggtcaccgtctcctca

FIG. 8B
4A5 VL (SEQ ID NO:05)
gacattgagctcacccagtctccaatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactcggcaatctggggtccctgatcgcttcacaggcagtggatctgggacagatttcactctcacc
atcagcagtgtgcaggctgaagacctggcagtttattactgcagcaatctttataatctactcacgttcggtcctgggac
caagctggagatcaaacgg

FIG. 8C
4H11 VH (SEQ ID NO:06)
gtgaagctgcaggagtcagggggaggcttcgtgaagcctggagggtccctcaaagtctcctgtgcagcctctggattcac
tttcagtagctatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctgcacctg
caaatgggcagtctgaggtctggggacacggccatgtattactgtgcaaggcagggatttggtaactacggtgattacta
tgctatggactactggggccaagggaccacggtcaccgtctcctca

FIG. 8D
4H11 VL (SEQ ID NO:07)
gacattgagctcacccagtctccaatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagtttattactgcagcaatctttataatctactcacgttcggtcctgggac
caagctggaggtcaaacgg

FIG. 8E
9B11 VH (SEQ ID NO:08)
gtgaagctggaggagtcagggggagacttggtgaagcctggagggtccctgaaactctcctgtgcagtctctggattcac
tttcagtagccattccatgtcttggattcgtcagactccagagaagaggctagagtgggtcgcatccgtgagtagtggtg
gtaggatctactattcggacagtgtgaaggccgattcaccgtcaccagagaaaatgacaggaacaccctgtatttgtta
atgagtagtctgagtctgaggacacggccatgtattattgtggaagaggacaggtatttatgctttggacaattgggg
ccaaggggaccacggtcaccgtctcctca

FIG. 8F
9B11 VL.A (SEQ ID NO:09)
gacattgagctcacccagtctccatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagtttattactgcagcaatctttataatctactcacgttcggtcctgggac
caagctggagatcaaacgg

FIG. 8G
9B11 VL.B (SEQ ID NO:10)
gacattgagctcacccagtctccaaagctcctgatctacaaggtttccaaccgattttctggggtcccagacaggttcag
tggcagtggatcagggacagatttcacactcaagatcagcagagtggaggctgaggatctgggagtttattactgcttc
aaggttcacatgttccgtggacgttcggtggagggaccaagctggagatcaaacgg

FIG. 8H
24B3-VH (SEQ ID NO:11)
GAGGTGAAGCTGGAGGAGTCAGGACCTGAACTGGTGAAGCCTGGGGCTTCAGTGAAGATATCCTGCAAGGCTTCTGGTTA
CTCATTTACTGGCTACTTTATGAACTGGGTGAAGCAGACCCATGGAAAGAGCCTTGAGTGGATTGGACGTATTAATCCTT
ACAATGGTGCTACTTTCTACAATCAGAAGTTCACGGGCAAGGCCACAATGACTGTAGACAAATCCTCTACCACAGCCCAC
ATGGAGCTCCTGAGCCTGACATCTGAGGACTCTGCAGTCTATTATTGTGCAAAGGGGAATTACTACGGCCCCTTTGATTA
CTGGGGCCAAGGGACCACGGTCACCGTCTCCTCA

FIG. 8I
24B3-VL (SEQ ID NO:12)
GACATTGAGCTCACCCAGTCTCCATCTTATCTTGCTGCATCTCCTGGAGAAACCATTACTATTAATTGCAGGGCAAGTAA
GAGCATTAGCAAATATTTAGCCTGGTATCAAAAGAAACCTGGGAAAACTAATAAGCTTCTTATCTACTCTGGATCCACTT
TGCAATCTGGAATTCCATCAAGGTTCAGTGGCAGTGGATCTGGTACAGATTTCACTCTCACCATCAGTAGCCTGGAGCCT
GAAGATTTTGCAATGTATTACTGTCAACAGCATAATGAATACCCGTGGACGTTCGGTGGAGGGACCAAGCTGGAGATCAA
ACGGGCGGCCGCA

FIG. 9A

Homo sapiens MUCIN-16 (GenBank NP_078966) (SEQ ID NO:13)

```
   1 mlkpsglpgs ssptrslmtg srstkatpem dsgltgatls pktstgaivv tehtlpftsp
  61 dktlasptss vvgrttqslg vmssalpest srgmthseqr tspslspqvn gtpsrnypat
 121 smvsglsspr trtsstegnf tkeastytlt vettsgpvte kytvptetst tegdstetpw
 181 dtryipvkit spmktfadst askenapvsm tpaettvtds htpgrtnpsf gtlyssfldl
 241 spkgtpnsrg etslelilst tgypfsspep gsaghsrist saplsssasv ldnkisetsi
 301 fsgqsltspl spgvpearas tmpnsaipfs mtlsnaetsa ervrstissl gtpsistkqt
 361 aetiltfhaf aetmdipsth iaktlasewl gspgtlggts tsalcttsps ttlvseetnt
 421 hhstsgkete gtlntsmtpl etsapgeese mtatlvptlg fttldskirs psqvssshpt
 481 relrttgsts grqssstaah gssedilratt sstskasswt sestaqqfse pqhtqwvets
 541 psmkterppa stsvaapitt svpsvvsgft tlktsstkgi wleetsadtl igestagptt
 601 hqfavptgis mtggsstrgs qgtthlltra tassetsadl tlatngvpvs vspavsktaa
 661 gssppggtkp sytmvssvip etsslqssaf regtslgltp lntrhpfssp epdsaghtki
 721 stsipllssa svledkvsat stfshhkats sittgtpeis tktkpssavl ssmtlsnaat
 781 spervrnats plthpspsge etagsvltls tsaettdspn ihptgtltse ssespstlsl
 841 psvsgvkttf ssstpsthlf tsgeeteets npsvsqpets vsrvrttlas tsvptpvfpt
 901 mdtwptrsaq fsshlvsel ratsstsvtn stgsalpkis hltgtatmsq tnrdtfndsa
 961 apqsttwpet sprfktglps atttvstsat slsatvmvsk ftspatssme atsirepstt
1021 ilttettngp gsmavastni pigkgyiteg rldtshlpig ttassetsmd ftmakesvsm
1081 svspsqsmda agsstpgrts qfvdtfsddv yhltsreiti prdgtssalt pqmtathpps
1141 pdpgsarstw lgilssspss ptpkvtmsst fstqrvttsm imdtvetsrw nmpnlpstts
1201 ltpsniptsg aigkstlvpl dtpspatsle aseggiptls typestntps ihlgahasse
1261 spstikltma svvkpgsytp ltfpsiethi hvstarmays sgsspemtap getntgstwd
1321 pttyitttdp kdtssaqvst phsvrtlrtt enhpktesat paaysgspki ssspnltspa
1381 tkawtitdtt ehstqlhytk laekssgfet qsapgpvsvv iptsptigss tleltsdvpg
1441 eplvlapseq ttitlpmatw lstslteema stdldissps spmstfaifp pmstpshels
1501 kseadtsair ntdsttldqh lgirslgrtg dlttvpitpl tttwtsvieh stqaqdtlsa
1561 tmspthvtqs lkdqtsipas aspshltsvy pelgtqgrss seattfwkps tdtlsreiet
1621 gptniqstpp mdntttgsss sgvtlgiahl pigtsspaet stnmalerrs statvsmagt
1681 mgllvtsapg rsisqslgrv ssvlsestte gvtdsskgss prlntqgnta lssslepsya
1741 egsqmstsip ltssptttpdv efiggstfwt kevttvmtsd iskssartes ssatlmstal
1801 gstentgkek lrtasmdlps ptpsmevtpw isltlsnapn ttdsldlshg vhtssagtla
1861 tdrslntgvt rasrlengsd tsskslsmgn sthtsmtyte ksevsssihp rpetsapgae
1921 ttltstpgnr aisltlpfss ipveeviatg itsgpdinsa pmthspitpp tivwtstgti
1981 eqstqplhav ssekvsvqtq stpyvnsvav saspthensv ssgsstsspy ssaslestds
2041 tisrrnaits wlwdlttslp tttwpstsls ealssghsgv snpsstttef plfsaastsa
2101 akqrnpetet hgpqntaast lntdassvtg lsetpvgasi ssevplpmai tsrsdvsglt
2161 sestanpslg tassagtklt rtislptses lvsfrmnkdp wtvsiplgsh pttntetsip
2221 vnsagppgls tvasdvidtp sdgaesiptv sfspspdtev ttishfpekt thsfrtissl
2281 theltsrvtp ipgdwmssam stkptgaspg itlgerrtit saapttspiv ltasftetst
2341 vsldnettvk tsdildarkt nelpsdssss sdlintsias stmdvtktas isptsisgmt
2401 assspslfss drpqvptstt etntatspsv ssntysldgg snvggtpstl ppftithpve
2461 tssallawsr pvrtfstmvs tdtasgenpt ssnsvvtsvp apgtwtsvgs ttdlpamgfl
2521 ktspageahs llastiepat aftphlsaav vtgssatsea sllttseska ihsspqtptt
```

FIG. 9B

```
2581 ptsganwets atpesllvvt etsdttltsk ilvtdtilfs tvstppskfp stgtlsgasf
2641 ptllpdtpai pltateptss latsfdstpl vtiasdslgt vpettltmse tsngdalvlk
2701 tvsnpdrsip gitiqgvtes plhpsstsps kivaprntty egsitvalst lpagttgslv
2761 fsqssenset talvdssaql erasvmpltt qsqgmassqq iresgsthstg tktfsslplt
2821 mnpgevtams eittnrltat qstapkgipv kptsaesgll tpvsasssps kafaslttap
2881 ptwgipqstl tfefsevpsl dtksaslptp gqslntipds dastassels kspeknprar
2941 mmtstkaisa ssfqstgfte tpegsaspsm agheprvpts gtgdpryase smsypdpska
3001 ssamtstsla sklttlfstq qaarsgssss pislsteket sflsptasts rktslflgps
3061 marqpnilvh lqtsaltlsp tstlnmsqee ppeltssqti aeeegttaet qtltftpset
3121 ptsllpvssp teptarrkss petwassisv paktslvett dgtlvttikm ssqaaqgnst
3181 wpapaeetgs spagtspgsp emsttlkims skepsispei rstvrnspwk tpettvpmet
3241 tvepvtlqst algsgstsis hlptgttspt ksptenmlat ervslspspp eawtnlysgt
3301 pggtrqslat mssvslespt arsitgtgqq sspelvsktt gmefsmwhgs tggttgdthv
3361 slstssnile dpvtspnsvs sltdkskhkt etwvsttaip stvlnnkima aeqqtsrsvd
3421 eaysstssws dqtsgsditl gaspdvtntl yitstaqtts lvslpsgdqg itsltnpsgg
3481 ktssassvts psigletlra nvsavksdia ptaghlsqts spaevsildv ttaptpgist
3541 tittmgtnsi stttpnpevg mstmdstpat errttstehp stwsstaasd swtvtdmtsn
3601 lkvarspgti stmhttsfla sstseldsmst phgritvigt slvtpssdas avktetstse
3661 rtlspsdtta stpistfsrv qrmsisvpdi letswtpsst eaedvpvsmv stdhastktd
3721 pntplstflf dslstldwdt grslssatat tsapqgattp qeltletmis patsqlpfsi
3781 ghitsavtpa amarssgvtf srpdptskka eqtstqlptt tsahpgqvpr saattldvip
3841 htaktpdatf qrqgqtaltt saratsdswn ekekstpsap witemmnsvs edtikevtss
3901 ssvlrtlntl dinlesgtts spswksspye riapssesttd keaihpstnt vettgwvtss
3961 ehashstipa hsassklsp vvttstreqa ivsmstttwp estrartepn sfltielrdv
4021 spymdtsstt qtsiisspgs taitkgprte itsskrisss flaqsmrssd spseaitrls
4081 nfpamtesgg milamqtspp gatslsaptl dtsataswtg tplattqrft ysekttlfsk
4141 gpedtsqpsp psveetssss slvpihatts psnilltsqg hspsstppvt svflsetsgl
4201 gkttdmsris lepgtslppn lsstageals tyeasrdtka ihhsadtavt nmeatssseys
4261 pipghtkpsk atsplvtshi mgditsstsv fgssetteie tvssvnqglq erstsqvass
4321 atetstvith vssgdatthv tktqatfssg tsissphqfi tstntftdvs tnpstslimt
4381 essgvtittq tgptgaatqg pylldtstmp yltetplavt pdfmqsekttt liskgpkdvs
4441 wtsppsvaet sypssltpfl vttippatst lqgqhtsspv satsvltsgl vkttdmlnts
4501 mepvtnspqn lnnpsneila tlaattdiet ihpsinkavt nmgtassahv lhstlpvsse
4561 pstatspmvp assmgdalas isipgsettd iegeptsslt agrkenstlq emnsttesni
4621 ilsnvsvgai teatkmevps fdatfiptpa qstkfpdifs vassrlsnsp pmtisthmtt
4681 tqtgssgats kiplaldtst letsagtpsv vtegfahski ttammndvkd vsqtnppfqd
4741 easspssqap vlvttlpssv aftpqwhsts spvsmssvlt sslvktagkv dtsletvtss
4801 pqsmsntldd isvtsaattd ietthpsint vvtnvgttgs afeshstvsa ypepskvtsp
4861 nvttstmedt tisrsipkss kttrtetett ssltpklret sisqeitsst etstvpykel
4921 tgattevsrt dvtsssstsf pgpdqstvsl distetntrl stspimtesa eitittqtgp
4981 hgatsqdtft mdpsnttpqa gihsamthgf sqldvttlms ripqdvswts ppsvdktssp
5041 ssflsspamt tpslisstlp edklsspmts lltsqlvkit dilrtrlepv tsslpnfsst
5101 sdkilatskd skdtkeifps inteetnvka nnsgheshsp aladsetpka ttqmvitttv
5161 gdpapstsmp vhgssettni kreptyfltp rlretstsqe ssfptdtsfl lskvptgtit
```

FIG. 9C

```
5221 evsstgvnss skistpdhdk stvppdtftg eiprvftssi ktksaemtit tqasppesas
5281 hstlpldtst tlsqggthst vtqgfpysev ttlmgmgpgn vswmttppve etssvsslms
5341 spamtspspv sstspqsips splpvtalpt svlvtttdvl gttspesvts sppnlssith
5401 erpatykdta hteaamhhst ntavtnvgts gsghksqssv ladsetskat plmsttstlg
5461 dtsvststpn isqtnqiqte ptaslsprlr esstsektss ttetntafsy vptgaitqas
5521 rteisssrts isdldrptia pdistgmitr lftspimtks aemtvttqtt tpgatsqgil
5581 pwdtsttlfq ggthstvsqg fphseittlr srtpqdvswm ttppveetss gfslmspsmt
5641 spspvsstsp esipssplpv talltsvlvt ttnvlgttsp epvtssppnl ssptqerltt
5701 ykdtahteam hasmhtntav anvgtsisgh esqssvpads htskatspmg itfamgdtsv
5761 ststpaffet riqtestssl ipglrdtrts eeintvtets tvlsevpttt ttevsrtevi
5821 tssrttisgp dhskmspyis tetitrlstf pfvtgstema itnqtgpigt isqatltldt
5881 sstaswegth spvtqrfphs eetttmsrst kgvswqspps veetsspssp vplpaitshs
5941 slysavsgss ptsalpvtsl ltsgrrktid mldthselvt sslpsassfs geiltseast
6001 ntetihfsen taetnmgttn smhklhssvs ihsqpsghtp pkvtgsmmed aivststpgs
6061 petknvdrds tspltpelke dstalvmnst tesntvfssv sldaatevsr aevtyydptf
6121 mpasaqstks pdispeasss hensppltis thktiatqtg psqvtslgql tldtstiats
6181 agtpsartqd fvdsettsvm nndlndvlkt spfsaeeans lssqapllvt tspspvtstl
6241 qehstsslvs vtsvptptla kitdmdtnle pvtrspqnlr ntlatseatt dthtmhpsin
6301 tavanvgtts spnefyftvs pdsdpykats avvitstsgd sivstsmprs samkkieset
6361 tfslifrlre tstsqkigss sdtstvfdka ftaattevsr teltsssrts iqgtekptms
6421 pdtstrsvtm lstfagltks eertiatqtg phratsqgtl twdtsittsq agthsamthg
6481 fsqldlstlt srvpeyisgt sppsvektss ssellslpai tspspvpttl pesrpsspvh
6541 ltslptsglv kttdmlasva slppnlgsts hkipttsedi kdtekmypst niavtnvgtt
6601 tsekesyssv payseppkvt spmvtsfnir dtivstsmpg sseitrieme stfslahglk
6661 gtstsqdpiv steksavlhk lttgatetsr tevassrrts ipgpdhstes pdistevips
6721 lpislgites snmtiitrtg pplgstsqgt ftldtpttss ragthsmatq efphsemttv
6781 mnkdpeilsw tippsiekts fssslmpspa mtsppvsstl pktihttpsp mtslltpslv
6841 mttdtlgtsp epttssppnl sstsheiltt dedttaieam hpststaatn vettssghgs
6901 qssvladssk tkatapmdtt stmghttvst smsvssettk ikrestyslt pglretsisq
6961 nasfstdtsi vlsevptgtt aevsrtevts sgrtsipgps qstvlpeist rtmtrlfasp
7021 tmtesaemti ptqtgpsgst sqdtltldts ttksqakths tltqrfphse mttlmsrgpg
7081 dmswqsspsl enpsslpsll slpattsppp isstlpvtis ssplpvtsll tsspvtttdm
7141 lhtspelvts sppklshtsd erlttgkdtt nteavhpstn taasnveips sghespssal
7201 adsetskats pmfitstqed ttvaistphf letsriqkes isslspklre tgssvetssa
7261 ietsavlsev sigatteisr tevtsssrts isgsaestml peisttrkii kfptspilae
7321 ssemtiktqt sppgstsest ftldtsttps lvithstmtq rlphseittl vsrgagdvpr
7381 psslpveets ppssqlslsa mispspvsst lpasshsssa svtslltpgq vkttevldss
7441 aepetsspps lsstsveila tsevttdtek ihpfsntavt kvgtsssghe spssvlpdse
7501 ttkatsamgt isimgdtsvs tltpalsntr kiqsepassl ttrlretsts eetslatean
7561 tvlskvstga ttevsrteai sfsrtsmsgp eqstmsqdis igtiprisas svltesakmt
7621 ittqtgpsss tlestlnlnt attpswveth siviqgfphp emttsmgrgp ggvswpsppf
7681 vketsppssp lslpavtsph pvsttflahi ppsplpvtsl ltsgpatttd ilgtstepqt
7741 sssssslstts herlttykdt ahteavhpst ntggtnvatt ssgyksqssv ladsspmctt
7801 stmgdtsvlt stpafletrr iqtelasslt pglressgse gtssgtkmst vlskvptgat
```

FIG. 9D

```
 7861 teiskedvts ipgpaqstis pdistrtvsw fstspvmtes aeitmmthts plgattqgts
 7921 tldtssttsl tmthstisqg fshsqmstlm rrgpedvswm sppllektrp sfslmsspat
 7981 tspspvsstl pesissspIp vtslltsgla kttdmlhkss epvtnspanl sstsveilat
 8041 sevttdtekt hpssnrtvtd vgtssseghes tsfvladsqt skvtspmvit stmedtsvst
 8101 stpgffetsr iqteptsslt lglrktssse gtslatemst vlsgvptgat aevsrtevts
 8161 ssrtsisgfa qltvspetst etitrlptss imtesaemmi ktqtdppgst pesthtvdis
 8221 ttpnwveths tvtqrfshse mttlvsrspg dmlwpsqssv eetssasssll slpattspsp
 8281 vsstlvedfp saslpvtsll npglvittdr mqisrepgts stsnlsstsh erlttledtv
 8341 dtedmqpsth tavtnvrtsi sghesqssvl sdsetpkats pmgttytmge tsvsistsdf
 8401 fetsriqiep tssltsglre tssserissa tegstvlsev psgattevsr tevissrgts
 8461 msgpdqftis pdisteaitr lstspimtes aesaitietg spgatsegtl tldtstttfw
 8521 sgthstaspg fshsemttlm srtpgdvpwp slpsveeass vssslsspam tstsffstlp
 8581 esissspIhpv talltIgpvk ttdmlrtsse petssppnls stsaeilats evtkdrekih
 8641 pssntpvvnv gtviykhlsp ssvladlvtt kptspmatts tlgntsvsts tpafpetmmt
 8701 qptssltsgl reistsqets satersasls gmptgattkv srtealslgr tstpgpaqst
 8761 ispeisteti tristpltt gsaemtitpk tghsqassqg tftldtssra swpgthsaat
 8821 hrsphsgmtt pmsrgpedvs wpsrpsvekt sppsslvsls avtspsplys tpseesshssp
 8881 lrvtslftpv mmkttdmldt slepvttspp smnitsdesl atskatmete aiqlsentav
 8941 tqmgtisarq efyssypqlp epskvtspvv tsstikdivs ttipasseit riemeststl
 9001 tptpretsts qeihsatkps tvpykaltsa tiedsmtqvm sssrgpspdq stmsqdiste
 9061 vitrlstspi ktestemtit tqtgspgats rgtltldtst tfmsgthsta sqgfshsqmt
 9121 almsrtpgdv pwlshpsvee assasfslss pvmtssspvs stlpdsihss slpvtsllts
 9181 glvkttellg tsseepetssp pnlsstsaei laitevttdt eklemtnvvt sgythespss
 9241 vladsvttka tssmgitypt gdtnvltstp afsdtsriqt ksklsltpgl metsiseets
 9301 satekstvls svptgattev srteaisssr tsipgpaqst mssdtsmeti tristpltrk
 9361 estdmaitpk tgpsgatsqg tftldsssta swpgthsatt qrfpqsvvtt pmsrgpedvs
 9421 wpsplsvekn sppsslvsss svtspsplys tpsgsshssp vpvtslftsi mmkatdmlda
 9481 slepettsap nmmnitsdesl aaskattete aihvfentaa shvettsate elyssspgfs
 9541 eptkvispvv tsssirdnmv sttmpgssgi trieiesmss ltpglretrt sqditsstet
 9601 stvlykmpsg atpevsrtev mpssrtsipg paqstmsldi sdevvtrlst spimtesaei
 9661 tittqtgysl atsqvtlplg tsmtflsgth stmsqglshs emtnlmsrgp eslswtsprf
 9721 vettrssssl tslplttsls pvsstlldss pssplpvtsl ilpglvkttte vldtssepkt
 9781 ssspnlssts veipatseim tdtekihpss ntavakvrts ssvheshssv ladsettiti
 9841 psmgitsavd dttvftsnpa fsetrripte ptfsltpgfr etstseetts itetsavlyg
 9901 vptsattevs mteimssnri hipdsdqstm spdiitevit rlssssmmse stqmtittqk
 9961 sspgataqst ltlatttapl arthstvppr flhsemttlm srspenpswk sslfvektss
10021 ssssllslpvt tspsvsstlp qsipsssfsv tslltpgmvk ttdtstepgt slspnlsqts
10081 veilaasevt tdtekihpss smavtnvgtt ssghelyssv sihsepskat ypvgtpssma
10141 etsistsmpa nfettgfeae pfshltsgfr ktnmsldtss vtptntpssp gsthllqssk
10201 tdftssakts spdwppasqy teipvdiitp fnaspsites tgitsfpesr ftmsvtesth
10261 hlstdllpsa etistgtvmp slseamtsfa ttgvpraisg sgspfsrtes gpgdatlsti
10321 aeslpsstpv pfssstfttt dsstipalhe itsssatpyr vdtslgtess ttegrlvmvs
10381 tldtssqpgr tssspildtr mtesvelgtv tsayqvpsls trltrtdgim ehitkipnea
10441 ahrgtirpvk gpqtstspas pkglhtggtk rmetttttalk ttttalktts ratlttsvyt
```

FIG. 9E

```
10501 ptlgtltpln asmqmastip temmittpyv fpdvpettss latslgaets talprttpsv
10561 fnresettas lvsrsgaers pviqtldvss sepdttaswv ihpaetiptv skttpnffhs
10621 eldtvsstat shgadvssai ptnispseld altplvtisg tdtsttfptl tksphetetr
10681 ttwlthpaet sstiprtipn fshhesdatp siatspgaet ssaipimtvs pgaedlvtsq
10741 vtssgtdrnm tiptltlspg epktiaslvt hpeaqtssai ptstispavs rlvtsmvtsl
10801 aaktsttnra ltnspgepat tvslvthpaq tsptvpwtts iffhsksdtt psmttshgae
10861 sssavptptv stevpgvvtp lvtssravis ttipiltlsp gepettpsma tshgeeassa
10921 iptptvspgv pgvvtslvts sravtsttip iltfslgepe ttpsmatshg teagsavptv
10981 lpevpgmvts lvassravts ttlptltlsp gepettpsma tshgaeasst vptvspevpg
11041 vvtslvtsss gvnstsiptl ilspgelett psmatshgae assavptptv spgvsgvvtp
11101 lvtssravts ttipiltlss sepettpsma tshgveassa vltvspevpg mvtslvtssr
11161 avtsttiptl tissdepett tslvthseak misaiptlav sptvqglvts lvtssgsets
11221 afsnltvass qpetidswva hpgteassvv ptltvstgep ftnislvthp aessstlprt
11281 tsrfshseld tmpstvtspe aesssaistt ispgipgvlt slvtssgrdi satfptvpes
11341 pheseatasw vthpavtstt vprttpnysh sepdttpsia tspgaeatsd fptitvspdv
11401 pdmvtsqvts sgtdtsitip tltlssgepe tttsfityse thtssaiptl pvspgaskml
11461 tslvissgtd stttfptlte tpyepettai qlihpaetnt mvprttpkfs hsksdttlpv
11521 aitspgpeas savstttisp dmsdlvtslv pssgtdtstt fptlsetpys pettatwlth
11581 paetsttvsg tipnfshrgs dtapsmvtsp gvdtrsgvpt ttippsipgv vtsqvtssat
11641 dtstaiptlt pspgepetta ssathpgtqt gftvpirtvp ssepdtmasw vthppqtstp
11701 verttssfsh sspdatpvma tsprteassa vlttispgap emvtsqitss gaatsttvpt
11761 lthspgmpet tallsthprt etsktfpast vfpqvsetta sltirpgaet stalptqtts
11821 alftllvtgt srvdlsptas pgvsaktapl sthpgtetst miptstlslg llettgllat
11881 sssaetstst ltltvspavs glssasittd kpqtvtswnt etspsvtsvg ppefsrtvtg
11941 ttmtlipsem ptppktshge gvsptttilrt tmveatnlat tgssptvakr ttffntlags
12001 lftplttpgm stlasesvts rtsynhrswi sttssynrry wtpatstpvt stfspgists
12061 sipsstaatv pfmvpftlnf titnlqyeed mrhpgsrkfn aterelqgll kplfrnssle
12121 ylysqcrlas lrpekdssat avdaicthrp dpedlgldre rlywelsnlt ngiqelgpyt
12181 ldrnslyvng fthrssmptt stpgtstvdv gtsgtpsssp spttagpllm pftlnftitn
12241 lqyeedmrrt gsrkfntmes vlqgllkplf kntsvgplys gcrltllrpe kdgaatgvda
12301 icthrldpks pglnreqlyw elskltndie elgpytldrn slyvngfthq ssvsttstpg
12361 tstvdlrtsg tpsslsspti maagpllvpf tlnftitnlq ygedmghpgs rkfnttervl
12421 qgllgpifkn tsvgplysgc rltslrsekd gaatgvdaic ihhldpkspg lnrerlywel
12481 sqltngikel gpytldrnsl yvngfthrts vptsstpgts tvdlgtsgtp fslpspatag
12541 pllvlftlnf titnlkyeed mhrpgsrkfn ttervlqtll gpmfkntsvg llysqcrltl
12601 lrsekdgaat gvdaicthrl dpkspgvdre qlywelsqlt ngikelgpyt ldrnslyvng
12661 fthwipvpts stpgtstvdl gsgtpsslps pttagpllvp ftlnftitnl kyeedmhcpg
12721 srkfntterv lqsllgpmfk ntsvgplysg crltllrsek dgaatgvdai cthrldpksp
12781 gvdreqlywe lsqltngike lgpytldrns lyvngfthqt sapntstpgt stvdlgtsgt
12841 psslpsptsa gpllvpftln ftitnlqyee dmhhpgsrkf ntervlqggl lgpmfkntsv
12901 gllysqcrlt llrpekngaa tgmdaicshr ldpkspglnr eqlywelsql thgikelgpy
12961 tldrnslyvn gfthrssvap tstpgtstvd lgtsgtpssl pspttavpll vpftlnftit
13021 nlqygedmrh pgsrkfntte rvlqggllgpl fknssvgply sgcrlislrs ekdgaatgvd
13081 aicthhlnpq spgldreqly wqlsqmtngi kelgpytldr nslyvngfth rssglttstp
```

FIG. 9F

```
13141  wtstvdlgts gtpspvpspt ttgpllvpft lnftitnlqy eenmghpgsr kfnitesvlq
13201  gllkplfkst svgplysgcr ltllrpekdg vatrvdaict hrpdpkipgl drqqlywels
13261  qlthsitelg pytldrdsly vngftqrssv pttstpgtft vqpetsetps slpgptatgp
13321  vllpftlnft itnlqyeedm rrpgsrkfnt tervlqgllm plfkntsvss lysgcrltll
13381  rpekdgaatr vdavcthrpd pkspgldrer lywklsqlth gitelgpytl drhslyvngf
13441  thqssmtttr tpdtstmhla tsrtpaslsg pmtaspllvl ftinftitnl ryeenmhhpg
13501  srkfntterv lqgllrpvfk ntsvgplysg crltllrpkk dgaatkvdai ctyrpdpksp
13561  gldreqlywe lsqlthsite lgpytldrds lyvngftqrs svpttsipgt ptvdlgtsgt
13621  pvskpgpsaa spllvlftln ftitnlryee nmqhpgsrkf nttervlqgl lrslfkstsv
13681  gplysgcrlt llrpekdgta tgvdaicthh pdpksprldr eqlywelsql thnitelgpy
13741  aldndslfvn gfthrssvst tstpgtptvy lgasktpasi fgpsaashll ilftlnftit
13801  nlryeenmwp gsrkfntter vlqgllrplf kntsvgplys gcrltllrpe kdgeatgvda
13861  icthrpdptg pgldreqlyl elsqlthsit elgpytldrd slyvngfthr ssvpttstqv
13921  vseepftlnf tinnlrymad mgqpgslkfn itdnvmqhll splfqrsslg arytgcrvia
13981  lrsvkngaet rvdllctylq plsgpglpik qvfhelsqqt hgitrlgpys ldkdslylng
14041  ynepgpdepp ttpkpattfl pplseattam gyhlktltln ftisnlqysp dmgkgsatfn
14101  stegvlqhll rplfqkssmg pfylgcqlis lrpekdgaat gvdttctyhp dpvgpgldiq
14161  qlywelsqlt hgvtqlgfyv ldrdslfing yapqnlsirg eyqinfhivn wnlsnpdpts
14221  seyitllrdi qdkvttlykg sqlhdtfrfc lvtnltmdsv lvtvkalfss nldpslveqv
14281  fldktlnasf hwlgstyqlv dihvtemess vyqptssssst qhfylnftit nlpysqdkaq
14341  pgttnyqrnk rniedalnql frnssiksyf sdcqvstfrs vpnrhhtgvd slcnfsplar
14401  rvdrvaiyee flrmtrngtq lqnftldrss vlvdgyspnr nepltgnsdl pfwaviligl
14461  agllgvitcl icgvlvttrr rkkegeynvq qqcpgyyqsh ldledlq
```

FIG. 9G

Peptide 1
14394                14410
    nfsplar rvdrvaiyee (SEQ ID NO:01)

FIG. 9H

Peptide 2
14425                14442
    tldrss vlvdgyspnr ne (SEQ ID NO:02)

FIG. 9I

Peptide 3
14472                14492
    cgvlvttrr rkkegeynvq qq (SEQ ID NO:03)

FIG. 9J

Transmembrane Region:
14452                14475
    fwaviligl agllgvitcl icgvl (SEQ ID NO:14)

FIG. 9K

Peptide containing the cysteine loop peptide:
14367                                14398
    ksyf sdcqvstfrs vpnrhhtgvd slcnfspl (SEQ ID NO:15)

CD8 leader sequence
ATGGCTC TCCCAGTGAC TGCCCTACTG CTTCCCCTAG CGCTTCTCCT GCATGCAGAG CD3 zeta chain intracellular domain
AGAGT CAAGTTCAGC AGGAGCGCAG AGCCCCCAGC GTACCAGCAG GGCCAGAACC AGCTCTATAA
CGAGCTCAAT CTAGGACGAA GAGAGGAGTA CGATGTTTTG GACAAGAGAC GTGGCCGGGA CCCTGAGATG
GGGGGAAAGC CGCGCAGAA GAACCCTCAG GAAGGCCTGT ACAATGAACT GCAGAAAGAT AAGATGGCG
GAGGCCTACAG TGAGATTGGG ATGAAAGGCG AGCGCCGGAG GGGCAAGGGG CACGATGGCC TTTACCAGGG
TCTCAGTACA GCCACCAAGG ACACCTACGA CGCCCTTCAC ATGCAGGCCC
TGCCCCCTCG (G4S)3 serine-glycine linker
[sequence redacted]

CD8 transmembrane domain
GCGGCCGCAC CCACCACGAC GCCAGCGCCG CGACCACCAA CCCCGGCGCC CACGATCGCG TCCCAGCCCC
TGTCCCTGCG CCCAGAGGCG TGCCGGCCAG CGGCGGGGGG CGCAGTGCAC ACGAGGGGGC TGGACTTCGC
CTGTGATATCTACATCTGGG CGCCCTTGGC CGGCACTTGT GGGGTCCTTC TCCTGTCACT GGTTATCACC
CTTTACTGCA ACCAC CD28 transmembrane + intracellular domains (-STOP)
CAA TTGAAGTTAT GTATCCTCCT CCTTACCTAG ACAATGAGAA GAGCAATGGA ACCATTATCC
ATGTGAAAGG GAAACACCTT TGTCCAAGTC CCCTATTTCC CGGACCTTCT AAGCCCTTTT GGGTGCTGGT
GGTGGTTGGT GGAGTCCTGG CTTGCTATAG CTTGCTAGTA ACAGTGGCCT TTATTATTTT CTGGGTGAGG
AGTAAGAGGA GCAGGCTCCT

Figure 18 top strand: SEQ ID NO:37
Figure 18 bottom strand: SEQ ID NO:38

7701  TTGGGATGAA AGGGGACGGC CGGAGGGGCA AGGGGCAGGA TGGCCTTTAC CAGGGTCTCA GTACAGCCAC CAAGGACACC TACGAGGCCC TTCACATGCA
      AACCCTACTT TCCGCTCGGG GGCTCCCCGT TCCCCGTGCT ACCGGAAATG GTCCCAGAGT CATGTCGGTG GTTCCTGTGG ATGCTCCGGG AAGTGTACGT
      CD3 zeta chain intracellular domain
      ──────────
      XhoI

7801  GGCCCTGCCC CTCGGTAAC AGCCACTCGA G
      CCGGGACGGG GGAGCGATTG TCGGTGAGCT C

Figure 19 top strand: SEQ ID NO:39
      Figure 19 bottom strand: SEQ ID NO:40

1. Mouse MUC16-CD Peptide 1 (SEQ ID NO:21):

TLDRKSVFVDGYSQNRDD                                19 AA

2. Mouse 1st Cysteine Loop peptide 2 (SEQ ID NO:22):

KSYFSDCQVLAFRSVSNNNNHTGVDSLCNFSPL                 33 AA

3. Mouse 2nd Cysteine Loop peptide 3 (SEQ ID NO:23):

SLYSNCRLASLRPKKNGTATGVNAICSYHQN                   32 AA

Figure 20B
Alignment of mouse MUC16 (SEQ ID NO:24) and human MUC16 (SEQ ID NO:25) amino acid sequences

```
                     Peptide 1 (C' ByFbB1A5 loop)
mouse complete   RLIRPLVQME---SLYSHSKLASLPKKNGIASSNAIGSYRQNPDHPELGTQELYTELT
8244
human complete   RLLRPLFQKSSMGPFYLGSQLFSLPPEKDGAATGVDTTSYHPDPVGPGLGIQQLYNELS
14167
                 **:***.*:,  .:*  *:*  *****:*:*:****::  *:***  :*  ** *:** :*:

mouse complete   QLTQGVTQLGSYMLDQNSIYVEGYVPLNITTQSFYQLNFSIINWNLNNTDPTSSEYITLE
8304
human complete   QLTEGVTQLGFYVLDRDSLFTNGYAPQELSIRGEYQINFRIVNWNLSNPDPTSSEYITLL
14227
                 *:**** *::::::*.*  *:::*:*: *:**  *:****.*.********* mouse complete   RDIEDKVTTLYTGSQLKEVFQCSLVTNMTSGSTVVTLEALFSSHLDPRLVKQVFLNKTLN
8364
human complete   RDIQDKVTTLYKGSQLHDTFRFSLVTNLTMDSVLVTVKALFSSNLDPSLVEQVFLDKTLN
14287
                 *:***:**::.*: ******:*:.*.* :.*.:*::**** mouse complete   ASSHWLGATYQLKDLHVIDMKTSILLPAEIPTTSSSSQHFNLNFTITNLPYSQDIAQPST
8424
human complete   ASFHWLGSTYQLVDIHVTEMESSVYQ----PTSSSSTQHFYLNFTITNLPYSQDKAQPGT
14343
                  :** *:**::*::::*:    .***:*.*********.  *.* mouse complete   TKYQQTKRGIENAINQLFRNSSI                     ARRV
8484
human complete   TNYQRNKRNIEDALNQLFRNSSIKSYFSESQVSTFRSVPN-PHHTGVDSINFSPLAKRV
14402
                 *:*   :************          :   :.:  *  ***** mouse complete   DKVAIYEEFLRMTHNGTQLLNF                       DVKKNSCLPFWAIILISLAV
8544
human complete   DKVAIYEEFLRMTKNGTQLQNFTLDRSSVLVDGYSPNRNEPLTGNSLPFWAVILIGLAG
14462
                 ***********.*                           :. *:*.*** mouse complete   LLVLITSLMSFLVTVSRKKEGDYQVQRHKLAYYLSHLDLRKLQ  8585
human complete   LLGVITSLISGVLVTTRRKKEGEYNVQQCSPGYYQSHLDLEDLQ 14507
                 ** :****:* :*** *****:*.**:   * ***** *
```

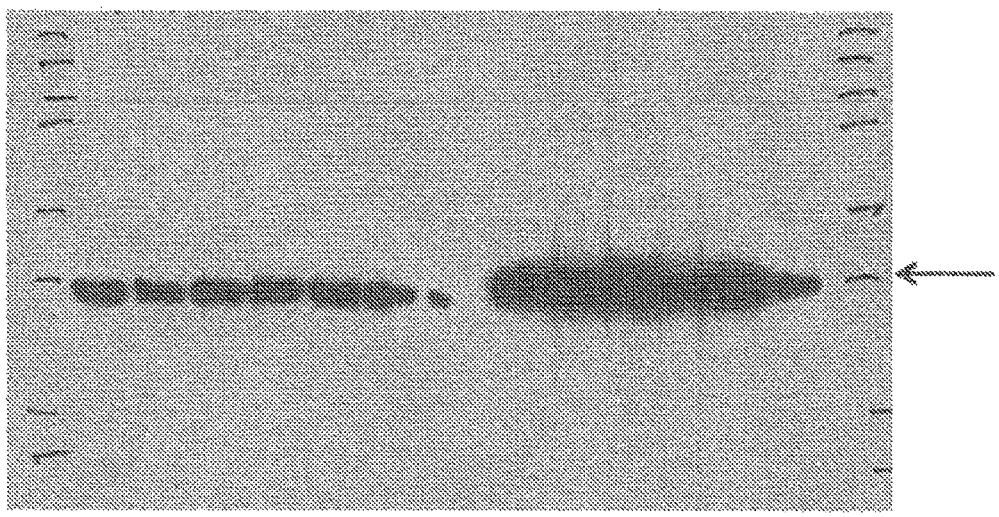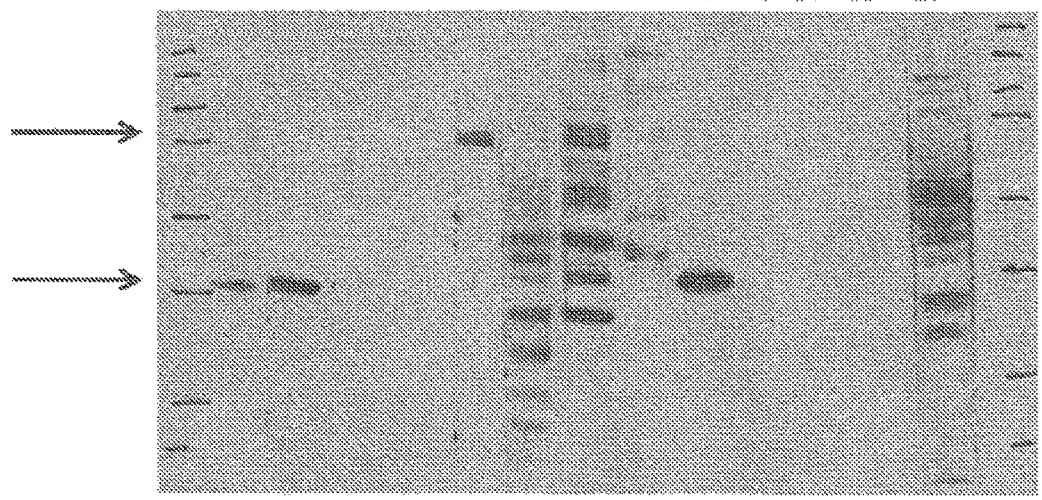
Figure 21

FIG. 24A  Nucleotide sequence encoding 12B10.3G10-V$_H$ (SEQ ID NO:26)

GAGGTGAAGCTGGAGGAGTCAGGTGGAGGATTGGTGCAGCCTAAAGGATCATTGAAACTCTCATGTGCCGCCTCT
GGTTTCACCTTCAATACCTATGCCGTGCACTGGGTCCGCCAGGCTCCAGGAAAGGGTATGGAATGGGTTGCTCGC
ATAAGAAGTAAAAGTGGAAATTATGCAACATATTATGCCGATTCAGTGAAAGACAGATTCACCATCTCCAGAAAT
GATTCACAGAGCATGCTCTATCTGCAAATGAACAACCTGAAAACTGAGGACACAGCCATATATTACTGTGTGAGA
GCGGGTAACAACGGGGCCTTTCCTTACTGGGGCCAAGGGACCACGGTCACCGTCTCCTCA

FIG. 24B  12B10.3G10-V$_H$ Amino Acid sequence (SEQ ID NO:27)

EVKLEESGGGLVQPKGSLKLSCAASGFTFNTYAVHWVRQAPGKGMEWVARIRSKSGNYAT
YYADSVKDRFTISRNDSQSMLYLQMNNLKTEDTAIYYCVRAGNNGAFPYWGQGTTVTVSS

FIG. 24C  Nucleotide sequence encoding 12B10.3G10-V$_L$ (SEQ ID NO:28)

Note the VL has an optional NotI site added by the primer for
cloning.

GACATTGAGCTCACCCAGTCTCCATCCTCACTGTCTGCATCTCTCGGAGGCAGAGTCACCATCACTTGCAAGGCT
AGCCAAGATATTAAGAAGTATATAGCTTGGTACCAACACAAGCCTGGAAAAACTCCTCGACTACTCATACATTTC
ACATCTACATTACAGACAGGCATCCCATCAAGGTTCAGTGGACGTGGGTCTGGAGAGACTATTCCTTCAGCATC
AGCAACCTGGAGTCTGAAGATATTGCAACTTATTATTGTCTACAGTATGATAGTCTGTACACGTTCGGAGGGGGG
ACCAAGCTGGAGATCAAACGGGCGGCCGCA

FIG. 24D  12B10.3G10-V$_L$ Amino Acid sequence (SEQ ID NO:29)

DIELTQSPSSLSASLGGRVTITCKASQDIKKYIAWYQHKPGKTPRLLIHFTSTLQTGIPS
RFSGRGSGRDYSFSISNLESEDIATYYCLQYDSLYTFGGGTKLEIKRAAA

ANTIBODIES TO MUC16 AND METHODS OF USE THEREOF

This application is a divisional of U.S. patent application Ser. No. 13/635,090, national stage of International Application No. PCT/US2011/030025, filed Mar. 25, 2011, which claims benefit of U.S. Provisional Application No. 61/317,964, filed on Mar. 26, 2010, each of which are hereby incorporated herein by reference in their entireties for all purposes.

This invention was made with government support under grant number CA052477 awarded by the National Institutes of Health. The government has certain rights in the invention.

FIELD OF THE INVENTION

The invention relates to antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

BACKGROUND OF THE INVENTION

Cell surface markers and shed antigens are used in the diagnosis of several cancers. For example, the CA125 antigen, recognized by the OC125 antibody, is a tissue-specific, circulating antigen expressed in ovarian cancer. The CA125 antigen is encoded by the MUC16 gene, cloned by Lloyd and Yin. The full-length gene describes a complex tethered mucin protein present primarily in a variety of gynecologic tissues, especially neoplasms. OC125 and other related antibodies react with glycosylation-dependent antigens present exclusively in the cleaved portion of the molecule.

A serum assay can detect elevated levels of the circulating CA125 antigen in many epithelial ovarian cancer patients, and this antigen, derived using the ovarian cell line OVCA433, is recognized by the OC125 antibody (1-2). The detection of circulating CA125 in serum has proven to be a useful tool for the management of ovarian cancer patients and clinical trials (3-4). However, CA125 is neither sufficiently sensitive nor specific for general cancer screening (5-6). A variety of CA125 linked antibodies including VK8 and M11 have subsequently been defined as present on ovarian cancer cells (7-9). Although these antibodies have been used to develop serum assays and various other studies in ovarian cancer, they have significant shortcomings for clinical use in screening or tissue delivery. These antibodies are not useful as screening tools, nor can they detect the proximal residual MUC16 protein fragment after cleavage. This has limited their diagnostic and therapeutic applications.

For example, OC125, M11, and most other antibodies prepared against ovarian cancer cell extracts are directed at complex, glycosylation-dependent antigens. These antigens are exclusively present in the shed portion of MUC16 and cannot be employed to follow the biology of the proximal portion of MUC16 and may not accurately reflect tissue distribution since the glycosylation patterns can vary substantially among tissues. Because the vast majority of MUC16-reactive antibodies, including OC125, react with the glycosylation-dependent antigen present exclusively in the cleaved portion of the molecule, the true distribution of MUC16 expression is not known (21). There is currently no antibody available to track the fate of the remaining MUC16 protein fragment after cleavage and CA125 release.

Thus, there remains a need for the identification of antibodies that are directed against sequences in the peptide backbone of MUC16, and that are useful for diagnosis and treatment of cancers in which MUC16 is expressed and/or overexpressed.

SUMMARY OF THE INVENTION

The invention provides an antibody, or an antigen-binding fragment thereof, that specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVD-SLC (SEQ ID NO:19). In one embodiment, the antibody internalizes into a cell. While not intending to limit the invention to a particular sequence of MUC16 ectodomain, in one embodiment, the MUC16 ectodomain polypeptide comprises a polypeptide selected from the group of Polypeptide 1 NFSPLARRVDRVAIYEE (SEQ ID NO:01) and Polypeptide 2 TLDRSSVLVDGYSPNRNE (SEQ ID NO:02). In another embodiment, the antibody lacks specific binding to a glycosylated MUC16 extracellular domain. In yet a further embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:06, and a variable light ($V_L$) chain encoded by SEQ ID NO:07. In yet another alternative embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:04, and a variable light ($V_L$) chain encoded by SEQ ID NO:05. In a further embodiment, the antibody specifically binds to the Polypeptide 1 (SEQ ID NO:01) of the MUC16 ectodomain polypeptide, and wherein the antibody comprises a variable heavy ($V_H$) chain encoded by SEQ ID NO:08, and a variable light ($V_L$) chain encoded by at least one of SEQ ID NO:09 and SEQ ID NO:10. In one embodiment, the MUC16 cytoplasmic domain polypeptide comprises VTTRR RKKEGEYNVQ QQ (SEQ ID NO:18). More preferably, but without limitation, the MUC16 cytoplasmic domain polypeptide comprises Polypeptide 3 CGVLVTTRRRK-KEGEYNVQQQ (SEQ ID NO:03). In an alternative embodiment, the MUC16 extracellular domain polypeptide that contains a cysteine loop polypeptide comprises CQVSTFRSVPNRHHTGVDSLC (SEQ ID NO:19). More preferably, but without limitation, the MUC16 extracellular domain polypeptide comprises Polypeptide 4 KSYF SDC-QVSTFRS VPNRHHTGVD SLCNFSPL (SEQ ID NO:15). In yet another alternative embodiment, the antibody specifically binds to the Polypeptide 4 (SEQ ID NO:15) of the MUC16 extracellular domain polypeptide, and wherein the antibody comprises a variable heavy ($V_H$) chain encoded by SEQ ID NO:11, and a variable light ($V_L$) chain encoded by SEQ ID NO:12. In a further alternative embodiment, the antibody is selected from the group of a chimeric antibody, a monoclonal antibody, a recombinant antibody, an antigen-binding fragment of a recombinant antibody, a humanized antibody, and an antibody displayed upon the surface of a phage. In another embodiment, the antigen-binding fragment is selected from the group of a Fab fragment, a F(ab')2 fragment, and a Fv fragment. In an alternative embodiment, the antibody, or antigen-binding fragment thereof, is covalently linked to a cytotoxic agent or a prodrug of a cytotoxic agent. In a preferred embodiment, the antibody is a monoclonal antibody produced by a hybridoma cell line.

The invention also provides an isolated monoclonal antibody, or an antigen-binding fragment thereof, produced by a hybridoma cell line, wherein the antibody specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19). In one embodiment, the MUC16 ectodomain polypeptide comprises Polypeptide 1 (SEQ ID NO:01) and the antibody is selected from the group of 9B11.20.16, 10A2, 2F4, 23D3, 30B1, and 31B2. In an alternative embodiment, the MUC16 ectodomain polypeptide comprises Polypeptide 2 (SEQ ID NO:02), and wherein the antibody is selected from the group of 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10. In yet a further embodiment, the MUC16 cytoplasmic domain polypeptide comprises Polypeptide 3 CGVLVTTRRRKKEGEYNVQQQ (SEQ ID NO:03), and wherein the antibody is selected from the group of 31A3.5.1, 19D1, 10F6, 22E10, 22F1, 3H8, 22F11, 4D7, 24G12, 19G4, 9A5, 4C2, 31C8, 27G4, and 6H2. In another alternative embodiment, the MUC16 extracellular domain polypeptide comprises Polypeptide 4 KSYF SDCQVSTFRS VPNRHHTGVD SLCNFSPL (SEQ ID NO:15), and wherein the antibody is selected from the group of 24B3 and 9C7.

The invention additionally provides a composition comprising (a) any one or more of the antibodies, or antigen-binding fragments thereof, that are described herein, and (b) a pharmaceutically acceptable carrier.

Also provided by the invention is a hybridoma cell line that produces a monoclonal antibody that specifically binds to a polypeptide, or antigenic portion thereof, selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19).

The invention additionally provides a method for detecting a disease that comprises overexpression of MUC16 in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of MUC16, comprising administering to a subject having the disease a therapeutically effective amount of any one or more of the antibodies, or antigen-binding fragments thereof, that are described herein. In one embodiment, the disease is cancer, as exemplified by ovarian cancer and breast cancer.

The invention also provides an isolated antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31). In one embodiment, the antibody is selected from the group of a monoclonal antibody, a chimeric antibody, a recombinant antibody, an antigen-binding fragment of a recombinant antibody, a humanized antibody, and an antibody displayed upon the surface of a phage. In a preferred embodiment, the antibody is a monoclonal antibody produced by hybridoma cells selected from the group of 12B10-3G10, 10C4-3H5, 10C4-1F2, 10C4-2H8, 10C4-1G7, 17F2-3G5, 17F2-3F6, 17F2-2F9, 17F2-1E11, 12B10-3F7, 12B10-2F6, 12B10-2F10, 25E9-3, 25E9-5, 25E9-1, 25E9-16, 21B8-1H11, 21B8-3G6, 21B8-3H9, 21B8-1G8, 21E1-1E3, 21E1-1G9, 21E1-2G7, 21E1-3G12, 4H1-2E1, 4H1-2E3, 4H1-3E1, 4H1-3H3, 15A8-2E2, 15A8-2E10, 15A8-2E11, 15A8-3D2, 22B5- 1F6, 22B5-3G9, 22B5-2G8, and 22B5-3F11. In a particular embodiment, the MUC16 polypeptide is TLDRKSVFVDGYSQNRDD (SEQ ID NO:21), and the antibody comprises a variable heavy ($V_H$) chain sequence SEQ ID NO:27, and a variable light ($V_L$) chain sequence SEQ ID NO:29, such as the monoclonal antibody produced by hybridoma cell 12B10-3G10. In an alternative embodiment, the antigen-binding fragment is selected from the group of a Fab fragment, a F(ab')2 fragment, and a Fv fragment. In a more preferred embodiment, the antibody, or antigen-binding fragment thereof, is covalently linked to a cytotoxic agent and/or to a prodrug of a cytotoxic agent. In a further embodiment, the antibody specifically binds to human MUC16 (SEQ ID NO:25). In another embodiment, the antibody internalizes into a cell. In an alternative embodiment, the antibody lacks specific binding to a glycosylated MUC16 extracellular domain.

The invention also provides a composition comprising (a) any one or more of the invention's antibodies and/or antigen-binding fragments thereof, and (b) a pharmaceutically acceptable carrier.

The invention further provides a hybridoma cell that produces an antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31).

The invention also provides an isolated nucleotide sequence comprising a polynucleotide that encodes at least one of a variable heavy ($V_H$) chain sequence and the variable light ($V_L$) chain sequence of an antibody that specifically binds to a MUC16 polypeptide, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31). In one embodiment, the MUC16 polypeptide is TLDRKS-VFVDGYSQNRDD (SEQ ID NO:21) and the polynucleotide encoding the variable heavy ($V_H$) chain sequence comprises SEQ ID NO:26, and wherein the polynucleotide encoding the variable light ($V_L$) chain sequence comprises SEQ ID NO:28.

The invention also provides a method for producing an antibody that specifically binds to a MUC16 polypeptide or to an antigenic portion thereof, comprising administering to a subject an immunologically effective amount of a MUC16 polypeptide selected from the group of a) TLDRKS-VFVDGYSQNRDD (SEQ ID NO:21), b) KSYFSDCQV-LAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31).

The invention additionally provides a method for identifying a subject as having disease, comprising determining the level, in a sample from the subject, of specific binding of any one or more of the invention's antibodies and/or antigen-binding fragments thereof, with the MUC16 polypeptide or with the antigenic portion thereof, wherein detecting an altered level of the specific binding relative to a control sample identifies the subject as having disease. In one embodiment, the disease is cancer exemplified by ovarian cancer and breast cancer. In another embodiment, the method further comprises detecting an altered level of binding of the antibody to the sample compared to a control sample. Optionally, the detecting is selected from the group of immunohistochemistry, enzyme-linked immunosorbent assay (ELISA), fluorescence-activated cell sorting (FACS), Western blot, immunoprecipitation, and radiographic imaging.

The invention also provides a method for reducing one or more symptoms of disease comprising administering to a subject in need thereof a therapeutically effective amount of any one or more of the invention's antibodies and/or antigen-binding fragment thereof. In one embodiment, the disease is cancer, exemplified by ovarian cancer and breast cancer. Optionally, the method further comprises detecting a reduction in one or more symptoms of the disease after the administration step.

BRIEF DESCRIPTION OF THE DRAWINGS

FIG. 1: Three MUC16 carboxy terminus peptides were synthesized at the MSKCC Microchemistry Core Facility. Polypeptide 1 is near the putative cleavage site, Polypeptide 2 is before the transmembrane, and Polypeptide 3 is the internal peptide, which is inside the transmembrane.

FIG. 3A: OC125 (Score 0); FIG. 3B: OC125 (Score 1); FIG. 3C: OC125 (Score 2); FIG. 3D: OC125 (Score 3); FIG. 3E: OC125 (Score 4); FIG. 3F: OC125 (Score 5); FIG. 3G: 4H11 (Score 0); FIG. 3H: 4H11 (Score 1); FIG. 3I: 4H11 (Score 2); FIG. 3J: 4H11 (Score 3); FIG. 3K: 4H11 (Score 4); FIG. 3L: 4H11 (Score 5).

FIG. 4A: Western blot analysis of GST-ΔMUC16$^{c114}$ fusion protein with monoclonal antibodies 9C9.21.5.13 and 4H11.2.5. FIG. 4B: Western blot analysis of SKOV3-phrGFP-ΔMUC16$^{c114}$ and SKOV3-phrGFP-ΔMUC16$^{c334}$ protein extract and probed with monoclonal antibodies 9C9.21.5.13 and 4H11.2.5.

FIGS. 8A-8I: Nucleotide sequence encoding antibody variable heavy ($V_H$) chain and antibody variable light ($V_L$) chain. FIG. 8A: 4A5 $V_H$ (SEQ ID NO:04), FIG. 8B: 4A5 $V_L$ (SEQ ID NO:05), FIG. 8C: 4H11 $V_H$ (SEQ ID NO:06), FIG. 8D: 4H11 $V_L$ (SEQ ID NO:07), FIG. 8E: 9B11 $V_H$ (SEQ ID NO:08), FIG. 8F: 9B11 $V_{LA}$ (SEQ ID NO:09), FIG. 8G: 9B11 $V_{LB}$ (SEQ ID NO:10), FIG. 8H: 24B3 $V_H$ (SEQ ID NO:11), FIG. 8I: 24B3 $V_L$ (SEQ ID NO:12).

FIGS. 9A-9F: *Homo sapiens* MUC16 (GenBank NP_078966) (SEQ ID NO:13), FIG. 9G: Polypeptide 1 (SEQ ID NO:01), FIG. 9H: Polypeptide 2 (SEQ ID NO:02), FIG. 9I: Polypeptide 3 (SEQ ID NO:03), FIG. 9J: Transmembrane domain (SEQ ID NO:14), FIG. 9K: Polypeptide 4 (SEQ ID NO:15) containing a cysteine loop polypeptide (SEQ ID NO:19).

FIG. 15A: Kaplan-Meier survival curve of SCID-Beige mice treated ip or iv with 4H11-28z$^+$ T cells. SCID-Beige mice were injected intraperitoneally with 3×10$^6$ OV-CAR3(MUC-CD/GFP-FF-Luc) tumor cells followed by either iv or ip infusion of 3×10$^7$ 4H11-28z$^+$ T cells. Tumor eradication is enhanced after either ip or iv infusion of 4H11-28z$^+$ T cells when compared to control treated mice. Both ip and iv 4H11-28z$^+$ T cell treated mice exhibited statistically enhanced survival (*p<0.0001 and p=0.0038, respectively) when compared to 19-28z$^+$ T cell treated control cohorts. Conversely, difference in survival between the ip and iv 4H11-28z$^+$ T cell cohorts was not statistically significant (p=0.22). FIG. 15B: BLI of tumor progression of representative ip and iv 4H11-28z$^+$ T cell treated mice with ultimately progressive disease following treatment compared to BLI of tumor progression in a representative control 19-28z$^+$ T cell treated mouse. FIG. 15C: Systemically injected CFSE stained 4H11-28z$^+$ T cells traffic to advanced ip OV-CAR(MUC-CD) tumors. Presence of iv injected CFSE labeled 19-28z$^+$ control T cells (left panel) and 4H11-28z$^+$ T cells (right panel) 1 day following infusion into SCID-Beige mice with advanced OV-CAR(MUC-CD) tumors (injected 7 days earlier), as assessed by FACS analysis of single cell OV-CAR3(MUC-CD) tumor suspensions, reveals a marked population of 4H11-28z$^+$ but not control 19-28z$^+$ T cells within peritoneal OV-CAR3(MUC-CD) tumors.

FIG. 16A: BLI of 4H11-28z+ T cell treated mice with either relapsed disease (middle row) or eradicated disease (bottom row) compared to a representative 19-28z+ T cell treated control mouse. FIG. 16B: Kaplan-Meier survival curve of SCID-Beige mice with advanced OV-CAR3(MUC-CD/GFP-FFLuc) tumors treated ip with 4H11-28z+ T cells. All 4H11-28z+ T cell treated mice demonstrated enhanced survival when compared to control 19-28z+ T cell treated mice (**p=0.0011), with an overall long-term survival of 25% at day 120.

FIG. 17: CD8 leader sequence (SEQ ID NO: 32), CD3 zeta chain intracellular domain sequence (SEQ ID NO: 33), (G45)3 serine-glycine linker sequence (SEQ ID NO: 34), CD8 transmembrane domain sequence (SEQ ID NO: 35), and CD28 transmembrane+intracellular domains (-STOP) sequence (SEQ ID NO: 36).

FIGS. 18A-18E: SFG_4H11z sequence.

FIGS. 19A-19F: SFG-4H11-28z sequence.

FIG. 20A: Mouse MUC16-CD Peptide 1 (SEQ ID NO:21), Mouse first Cysteine Loop Peptide 2 (SEQ ID NO:22), and Mouse second Cysteine Loop Peptide 3 (SEQ ID NO:23). FIG. 20B: Alignment of mouse MUC16 (SEQ ID NO:24) and human MUC16 (SEQ ID NO:25) amino acid sequences. A cysteine was added to the peptide sequence at the N terminus of Peptide 1 and Peptide 3 for better conjugation with KLH.

FIG. 21: IDB extract with 1:10 dilution of Mouse MUC16 monoclonal Primary Supernatants.

FIG. 24A: Nucleotide sequence encoding 12B10-3G10-$V_H$ (SEQ ID NO:26), FIG. 24B: 12B10-3G10-$V_H$ Amino Acid sequence (SEQ ID NO:27), FIG. 24C: Nucleotide sequence encoding 12B10-3G10-$V_L$ (SEQ ID NO:28) (Note the VL has an optional NotI site added by the primer for cloning, and FIG. 24D: 12B10-3G10-$V_L$ Amino Acid sequence (SEQ ID NO:29).

DEFINITIONS

Figure 2:
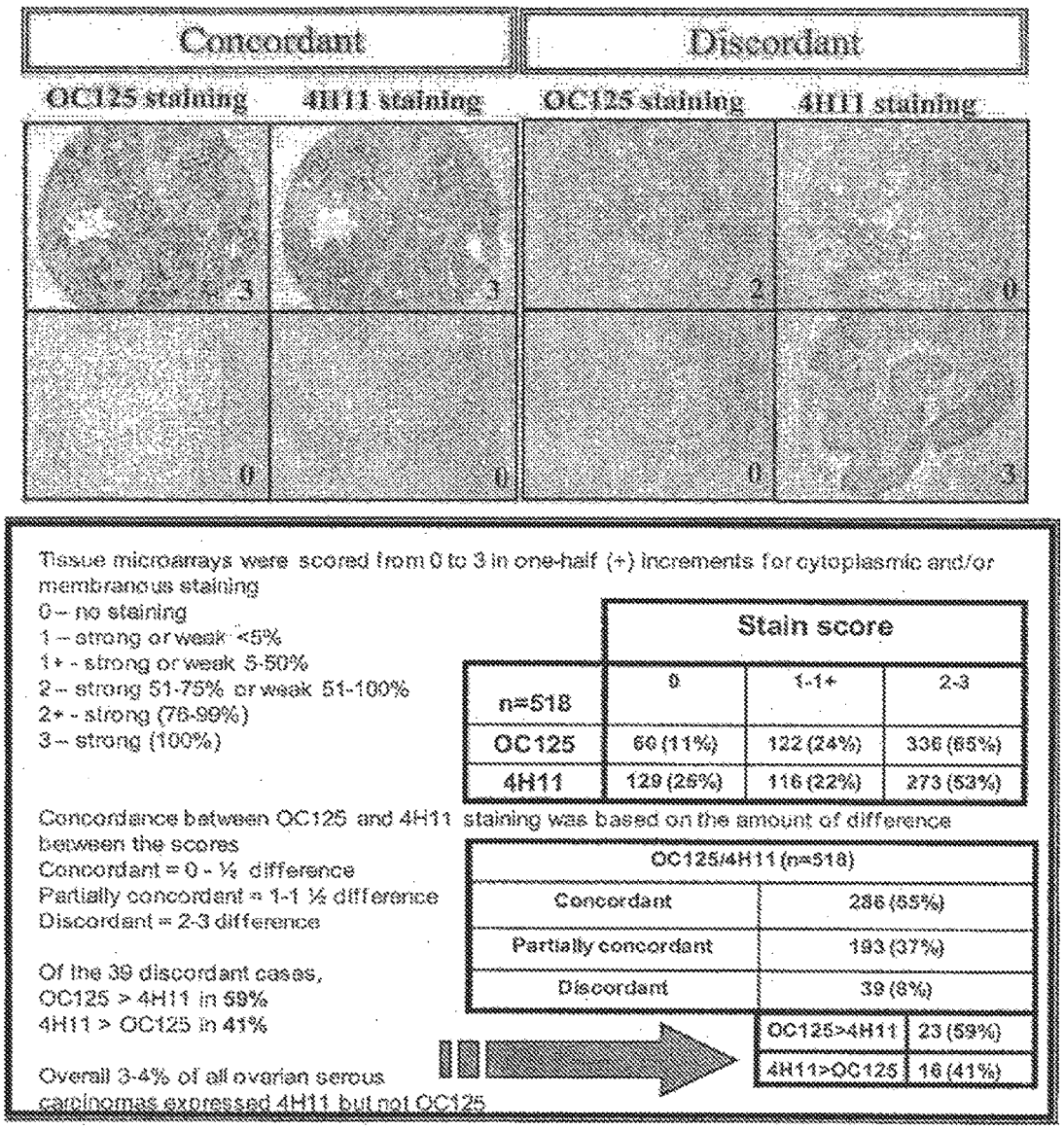
FIG. 2: Comparison staining of high-grade serous ovarian carcinomas using OC125 (left panel) and 4H11 (right panel)
Figure 3A:
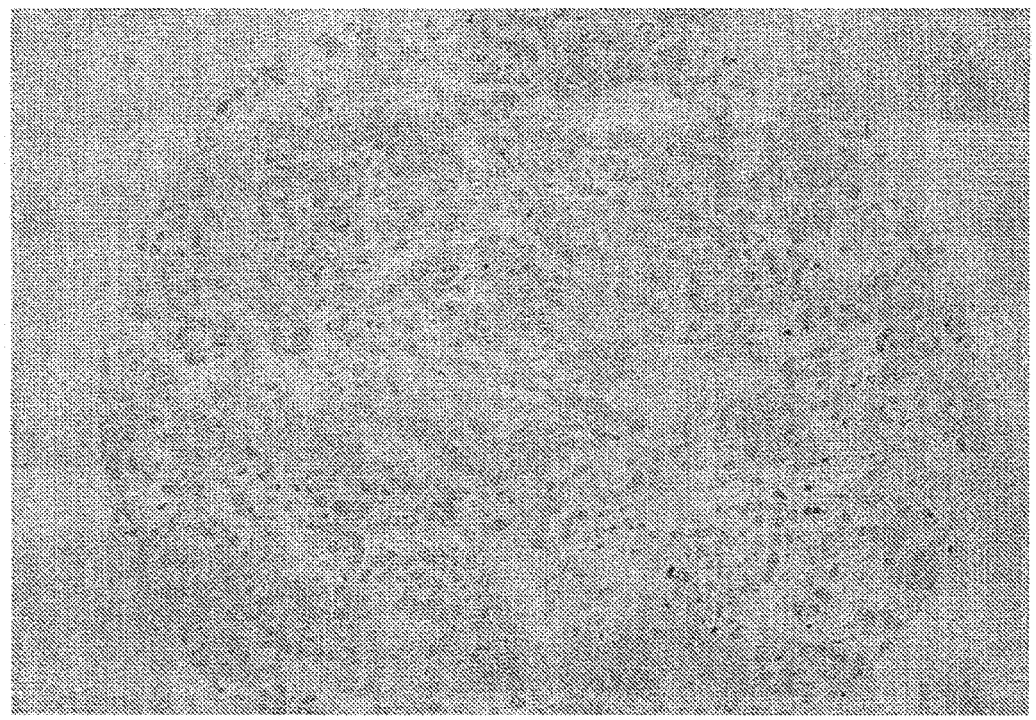
FIG. 3A-FIG. 3L: Immunohistochemical scoring of OC125 and 4H11 on tissue microarrays of high-grade ovarian serous carcinoma. Only membranous and/or cytoplasmic staining was considered positive. Score 0: No staining; Score 1: <5% strong or weak; Score 2: 5-50% strong or weak; Score 3: 51-75% strong or 51-100% weak; Score 4: 76-99% strong; Score 5: 100% strong.
Figure 3B:
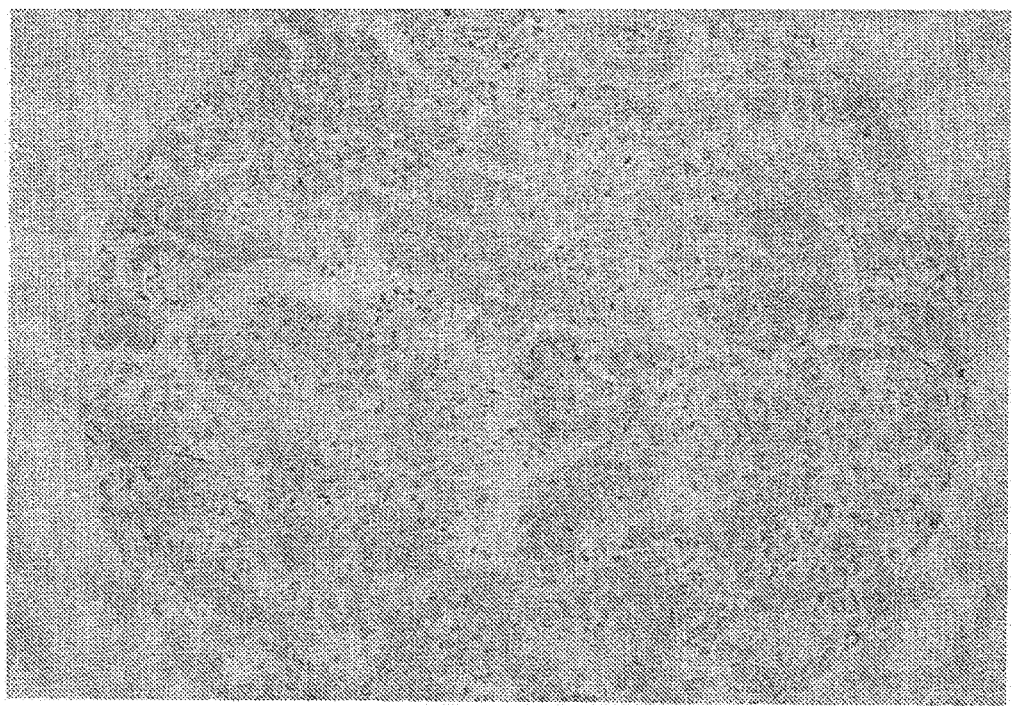
Figure 3C:
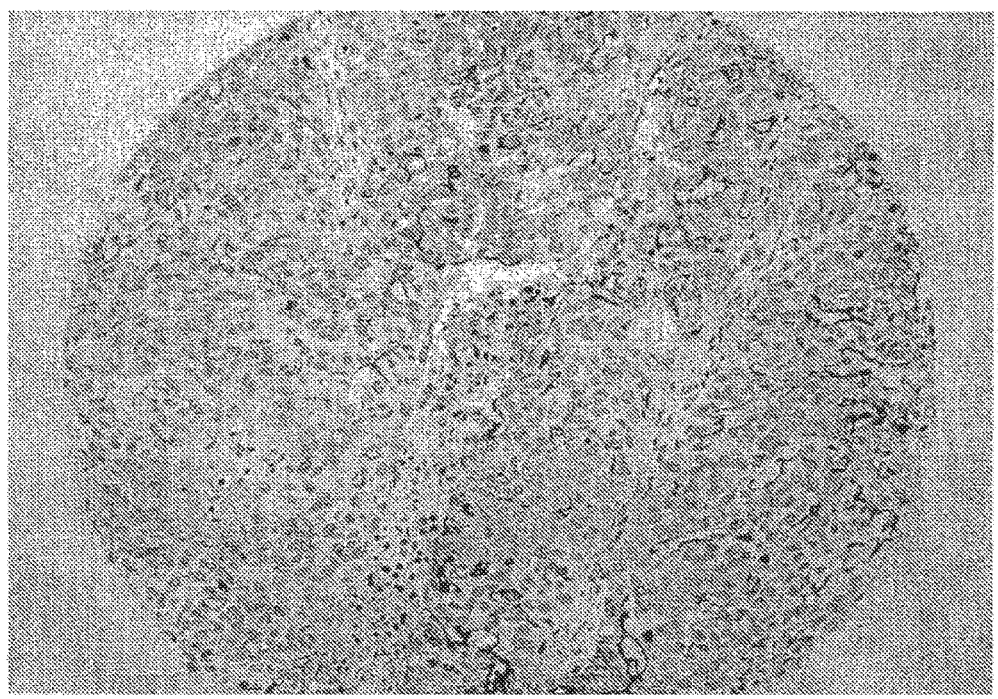
Figure 3D:
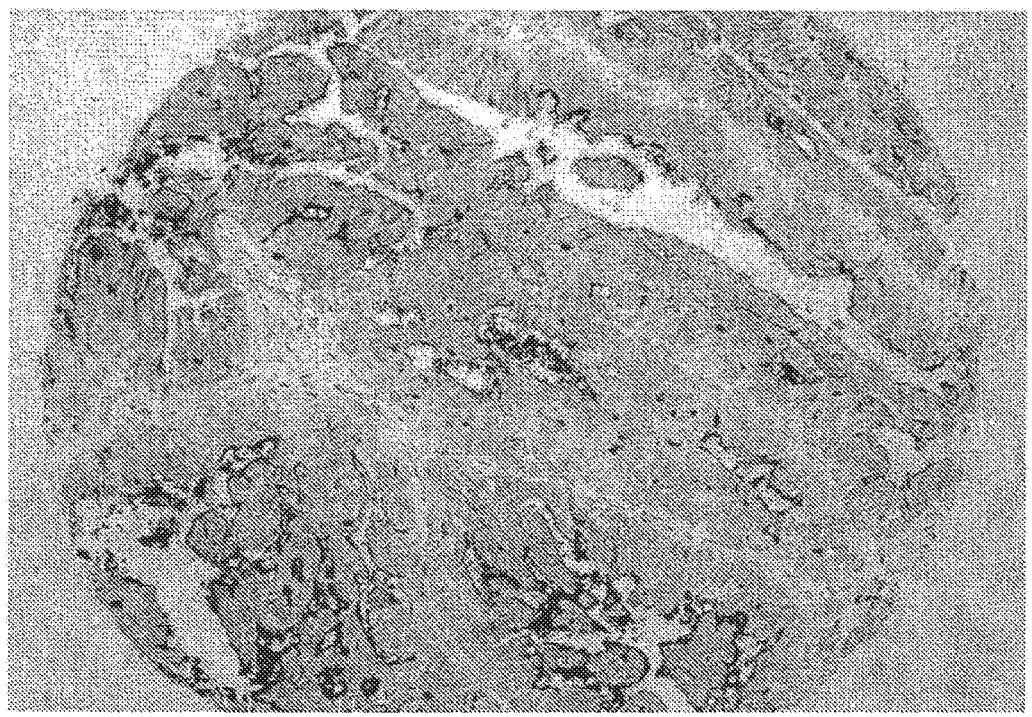
Figure 3E:
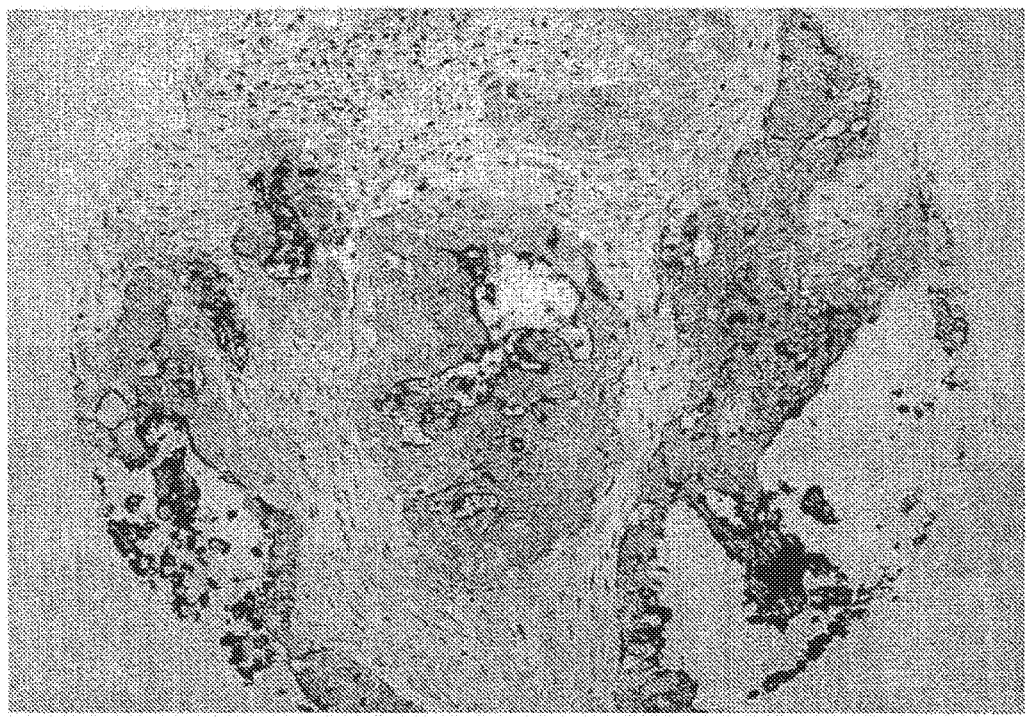
Figure 3F:
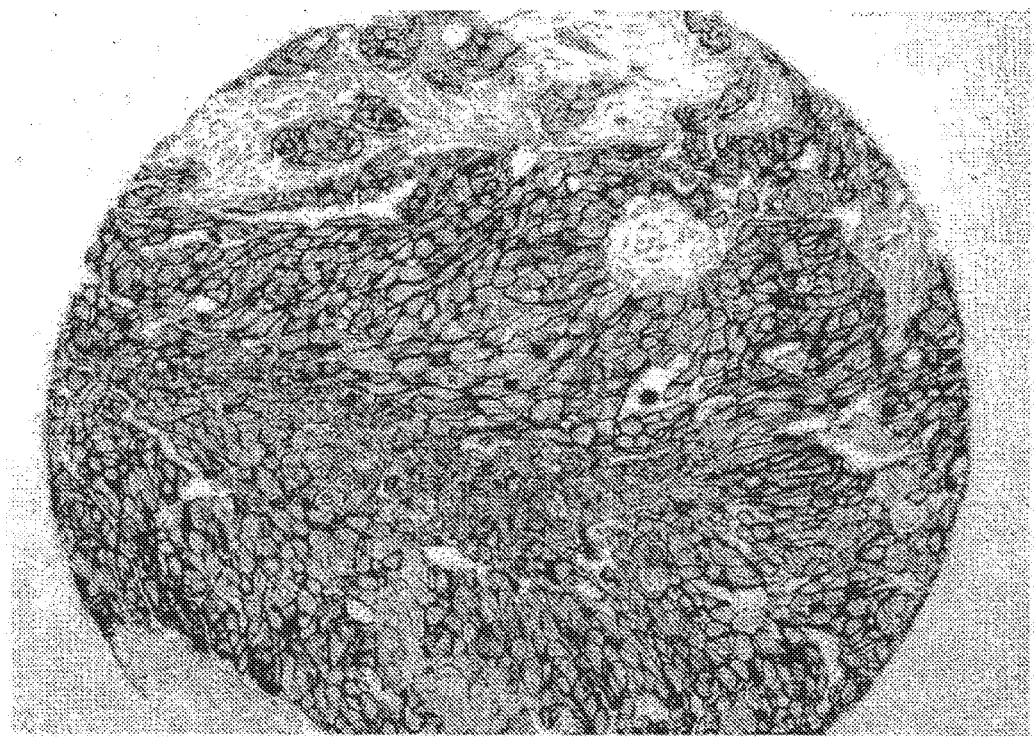
Figure 3G:
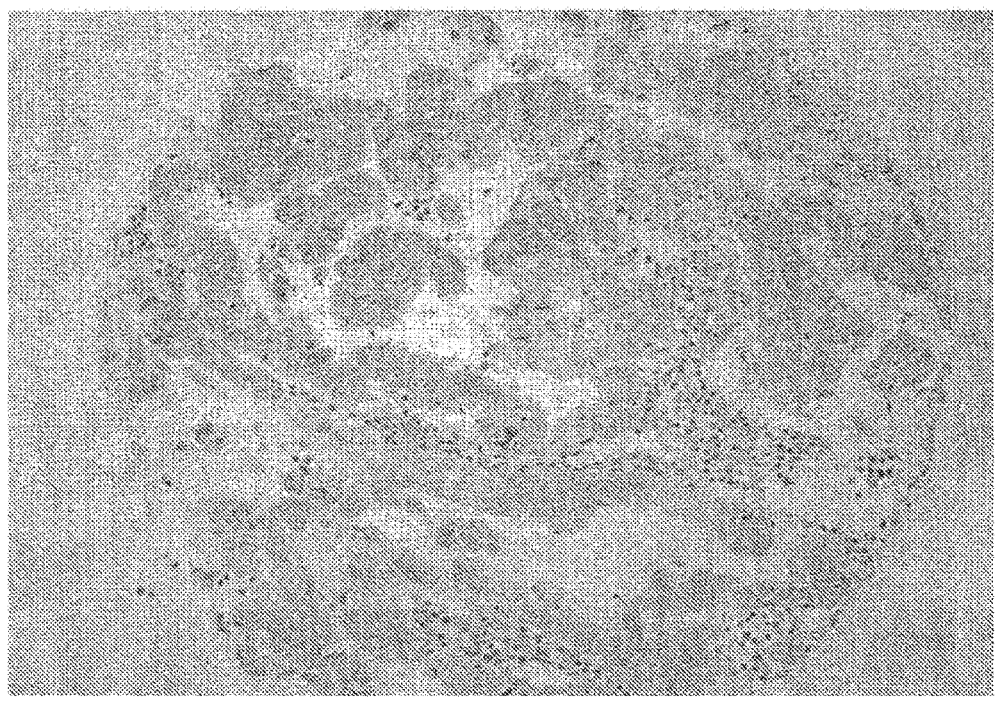
Figure 3H:
Figure 3I:
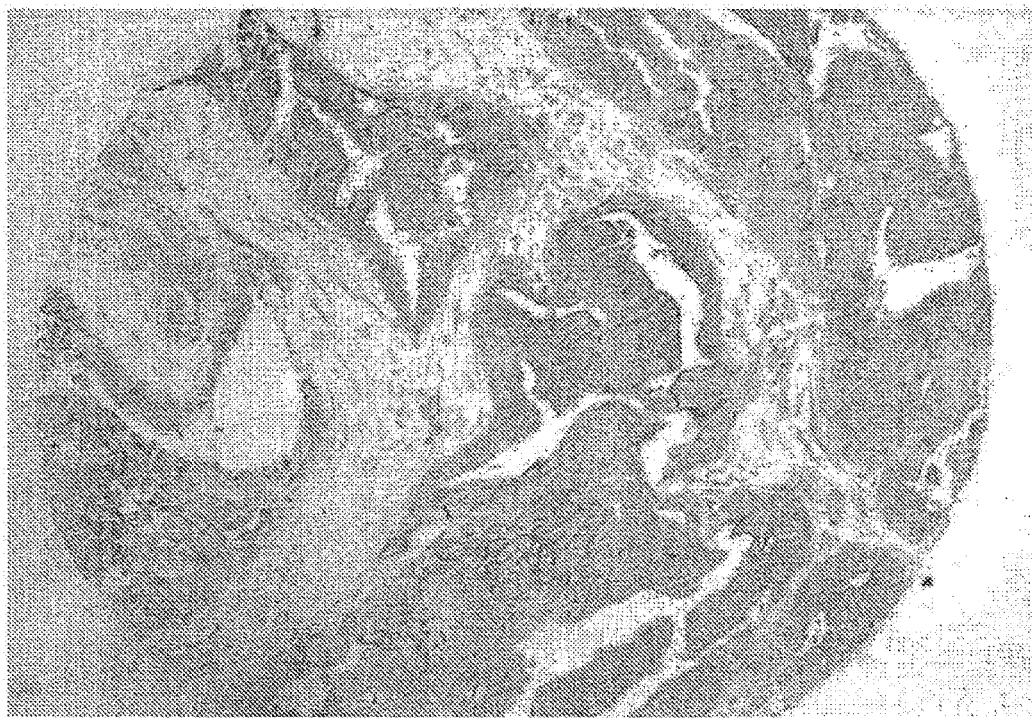
Figure 3J:
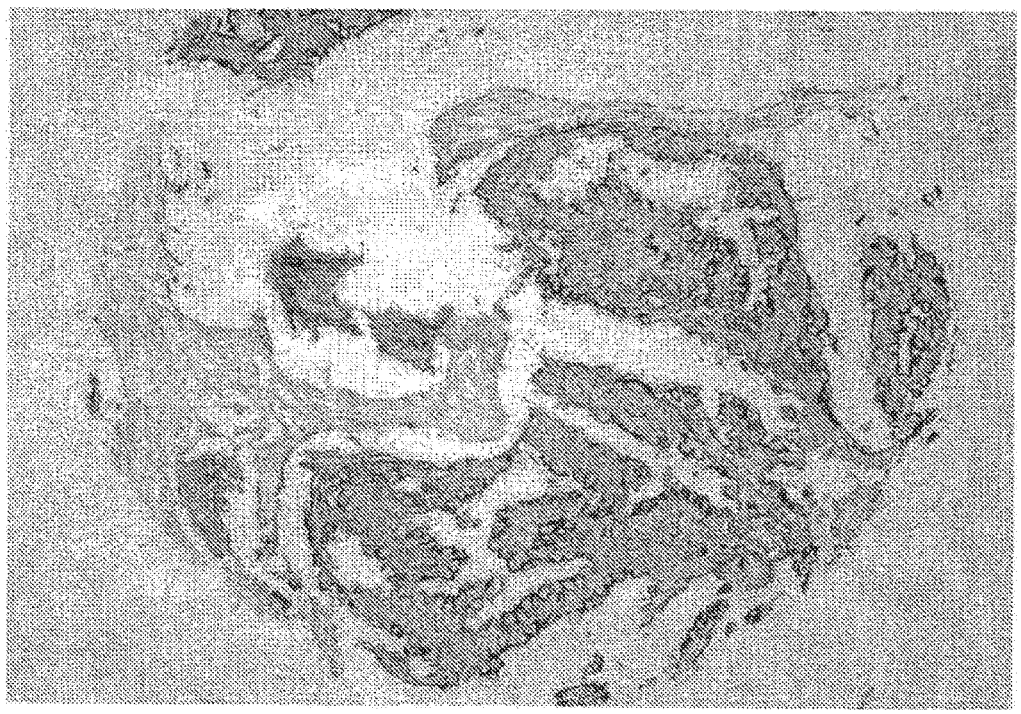
Figure 3K:
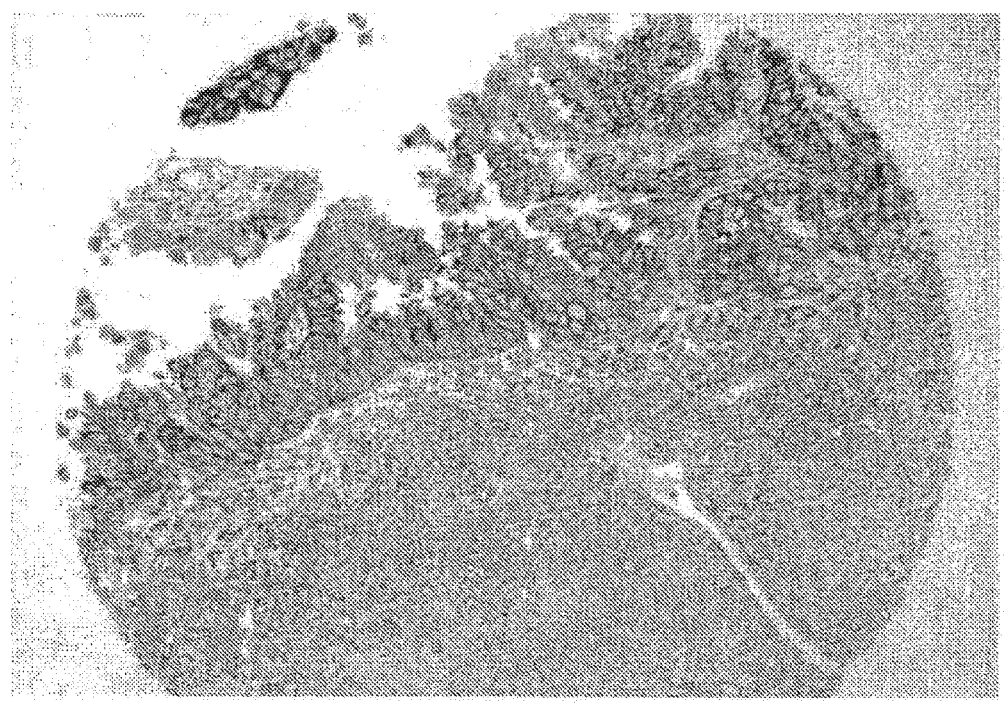
Figure 3L:
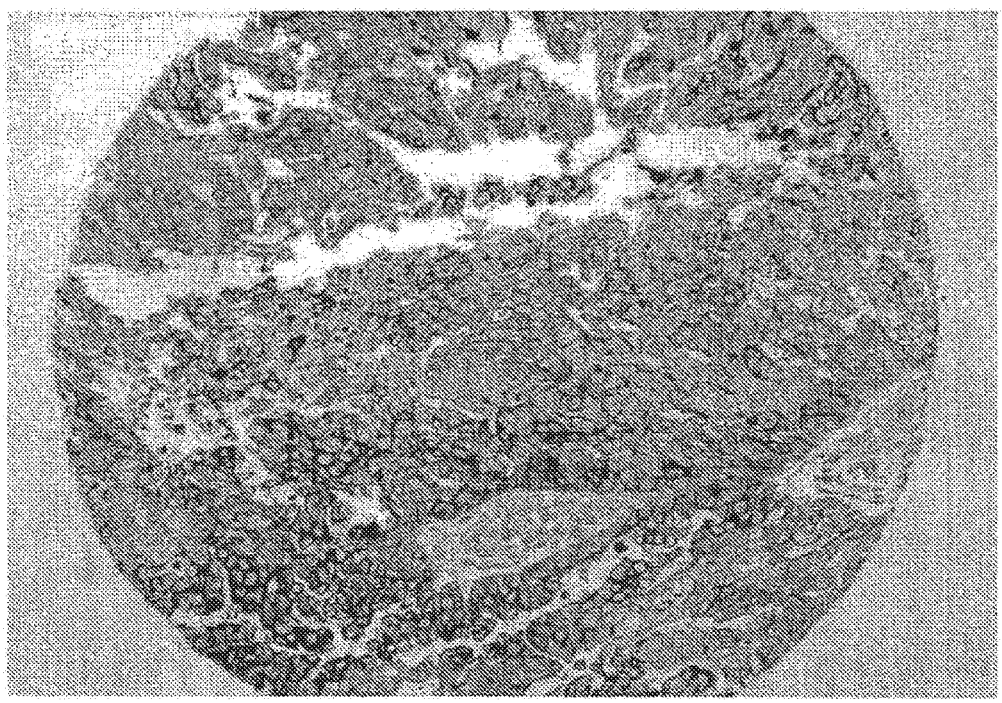

To facilitate understanding of the invention, a number of terms are defined below.

The terms "purified," "isolated," and grammatical equivalents thereof as used herein, refer to the reduction in the amount of at least one undesirable component (such as cell, protein, nucleic acid sequence, carbohydrate, etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable component cell, protein, nucleic acid sequence, carbohydrate, etc.).

The term "antibody" refers to an immunoglobulin (e.g., IgG, IgM, IgA, IgE, IgD, etc.). The basic functional unit of each antibody is an immunoglobulin (Ig) mononer (containing only one immunoglobulin ("Ig") unit). Included within this definition are polyclonal antibody, monoclonal antibody, and chimeric antibody.

The variable part of an antibody is its "V domain" (also referred to as "variable region"), and the constant part is its "C domain" (also referred to as "constant region") such as the kappa, lambda, alpha, gamma, delta, epsilon and mu constant regions. The "variable domain" is also referred to as the "$F_V$ region" and is the most important region for binding to antigens. More specifically, variable loops, three each on the light ($V_L$) and heavy ($V_H$) chains are responsible for binding to the antigen. These loops are referred to as the "complementarity determining regions" ("CDRs" and "idiotypes."

The immunoglobulin (Ig) monomer of an antibody is a "Y"-shaped molecule that contains four polypeptide chains: two light chains and two heavy chains, joined by disulfide bridges.

Light chains are classified as either (λ) or kappa (κ). A light chain has two successive domains: one constant domain ("$C_L$") and one variable domain ("$V_L$"). The variable domain, $V_L$, is different in each type of antibody and is the active portion of the molecule that binds with the specific antigen. The approximate length of a light chain is 211 to 217 amino acids.

Each heavy chain has two regions, the constant region and the variable region. The There are five types of mammalian Ig heavy denoted a α, δ, ε, γ, and μ. The type of heavy chain present defines the class of antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region ("$C_H$") and the variable ("$V_H$") region. The constant region ($C_H$) is identical in all antibodies of the same isotype, but differs in antibodies of different isotypes. Heavy chains γ, α and δ have a constant region composed of three tandem (in a line) Ig domains, and a hinge region for added flexibility. Heavy chains μ and ε have a constant region composed of four immunoglobulin domains. The variable region ($V_H$) of the heavy chain differs in antibodies produced by different B cells, but is the same for all antibodies produced by a single B cell or B cell clone. The variable region of each heavy chain is approximately 110 amino acids long.

The term "specifically binds" and "specific binding" when made in reference to the binding of two molecules (e.g. antibody to an antigen, etc.) refer to an interaction of the two molecules that is dependent upon the presence of a particular structure on one or both of the molecules. For example, if an antibody is specific for epitope "A" on the molecule, then the presence of a protein containing epitope A (or free, unlabelled A) in a reaction containing labeled "A" and the antibody will reduce the amount of labeled A bound to the antibody.

The term "capable of binding" when made in reference to the interaction between a first molecule (such as antibody, polypeptide, glycoprotein, nucleic acid sequence, etc.) and a second molecule (such as antigen, polypeptide, glycoprotein, nucleic acid sequence, etc.) means that the first molecule binds to the second molecule in the presence of suitable concentration of salts, and suitable temperature, and pH. The conditions for binding molecules may be determined using routine and/or commercially available methods The terms "antigen," "immunogen," "antigenic," "immunogenic," "antigenically active," "immunologic," and "immunologically active" when made in reference to a molecule, refer to any substance that is capable of inducing a specific humoral immune response (including eliciting a soluble antibody response) and/or cell-mediated immune response (including eliciting a CTL response). Antigenic peptides preferably contain at least 5, at least 6, at least 7, at least 8, at least 9, and more preferably at least 10 amino acids. To elicit antibody production, in one embodiment, antigens may be conjugated to keyhole limpet hemocyanin (KLH) or fused to glutathione-S-transferase (GST).

A "cognate antigen" when in reference to an antigen that binds to an antibody, refers to an antigen that is capable of specifically binding to the antibody.

In one embodiment, the antigen comprises an epitope. The terms "epitope" and "antigenic determinant" refer to a structure on an antigen, which interacts with the binding site of an antibody or T cell receptor as a result of molecular complementarity. An epitope may compete with the intact antigen, from which it is derived, for binding to an antibody.

As used herein the terms "portion" and "fragment" when made in reference to a nucleic acid sequence or protein sequence refer to a piece of that sequence that may range in size from 2 contiguous nucleotides and amino acids, respectively, to the entire sequence minus one nucleotide and amino acid, respectively.

A "subject" that may benefit from the invention's methods includes any multicellular animal, preferably a mammal. Mammalian subjects include humans, non-human primates, murines, ovines, bovines, ruminants, lagomorphs, porcines, caprines, equines, canines, felines, ayes, etc.). Thus, mammalian subjects are exemplified by mouse, rat, guinea pig, hamster, ferret and chinchilla. The invention's compositions and methods are also useful for a subject "in need of reducing one or more symptoms of" a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease (such as cancer) refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic cells (i.e., "hyperplastic cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia.

"Sample" and "specimen" as used herein are used in their broadest sense to include any composition that is obtained and/or derived from a biological source, as well as sampling devices (e.g., swabs), which are brought into contact with biological or environmental samples. "Biological samples" include those obtained from a subject, including body fluids (such as urine, blood, plasma, fecal matter, cerebrospinal fluid (CSF), semen, sputum, and saliva), as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. These examples are illustrative, and are not to be construed as limiting the sample types applicable to the present invention.

"Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

"Internalize" when in reference to a cell refers to entry from the extracellular medium into the cell membrane and/or cytoplasm.

"Glycosylated" when in reference to a sequence (e.g., an amino acid sequence or nucleotide sequence) refers to a sequence that is covalently linked to one or more saccharides.

"Pharmaceutical" and "physiologically tolerable" composition refers to a composition that contains pharmaceutical molecules, i.e., molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutical molecule does not substantially reduce the activity of the invention's compositions. Pharmaceutical molecules include "diluent" (i.e., "carrier") molecules and excipients.

"Immunogenically effective" and "antigenically effective" amount of a molecule interchangeably refer to an amount of the molecule that is capable of inducing a specific humoral immune response (including eliciting a soluble antibody response) and/or cell-mediated immune response (including eliciting a cytotoxic T-lymphocyte (CTL) response).

"Treating" a disease refers to reducing one or more symptoms (such as objective, subjective, pathological, clinical, sub-clinical, etc.) of the disease.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "alter" and "modify" when in reference to the level of any molecule and/or phenomenon refer to an increase or decrease.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

DESCRIPTION OF THE INVENTION

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

Using synthetic peptides, the inventors raised novel-specific antibodies to the carboxy-terminal portion of MUC16, retained by the cell, proximal to the putative cleavage site. These antibodies were characterized using fluorescence-activated cell-sorting analysis, enzyme-linked immunoassay, Western blot analysis, and immunohistochemistry. Each of the selected monoclonal antibodies was reactive against recombinant GST-ΔMUC16$^{c114}$ protein and the MUC16 transfected SKOV3 cell line. Three antibodies, 4H11, 9C9, and 4A5 antibodies demonstrated high affinities by Western blot analysis and saturation-binding studies of transfected SKOV3 cells, and displayed antibody internalization. Immunohistochemical positivity with novel antibody 4H11 was similar to OC125, but with important differences, including diffuse positivity in lobular breast cancer and a small percentage of OC125-negative ovarian carcinomas which showed intense and diffuse 4H11 antibody binding.

The invention's compositions and methods are useful for diagnostic and therapeutic applications, as well as biologic studies such as membrane receptor trafficking and intracellular events. Diagnostic applications include, for example, detection of cancer using immunohistochemical, radiographic imaging, enzyme-linked immunosorbent assay (ELISA), fluorescence-activated cell sorting (FACS), Western blot, and/or immunoprecipitation detection.

The invention is further described under (A) MUC16, (B) Prior Art Antibodies, (C) Invention's Antibodies, (D) Hybridoma Cell Lines, (E) Conjugates Of The Invention's Antibodies Linked To Cytotoxic Agents And/Or Prodrugs, (F) Detecting Muc16 Portions And Diagnostic Applications, and (G) Therapeutic Applications.

A. MUC16

Figure 10:
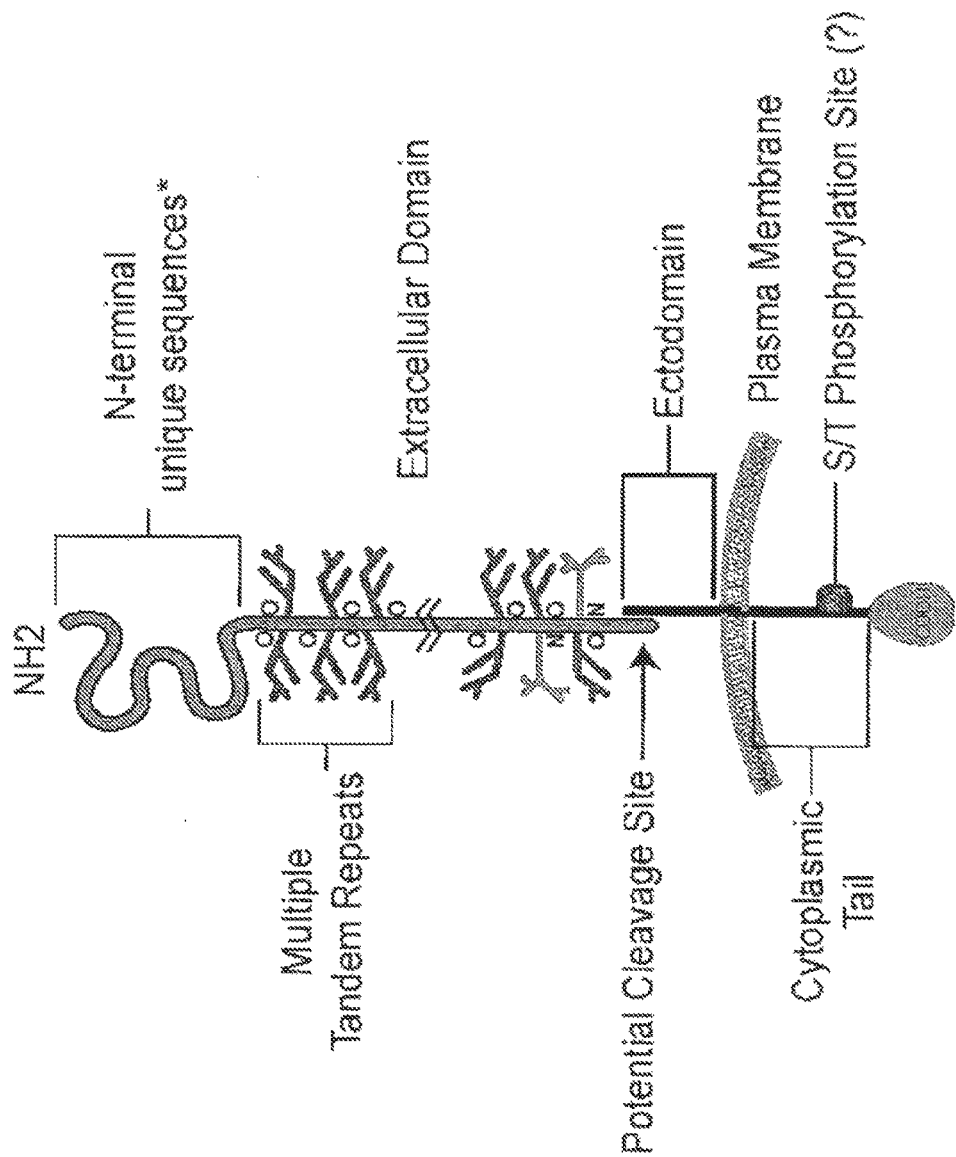
FIG. 10: Schematic of MUC16 structure.

"MUC16," "MUC-16" and "Mucin 16" interchangeably refer to a type I membrane protein that is part of a family of tethered mucins. A schematic of Muc16 is in FIG. 10, and an exemplary human Muc16 amino acid sequence (SEQ ID NO:13) is shown in FIGS. 9A-9F. An alignment of mouse MUC16 (SEQ ID NO:24) and human MUC16 (SEQ ID NO:25) amino acid sequences is shown in FIG. 20B. The term "type 1 protein" refers to a "membrane protein" that is at least partially embedded in the lipid bilayer of a cell, virus and the like, and that contains a transmembrane domain (TM) sequence embedded in the lipid bilayer of the cell, virus and the like. The portion of the protein on the NH$_2$-terminal side of the TM domain is exposed on the exterior side of the membrane, and the COOH-terminal portion is exposed on the cytoplasmic side.

Recently, the sequence of the cDNA-encoding MUC16/CA125 was described by Yin and Lloyd in 2001 and completed by O'Brien in 2002 (10-12). The complete MUC16 protein has various components consisting of a cytoplasmic tail with potential phosphorylation sites, a transmembrane domain, and an external domain proximal to an apparent cleavage site. Distal to the cleavage site, the released external domain contains 16-20 tandem repeats of 156 amino acids, each with many potential glycosylation sites (11). The overall repeat structure (FIG. 10) is well conserved across mammals, but the repeats are not completely identical in exact amino acid composition.

The MUC16 protein is part of a family of tethered mucins that includes both MUC1 and MUC4 (13). MUC1 is present in a variety of tissues and appears to signal through a beta catenin pathway, interact with EGF receptor, mediates drug resistance and can act as an oncogene (14-17). The MUC4 protein is also expressed in a variety of tissues but is common on neoplasms of the gastrointestinal track (18-20). In contrast, the CA125 antigen has been more restricted in its distribution and is present primarily in gynecologic tissues and overexpressed in Müllerian neoplasms (21). However, the CA125 antigen, recognized by the OC125 antibody, is a heavily glycosylated antigen expressed in the tandem repeat region of the larger MUC16 protein. This glycoprotein is typically shed from a putative cleavage site in the extracellular domain of the MUC16 peptide backbone.

Thus, "MUC16" protein contains (a) a "cytoplasmic domain," (b) a "transmembrane domain," and (c) a "extracellular domain." The MUC16 extracellular domain contains a cleavage site between a non-glycosylated ectodomain and a large glycosylated ectodomain of tandem repeats.

The terms "cytoplasmic domain," "cytoplasmic tail," and "CT" are used interchangeably to refer to a protein sequence, and portions thereof, that is on the cytoplasmic side of the lipid bilayer of a cell, virus and the like. Methods for determining the CT of a protein are known in the art Elofsson et al. (2007) Annu. Rev. Biochem. 76:125-140; Bernsel et al. (2005) Protein Science 14:1723-1728).

The terms "transmembrane domain" and "TM" are used interchangeably to refer to a protein sequence, and portions thereof, that spans the lipid bilayer of a cell, virus and the like. Methods for determining the TM of a protein are known in the art (Elofsson et al. (2007) Annu. Rev. Biochem. 76:125-140; Bernsel et al. (2005) Protein Science 14:1723-1728).

The terms "ectodomain" and "extracellular domain" are interchangeably used when in reference to a membrane protein to refer to the portion of the protein that is exposed on the extracellular side of a lipid bilayer of a cell, virus and the like. Methods for determining the ectodomain of a protein are known in the art (Singer (1990) Annu. Rev. Cell Biol. 6:247-296 and High et al. (1993) J. Cell Biol. 121: 743-750, and McVector software, Oxford Molecular).

The exemplary Muc16 of FIGS. 9A-9F contains (a) a "MUC16 cytoplasmic domain" from amino acid 14476 to 14507, vttrr rkkegeynvq qqcpgyyqsh ldledlq (SEQ ID NO:16), that interacts with the intracellular signal transduction machinery; (b) a "MUC16 transmembrane domain" from amino acid 14452 to 14475, fwaviligl agllgvitcl icgvl (SEQ ID NO:14) that spans the plasma membrane; and (c) a "MUC16 extracellular domain" amino acid 1 to 14392 (SEQ ID NO:13) that contains a cleavage site between an non-glycosylated ectodomain and a large glycosylated ectodomain of tandem repeats. The "MUC16 ectodomain" is exemplified by nfsplar rvdrvaiyee flrmtrngtq lqnftldrss vlvdgyspnr nepltgnsdl p (SEQ ID NO:17) from amino acid 14394 to 14451 of SEQ ID NO:13 of FIGS. 9A-9F.

The exemplary MUC16 ectodomain contains both Polypeptide 1 (nfsplar rvdrvaiyee (SEQ ID NO:01), which is from amino acid 14394 to 14410 of SEQ ID NO:13), and Polypeptide 2 (tldrss vlvdgyspnr ne (SEQ ID NO:02), which is from amino acid 14425 to 14442 of SEQ ID NO:13), against which the invention's exemplary antibodies were produced. Polypeptide 3, cgvlvttrr rkkegeynvq qq (SEQ ID NO:03) is from amino acid 14472 to 14492 of SEQ ID NO:13, and contains both a transmembrane domain portion (cgvl) and a cytoplasmic domain portion (vttrr rkkegeynvq qq (SEQ ID NO:18)). Thus, the CGVL is optional in SEQ ID NO:03, as it is part of the transmembrane domain.

Polypeptide 4 (ksyf sdcqvstfrs vpnrhhtgvd slcnfspl (SEQ ID NO:15), is located in a non-glycosylated portion of the Muc16 extracellular domain, is from amino acid 14367 to 14398 of SEQ ID NO:13, and contains a cysteine loop polypeptide cqvstfrsvpnrhhtgvdslc (SEQ ID NO:13).

B. Prior Art Antibodies

The expression of the MUC16/CA125 antigen has long been associated with gynecologic tissues. "CA125," "CA-125," "Cleaved CA125," and "cleaved CA-125," interchangeably refer to the glycosylated external domain of the tethered mucin MUC16, that is distal to the cleavage site (Payne et al., U.S. Pat. No. 7,202,346). This released external domain contains 16-20 tandem repeats of 156 amino acids, each with potential glycosylation sites. An apparent cysteine-based disulfide loop of 19 amino acids is present in all repeats and the N-terminal end contains a hairbrush structure that is heavily 0-glycosylated (11). The deduced size would be 2.5 MD for the protein part, and with added carbohydrates, this could increase to 5 MD (10, 26).

CA125, though it is not sensitive or specific enough to be used as a general screening tool, is routinely used to monitor patients with ovarian carcinoma. The tests used to measure CA125 are antibody based detection methods, as are the immunohistochemical stains routinely performed for diagnostic purposes. The epitope specificity of 26 antibodies to MUC16 was studied in the first report from the International Society of Oncodevelopmental Biology and Medicine (ISOBM) TD-1 Workshop and the application of 22 antibodies to immunohistochemistry was reported in the second report from the TD-1 workshop (7, 21). The existing antibodies were grouped as OC125-like, M11-like, or OV197-like and all of the known antibodies recognized CA125 epitopes in the repeating, glycosylated elements in the external domain of the tethered mucin MUC16, distal to the putative cleavage site.

The vast majority of MUC16-reactive antibodies, including OC125, react with the glycosylation-dependent antigen present exclusively in the cleaved portion of the molecule so the true distribution of MUC16 expression is not known (21). There is currently no antibody available to track the fate of the remaining MUC16 protein fragment after cleavage and CA125 release.

C. Invention's Antibodies

In order to better explore the biology of human MUC16, the inventors have derived monoclonal antibodies against the extracellular portion of the MUC16-carboxy terminus, proximal to the putative cleavage site, as well as one monoclonal antibody against the internal cytoplasmic domain. In contrast to prior antibodies, these are derived against the peptide backbone of MUC16 and are not directed at complex glycoprotein epitopes. Since these epitopes are proximal to the cleavage site, they are unlikely to be found in the circulation and provide novel targets for diagnostic methods and therapeutic interventions. Data herein demonstrate the identification and characterization of exemplary antibodies developed against the MUC16 peptide backbone.

The inventors have developed novel antibodies that are directed at the non-cleaved, non-glycosylated peptide backbone of MUC16. These are exemplified by both 4H11 and 9C9 antibodies, which react with peptide sequences in the non-cleaved ectodomain of MUC16 and are detectable on the surface of ovarian cancer cell lines and in paraffin-fixed tissues from human ovarian cancer surgical specimens. The antibodies show high affinity and are readily internalized by ovarian cancer cells when bound to the ectodomain of MUC16. This suggests that the proximal portion of MUC16 has an independent biology from the more distal, cleaved portion of the mucin. It also suggests that the proximal portions of MUC16 could provide convenient targets for diagnostic and therapeutic interventions. Targeting the peptide backbone of MUC16 provides highly specific tissue delivery for genetically engineered cells, liposomes, or antibody conjugates, including conjugates with the invention's antibodies.

The invention's antibodies, exemplified by antibody 4H11, are useful as tools in immunohistochemistry. Date herein show that 4H11 is relatively specific to high-grade ovarian serous carcinoma. Invasive lobular breast carcinoma is the major exception and shows extensive MUC16 protein as detected by 4H11. Lobular carcinoma of the breast has unique biology which is characterized by a propensity to metastasize to serosal surfaces (27). Since MUC16 is the cognate binding partner of mesothelin, this may have important implications for lobular cancer (28). The discordance rates for OC125 and 4H11 also suggest that 4H11 might provide additional, independent information from OC125 in a subset of ovarian carcinomas. Some tumors that are negative with OC125 retain cytoplasmic and extracellular portions of the MUC16 glycoprotein, portions of the molecule that are likely involved in transduction of signals potentially important in the malignant phenotype.

Thus, in one embodiment, the invention provides an isolated antibody, or an antigen-binding fragment thereof, that specifically binds to a polypeptide, or antigenic portion thereof, wherein the polypeptide is exemplified by a) MUC16 ectodomain polypeptide (exemplified by NFSPLAR RVDRVAIYEE FLRMTRNGTQ LQNFTL-DRSS VLVDGYSPNR NEPLTGNSDL P (SEQ ID NO:17)), b) MUC16 cytoplasmic domain polypeptide (exemplified by VTTRR RKKEGEYNVQ QQ (SEQ ID NO:18), which is contained within each of CGVLVTTRR RKKEGEYNVQ QQ (SEQ ID NO:03) and LVTTRR RKKEGEYNVQ QQ (SEQ ID NO:20)), and c) MUC16 extracellular domain polypeptide that contains a cysteine loop polypeptide CQVSTFRSVPNRHHTGVDSLC (SEQ ID NO:19).

Figure 5A:
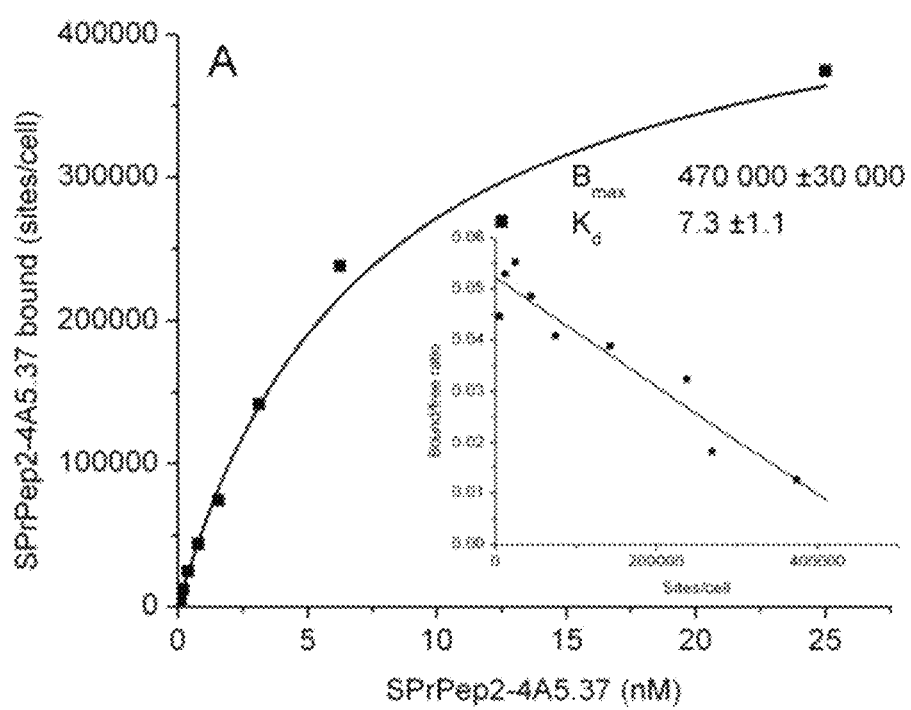
FIG. 5A-5D: MUC16 carboxy terminus monoclonal antibodies binding affinity on OVCAR3 cells.
Figure 5B:
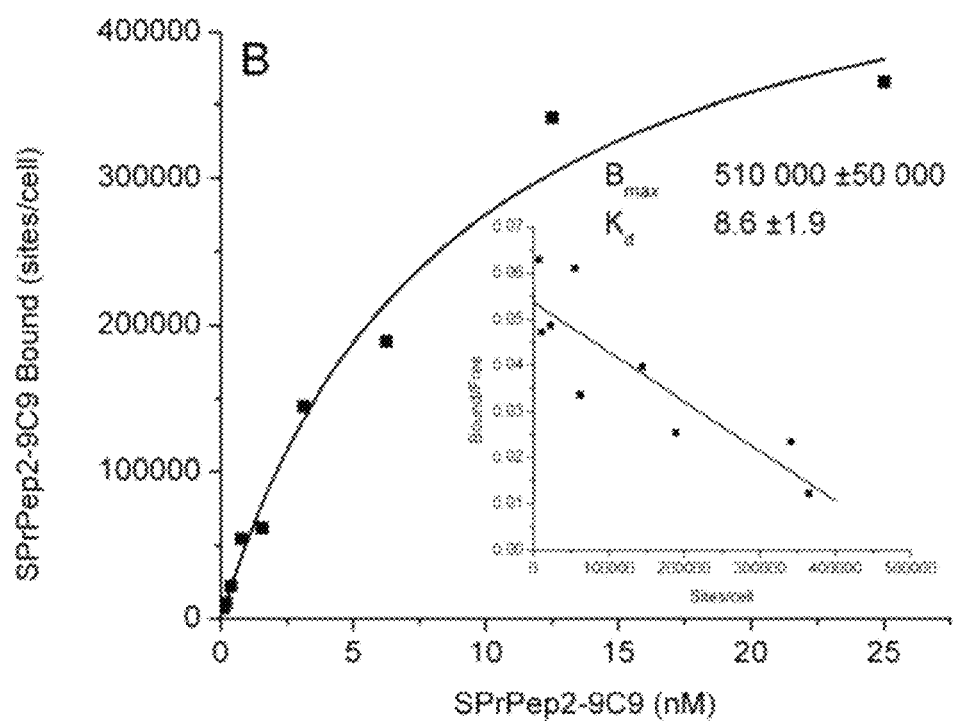
Figure 5C:
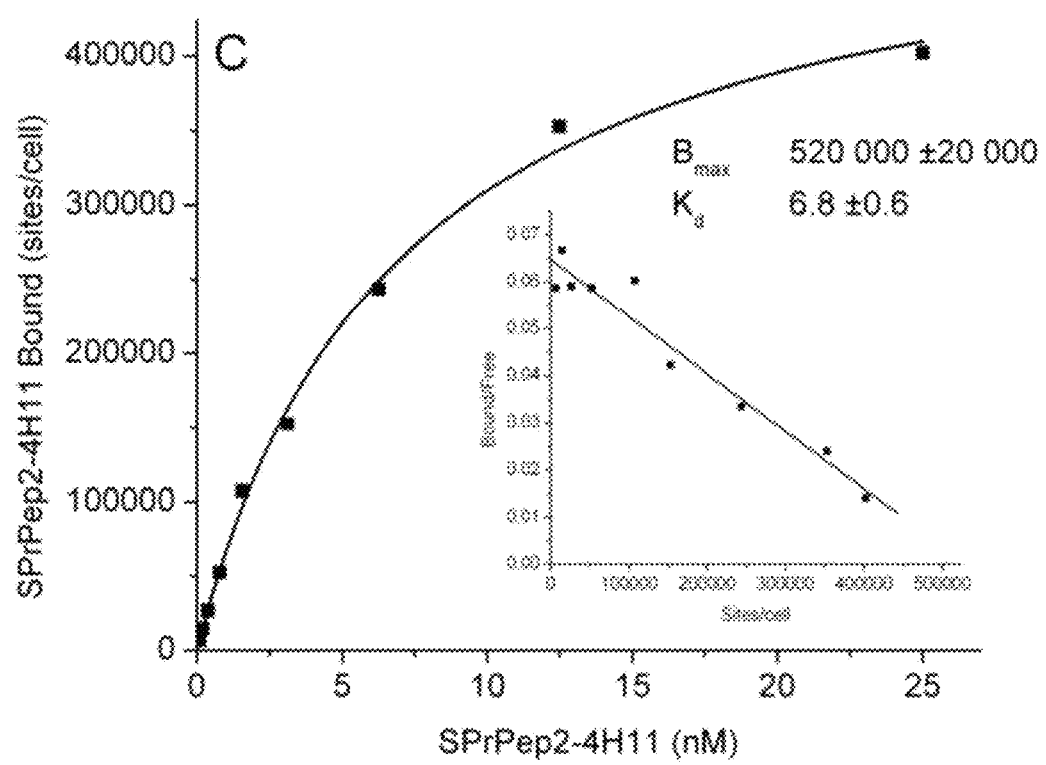
Figure 5D:
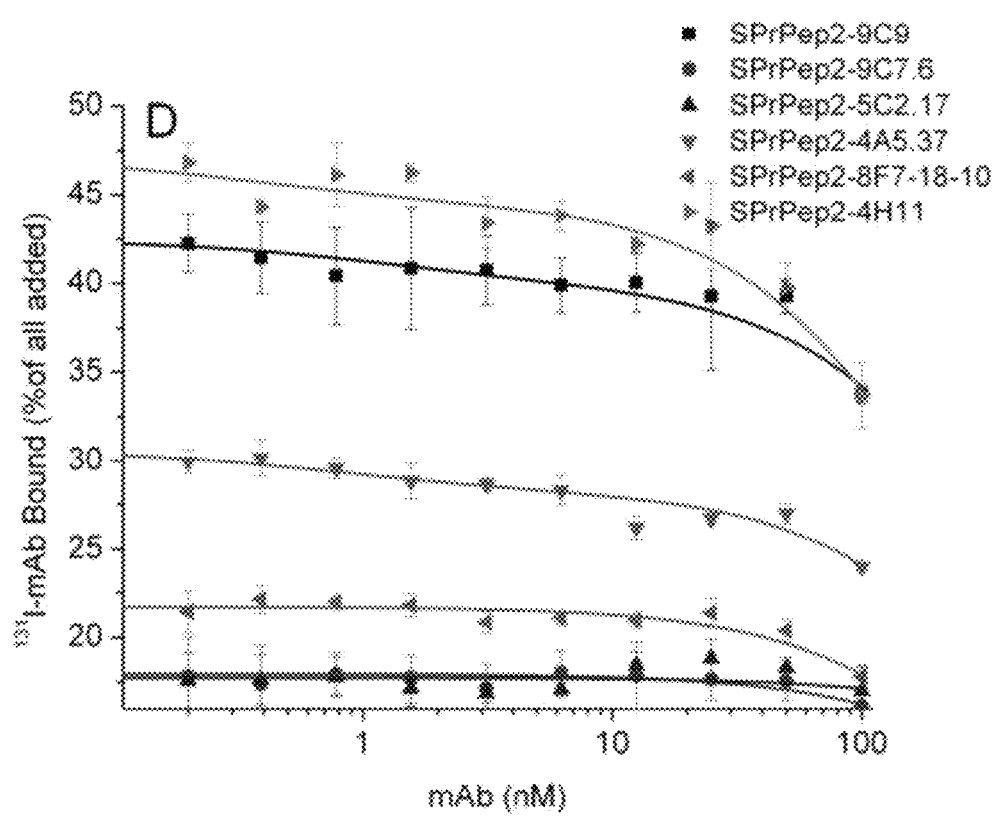
Figure 5E:
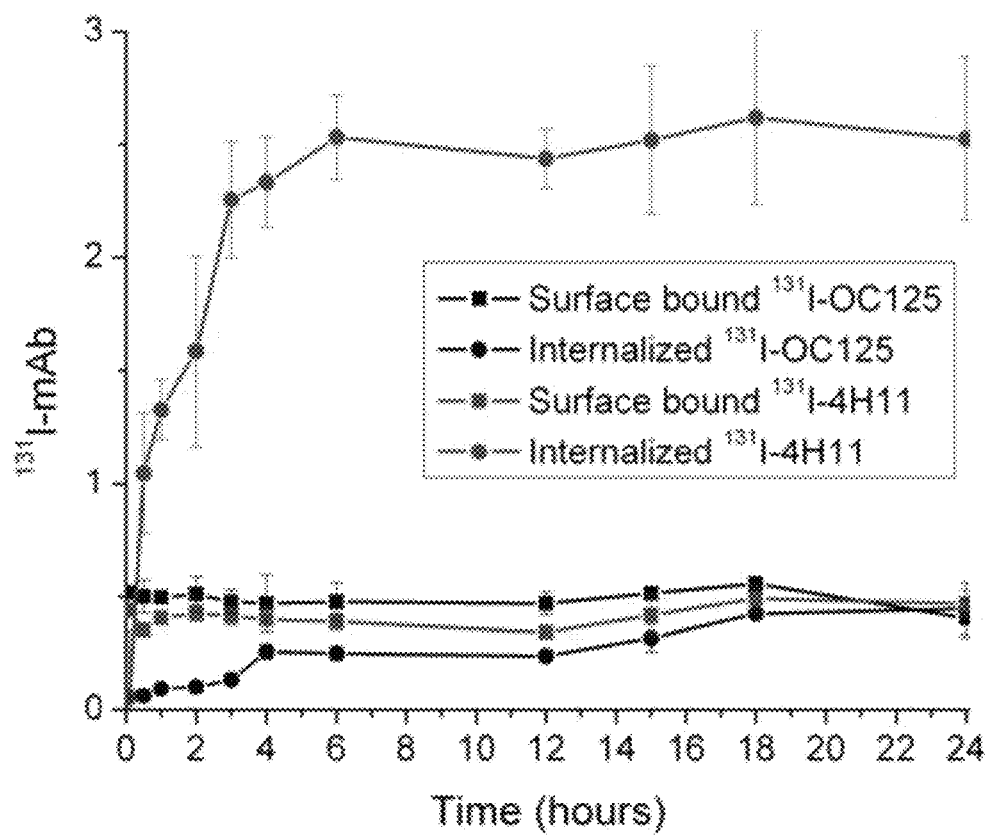
FIG. 5E: Internalization of radio-labeled 4H11 and OC125 antibodies on SKOV3-phrGFP-ΔMUC16$^{c334}$ stable transfected cells.
Figure 6A:
FIG. 6A-D: Comparison staining intensities of OC125 and 4H11 monoclonal antibodies on tissue microarrays containing cancers of the prostate (2A, concordant), lung (2B, discordant), breast (2C, discordant), and pancreas (2D, discordant).
Figure 6B:
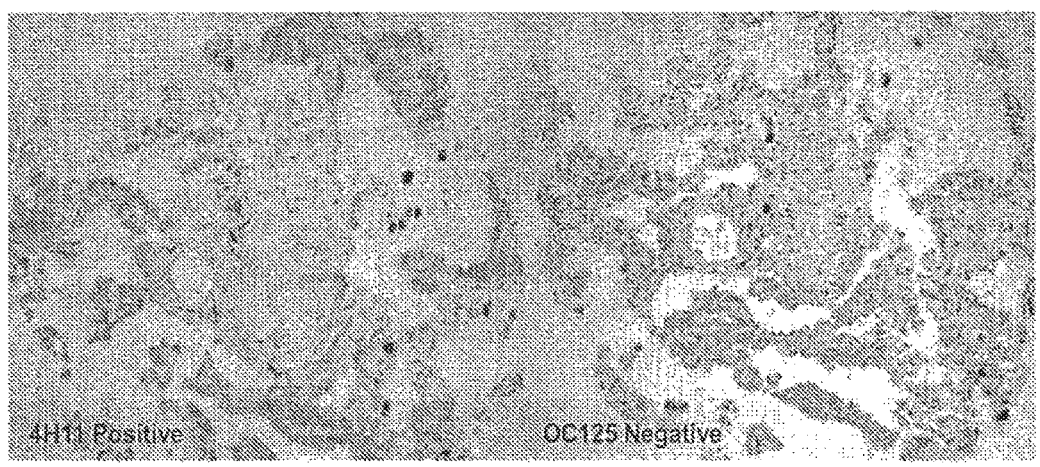
Figure 6C:
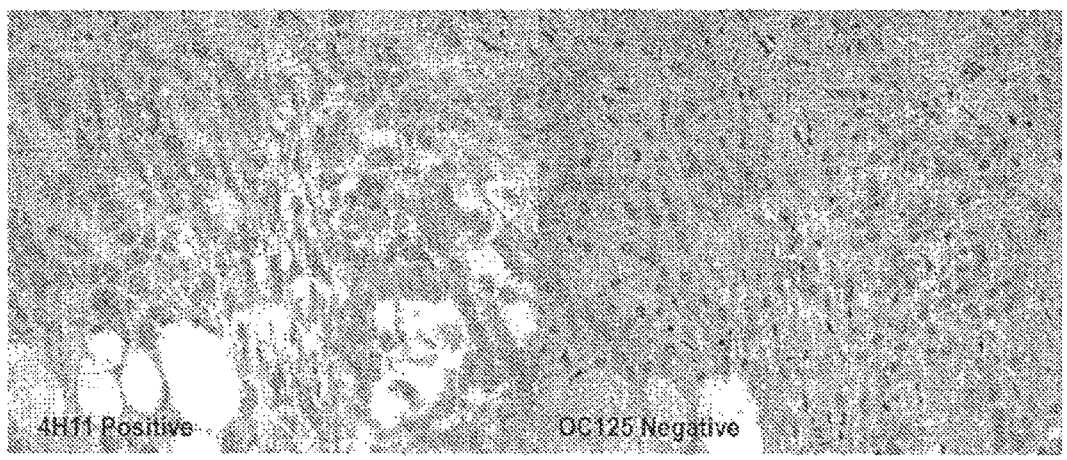
Figure 6D:

One advantage of the invention's antibodies is that the antibody internalizes into a cell, thereby being useful in applications for delivery inside a cell, such as disease therapy. "Internalized" when in reference to a molecule that is internalized by a cell refers to passage of the molecule that is in contact with the extracellular surface of a cell membrane across the cell membrane to the intracellular surface of the cell membrane and/or into the cell cytoplasm. Methods for determining internalization are disclosed herein, including the detection of radiolabeled molecule inside the cell (FIG. 5E).

In one embodiment, the invention's antibodies specifically bind to MUC16 ectodomain polypeptide that comprises a polypeptide selected from the group consisting of Polypeptide 1 NFSPLARRVDRVAIYEE (SEQ ID NO:01) and Polypeptide 2 TLDRSSVLVDGYSPNRNE (SEQ ID NO:02). Data herein show that the invention's antibodies specifically bind to GST-ΔMUC16$^{c114}$ (Example 2, Table 1A). The specificity of the invention's antibodies is in contrast to prior art antibodies (e.g., VK8, M11 and OC125 antibodies) that did not bind to GST-ΔMUC16$^{c114}$ purified protein or cell lysates of the SKOV3-phrGFP-ΔMUC16$^{c114}$ cell line (Example 2, FIG. 2).

In a further embodiment, the invention's antibodies lack specific binding to a glycosylated MUC16 extracellular domain, exemplified by the cleaved CA-125 described in Payne et al., U.S. Pat. No. 7,202,346.

While not intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:06 (i.e., the antibody 4H11 variable heavy (VH) chain amino acid sequence of FIG. 8C), and a variable light ($V_L$) chain encoded by SEQ ID NO:07 (i.e., the antibody 4H11 variable light ($V_L$) chain amino acid sequence of FIG. 8D). In a particular embodiment, the antibody is chimeric, wherein at least one of the $V_L$ and $V_H$ chains is fused to a human immunoglobulin constant region.

Also without intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:04 (i.e., the antibody 4A5 variable heavy ($V_H$) chain nucleotide sequence of FIG. 8A), and a variable light ($V_L$) chain encoded by SEQ ID NO:05 (i.e., the antibody 4A5 variable light ($V_L$) chain nucleotide sequence of FIG. 8B). In a particular embodiment, the antibody is chimeric wherein at least one of the $V_L$ and $V_H$ chains is covalently linked to a human immunoglobulin constant region.

Still without intending to limit the sequence of the $V_L$ and $V_H$ regions of the invention's antibodies, in one embodiment, the antibody specifically binds to the Polypeptide 1 (SEQ ID NO:01) of the MUC16 ectodomain polypeptide, wherein the antibody comprises a variable heavy ($V_H$) chain encoded by SEQ ID NO:08 (i.e., the antibody 9B11 variable heavy (VH) chain nucleotide sequence of FIG. 8E), and a variable light ($V_L$) chain encoded by at least one of SEQ ID NO:09 (i.e., antibody 9B11 variable light ($V_{LA}$) chain nucleotide sequence of FIG. 8F), and SEQ ID NO:10 (i.e., the antibody 9B11 variable light ($V_{LB}$) chain nucleotide sequence of FIG. 8G). In a particular embodiment, the antibody is chimeric wherein at least one of the $V_L$ and $V_H$ chains is covalently linked to a human immunoglobulin constant region.

While not intending to restrict the source of antigen to which the invention's antibodies bind, in one embodiment, the MUC16 ectodomain polypeptide is expressed by a cell. Data herein show that the invention's exemplary antibodies bind to SKOV3 cells transduced with phrGFP-ΔMUC16$^{c114}$ (Example 2).

While not limiting the sequence of antigen to which the invention's antibodies bind, in a further embodiment, the invention's antibodies specifically bind to a MUC16 cytoplasmic domain polypeptide that comprises VTTRR RKKEGEYNVQ QQ (SEQ ID NO:18). In a particular embodiment, the MUC16 cytoplasmic domain polypeptide comprises Polypeptide 3 CGVLVTTRRRKKEGEYN-VQQQ (SEQ ID NO:03). In some embodiment, the MUC16 cytoplasmic domain polypeptide is expressed by a cell. For example, data herein show that the invention's exemplary antibody binds to SKOV3 cells transduced with phrGFP-ΔMUC16$^{c114}$ (Example 2). In a particular embodiment, the cell is permeabilized to facilitate internalization of the antibody into the cell so that it comes into contact with its cytoplasmic antigen.

Still without limiting the sequence of antigen to which the invention's antibodies bind, in a further embodiment, the invention's antibodies bind to a MUC16 extracellular domain polypeptide that contains a cysteine loop polypeptide CQVSTFRSVPNRHHTGVDSLC (SEQ ID NO:19). In a more preferred embodiment, the MUC16 extracellular domain polypeptide comprises Polypeptide 4 KSYF SDC-QVSTFRS VPNRHHTGVD SLCNFSPL (SEQ ID NO:15).

Still without intending to limit the sequence of the $V_L$ and $V_H$ regions of the invention's antibodies, in one embodiment, the antibody specifically binds to Polypeptide 4 (SEQ ID NO:15) of the MUC16 extracellular domain polypeptide, wherein the antibody comprises a variable heavy ($V_H$) chain encoded by SEQ ID NO:11 (i.e., the antibody 24B3 variable heavy ($V_H$) chain amino acid sequence of FIG. 8H), and a variable light ($V_L$) chain encoded by SEQ ID NO:12 (i.e., the antibody 24B3 variable light ($V_L$) chain amino acid sequence of FIG. 8I).

The invention contemplates chimeric antibodies (see U.S. Pat. No. 7,662,387), monoclonal antibodies, recombinant antibodies, an antigen-binding fragment of a recombinant antibody, a humanized antibody, and an antibody displayed upon the surface of a phage (U.S. Pat. No. 7,202,346). In particular, the invention contemplates antibody fragments that contain the idiotype ("antigen-binding region" or "antigen-binding fragment") of the antibody molecule. For example, such antigen-binding fragments include, but are not limited to, the Fab region, F(ab')2 fragment, pFc' fragment, and Fab' fragments.

The "Fab region" and "fragment, antigen binding region," interchangeably refer to portion of the antibody arms of the immnoglobulin "Y" that function in binding antigen. The Fab region is composed of one constant and one variable domain from each heavy and light chain of the antibody. Methods are known in the art for the construction of Fab expression libraries (Huse et al., Science, 246:1275-1281 (1989)) to allow rapid and easy identification of monoclonal Fab fragments with the desired specificity. In another embodiment, Fc and Fab fragments can be generated by using the enzyme papain to cleave an immunoglobulin monomer into two Fab fragments and an Fc fragment. The enzyme pepsin cleaves below the hinge region, so a "F(ab')2 fragment" and a "pFc' fragment" is formed. The F(ab')2 fragment can be split into two "Fab' fragments" by mild reduction.

The invention also contemplates a "single-chain antibody" fragment, i.e., an amino acid sequence having at least one of the variable or complementarity determining regions (CDRs) of the whole antibody, and lacking some or all of the constant domains of the antibody. These constant domains are not necessary for antigen binding, but constitute a major portion of the structure of whole antibodies. Single-chain antibody fragments are smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies. Techniques for the production of single-chain antibodies are known (U.S. Pat. No. 4,946,778). The variable regions of the heavy and light chains can be fused together to form a "single-chain variable fragment" ("scFv fragment"), which is only half the size of the Fab fragment, yet retains the original specificity of the parent immunoglobulin.

The "Fc region" and "Fragment, crystallizable region" interchangeably refer to portion of the base of the immnoglobulin "Y" that function in role in modulating immune cell activity. The Fc region is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. In an experimental setting, Fc and Fab fragments can be generated in the laboratory by cleaving an immunoglobulin monomer with the enzyme papain into two Fab fragments and an Fc fragment.

The invention contemplates polyclonal antibodies and monoclonal antibodies. "Polyclonal antibody" refers to an immunoglobulin produced from more than a single clone of plasma cells; in contrast "monoclonal antibody" refers to an immunoglobulin produced from a single clone of plasma cells. Generic methods are available for making polyclonal and monoclonal antibodies that are specific to a desirable polypeptide. For the production of monoclonal and polyclonal antibodies, various host animals can be immunized by injection with the peptide corresponding to any molecule of interest in the present invention, including but not limited to hamsters, rabbits, mice, rats, sheep, goats, etc. For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 (1975)), techniques using germ-free animals and utilizing technology such as that described in PCT/US90/02545, as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)). In some particularly preferred embodiments of the present invention, the present invention provides monoclonal antibodies.

Also contemplated are chimeric antibodies. As used herein, the term "chimeric antibody" contains portions of two different antibodies, typically of two different species. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al. Chimeric antibodies include monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a Hc region that aggregates (e.g., IgM H chain).

The invention also contemplates "humanized antibodies," i.e., chimeric antibodies that have constant regions derived substantially or exclusively from human antibody constant regions, and variable regions derived substantially or exclusively from the sequence of the variable region from a mammal other than a human. Humanized antibodies preferably have constant regions and variable regions other than the complement determining regions (CDRs) derived substantially or exclusively from the corresponding human antibody regions and CDRs derived substantially or exclusively from a mammal other than a human. Thus, in one embodiment, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. Humanized antibodies may be generated using methods known in the art, e.g., U.S. Pat. No. 5,225,539 to Winter et al., including using human hybridomas (Cote et al., Proc. Natl. Acad. Sci. U.S.A. 80:2026-2030 (1983)) or by transforming human B cells with EBV virus in vitro (Cole et al., in Monoclonal Antibodies and Cancer Therapy, Alan R. Liss, pp. 77-96 (1985)). Additional methods include, for example, generation of transgenic non-human animals which contain human immunoglobulin chain genes and which are capable of expressing these genes to produce a repertoire of antibodies of various isotypes encoded by the human immunoglobulin genes (U.S. Pat. Nos. 5,545,806; 5,569,825 and 5,625,126). Humanized antibodies may also be made by substituting the complementarity determining regions of, for example, a mouse antibody, into a human framework domain (PCT Pub. No. WO92/22653).

Importantly, early methods for humanizing antibodies often resulted in antibodies with lower affinity than the non-human antibody starting material. More recent approaches to humanizing antibodies address this problem by making changes to the CDRs. See U.S. Patent Application Publication No. 20040162413, hereby incorporated by reference. In some embodiments, the invention's humanized antibodies contain an optimized heteromeric variable region (e.g. that may or may not be part of a full antibody other molecule) having equal or higher antigen binding affinity than a donor heteromeric variable region, wherein the donor heteromeric variable region comprises three light chain donor CDRs, and wherein the optimized heteromeric variable region comprises: a) a light chain altered variable region comprising; i) four unvaried human germline light chain framework regions, and ii) three light chain altered variable region CDRs, wherein at least one of the three light chain altered variable region CDRs is a light chain donor CDR variant, and wherein the light chain donor CDR variant comprises a different amino acid at only one, two, three or four positions compared to one of the three light chain donor CDRs (e.g. the at least one light chain donor CDR variant is identical to one of the light chain donor CDRs except for one, two, three or four amino acid differences).

Chimeric antibodies containing amino acid sequences that are fused to constant regions from human antibodies, or to toxins or to molecules with cytotoxic effect, are known in the art (e.g., U.S. Pat. Nos. 7,585,952; 7,227,002; 7,632,925; 7,501,123; 7,202,346; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 6,429,295; 7,666,425; and 5,057,313).

Antibodies that are specific for a particular antigen may be screened using methods known in the art (e.g., U.S. Pat. No. 7,202,346) and disclosed herein. For example, In the production of antibodies, screening for the desired antibody can be accomplished by radioimmunoassay, ELISA (enzyme-linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In one embodiment, the invention's antibodies are monoclonal antibodies produced by a hybridoma cell line. In a particular embodiment, the monoclonal antibody specifically binds to a MUC16 ectodomain polypeptide that comprises Polypeptide 1 (SEQ ID NO:01), as exemplified by the antibody selected from the group consisting of 9B11.20.16, 10A2, 2F4, 23D3, 30B1, and 31B2 (Tables 1 and 2). In a preferred embodiment, the antibody is 9B11.

In another embodiment, the monoclonal antibody specifically binds to a MUC16 ectodomain polypeptide that comprises Polypeptide 2 (SEQ ID NO:02), wherein the antibody is exemplified by 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10 (Tables 1 and 2). In a preferred embodiment, the antibody is exemplified by 4H11.2.5, 4A5.37, 9C9.21.5.13, 28F7.18.10, 9C7.6, and 5C2.17.

In a further embodiment, the monoclonal antibody specifically binds to a MUC16 cytoplasmic domain polypeptide that comprises Polypeptide 3 CGVLVTTRRRKKEGEYNVQQQ (SEQ ID NO:03), wherein the antibody is exemplified by 31A3.5.1, 19D1, 10F6, 22E10, 22F1, 3H8, 22F11, 4D7, 24G12, 19G4, 9A5, 4C2, 31C8, 27G4, and 6H2 (Tables 1 and 2). In a preferred embodiment, the antibody is 31A3.5.1.

In another embodiment, the monoclonal antibody specifically binds to a MUC16 extracellular domain polypeptide that comprises Polypeptide 4 KSYF SDCQVSTFRS VPNRHHTGVD SLCNFSPL (SEQ ID NO:15), wherein the antibody is exemplified by 24B3 and 9C7 (Table 2).

The invention's antibodies and methods for their use (both diagnostic and therapeutic) are disease specific. "Specificity" of a method and/or molecule for disease, such as "specificity for cancer" which is interchangeably used with "cancer specificity", refers to the proportion (e.g., percentage, fraction, etc.) of negatives (i.e., healthy individuals not having disease) that are correctly identified, i.e., the percentage of healthy subjects who are correctly identified as not having disease. Specificity may be calculated according to the following equation:

Specificity=number of true negatives/(number of true negatives+number of false positives).

Thus, in some embodiments, the invention's compositions and/or methods have a "cancer specificity" greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% specificity is most desirable, i.e., not predicting anyone from the healthy group as having cancer, it is not necessary. Data herein demonstrate the invention's cancer specificity (Table 3).

In alternative embodiments, specificity is expressed (together with sensitivity) as a statistical measure of the performance of a binary classification test, such as using a Receiver Operator Characteristic (ROC) curve". For any test, there is usually a trade-off between specificity and sensitivity. For example: in cancer screening tests of human subjects, it is undesirable to risk falsely identifying healthy people as having cancer (low specificity), due to the high costs. These costs are both physical (unnecessary risky procedures) and financial. This trade-off can be represented graphically using a ROC curve. "Receiver Operator Characteristic curve" and "ROC curve" refer to a plot of the true positive rate (AKA sensitivity) versus true negative rate (AKA 1-specificity). The measured result of the test is represented on the x axis while the y axis represents the number of control (e.g., healthy) or case (e.g., cancer) subjects. For any given cut point (each point along the x axis) a sensitivity and specificity of the assay can be measured. The range of sensitivity and specificity for any given assay can range from 0% to 100%, depending on the selected cut point. For this reason, in some preferred embodiments, the AUC is used as the standard measure of an assay's specificity and/or sensitivity. The "area under the curve" ("AUC") for the ROC curve plot is equal to the probability that a classifier will rank a randomly chosen positive instance higher than a randomly chosen negative one. Thus, AUC is a general measure of a tests ability to successfully discriminate between case (e.g., cancer) and control (e.g., healthy) subjects. Random chance would generate an AUC of 0.5. Therefore, in one embodiment, useful tests preferably have AUC's greater than 0.50, including any value from 0.51 to 1.00, such as from 0.55 to 1.00, from 0.60 to 1.00, from 0.65 to 1.00, from 0.70 to 1.00, from 0.75 to 1.00, from 0.80 to 1.00, from 0.85 to 1.00, from 0.90 to 1.00, from 0.95 to 1.00, and most preferably 1.00. AUC values greater than 0.50 include 0.51, 0.52, 0.52, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, and 0.99.

The invention's antibodies and methods for their use (both diagnostic and therapeutic) are disease sensitive. "Sensitivity" of a method and/or molecule for disease, such as "sensitivity for cancer" which is interchangeably used with "cancer sensitivity," refers to the proportion (e.g., percentage, fraction, etc.) of positives (i.e., individuals having cancer) that are correctly identified as such (e.g. the percentage of people with cancer who are identified as having the condition). Sensitivity may be calculated according to the following equation; Sensitivity=number of true positives/(number of true positives+number of false negatives).

Thus, in some embodiments, the invention's compositions and/or methods have a "disease sensitivity," such as "cancer sensitivity," greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% sensitivity is most desirable (i.e., predicting all subjects from the cancer group as having cancer), it is not necessary.

In alternative embodiments, the invention's compositions and/or methods have a "disease sensitivity," such as "cancer sensitivity," equal to or lower than 50%, including any numerical value from 0% to 50%, such as 1%, 2%, 3%, 4%, 6%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, and 49%.

In some embodiments, sensitivity is expressed (together with specificity) as a statistical measure of the performance of a binary classification test, such as using AUC of a ROC curve, as discussed above with respect to specificity.

D. Hybridoma Cell Lines

In addition to the invention's novel antibodies, the invention also provides hybridoma cell lines that produce these antibodies. "Hybridoma cell" refers to a cell line produced by fusing a specific antibody-producing B cell with a myeloma (B cell cancer) cell that is selected for its ability to grow in tissue culture and for an absence of antibody chain synthesis. The antibodies produced by the hybridoma cell are all of a single specificity and are therefore monoclonal antibodies (in contrast to polyclonal antibodies).

In a particular embodiment, the invention provides hybridoma cell lines that produce a monoclonal antibody that specifically binds to a polypeptide, or antigenic portion thereof, selected from the group consisting of a) MUC16 ectodomain polypeptide (e.g., NFSPLAR RVDRVAIYEE FLRMTRNGTQ LQNFTLDRSS VLVDGYSPNR NEPLTGNSDL P (SEQ ID NO:17)), b) MUC16 cytoplasmic domain polypeptide (e.g., VTTRR RKKEGEYNVQ QQ (SEQ ID NO:18)), and c) MUC16 extracellular domain polypeptide that contains a cysteine loop polypeptide CQVSTFRSVPNRHHTGVDSLC (SEQ ID NO:19). The MUC16 polypeptide SEQ ID NO:18 is contained within LVTTRR RKKEGEYNVQ QQ (SEQ ID NO:20). Thus, SEQ ID NO:20 contains both a transmembrane domain amino acid (L) and a cytoplasmic domain portion VTTRR RKKEGEYNVQ QQ (SEQ ID NO:18), i.e., the L is optional, as it is part of the transmembrane domain. The MUC16 polypeptide SEQ ID NO:18 is also contained within CGVLVTTRR RKKEGEYNVQ QQ (SEQ ID NO:03). Thus, SEQ ID NO:03 contains both a transmembrane domain portion (CGVL) and a cytoplasmic domain portion VTTRR RKKEGEYNVQ QQ (SEQ ID NO:18), i.e., the CGVL is optional, as it is part of the transmembrane domain.

E. Conjugates of the Invention's Antibodies Linked to Cytotoxic Agents and/or Prodrugs The invention contemplates conjugate antibodies. A "conjugate" antibody refers to an antibody of the present invention covalently linked to a cytotoxic agent and/or a prodrug of a cytotoxic agent.

"Cytotoxic agent" refers any agent that is capable of reducing the growth of, and/or killing, a target cell. A "prodrug" represents an analog of a cytotoxic agent that substantially lacks cytotoxic activity until subjected to an activation step. Activation steps may include enzymatic cleavage, a chemical activation step such as exposure to a reductant, or a physical activation step such as photolysis.

The covalent linkage between the invention's antibodies and the cytotoxic agent or prodrug can include cleavable linkages such as disulfide bonds, which may advantageously result in cleavage of the covalent linkage within the reducing environment of the target cell. Such conjugates are useful as tumor-cell specific therapeutic agents.

In one embodiment, the cytotoxic agent is a small drug molecule (Payne et al., U.S. Pat. No. 7,202,346). In another embodiment, the cytotoxic agent a maytansinoid, an analog of a maytansinoid, a prodrug of a maytansinoid, or a prodrug of an analog of a maytansinoid (U.S. Pat. Nos. 6,333,410; 5,475,092; 5,585,499; 5,846,545; 7,202,346). In another embodiment, the cytotoxic agent may be a taxane (see U.S. Pat. Nos. 6,340,701 & 6,372,738 & 7,202,346) or CC-1065 analog (see U.S. Pat. Nos. 5,846,545; 5,585,499; 5,475,092 & 7,202,346).

In another embodiment, the cytotoxic agent is exemplified by an auristatin, a DNA minor groove binding agent, a DNA minor groove alkylating agent, an enediyne, a duocarmycin, a maytansinoid, and a vinca alkaloid (U.S. Pat. No. 7,662, 387).

In a further embodiment, the cytotoxic agent is an anti-tubulin agent (U.S. Pat. No. 7,662,387). In yet another embodiment, the cytotoxic agent is exemplified by dimethylvaline-valine-dolaisoleuine-dolaproine-phenylalanine-p-phenylenediamine (AFP), dovaline-valine-dolaisoleunine-dolaproine-phenylalanine (MMAF), and monomethyl auristatin E (MAE) (U.S. Pat. No. 7,662,387).

In an additional embodiment the toxic agent is exemplified by radioisotope emitting radiation, immunomodulator, lectin, and toxin (U.S. Pat. No. 6,429,295). In particular, the radioisotope emitting radiation is an alpha-emitter selected from the group consisting of $^{212}$Bi, $^{213}$Bi, and $^{211}$At, or a beta-emitter selected from the group consisting of $^{186}$Re and $^{90}$Y, or a gamma-emitter $^{131}$I (U.S. Pat. No. 7,666,425).

In an alternative embodiment, the toxin is exemplified by ricin, the A-chain of ricin, and pokeweed antiviral protein (U.S. Pat. No. 5,057,313).

In yet another embodiment, the cytotoxic agent is an anti-cancer drug selected from the group consisting of methotrexate, 5-fluorouracil, cycloheximide, daunomycin, doxorubicin, chlorambucil, trenimon, phenylenediamine mustard, adriamycin, bleomycin, cytosine arabinoside or Cyclophosphamide (U.S. Pat. No. 5,057,13).

F. Detecting Muc16 Portions and Diagnostic Applications

The invention provides a method for detecting a disease that comprises overexpression of MUC16 in a subject, wherein the method comprises a) providing i) a sample from a subject, and ii) any one or more of the invention's antibodies, b) contacting the sample with the antibody under conditions for specific binding of the antibody with its cognate antigen, and c) detecting an increased level of binding of the antibody to the sample compared to a control sample lacking the disease, thereby detecting the disease in the subject. Generic methods for detecting disease using antibodies are known in the art (Payne et al., U.S. Pat. No. 7,202,346). The invention's methods are particularly useful in detecting cancer, such as ovarian cancer and breast cancer.

The invention's methods are not limited to a particular approach to detecting binding of the invention's antibodies to their antigens. In one embodiment, detecting binding to the invention's antibodies typically involves using antibodies that are labeled with a detectable moiety, such as radioisotope (e.g., $^3$H, $^{14}$C, $^{32}$P, $^{35}$S, and/or $^{125}$I) fluorescent or chemiluminescent compound (e.g., fluorescein isothiocyanate, rhodamine, and/or luciferin) and/or an enzyme (e.g., alkaline phosphatase, beta-galactosidase and/or horseradish peroxidase).

Methods for conjugating antibodies to a detectable moiety are known in the art (e.g., Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

Thus, the invention's antibodies may be employed in immunoassays, such as competitive binding assays, direct and indirect sandwich assays, and immunoprecipitation assays, including immunohistochemistry, enzyme-linked immunosorbent assay (ELISA), fluorescence-activated cell sorting (FACS), and Western blots.

For example, with respect to immunohistochemical detection, data herein demonstrate that antibody 4H11 is useful in detecting high-grade ovarian serous carcinoma, lobular cancer (28), and a subset of ovarian carcinomas that are negative with OC125 and that retain cytoplasmic and extracellular portions of the MUC16 glycoprotein.

The antibodies of the invention also are useful for radiographic in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies.

The invention's antibodies are additionally useful as affinity purification agents. In this process, the antibodies are immobilized on a suitable support, such a Sephadex resin or filter paper, using methods well known in the art, to capture and purify molecules that contain antigens that specifically bind to the invention's antibodies.

G. Therapeutic Applications

The invention provides methods for treating a disease that comprises overexpression of MUC16, comprising administering to a subject having the disease a therapeutically effective amount of any one or more of the invention's antibodies. Generic methods for treating disease with antibodies are known in the art (Payne et al., U.S. Pat. No. 7,202,346). The invention's methods are particularly useful in treating cancer, such as ovarian cancer and breast cancer. These methods are also applicable to primary cancer, metastatic cancer, and recurrent cancer.

The term "administering" to a subject means providing a molecule to a subject. This may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The invention's compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical and sublingual forms. Parenteral routes of administration include, for example, subcutaneous, intravenous, intramuscular, intrastemal injection, and infusion routes.

In one embodiment, the invention's compositions comprise a lipid for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29; Song et al. (2008) Int J Pharm 363, 155-161; Voinea et al. J Cell Mol Med 6, 465-474).

Antibody treatment of human beings with cancer is known in the art, for example in U.S. Pat. Nos. 5,736,137; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 7,662,387; 6,429,295; 7,666,425; 5,057,313.

The invention's antibodies may be administered with pharmaceutically acceptable carriers, diluents, and/or excipients. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The invention's antibodies are typically administered in a therapeutic amount. The terms "therapeutic amount," "pharmaceutically effective amount," "therapeutically effective amount," and "biologically effective amount," are used interchangeably herein to refer to an amount that is sufficient to achieve a desired result, whether quantitative or qualitative. In particular, a pharmaceutically effective amount is that amount that results in the reduction, delay, and/or elimination of undesirable effects (such as pathological, clinical, biochemical and the like) that are associated with disease. For example, a "therapeutic amount that reduces cancer" is an amount that reduces, delays, and/or eliminates one or more symptoms of cancer.

For example, specific "dosages" of a ""therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors, which those skilled in the art will recognize. The dosage amount and frequency are selected to create an effective level of the compound without substantially harmful effects.

When present in an aqueous dosage form, rather than being lyophilized, the antibody typically will be formulated at a concentration of about 0.1 mg/ml to 100 mg/ml.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs.

The methods of the present invention can be practiced in vitro, in vivo, or ex vivo.

EXPERIMENTAL

The following examples serve to illustrate certain preferred embodiments and aspects of the present invention and are not to be construed as limiting the scope thereof.

Example 1

Materials and Methods

The following is a brief description of the exemplary materials and methods used in the subsequent Examples.
Cell Cultures:

OVCAR3, SKOV3, and A2780 cell lines were obtained through the American Type Culture Collection (ATCC, Manassas, Va.) and sustained in culture according to the ATCC literature. For the creation of MUC16+ transfected cell lines, the carboxyterminus portion of the MUC16 cDNA was introduced as green fluorescent protein fusion proteins using the Vitality phrGFP vector expression system (Stratagene, La Jolla, Calif.). Stable cell lines were selected using geneticin (G418, Invitrogen, Grand Island, N.Y.) in their respective culture media and isolated by expression of Green Fluorescence Protein. Stable transfectants were routinely maintained in G418 in their culture media respectively. The $\Delta MUC16^{c114}$ transfectants have cell surface expression of MUC16 protein from the putative cleavage site to the carboxyterminus (AA 1776 to 1890) (12).
Monoclonal Preparation:

Using the MUC16 sequence, peptide sequences encoding elements of the $\Delta MUC16^{c114}$ amino acid sequence were synthesized at the Memorial Sloan-Kettering Cancer Center (MSKCC) Microchemistry Core Facility. The inventors synthesized 3 polypeptides (FIG. 1) and modified Polypeptide 1 and Polypeptide 2 with a cysteine at the N-terminus for better conjugation to KLH. Equal concentrations of the KLH-conjugated peptides were mixed and then used as the immunogen for 5 BALB/c mice. The inventors selected 1 of the 5 mice whose serum showed the highest reactivity to individual peptides by ELISA, and the MSKCC Monoclonal Antibody Core Facility performed the fusion and selected the antibodies using standard protocols. After 10 days of fusion, supernatants were selected and screened for reactivity by ELISA against the individual synthetic peptides.
ELISA:

Sandwich ELISA was performed to see the positivity of the antibodies to individual peptides and GST-$\Delta MUC16^{c114}$ fusion protein following routine core facility protocol for ELISA assay.
FACS Analyses:

Adherent target cells were removed by 0.05% Trypsin and 0.1% EDTA, washed, and counted by a hemocytometer. Cells were distributed into multiple Eppendorf tubes with at least $0.5-1\times10^6$ cells per tube. Cells were washed with phosphate buffered saline (PBS) containing 1% FCS and 0.025% Sodium Azide (FACS buffer). For internal FACS staining, cells in the Eppendorf tubes were permeabilized with 1:10 diluted FACS Permeabilizing Solution 2 (BD BioSciences, San Jose, Calif.) for 10 minutes at room temperature and then washed twice with ice cold FACS buffer. Then they were incubated either without (for antibody control) or with 1 µg/tube of bioreactive supernatants of mouse MUC16 monoclonals for 30 minutes on ice. For surface FACS staining, cells were incubated either without (for second antibody control) or with 1 µg/tube of bioreactive supernatants of MUC16 monoclonals (9B11.20.16, 9C9.21.5.13 and 4H11.2.5), Mouse anti-human OC125 (M3519), Mouse anti-human M11 (M3520) (DakoCytomation, Dako North America Inc., Carpinteria, Calif.) or VK8 (kindly provided by Dr. Beatrice Yin and Dr. Ken Lloyd, MSKCC, New York, N.Y.) for 30 minutes on ice. Cells in Eppendorf tubes were also surface stained with 1 µg/tube of non-specific isotype matched control mouse antibodies (13C4 for IgG1 and 4E11 for IgG2b monoclonals obtained from MSKCC Monoclonal Core Facility) and incubated on ice for 30 minutes. All cells were washed three times with FACS buffer. Cells were incubated with 1 µg/tube of second antibody Goat anti-mouse IgG1-PE or IgG2b-PE for 30 minutes on ice and then washed three times with FACS buffer. The cells were analyzed by a FACS Calibur machine at the MSKCC Flow Cytometry Core Facility.
Western Blot Analysis:

Stable cell lines were cultured in 10 cm dishes in their respective culture media and incubated with 5% $CO_2$ at 37° C. for 3 days. They were washed twice with ice cold PBS to remove the serum-containing media. Adherent cells were scraped with 1-2 ml of ice cold PBS, and the cells were spun down in an Eppendorf tube at 4° C. in an Eppendorf centrifuge. Supernatant was discarded, and the cells were lysed with 0.2 ml of modified Ripa lysis buffer (20 mM Tris-HCL; pH 7.4; 150 mM NaCl; 1% NP-40; 1 mM Na3VO4; 1 mM PMSF; 1 mM DTT; 10 µg/ml leupeptin; and 10 µg/ml aprotinin) for 30 minutes on ice and spun at 4° C. for 10 minutes. The soluble solution was separated into a tube and the debris pellet was discarded. Protein concentration was measured using the Bio-Rad Protein Assay (Bio-RaD Laboratories, Hercules, Calif.). Equal amounts of proteins (GST-MUC16-CD-fusion protein or stable cell line extracts) were separated by sodium dodecyl sulfate polyacrylamide gel electrophoresis (SDS-PAGE) and transferred to nitrocellulose membrane using a BioRad transfer apparatus in a cold room at 4° C. The membranes were blocked with 3% bovine serum albumin (BSA) in PBS with 0.1% Tween-20 (PBST) at 4° C. overnight. Membranes were probed with primary antibody (1:1000 dilution) for 1 hr at room temperature and then washed three times with PBST. Then the membranes were stained with corresponding second antibody, anti-Mouse IgG Horse Radish Peroxidase (HRP) linked whole antibody from sheep (GE Healthcare, UK) (1:5000 dilution), for 1 hr at room temperature. Membranes were washed three times with PBST and developed with a Western Lightning® chemiluminescence reagent (ECL, Perkin Elmer, Waltham, Mass.) for 1-5 minutes at room temperature, and the signals were developed on Kodak BioMax Film.

Binding and internalization studies with monoclonal antibodies and OVCAR3 and SKOV3 stable transfectants:

Purified monoclonal antibodies were labeled with $^{131}I$ using the iodogen method and purified by size exclusion chromatography (22). Saturation binding studies were performed with radiolabeled antibodies using substrates of intact OVCAR-3 cells. Briefly, 10 test solutions were prepared (in triplicate) and they contained increasing amounts of the radioiodinated antibodies, 3-500 000 cells in a total volume of 500 µL of PBS (0.2% BSA; pH 7.4). The cells were isolated by rapid filtration through a glass fiber membrane and washed with ice cold tris buffered saline. Cells were counted in a gamma counter with standards of total activity added. For each concentration of radiolabeled antibody, non-specific binding was determined in the presence of 100 nM of the unmodified antibody. The data were analyzed with a least squares regression method (Origin, Microcal, Software Inc., Northampton, Mass.) to determine the $K_d$ and $B_{max}$ values, and a Scatchard transformation was performed.

Antibody cell internalization studies were performed with $^{131}$I-4H11 and $^{131}$I-OC125 monoclonal antibodies and SKOV3-phrGFP-ΔMUC16$^{c334}$ stable transfected cells. Briefly, radiolabeled antibody (370 MBq/mg, 100 kcpm) in 2 mL of medium was added to SKOV3 cells plated in a 6-well plate. The plates were incubated at 37° C. for up to 24 hours. At various time points, the medium was removed from three wells and the cells washed with 2×2 mL PBS. Cell surface bound activity was then stripped and collected with 2×2 mL of an ice cold acid wash (100 mM acetic acid 100 mM glycine; pH 3.0). The cells were then dissolved with 2×1 ml 1 M NaOH and collected. At the end of the study all samples were counted with a gamma counter together with standards, representing the initial amount of radioactivity added. All the media samples were analyzed by ITLC-SG with mobile phases of 5% TCA to determine unbound $^{131}$I.

Tissue Microarray (TMA):

Tissue microarrays were either constructed within our institution or bought from a commercial laboratory if not available internally. Briefly, core-needle biopsies of pre-existing paraffin-embedded tissue were obtained from the so-called donor blocks and then relocated into a recipient paraffin-arrayed "master" block by using the techniques by Kononen et al. and subsequently modified by Hedvat et al (23-24). A manually operated Tissue Arrayer MTA-1 from Beecher Instruments Inc. (Sun Prairie, Wis.) was used to produce sample circular spots (cores) that measured 0.6 to 1.0 mm in diameter. The cores were arrayed 0.3 to 0.4 mm apart from each other. A layer of control tissues was strategically laid around the actual tissue microarrays in order to avoid edging effects. The specific composition of each tissue microarray is delineated below. Slides of tissue microarrays for ovarian cancer, prostate cancer, adenocarcinoma of the lung, mucinous neoplasms of the pancreas, and invasive ductal and invasive lobular breast carcinoma were prepared by cutting 4 um sections from formalin-fixed paraffin-embedded tissue. Normal adult and fetal tissue microarrays were obtained from a commercial source (Biomax, US). OVCAR3 cells were used as positive controls.

Immunohistochemistry:

Immunohistochemistry was performed on the tissue microarrays with both standard OC125 (Ventana, Tucson, Ariz.) and the novel monoclonal antibodies. Sections of the tissue microarrays were cut at 4 microns, placed on Superfrost/Plus microscope slides (Fisher brand) and baked in a 60° oven for at least 60 minutes. The slides were then deparaffinized and hydrated to distilled water, soaked in citrate buffer at pH 6.00 for 30 minutes at 97° C., washed in running water for 2-5 minutes, incubated for 5 minutes in 3% hydrogen peroxide diluted in distilled water. Slides were washed in distilled water for 1 minute, transferred to a bath of phosphate buffered saline (PBS), pH 7.2, for two changes of 5 minutes each and placed in 0.05% BSA diluted in PBS for a minimum of 1 minute. After drying around tissue sections, normal serum was applied at a 1:20 dilution in 2% BSA/PBS and incubated for a minimum of 10 minutes at room temperature in a humidity chamber. The serum was then suctioned off without allowing the sections to dry, and approximately 150 lambda of novel antibody at a dilution of 1:1000 was placed on the tissue. The slide was incubated overnight (approximately 15-18 hours) at 4° C. in a humidity chamber. Primary antibody was washed off using three changes of PBS for 10 minutes each. Secondary antibody, biotinylated α-mouse from Vector laboratories (Burlingame, Ca), was applied at 1:500 dilution in 1% BSA/PBS and incubated for 45-60 minutes at room temperature in humidity chamber. The antibody was washed off again using three changes of PBS as above. Slides were then transferred to a bath of diaminobenzidine (DAB), diluted in PBS for 5-15 minutes. The slides were then washed in tap water for 1 minute, counterstained using Harris modified hematoxylin (Fisher), decolorized with 1% acid alcohol and blue in ammonia water, dehydrated with 3 changes each of 95% ethanol, 100% ethanol and xylene for 2 minutes each and coverslipped with permanent mounting medium.

Immunohistochemistry Scoring:

Commercially available antibodies, such as OC125 and M11, target complex glycosylation-dependent epitopes. Our hypothesis is that glycosylation may be tissue specific; therefore, it was important to examine the utility of the peptide-directed antibodies in paraffin-fixed tissues and survey the prevalence of MUC16 expression. The three candidate antibodies, 4H11, 9C9 and 4A5, were characterized using OVCAR3 cell line pellets. Of the three, the 4H11 antibody showed the strongest, most diffuse and consistent staining pattern at multiple dilutions, with the least amount of background staining and, therefore, was optimized for use in human tissues in the pathology core facility.

Using 4H11, the inventors stained and scored positivity using tissue microarrays from high-stage, high-grade ovarian serous carcinomas (FIG. 2), these tumors being the most common type of ovarian cancer, representing approximately 80-85% of all ovarian carcinomas in Western industrialized nations (25). To test the specificity of the novel antibody, the inventors also stained tissue microarrays of cancers of the prostate, lung, breast, and pancreas and compared their staining intensities with that of OC125 monoclonal antibody (FIG. 6A-D). To determine whether there would be any cross-reactivity with normal human tissues, the antibodies were also tested on normal human adult and fetal TMAs.

All of the stained sections were reviewed by a reference pathologist (KJP). A subset of cores for which there was equivocal staining was also independently scored by a second pathologist (RAS) to ensure consistency in scoring methods. Only cytoplasmic and/or membranous staining was considered positive. If a portion of the cell showed membranous staining, that was considered partial staining. A scoring system was devised to provide a semiquantitative assessment of staining distribution and intensity in individual cores. At the same time, it was designed to be useful for comparing the staining distribution and intensity between OC125 and the novel antibodies. The score incorporated the percentage of cells, the intensity and pattern of the staining according to the following standards: score 0: no staining; score 1: <5% strong or weak; score 2: 5-50% strong or weak; score 3: 51-75% strong or 51-100% weak; score 4: 76-99% strong; and score 5: 100% strong staining (FIG. 3A-FIG. 3L). The pathologist first reviewed all tissue microarrays stained with OC125 and scored each core. Then the same cores stained with the novel antibodies were scored 1 to several days after OC125 without reference to the previous results. Direct comparison of the scoring between the stains for each core was made only after all of the scoring was completed. The same process was used for all non-ovarian tissue microarrays. After comparison, core staining was determined to be concordant, equivocal, or discordant based on the point differentials. Concordant cores differed by 0 to 1 point, equivocal cores differed by 2 points, and discordant cores differed by 3 to 5 points. The one exception to this rule was when the difference of 1 point was between a score of 0 and 1, in which case, the differences were considered equivocal. This was in order to truly separate negative cases from even focally positive ones.

Example 2

Generation and Characterization of Anti-MUC16 Monoclonal Antibodies

MUC16-directed monoclonal antibodies were isolated by ELISA-based screening using both the individual peptides and recombinant GST-ΔMUC16$^{c114}$ protein followed by sequential subcloning for single cell clones.

Tables 1A and 1B:

MUC16-carboxyterminus monoclonal antibodies showing their reactivity to GST-ΔMUC16$^{c114}$ western, FACS analysis on OVCAR3 wild type cells

TABLE 1A

| Peptide 1 | | | | Peptide 2 | | | | Peptide 3 | | | |
| --- | --- | --- | --- | --- | --- | --- | --- | --- | --- | --- | --- |
| ELISA Hybridoma Sups (1:1) | (1:10) GST-MucCD Western +/− | (1:1) OVCAR3 FACS +/− | Isotype | ELISA Hybridoma Sups (1:1) | (1:10) GST-MucCD Western +/− | (1:1) OVCAR3 FACS +/− | Isotype | ELISA Hybridoma Sups (1:1) | (1:10) GST-MucCD Western +/− | (1:1) OVCAR3 FACS +/− | Isotype |
| 10A2 | + | − | IgG1, IgM | 13H1 | Weak | − | IgG1 | 22E10 | + | − | IgG2b |
| 23D4 | − | − | missing | 28F8 | + | + | IgG1, IgM | 22F11 | Weak | − | IgM |
| 2F4 | Weak | − | IgG1, IgM | 11B6 | − | − | IgM | 19G4 | Weak | − | IgG1, IgM |
| 9B11 | Weak | +/− | IgG1 | 4C7 | + | − | IgG1 | 31A3 | Weak | − | IgG1 |
| 23D3 | Weak | + | IgG1, IgG2b | 28F7 | + | + | IgG1 | 4C2 | + | − | IgG1, IgM |
| 30B1 | − | − | IgG1 | 9C7 | + | + | IgG1 | 27G4 | + | − | IgM |
| 31B2 | + | − | IgM | 9C9 | + | + | IgG1, IgG2b | 19D1 | + | − | IgG2b |
| | | | | 4H11 | + | + | IgG2b, IgM | 22F1 | + | − | IgG2b, IgM |
| | | | | 4A2 | − | − | IgG1 | 4D7 | + | − | IgG3 |
| | | | | 4A5 | + | + | IgG1 | 9A5 | − | − | IgM |
| | | | | 29G9 | + | − | IgG1 | 31C8 | − | − | IgG2b |
| | | | | 5C2 | + | + | IgG1 | 6H2 | Weak | − | IgG1, IgM |
| | | | | 23G12 | − | − | IgG1, IgG2a | 10F6 | − | − | IgG1 |
| | | | | 25G4 | − | − | IgG1, IgM | 3H8 | + | − | IgG1, IgM |
| | | | | 26B2 | + | + | IgG1, IgG2b, IgM | 24G12 | − | − | IgG1, IgM |
| | | | | 25H3 | − | − | IgG1, IgM | | | | |

TABLE 1B

| Peptide 1 | | | Peptide 2 | | | Peptide 3 | | |
| --- | --- | --- | --- | --- | --- | --- | --- | --- |
| | OVCAR3 FACS +/− | Isotype | | OVCAR3 FACS +/− | Isotype | | OVCAR3 FACS +/− | Isotype |
| 9B11.20.16 | +/− | IgG1 | 9C9.21.5.13 | + | IgG2b | 31A3.5.1 | − | IgG1 |
| | | | 4H11.2.5 | + | IgG2b | | | |
| | | | 9C7.6 | + | IgG1 | | | |
| | | | 5C2.17 | + | IgG1 | | | |
| | | | 4A5.37 | + | IgG1 | | | |
| | | | 28F7.18.10 | + | IgG1 | | | |

TABLE 2

Antibodies specific for exemplary portions of MUC16

```
1. Muc16 Polypeptide 1:
14394                14410                                          (MUC16 sequence)
    NFSPLARRVDRVAIYEE (SEQ ID NO: 01)                                        17 aa Mouse monoclonals which are specific to this peptide are:
9B11.20.16 (IgG1)
10A2 (IgG1, IgM)
2F4 (IgG1, IgM)
23D3 (IgG1, IgG2b)
30B1 (IgG1)
31B2 (IgM)
```

```
2. Muc16 Polypeptide 2:
14425                14442                                          (MUC16 sequence)
    TLDRSSVLVDGYSPNRNE (SEQ ID NO: 02)                                       18 aa Mouse monoclonals which are specific to this peptide are:
4H11.2.5 (IgG2b)                13H1 (IgG1)              29G9 (IgG1)
9C9.21.5.13 (IgG2b)             28F8 (IgG1, IgM)         23G12 (IgG1, IgG2a)
9C7.6 (IgG1)                    11B6 (IgM)               25G4 (IgG1, IgM)
5C2.17 (IgG1)                   4C7 (IgG1)               26B2 (IgG1, IgG2b, IgM)
4A5.37 (IgG1)                   4A2 (IgG1)               25H3 (IgG1, IgM)
28F7.18.10 (IgG1)
```

TABLE 2-continued

Antibodies specific for exemplary portions of MUC16

3. Muc16 Polypeptide 3 (SEQ ID NO: 03)

```
14472                  14492                                              (MUC16 sequence)
    CGVLVTTRRRKKEGEYNVQQQ                                                      21 aa
```

Mouse monoclonals which are specific to this peptide are:

| | | |
|---|---|---|
| 31A3.5.1 (IgG1) | 19D1 (IgG2b) | 10F6 (IgG1) |
| 22E10 (IgG2b) | 22F1 (IgG2b, IgM) | 3H8 (IgG1, IgM) |
| 22F11 (IgM) | 4D7 (IgG3) | 24G12 (IgG1, IgM) |
| 19G4 (IgG1, IgM) | 9A5 (IgM) | |
| 4C2 (IgG1, IgM) | 31C8 (IgG2b) | |
| 27G4 (IgM) | 6H2 (IgG1, IgM) | |

```
14452            14475
    FWAVILIGLAGLLGLITCLICGVL (SEQ ID NO: 14) is Transmembrane region                     24 aa
```

4. Muc16 Polypeptide 4 (SEQ ID NO: 15) containing a cysteine loop polypeptide (SEQ ID NO: 19):

```
14367                                    14398                            (MUC16 sequence)
    KSYFSDCQVSTFRSVPNRHHTGVDSLCNFSPL (SEQ ID NO: 15)                             32 aa
          |_____ S-S _____|
```

Mouse monoclonals which are specific to this peptide are:
24B3 (IgM)
9C7 (IgM)

| | |
|---|---|
| 4F12 | IgM kappa |
| 6H6 | IgM kappa |
| 25C2 | IgM kappa |
| 6E8 | IgM kappa |
| 2A3 | IgM, IgG1, IgG2b, kappa |
| 2G4 | IgM, IgG1, kappa |
| 4C8 | IgM, kappa |
| 2A6 | IgG1 kappa |
| 24G12 | IgG1 kappa |
| 15D5 | IgG1 kappa |
| 6E2 | IgM, IgG1, IgG3, IgG2a, kappa |
| 7E6 | IgM, kappa, lambda |
| 7G11 | IgM kappa |
| 20C3 | IgG1, IgG2b |
| 9A3 | IgM kappa |
| 15B6 | IgM kappa |
| 19D3 | IgM kappa |
| 5H8 | IgM, IgG1, IgG2b, kappa |
| 24A12 | IgM kappa |
| 2D10 | IgG3, IgM kappa |
| 5B2 | IgM, IgG3, IgG2b, IgG2a, IgG1, kappa |
| 8B6 | IgG2a, IgG3, kappa |
| 5A11 | IgM, kappa |
| 7D11 | light kappa only |
| 9F10 | IgM, kappa |
| 15D10 | IgM, kappa |
| 18D2 | IgM, kappa |
| 13A11 | IgM, kappa |
| 1A9 | IgM, kappa |
| 3B2 | IgM, kappa |
| 24F6 | IgM, kappa |
| 24E4 | IgM, kappa |
| 5A1 | IgG2a, IgM, kappa |
| 7B9 | IgM, kappa |
| 22F4 | IgM, kappa |

The identified monoclonal antibodies are listed in Table 1A and Table 2. Each of the selected monoclonal antibodies was reactive against GST-ΔMUC16$^{c114}$. The commercial MUC16-directed antibodies (OC125, M11, or VK8) did not bind to GST-ΔMUC16$^{c114}$ in ELISA or Western blotting. The clones were tested in FACS against OVCAR3 ovarian cancer cells and in Western blot analysis against GST-ΔMUC16$^{c114}$ (Table 1B), and selected purified monoclonal antibodies were isolated.

Figure 7A:
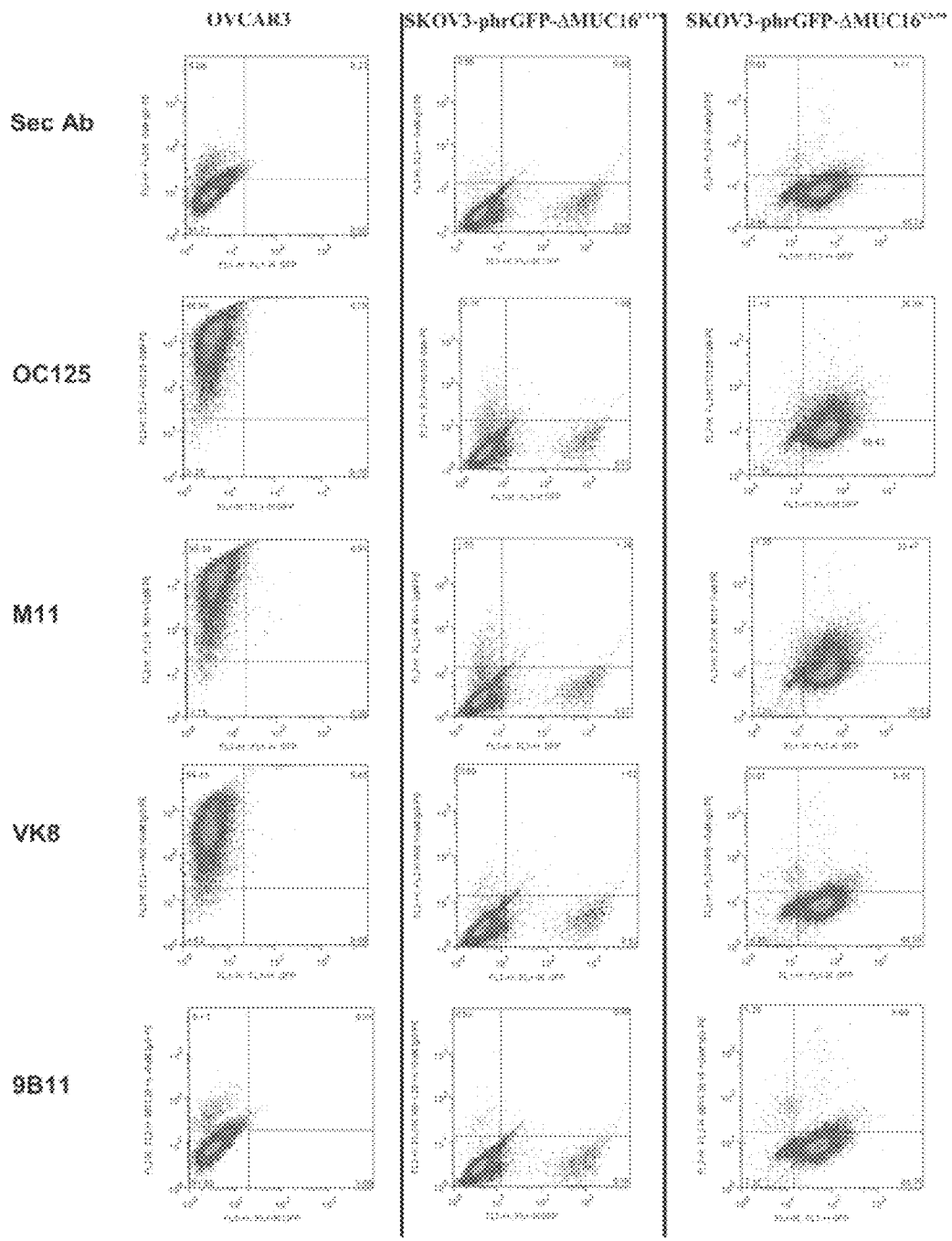
FIGS. 7A-7B: FACS analysis as described in the Material and Methods section was performed with commercial antibodies and MUC16 carboxy terminus monoclonal antibodies on OVCAR3 wt, SKOV3-phrGFP-ΔMUC16$^{c114}$ and SKOV3-phrGFP-ΔMUC16$^{c334}$ stable transfected cell lines.
Figure 7B:
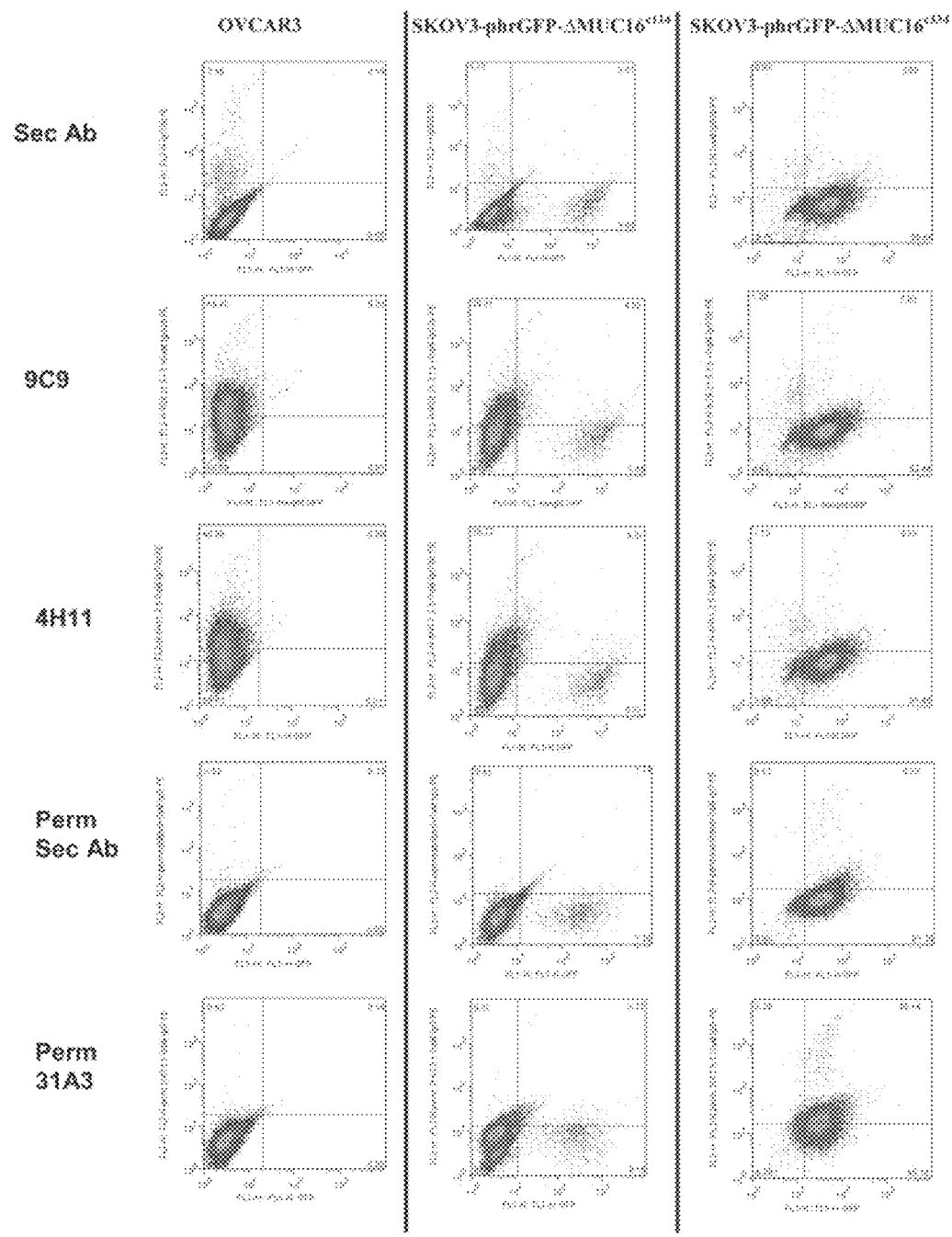

The inventors used the OVCAR3 wild type and the SKOV3 cells transduced with phrGFP-ΔMUC16$^{c114}$ to characterize the selected antibodies by FACS analysis. All of the selected monoclonal antibodies bound to both cell lines while commercial VK8, M11 and OC125 antibodies bound to the OVCAR3 cells but not to the SKOV3-phrGFP-ΔMUC16$^{c114}$ cell line. The antibodies against Polypeptide 3 required permeabilization since it is an internal epitope (FIGS. 7A-7B).

Figure 4A:
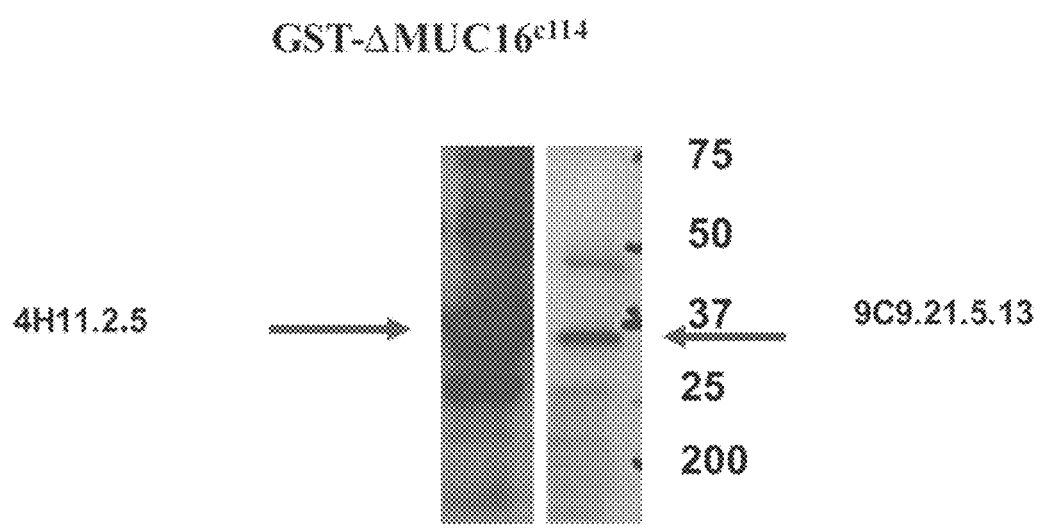
FIG. 4A and FIG. 4B: Western blot analysis.
Figure 4B:
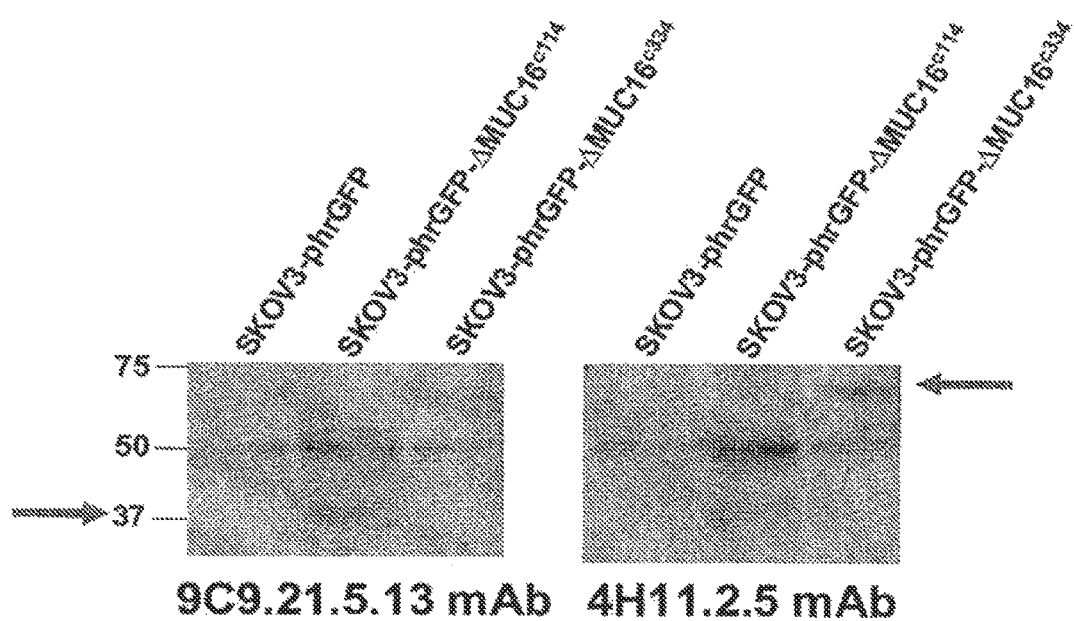

Western blot analysis using the GST-ΔMUC16$^{c114}$ purified protein showed strong binding with 4H11 and 9C9 antibodies (FIG. 4A), while the other selected antibodies showed less binding. The SKOV3-phrGFP-ΔMUC16$^{c114}$ transfectant was also positive by Western blot analysis using 4H11 and 9C9 antibodies (FIG. 4B). As before, the commercial antibodies did not interact with the GST-ΔMUC16$^{c114}$ purified protein or cell lysates of the SKOV3-phrGFP-ΔMUC16$^{c114}$ cell line.

The binding of six monoclonal antibodies against OVCAR3 MUC16 were examined in affinity binding studies. Three antibodies—9C7, 5C2 and 28F7—showed only modest levels of binding compared to the nonspecific binding of these antibodies to the OVCAR3 cells, which carry large numbers of MUC16 binding sites. In contrast, 4H11, 9C9, and 4A5 monoclonal antibodies showed highly specific binding affinity, as shown in FIGS. 5A-5D, with binding affinities of 6.8-8.6 nM against the cell surface epitopes of OVCAR3 cells. The inventors also examined the internalization of antibody bound to cell surface MUC16 protein. The inventors examined internalization in the transfected SKOV3-phrGFP-ΔMUC16$^{c334}$ cell line which bears the carboxy terminus of MUC16, including the 4H11 epitope and a single degenerate tandem repeat sequence to interact with the OC125 antibody. The commercial antibodies OC125, M11, and VK8 all bind to the cell surface of this transduced cell line. The $^{131}$I-labeled 4H11 showed rapid internalization at a high level, whereas $^{131}$I-labeled OC125 antibody was internalized at a much lower rate (FIG. 5E).

Example 3

Immunohistochemistry Results

Given their highly specific binding affinities, the antibodies 9C9, 4A5, and 4H11 were characterized for utility in immunohistochemistry using OVCAR3 cell lines. Of the three, the 4H11 antibody was selected to be optimized for use in human tissues based on its robust, sensitive and specific staining pattern as compared to the other two antibodies.

A. Ovary

Two high-stage, high-grade ovarian serous carcinoma tissue microarray slides composed of 419 cores, representing primary, metastatic and recurrent tumors from 40 patients were stained with both OC125 and 4H11 monoclonal antibodies (FIG. 2). The OC125 tissue microarrays showed 279 (66%) cores with 3-5 staining, 99 (24%) with 1-2 staining, and 41 (10%) with no staining. The 4H11 tissue microarrays showed 236 (56%) with 3-5 staining, 91 (22%) with 1-2 staining, and 92 (22%) with no staining. The two antibodies were concordant in 233 (56%) cores, equivocal in 161 (38%), and discordant in 25 (6%). Of the 25 discordant cores, 12 (48% of discordant cases, 3% of all cases) showed greater 4H11 positivity than OC125. Nine were discordant by a difference of 4 points, and 3 were discordant by a difference of 5 points. There was a total of 186 discordant and equivocal cores together, 48 (26%) of which showed greater staining with 4H11 than OC125. The staining pattern of both 4H11 and OC125 was cytoplasmic and membranous, although the membranous pattern of OC125 was stronger and better defined than 4H11 in the majority of cases. Discordant cases demonstrated higher levels of 4H11 than other cases.

B. Breast Cancer

A variety of other tissues were also examined for 4H11 staining to test the antibody's specificity. Of the 50 cores of invasive ductal carcinomas of the breast (number of patients unavailable), only 2 (4%) showed a score of 4 or greater 4H11 staining and none had scores of 3-5 for OC125 staining. The staining pattern with OC125 was mostly apical/luminal with some granular cytoplasmic staining. Some tumors with intracytoplasmic lumina also picked up the OC125 stain. 4H11 showed a more diffuse cytoplasmic blush without membranous accentuation.

In contrast, the invasive lobular breast carcinoma tissue microarray (composed of 179 cores with viable tumor, number of patients unavailable) had frequent MUC16 staining with 4H11. In this tissue microarray, 168 cores (94%) showed no staining for OC125, 5 (3%) showed 1-2 staining, and only 6 (3%) showed a staining intensity of 3. 4H11 staining was different in its distribution pattern, with 49 (27%) showing no staining, 81 (45%) showing 1-2 staining, and 49 (27%) showing 3-4 staining. Neither OC125 nor 4H11 had cores with a staining intensity of 5. The staining pattern was of cytoplasmic, luminal/membranous, or intraluminal for both OC125 and 4H11. The intraluminal pattern was strong and intense for both stains and highlighted the intracytoplasmic lumen that is commonly present in lobular carcinomas. The concordance rates were 34% concordant, 43% equivocal, and 23% discordant. Of the equivocal and discordant cases, there was none in which the OC125 was greater than the 4H11. All 42 discordant cases and 76 of 77 equivocal cases had 4H11 greater than OC125. There was also focal luminal staining with 4H11 in benign breast ducts and lobular carcinoma in situ.

C. Lung, Pancreatic and Prostatic Adenocarcinomas

Tumors from other organs were not reactive with either antibody. The lung adenocarcinoma TMA had 237 cores from 86 patients containing viable tumor. In the pancreatic TMA there were 92 cores from 21 patients containing pancreatic mucinous tumors, including intraductal papillary mucinous neoplasms (IPMN) and invasive ductal carcinomas. In the prostate cancer TMA there were 169 cores (number of patients not available). None of these cancer tissue microarrays had significant binding to either OC125 or 4H11. This information is summarized in Table 3.

TABLE 3

Staining intensity of OC125 as compared to 4H11 in tissue microarrays

| | OC125 vs. 4H11 staining intensity score (%) | | | | | |
| --- | --- | --- | --- | --- | --- | --- |
| | 0 | | 1-2 | | 3-5 | |
| Site | OC125 | 4H11 | OC125 | 4H11 | OC125 | 4H11 |
| Ovary high grade serous | 10 | 28 | 24 | 22 | 66 | 56 |
| Breast invasive ductal | 68 | 78 | 32 | 18 | 0 | 4 |
| Breast invasive lobular | 94 | 27 | 3 | 45 | 3 | 27 |
| Lung adenocarcinoma | 63 | 77 | 24 | 18 | 13 | 5 |
| Pancreas mucinous neoplasms | 98 | 88 | 2 | 10 | 0 | 2 |
| Prostate adenocarcinoma | 0 | 0 | 0 | 0 | 0 | 0 |

Score
0: 0% staining;
1: <5% strong or weak;
2: 5-50% strong or weak;
3: 51-75% strong or 51-100% weak;
4: 76-99% strong
5: 100% strong D. Normal Tissues There was no staining with OC125 or 4H11 in normal adult colon, rectum, ectocervix, small intestine, ovary, liver, pancreatic ducts, spleen, kidney, and skin. OC125 and 4H11 both stained endocervical glands (OC125 luminal, 4H11 weak cytoplasmic), esophageal glands (luminal), bronchial epithelium (OC125 luminal, 4H11 intracytoplasmic granules), and thymic corpuscles (cytoplasmic). 4H11 demonstrated weak to moderate staining of the gastric glands, particularly at the crypts, with an intracytoplasmic granular pattern. Other organs that showed punctuate intracytoplasmic staining with 4H11 only were prostate, seminiferous tubules of the testes, and the islet cells of the pancreas. The staining in the pancreatic islets cells was particularly strong and consistent. There was also nonspecific staining of liver, kidney and brain with 4H11. There were no cases that stained with OC125 and not 4H11.

Similarly, there was no staining with either OC125 or 4H11 in fetal heart, gallbladder, colon, small intestine, liver, rectum, adrenal, thyroid, spleen, skin, bone, epididymis, brain, lung, muscle, smooth muscle, kidney, eye, umbilical cord, and placenta. OC125 only stained thymic corpuscles in a pattern similar to that in adult tissue. 4H11 stained both fetal pancreatic endocrine cells and endocervical glands in a similar pattern to that of their adult counterparts. Islet cells showed a granular cytoplasmic pattern, and endocervical glands showed a linear luminal pattern, which was more similar to the OC125 pattern in the adult tissue.

Example 4

Successful Eradication of Established Peritoneal Ovarian Tumors in SCID-Beige Mice Following Adoptive Transfer of T Cells Genetically Targeted to the MUC16 Antigen Purpose:

Most patients diagnosed with ovarian cancer will ultimately die from their disease. For this reason, novel approaches to the treatment of this malignancy are needed. Adoptive transfer of a patients own T cells, genetically modified ex vivo through the introduction of a gene encoding an chimeric antigen receptor (CAR), an artificial T cell receptor, targeted to a tumor associated antigen, is a novel and promising approach to cancer therapy applicable to the treatment of ovarian cancer.

Experimental Design:

We have generated several CARs targeted to the retained extracellular domain of MUC16, termed MUC-CD, an antigen highly expressed on a majority of ovarian carcinomas. We investigate the in vitro biology of human T cells retrovirally transduced to express these CARs by co-culture assays on artificial antigen presenting cells (AAPCs) generated from NIH3T3 fibroblasts genetically modified to express the target MUC-CD antigen, as well as by cytotoxicity assays utilizing the human OV-CAR3(MUC-CD) ovarian tumor cell line and primary patient tumor cells. Finally, we assess the in vivo anti-tumor efficacy of MUC-CD targeted T cells in a SCID-Beige orthotopic, xenogeneic OV-CAR3(MUC-CD) murine tumor model.

Exemplary sequences used in this work are in FIG. 17-19.

Results:

CAR modified MUC-CD targeted T cells derived from both healthy donors and ovarian cancer patients exhibited efficient in vitro cytolytic activity against both human ovarian cell lines as well as primary ovarian carcinoma cells. MUC-CD targeted T cells may be further expanded ex vivo through multiple cycles of co-culture on 3T3(MUC-CD/B7.1) AAPCs. Expanded MUC-CD targeted T cells infused into SCID-Beige mice bearing intraperitoneal human OV-CAR3(MUC-CD) tumors either delayed progression or fully eradicated tumor even in the setting of advanced disease.

Conclusion:

These promising pre-clinical studies justify further investigation of MUC-CD targeted T cells as a potential therapeutic approach in the clinical setting treating patients with high risk MUC-16$^+$ ovarian carcinomas.

INTRODUCTION

Ovarian cancer is the sixth most common cancer worldwide and the seventh leading cause of cancer-related deaths in women (1, 2). Despite multimodality therapy with surgery and chemotherapy, most patients with ovarian carcinomas have a poor prognosis. For this reason, alternative approaches to treating this disease are urgently needed.

Infusion of a patient's own T cells genetically targeted ex vivo to antigens expressed on the surface of tumor cells is a promising novel approach to the adoptive immunotherapy of cancer, and one which has only recently been explored in earnest in the clinical setting. T cells may be genetically modified to target tumor associated antigens through the retroviral introduction of genes encoding artificial T cell receptors termed chimeric antigen receptors (CARs). Genetic engineering of T cells to express artificial T cell receptors that direct cytotoxicity toward a tumor cell presents a means to enhance immune recognition and elimination of cancer cells. CARs are most commonly composed of a single chain fragment length antibody (scFv), derived from a murine monoclonal antibody targeting a given tumor associated antigen, fused to a transmembrane domain (typically CD8, CD28, OX-40, and 4-1BB), fused to the TCR chain cytoplasmic signaling domain (3-13). When used to reprogram T-cell specificity, these fusion receptors permit recognition of native antigen. When expressed by the T cells, the resulting construct, upon engagement with the targeted antigen, induces T cell activation, proliferation, and lysis of targeted cells. These fusion receptors transduce a functional antigen-dependent co-stimulatory signal in primary T cells, permitting sustained T-cell proliferation when both endogenous TCR and a chimeric receptor for stimulatory signaling are engaged. To date, preclinical studies utilizing CAR-modified T cells have demonstrated promising results in a wide variety of malignancies (3, 4, 11, 14-18). More recently this approach been investigated clinically in the form of phase I trials (6, 19-21). These genetic approaches offer a means to enhance immune recognition and elimination of cancer cells.

Ovarian carcinomas appear to be relatively immunogenic tumors capable of inducing an endogenous immune response based on the fact that long-term prognosis of patients is markedly influenced by the degree and quality of the endogenous immune response to the tumor.

Specifically, it has been well documented that the presence of endogenous effector T cells within the ovarian cancer tumor microenvironment directly correlates to prolonged patient survival (22-25). In contrast, increasing numbers of immune suppressive CD4$^+$ CD25$^{hi}$ regulatory T cells (Tregs) within the tumor, which in turn presumably abrogate the anti-tumor activity of infiltrating effector T cells, correlates with shorter patient survival (26-29). In fact, it appears that it is the ratio of Tregs to effector T cells within the tumor microenvironment which ultimately dictates whether the endogenous immune response to the cancer is of benefit or detriment to the patient (24, 28). In this setting, the ability to generate and subsequently expand a population of tumor targeted effector T cells ex vivo which are subsequently infused back into the patient, may in turn skew the Treg to effector T cell ratio to one more favorable to eradicating the disease.

Mucins are important biomolecules for cellular homeostasis and protection of epithelial surfaces. Changes to expression of mucins in ovarian cancer might be exploited in diagnosis, prognosis and treatment (1). MUC16 is one such mucin which is over expressed on most ovarian carcinomas and is an established surrogate serum marker (CA-125) for the detection and progression of ovarian cancers (30-33). MUC16 is a high-glycosylated mucin composed of a large cleaved and released domain, termed CA-125, consisting of multiple repeat sequences, and a retained domain (MUC-CD) which includes a residual non-repeating extracellular fragment, a transmembrane domain, and a cytoplasmic tail (34). Since the antigen is otherwise only expressed at low levels in the uterus, endometrium, fallopian tubes, ovaries, and serosa of the abdominal and thoracic cavities, MUC16 is a potentially attractive target for immune-based therapies.

However, the fact that most of the extracellular domain of MUC16 is cleaved and secreted limits the utility of MUC16 as a target antigen on ovarian carcinomas. In fact, to date, all reported MAbs to MUC16 bind to epitopes present on the large secreted CA-125 fraction of the glycoprotein, with none known to bind to the retained extra-cellular fraction (MUC-CD) of the antigen (35-37). Since the MUC-CD fraction of the antigen is retained on cell surface, generating T cells specific to this portion of MUC16 may largely overcome the limitation of MUC16 as a target for adoptive cellular immunotherapy. To this end, we have previously generated a series of murine MAbs specific to the retained MUC-CD extracellular domain (38). Utilizing a hybridoma which expresses one such MAb, 4H11, we have successfully constructed several CARs specific to the MUC-CD antigen. This invention provides a nucleic acid encoding a chimeric T cell receptor, composed of, at least a zeta chain, a signaling region and a binding element that specifically interacts with a selected target as well as the chimeric T cell receptor comprising a zeta chain portion, a signaling region and a binding element.

In this report, we demonstrate highly efficient retroviral transduction of these MUC-CD targeted CARs into human T cells with resulting T cells able to specifically target and lyse MUC-CD$^+$ tumor cells in vitro. Furthermore, we demonstrate efficient MUC-CD targeted T cell expansion in vitro through repeated co-culture on NIH (3T3) fibroblasts genetically modified to express MUC-CD and the co-stimulatory ligand B7.1 (CD80). Successful expansion of modified T cells allowed us to subsequently generate sufficient T cell numbers to conduct in vivo studies in immune compromised SCID-Beige mice bearing established intraperitoneal MUC-CD$^+$ human ovarian tumors. Significantly, in these studies we demonstrate marked anti-tumor efficacy of MUC-CD targeted T cells, both following direct intraperitoneal as well as intravenous injection when compared to either untreated mice, or mice treated with T cells bearing a CAR targeted to an irrelevant antigen. In addition, we demonstrate significant cytotoxicity of 4H11-28z$^+$ patient's T cells and healthy donor's T cells targeting primary ascites-derived ovarian carcinoma cells from cancer patients.

To our knowledge this is the first report wherein T cells genetically targeted to the MUC16 antigen demonstrate marked anti-tumor efficacy against MUC16$^+$ tumors either in vitro or in vivo. These data serve as a rationale for proposing future clinical trials utilizing this approach in patients with high risk ovarian carcinomas.

Materials and Methods

Cell Lines and T Cells

The OV-CAR3 tumor cell line was cultured in RPMI 1640 (Invitrogen, Grand Island, N.Y.) supplemented with 10% heat-inactivated FBS, nonessential amino acids, HEPES buffer, pyruvate, and BME (Invitrogen). The PG13 and gpg29 retroviral producer cell lines were cultured in DMEM (Invitrogen) supplemented with 10% FCS, and NIH-3T3 artificial antigen-presenting cells (AAPC), described previously (3), were cultured in DMEM supplemented with 10% heat-inactivated donor calf serum. T cells were obtained from peripheral blood of healthy donors under IRB approved protocol #95-054, in BD Vacutainer CPT tubes (Becton Dickinson, Franklin Lakes, N.J.) as per the manufacturers instructions. All media were supplemented with 2 mmol/L L-glutamine (Invitrogen), 100 units/mL penicillin, and 100 μg/mL streptomycin (Invitrogen). T cells were cultured RPMI 1640 media as above supplemented with 20 IU/ml IL-2 (Novartis Pharmaceuticals, East Hanover, N.J.) and where indicated, medium was supplemented with 10 ng/mL interleukin 15 (R&D Systems, Minneapolis, Minn.).

Isolation of Patients Ascites-Derived Cancer Cells

Primary human ascites-derived cancer cells were obtained from ovarian cancer patients undergoing surgery for newly diagnosed advanced serous ovarian carcinoma under IRB approved protocol #97-134. The tumor cells were isolated from ascitic fluid of patients by centrifugation at 600 g for 10 min at room temperature. Cells were washed once with 1×PBS and cultured in RPMI 1640 media supplemented with 10% FBS for future analysis.

Generation of the MUC-CD Targeted 4H11z and 4H11-28z CARs

The heavy and light chain variable regions of the 4H11 monoclonal antibody were derived from the hybridoma cell line 4H11. Utilizing cDNA generated from 4H11 RNA we isolated the $V_H$ coding region by RACE PCR utilizing modified primers as described elsewhere (39, 40). The $V_L$ chain variable region was cloned by standard PCR utilizing modified primers as described by Orlandi et al (41, 42). The resulting $V_H$ and $V_L$ fragments were subcloned into the TopoTA PCR 2.1 cloning vector (Invitrogen) and sequenced. The $V_H$ and $V_L$ fragments were subsequently ligated to a (Gly$_4$Ser)$_3$ spacer domain, generating the 4H11 scFv and fused to the human CD8 leader peptide (CD8L) by overlapping PCR (9, 41). In order to construct the MUC-CD targeted 4H11 CARs, the coding region of the CD8L-4H11 scFv was fused to the human CD8 hinge and transmembrane domains (to generate the 4H11z CAR), or alternatively to the CD28 transmembrane and cytoplasmic signaling domains (to generate the 4H11-28z CAR), fused to the T cell receptor CD3ζ-signaling domain (3, 9, 43). The resulting CAR constructs were subsequently sub-cloned into the modified MMLV retroviral vector SFG (44). VSV-G preudotyped retroviral supernatants derived from transduced gpg29 fibroblasts were used to construct stable PG13 gibbon ape leukemia virus (GaLV) envelope-pseudotyped retroviral producing cell lines (41).

Retroviral Gene Transfer

Isolated healthy donor peripheral blood mononuclear cells (PBMCs) were activated with phytohemagglutinin (PHA) at 2 μg/ml (Sigma. St. Louis, Mo.) and retrovirally transduced on retronectin coated non-tissue culture plates (45). Briefly, six-well non-tissue culture plates (BD Biosciences, San Jose, Calif.) were coated with RetroNectin (RN) (Takara Biomedicals, Otsu, Japan) as per manufacturer's instructions. Forty-eight hours after PHA activation, aliquots of 1×10$^6$ T cells in 1 ml of supplemented RPMI medium were placed in each well of the RN-coated plates, along with 1 ml of SFG retroviral supernatant. T cells were centrifuged daily for 3 consecutive days with fresh retroviral supernatant added daily at 2000 g at 30° C. for 1 hr (45). Gene transfer was assessed on day 7 by FACS.

In order to generate the relevant NIH-3T3 murine fibroblast artificial antigen presenting cells, a MUC-CD construct encoding the retained extracellular, transmembrane and cytoplasmic domains of the MUC-16 antigen was initially subcloned into SFG retroviral vector, SFG(MUC-CD). 3T3 (MUC-CD) AAPCs were generated by retroviral transduction of SFG(MUC-CD) into wild-type NIH-3T3 fibroblasts, while 3T3(MUC-CD/B7.1) AAPCs were generated by retroviral transduction of previously established 3T3(B7.1) fibroblasts (41, 46). Highly enriched cell lines were isolated by FACS.

To generate the OV-CAR3(MUC-CD) and OV-CAR3 (MUC-CD/GFP-FFLuc) cell lines, we retrovirally transduced the WT OV-CAR3 human ovarian cancer cell line with SFG(GFP-FFLuc) as described previously (47) and/or SFG(MUC-CD) VSV-G pseudotyped retroviral supernatants derived from gpg29 fibroblasts as described elsewhere (44). Resulting tumor cells were sorted by FACS for either MUC-CD expression alone for the OVCAR3(MUC-CD) cell line, or dual MUC-CD and GFP expression for the OVCAR3(MUC-CD/GFP-FFLuc) cell line. MUC-CD expression by FACS was assessed using the 4H11 MAb.

In Vitro Analyses of CAR$^+$ Human T Cells

To assess in vitro expansion and cytokine release upon stimulation, transduced T cells were co-cultured for 7 days after retroviral transduction in 6-well tissue culture plates (BD Biosciences) on confluent NIH 3T3 AAPCs in RPMI medium supplemented with 10% FBS in the absence of supplemented cytokines. In order to generate sufficient numbers of CAR-modified T cells for in vivo studies, transduced T cells were co-cultured on B7.1$^+$ AAPCs (3T3(MUC-CD/B7.1)) in RPMI medium supplemented with 20 IU IL-2/mL and 10 ng/mL IL-15 as described previously (3, 43). Patients T cells were activated and expanded with human CD3/CD28 beads (DYNAL®, Invitrogen, Carlsbad, Calif.) following manufacturer's recommendations.

Western Blot Analysis of CAR Expression

Western blot analysis of T-cell lysates under reducing conditions with 0.1 mol/L DTT (Sigma) was performed as previously described (46). Briefly, transduced T cells were washed in PBS and resuspended in radioimmunoprecipitation assay (RIPA) buffer (Boston BioProducts, Worcester, Mass.) with mini complete protease inhibitor as per the manufacturer's instructions (Roche Diagnostics, Indianapolis, Ind.). Resulting proteins were separated on 12% SDS-PAGE mini gels (Bio-Rad, Hercules, Calif.) after the addition of 6× reducing loading buffer (Boston BioProducts, Worcester, Mass.) and heating at 100° C. for 10 min. Separated proteins were subsequently transferred to Immobilon membranes and probed using an anti-human CD3ζ chain monoclonal antibody (BD Biosciences). Antibody binding was detected by probing the blot with goat anti-mouse horse radish peroxidase-conjugated antibody followed by luminescent detection using Western Lighting Chemiluminescence Reagent Plus (Perkin-Elmer Life Sciences, Boston, Mass.) as per the manufacturer's instructions.

Cytotoxicity Assays

In vitro modified T cell cytotoxicity was assessed using the DELFIA® EuTDA assay (PerkinElmer LAS, Inc, Boston, Mass.) following manufacturer's recommendations. Cytotoxocity was assessed at 2 hours at effector T cell to target OV-CAR3(MUC-CD) or primary tumor cells (E:T) at indicated ratios. Effector T cells in these assays represent the number of CD8$^+$ CAR$^+$ T cells.

Cytokine Detection Assays

Cytokine assays were performed as per manufacturer's specifications using a multiplex Human Cytokine Detection assay to detect IL-2 and IFNγ (Millipore Corporation, Billerica, Mass.) utilizing the Luminex IS 100 system. Cytokine concentrations were assessed using IS 2.3 software (Luminex Corp., Austin, Tex.).

In Vivo SCID-Beige Mouse Tumor Models

In all in vivo studies, 8-12 week-old FOX CHASE C.B.-17 (SCID-Beige mice) (Taconic, Hudson, N.Y.) were initially injected ip with either 3×10$^6$ OV-CAR3(MUC-CD), or for bioluminescent imaging (BLI) studies 3×10$^6$ OV-CAR3(MUC-CD/GFP-FFLuc) tumor cells. Subsequently, 3×10$^7$ CAR$^+$ T cells were injected ip or iv on day 1 or 7 following tumor injection as indicated. Mice were monitored for distress as assessed by increasing abdominal girth, ruffled fur, and decreased response to stimuli. Distressed mice were euthanized. All murine studies were done in context of an Institutional Animal Care and Use Committee-approved protocol (#00-05-065).

Bioluminescent Imaging (BLI) of OVCAR3(MUC-CD/GFP-FFLuc) Tumor Cells in SCID-Beige Mice BLI was performed using Xenogen IVIS imaging system with Living Image software (Xenogen; Alameda, Calif.). Briefly, OVCAR3(MUC-CD/GFP-FFLuc) tumor bearing mice were injected by ip with D-luciferin (150 mg/kg; Xenogen) suspended in 200 μl PBS and imaged under 2% isoflurane anesthesia after 10 min. Image acquisition was done on a 25-cm field of view at medium binning level for 0.5-min exposure time (3, 43).

Flow Cytometry

All flow cytometric analyses of T cells and tumor cells was performed using a FACScan cytometer with Cellquest software (BD Biosciences). T cells were analyzed using CAR-specific polyclonal goat Alexa Fluor 647 antibody (Molecular probes, Eugene, Oreg.) phycoerythrin-labeled anti-human CD4, CD8, B7.1 (Caltag Laboratories, Burlingame, Calif.), B7.2 (Invitrogen, Camarillo, Calif.), 4-1BBL, and OX40 antibodies (Ancell Corporation, Bayport, Minn.). 3T3(MUC-CD) and OV-CAR3(MUC-CD) cells were stained with Alexa Fluor 647 labeled 4H11 antibody (generated and labeled in the MSKCC monoclonal antibody core facility).

CFSE Labeling of CAR$^+$ T Cells

CAR$^+$ T cells were stained with CFSE using the CellTrace™ CFSE cell proliferation kit following manufacturer's recommendations (Molecular Probes, Eugene, Oreg.). Proliferation of CFSE labeled T cells was analyzed by FACS. For detection of CFSE labeling T cells in vivo, ovarian tumors were macerated through 40 μm cell strainer (BD Falcon, Franklin Lakes, N.J.) and washed twice with 2% FBS/PBS before antibody staining and FACS analysis.

Statistics

Survival data assessed by log-rank analysis using Graph-Pad Prism software (GraphPad Prism software, San Diego, Calif.). Cytokine data were analyzed by Student's one-tailed t-test.

Results

Figure 11:
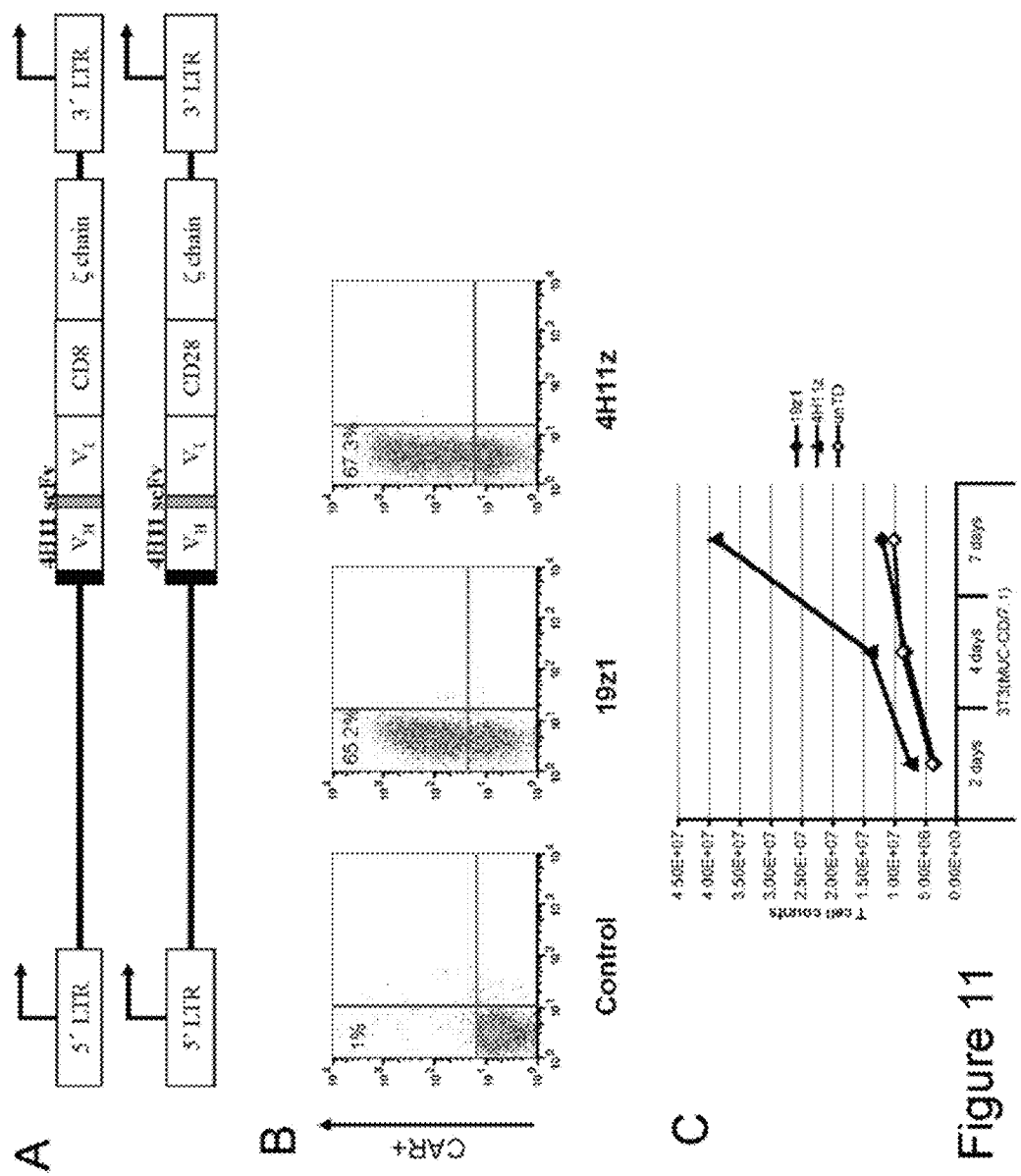
FIG. 11. Design and in vitro analysis of MUC-CD targeted CARs. (A) Schematic diagram of the first generation 4H11z and second generation 4H11-28z retroviral vectors. 4H11scFv: MUC16 specific scFv derived from the heavy ($V_H$) and light ($V_L$) chain variable regions of the monoclonal antibody 4H11; CD8: CD8 hinge and transmembrane domains; CD28: CD28 transmembrane and cytoplasmic signaling domains; ζ chain: T cell receptor ζ chain cytoplasmic signaling domain; LTR: long terminal repeat; black box: CD8 leader sequence; grey box: (Gly$_4$Ser)$_3$ linker; arrows indicate start of transcription. (B) FACS analysis of human T cells retrovirally transduced to express either the 4H11z or 19z1 CAR. (C) 4H11z$^+$ but not 19z1$^+$ T cells expand on 3T3(MUC-CD/B7.1) AAPC. CAR$^+$ were co-cultured on 3T3(MUC-CD/B7.1) AAPC monolayers at 3×10$^6$ CAR$^+$ T cells/well of a 6 well plate. Proliferation of CAR$^+$ T cells, normalized to the CAR$^+$ T cell fraction as assessed by FACS for the CAR$^+$ fraction in combination with viable T cell counts obtained on days 2, 4 and 7, as assessed by trypan blue exclusion assays.

We have constructed SFG retroviral vectors encoding first (4H11z) and second generation (4H11-28z) CARs targeted to the MUC-CD antigen using the 4H11 hybridoma which generates a MAb specific to the MUC-CD antigen (FIG. 11A). We confirmed expression of appropriately sized CAR proteins by Western blot analysis of resulting PG-13 retroviral producer cells (SFG-4H11z and SFG-4H11-28z) probed with ζ-chain specific antibody (data not shown).

In order to assess the function of the first generation 4H11z CAR, healthy donor T cells isolated from peripheral blood were retrovirally transduced to express the 4H11z and control 19z1 CARs (FIG. 11B). Function of the 4H11z CAR was assessed by proliferation of 4H11z transduced T cells following co-culture on 3T3(MUC-CD/B7.1) AAPCs. Results demonstrate specific proliferation of 4H11z transduced T cells, when compared to 19z1 modified T cells (FIG. 11C). These data are consistent 4H11z CAR mediated specific binding to the MUC-CD antigen and subsequent T cell activation.

Figure 12:
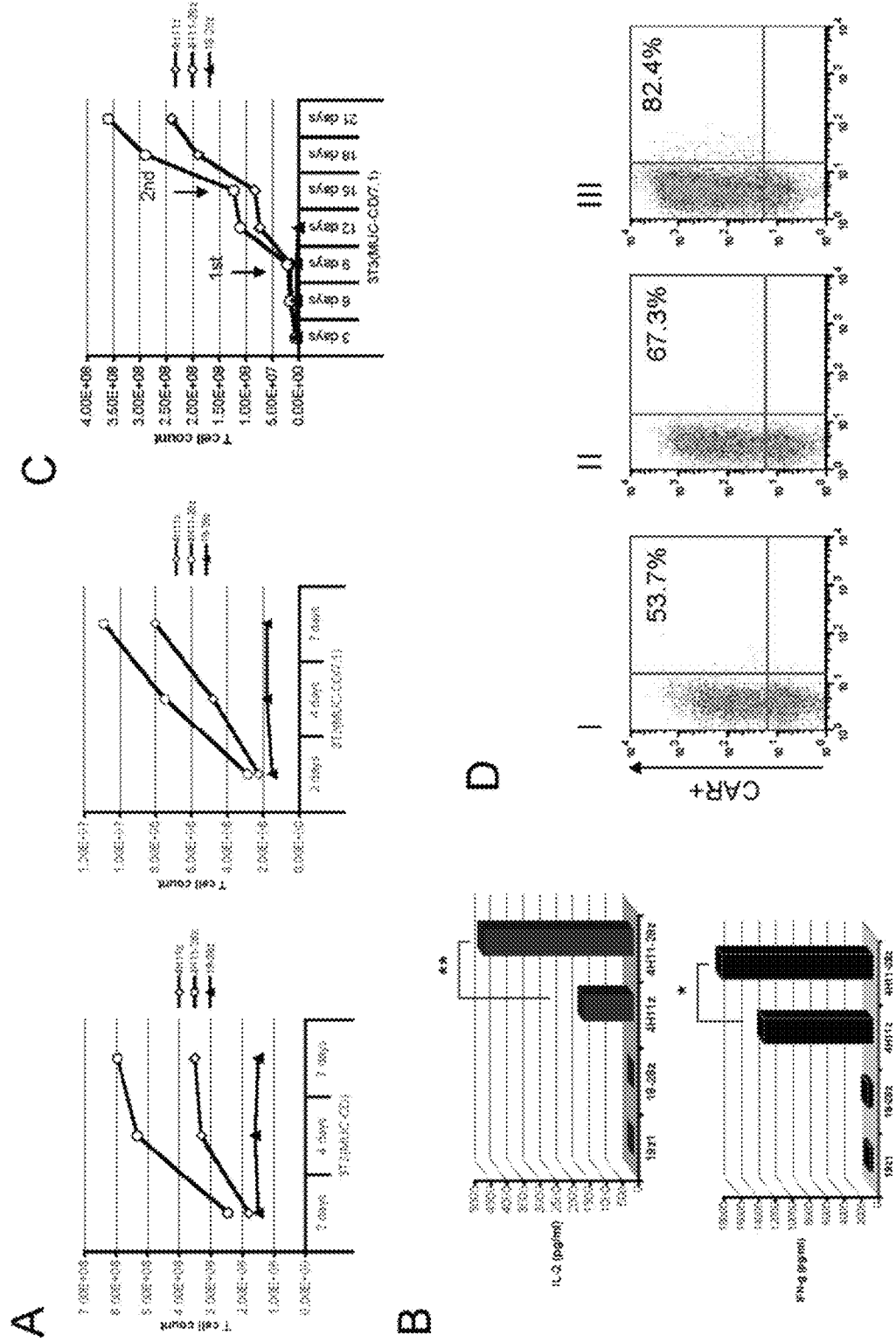
FIG. 12. In vitro comparison of T cells modified to express the first generation 4H11z CAR to T cells modified to express the second generation co-stimulatory 4H11-28z CAR. (A) CAR$^+$ T cells were co-cultured on MUC-CD monolayers with (right panel) or without B7.1 (left panel). 3×10$^6$ CAR$^+$ T cells were co-cultured on AAPC monolayers in 6 well tissue culture plates in cytokine-free medium. Total viable T cell counts were assessed on days 2, 4 and 7, by trypan blue exclusion assays. 4H11-28z$^+$ T cells markedly expanded when compared to 4H11z$^+$ T cells upon co-culture with 3T3(MUC-CD) AAPCs, p=0.0023 (4H11z compared to 4H11-28z). In contrast, both 4H11z$^+$ and 4H11-28z$^+$ T cells expanded similarly on 3T3(MUC-CD/B7.1) AAPCs, p=0.09, (4H11z compared to 4H11-28z). Control 19-28z$^+$ T cells did not proliferate on 3T3(MUC-CD), p=0.0056 (19-28z compared to 4H11z), p=0.0011 (19-28z compared to 4H11-28z), or on 3T3(MUC-CD/B7.1), p=0.0026 (19-28z compared to 4H11z), p=0.008'7 (19-28z compared to 4H11-28z). (B) 4H11-28z$^+$ but not 4H11z$^+$ T cells secrete IL-2 upon co-culture with 3T3(MUC-CD) AAPCs. Tissue culture supernatants at day 2 following activation on 3T3(MUC-CD) AAPCs were analyzed for cytokine secretion. 4H11-28z$^+$ T cells, in contrast to 4H11z$^+$ T cells, demonstrated enhanced secretion of IL-2 consistent with T cell co-stimulation mediated through the 4H11-28z CAR. *p=0.0008 (19z1 or 19-28z compared to 4H11z), p=0.0026 (19z1 or 19-28z compared to 4H11-28z), p=0.0046 (4H11z compared to 4H11-28z). Furthermore, both 4H11-28z$^+$ and 4H11z$^+$ T cells secreted IFNγ. *p=0.011 (4H11z compared to 4H11-28z). Control 19z1 and 1928z transduced T cells failed to secrete either IL-2 or IFNγ. p=0.0034 (19z1 compared to 4H11z), p=0.036 (19-28z compared to 4H11z), ***p=0.0008 (19-28z compared to 4H11-28z). (C) Expansion of CAR$^+$ T cells following 3 cycles of stimulation on 3T3(MUC-CD/B7.1). Human T cells transduced to express either 4H11z or 4H11-28z CARs demonstrated a >2 log expansion over 2 cycles of stimulation on 3T3(MUC-CD/B7.1) AAPCs. Arrows indicate 1st and 2nd cycles of restimulation on AAPCs. (D) FACS analysis of the CAR$^+$ T cell fraction of 4H11-28z$^+$ T cells increased following each weekly cycle of stimulation. (I) FACS following initial transduction, (II) FACS at 7 days following first stimulation on AAPCs, (III) FACS at 7 days following second stimulation on AAPCs. These data are representative of one of three different experiments using three different healthy donor T cell populations, all of which demonstrated similar proliferation and cytokine secretion patterns.

Since most malignancies fail to express co-stimulatory ligands, we further modified the 4H11z CAR to express the CD28 transmembrane and cytoplasmic co-stimulatory signaling domains, constructing the second generation 4H11-28z CAR (FIG. 11A). To assess whether the 4H11-28z CAR, when expressed by human T cells, was capable of generating both a primary activating signal (termed "signal 1") through the chain, as well as a co-stimulatory signal (termed "signal 2") through the CD28 cytoplasmic domain, which in turn allows for efficient T cell proliferation in the absence of exogenous co-stimulatory ligands, we compared T cell proliferation following co-culture on either 3T3(MUC-CD) or 3T3(MUC-CD/B7.1) AAPCs in the absence of exogenous cytokines. As expected, the second generation 4H11-28z$^+$ T cells markedly expanded when compared to 4H11z$^+$ T cells upon co-culture with 3T3(MUC-CD) AAPCs. In contrast, both 4H11z$^+$ and 4H11-28z$^+$ T cells expanded similarly on 3T3(MUC-CD/B7.1) AAPCs (FIG. 12A). Co-stimulation mediated by the 4H11-28z CAR was further verified by analysis of day 2 tissue culture supernatants from co-culture experiments on 3T3(MUC-CD) AAPCs demonstrating enhanced IL-2 secretion, a cytokine typically secreted in the context of T cell co-stimulation, when compared to control 19z1$^+$ and 19-28z$^+$ T cells and first generation 4H11z$^+$ T cells (FIG. 12B). Secretion of IFNγ was comparable between 4H11z$^+$ and 4H11-28z$^+$ activated T cells.

We next assessed the ability of MUC-CD targeted T cells to expand following weekly re-stimulations through co-culture on 3T3(MUC-CD/B7.1) AAPCs in the context of exogenous IL-2 and IL-15 (3). Both 4H11z$^+$ and 4H11-28z$^+$ T cells expanded greater than 2 logs over 3 weeks (FIG. 12C). T cells transduced with the 4H11-28z were further analyzed by FACS for CAR expression 7 days after initial activation on AAPCs and following two subsequent co-stimulations on AAPCs demonstrating an expected enrichment of the CAR$^+$ T cell fraction (FIG. 12D). Similar data was generated with expanded 4H11z$^+$ T cells (data not shown).

In Vitro Cytotoxicity and Proliferation of MUC-CD Targeted T Cells Following Co-Culture with OV-CAR3(MUC-CD) and Freshly Isolated Ascites Derived Ovarian Tumor Cells.

Figure 13:
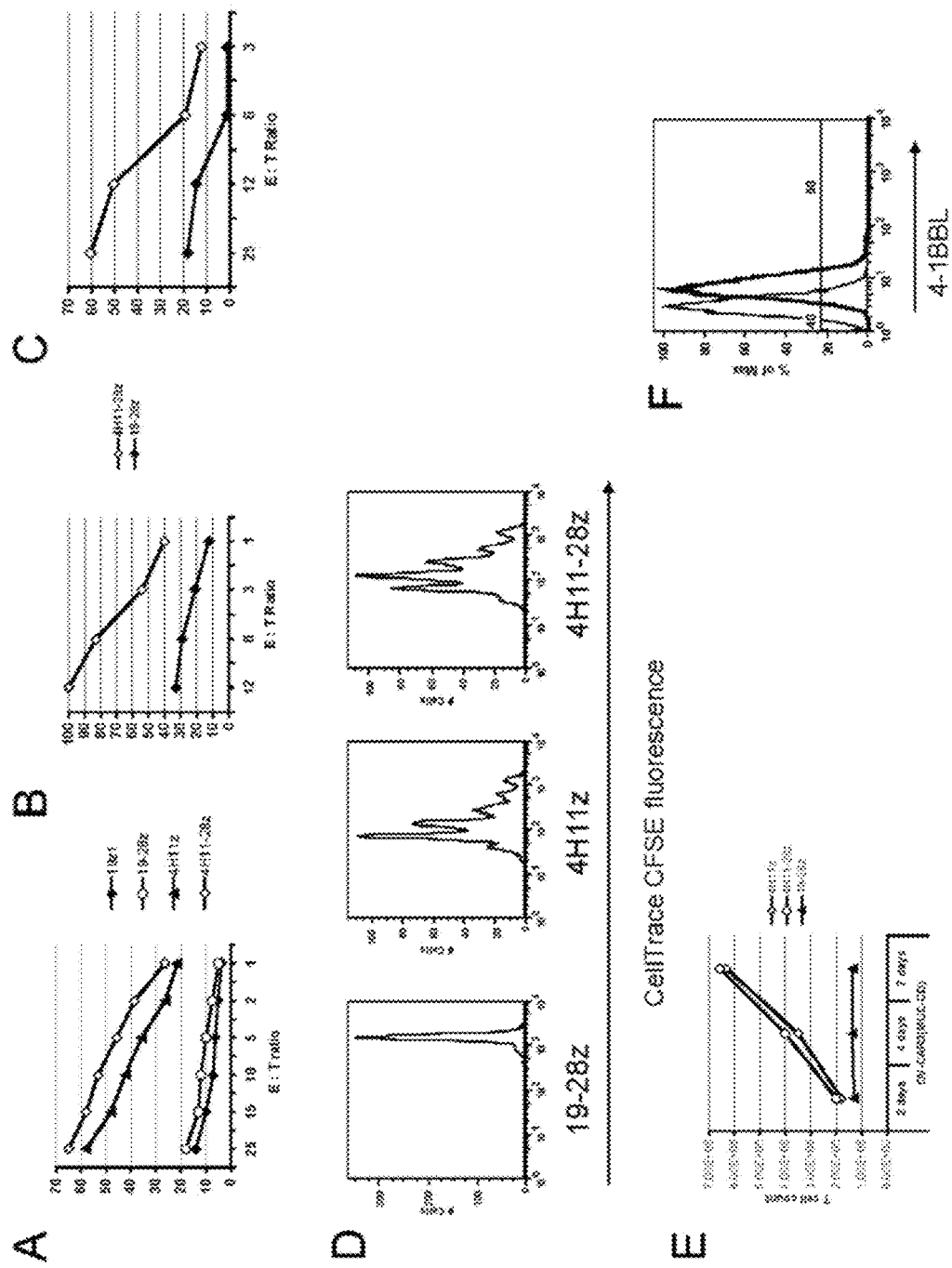
FIG. 13. MUC-CD targeted T cells specifically expand and lyse MUC-CD$^+$ tumor cells. (A) Cytotoxicity assay of 4H11z$^+$ and 4H11-28z$^+$ T cells targeting OV-CAR(MUC-CD) tumor cells demonstrates efficient cytotoxicity mediated by T cells from healthy donors modified to express the first and second generation MUC-CD targeted CARs. Control T cells modified to express the first and second generation CD19-targeted 19z1 and 19-28z CARs failed to demonstrate significant lysis of target tumor cells. (B) Healthy donor T cells modified to express the 4H11-28z CAR equally lyse primary patient ascites-derived MUC-CD$^+$ tumor cells when compared to T cells modified to express the control 19-28z CAR. This data represents 1 or 3 experiments targeting primary tumor cells from 3 ovarian carcinoma patients with similar results. (C) Autologous T cells isolated from peripheral blood, when modified with the 4H11-28z CAR, exhibit significant lysis of autologous MUC-CD$^+$ ascites-derived tumor cells when compared to control 19-28z$^+$ autologous T cells. These data represent 1 of 3 experiments utilizing T cells and autologous tumor cells from 3 different ovarian carcinoma patients with similar results. (D) Antigen specific proliferation of MUC-CD targeted CFSE labeled T cells after co-culture with OV-CAR3 (MUC-CD) tumor cells. CFSE labeled CAR$^+$ T cells were co-cultured with MUC-CD expressing OV-CAR3 tumor cells at 1:1 ratio for 5 days. Proliferation of CFSE labeled T cells was assessed by FACS demonstrating efficient proliferation of both 4H11z$^+$ and 4H11-28z$^+$ T cells but not control 19-28z$^+$ T cells. (E) CFSE results were further confirmed by absolute T cell numbers assessed on days 2, 4 and 7 following co-culture with OV-CAR3(MUC-CD) tumor cells. (F) FACS analysis of the expression of 4-1BBL on OVCAR3(MUC-CD) cells. OV-CAR3(MUC-CD) cells were stained with anti-human 4-1BBL antibody (thick line) or with isotype control (thin line). FACS analysis demonstrated expression of 4-1BBL on OV-CAR3(MUC-CD) tumor cells. Further FACS analyses failed to reveal expression of the co-stimulatory ligands B7.1, B7.2, or OX-40L.

In order to assess the ability of 4H11z$^+$ and 4H11-28z$^+$ T cells to target and lyse human ovarian carcinoma tumors, we utilized the human OV-CAR3 cell line which was genetically modified to express the MUC-CD antigen thereby better reflecting the majority of clinical ovarian tumor samples which express the 4H11-targeted MUC-CD antigen (48). We initially verified specific lysis by MUC-CD targeted T cells demonstrating similar significant cytotoxic activity of 4H11z and 4H11-28z CAR modified T cells targeting OV-CAR3(MUC-CD) tumor cells when compared control T cells expressing the irrelevant first and second generation CD19-targeted 19z1 and 1928z CARs (FIG. 13A). Healthy donor T cells modified to express the 4H11-28z CAR similarly exhibited lysis of freshly isolated ascites derived MUC-CD$^+$ ovarian carcinoma cells when compared to 19-28z transduced T cells (FIG. 13B). Moreover, patient's peripheral blood T cells modified to express the 4H11-28z CAR similarly lysed autologous primary MUC-CD$^+$ tumor cells derived from the same ascites sample when compared to T cells modified to express the control 19-28z CAR (FIG. 13C).

We further assessed the ability of 4H11z$^+$ and 4H11-28z$^+$ T cells from healthy donors to proliferate following co-culture on OV-CAR3(MUC-CD) as assessed by FACS of CFSE labeled T cells, as well as absolute T cells numbers over 7 days following co-culture with tumor (FIGS. 13D and E). Surprisingly, we found that both 4H11z$^+$ and 4H11-28z$^+$ T cells expanded equally well following co-culture with OV-CAR3(MUC-CD) tumor cells suggesting the ability of this tumor cell line to co-stimulate T cells through expression of a co-stimulatory ligand. To address this possibility, we conducted further FACS analyses of OV-CAR3(MUC-CD) tumor cells demonstrating expression of the co-stimulatory 4-1BBL ligand (FIG. 13F), but not the B7.1, B7.2, or OX-40L co-stimulatory ligands (data not shown).

In Vivo Anti-Tumor Activity of MUC-CD Targeted T Cells in SCID-Beige Mice.

Figure 14:
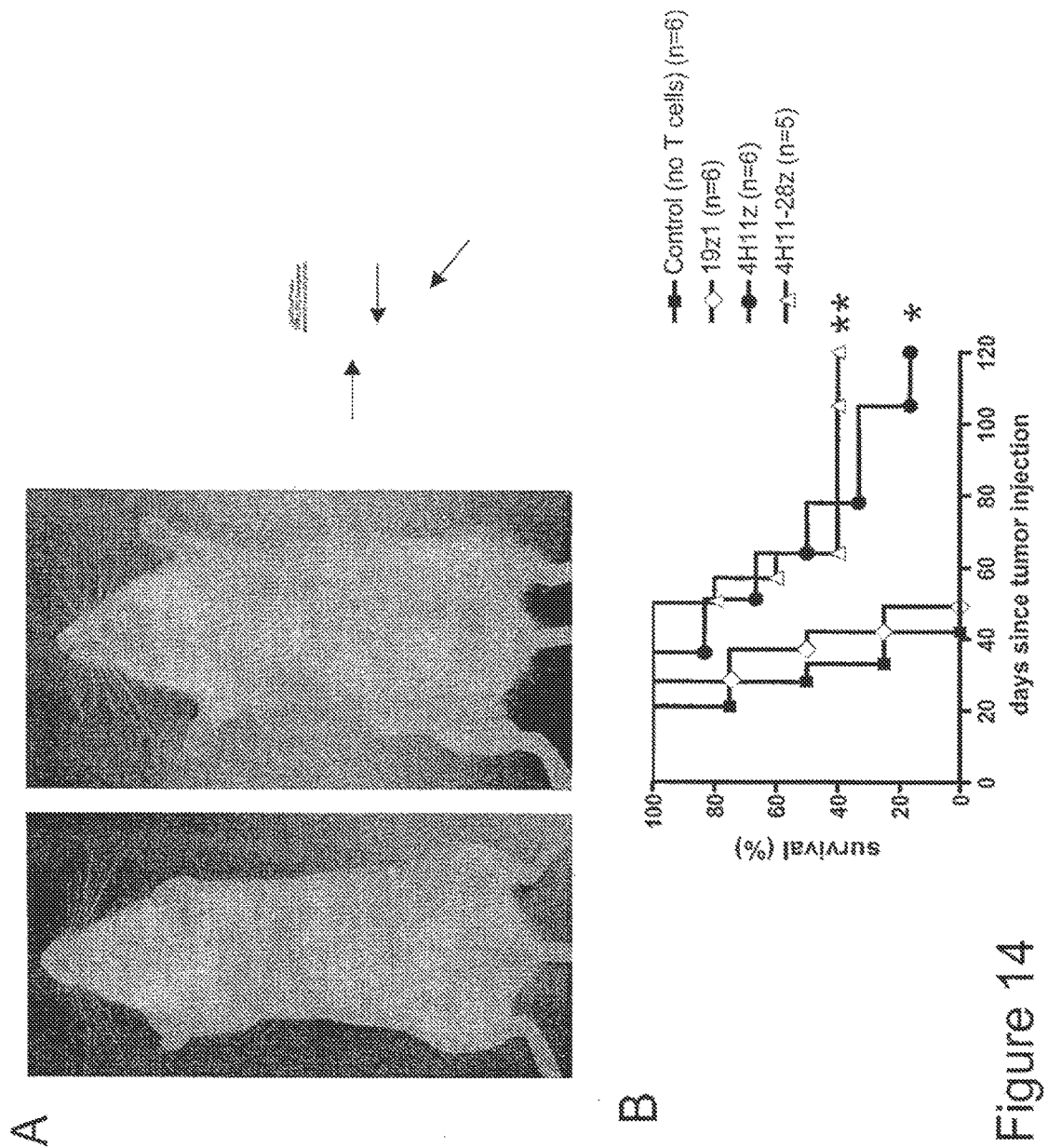
FIG. 14. Eradication of OV-CAR3(MUC-CD) tumors after intra-peritoneal treatment with first and second generation of MUC-CD targeted T cells. (A) Intraperitoneal injection of OV-CAR3(MUC-CD) tumors in untreated SCID-Beige mice results in abdominal distension and nodular peritoneal tumors. SCID-Beige mice were injected intraperitoneally with 3×10$^6$ OV-CAR3(MUC-CD) cells. At 5 weeks post intraperitoneal injection of OV-CAR3(MUC-CD) tumor cells mice developed ascites as evidenced by a distended abdomen (center panel) when compared to a tumor free mouse (left panel). Post mortem visualization of the peritoneum demonstrates nodular tumor masses (arrows) within the abdominal cavity (right panel). (B) Intraperitoneal injection of 4H11z$^+$ and 4H11-28z$^+$ T cells either delay tumor progression or fully eradicate disease. Kaplan-Meier survival curve of SCID-Beige mice treated with first or second generation of MUC-CD targeted T cells. SCID-Beige mice were infused ip with 3×10$^6$ OV-CAR3(MUC-CD) tumor cells on day 1 followed by 3×10$^7$ 4H11z$^+$ or 4H11-28z$^+$ T cells on day 2. All untreated mice or mice treated with control 19z1$^+$ T cells developed established tumors and were sacrificed by day 50. In contrast, 27% of mice treated with either 4H11z$^+$ or 4H11-28z$^+$ T cells remained without clinical evidence of disease by day 120. *p=0.01 (4H11z compared to 19z1), **p=0.0023 (4H11-28z compared to 19z1), p=0.63 (4H11z compared to 4H11-28z).

To assess the in vivo anti-tumor activity of 4H11z$^+$ and 4H11-28z$^+$ T cells, we next generated an orthotopic xenotransplant ovarian cancer tumor model by ip injection of OV-CAR3(MUC-CD) tumor cells into SCID-Beige mice. If left untreated, these mice developed marked ascites and multiple nodular peritoneal tumors by 3 weeks following tumor cell injection (FIG. 14A). All untreated tumor bearing mice had to be euthanized by 7 weeks following tumor cell injection due to evidence of distress.

To assess the in vivo anti-tumor efficacy of MUC-CD-targeted T cells, SCID-Beige mice were injected ip with OV-CAR3(MUC-CD/GFP-FFLuc) tumor cells on day 1 followed by ip injection of 4H11z$^+$ or 4H11-28z$^+$ T cells on day 2. For negative controls, tumor bearing mice were either untreated or treated with T cells modified to express the irrelevant CD19-targeted CAR. Collectively, we found that 27% of all mice treated with MUC-CD targeted T cells (3/11 mice) remained alive without clinical evidence of disease 120 days out from tumor injection with no statistically significant difference in survival when comparing the 4H11z$^+$ and 4H11-28z$^+$ T cell treated cohorts (FIG. 14B). In contrast, both MUC-CD-targeted T cell treated cohorts demonstrated statistically significant enhanced survival when compared to untreated and 19z1$^+$ T cell treated control cohorts.

Figure 15A:
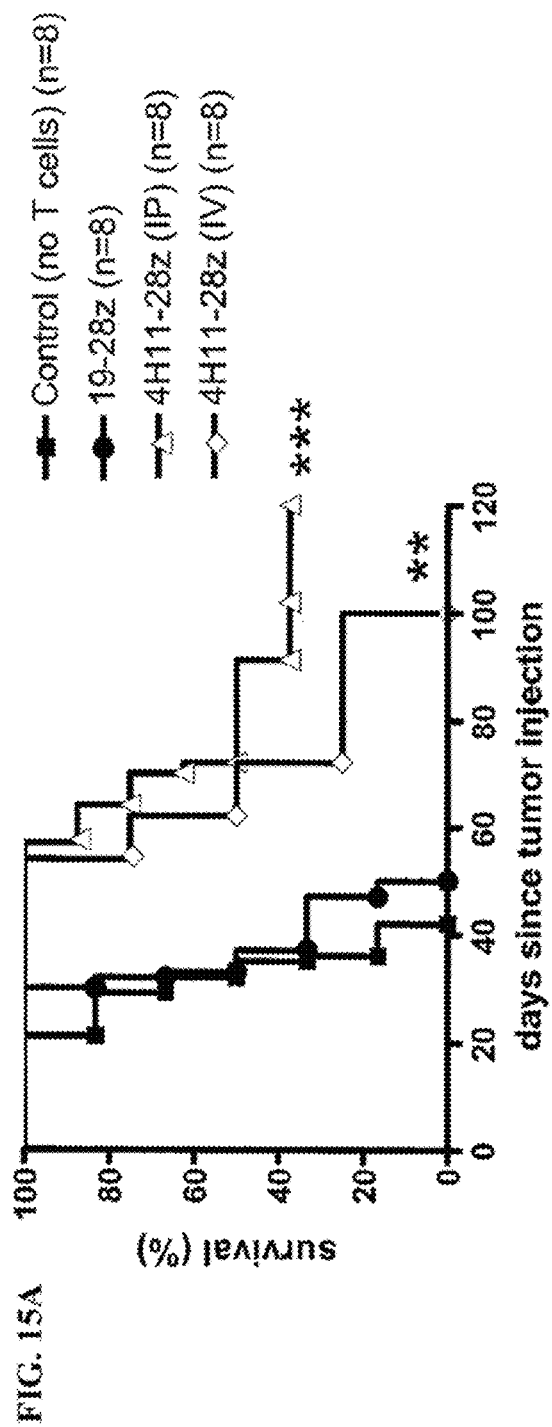
FIGS. 15A-15C: MUC-CD targeted 4H11-28z$^+$ T cells successfully traffic to ip OV-CAR3(MUC-CD/GFP-FFLuc) tumors following systemic intravenous infusion resulting in equally efficient anti-tumor efficacy when compared to ip 4H11-28z$^+$ treated tumor bearing mice.
Figure 15B:
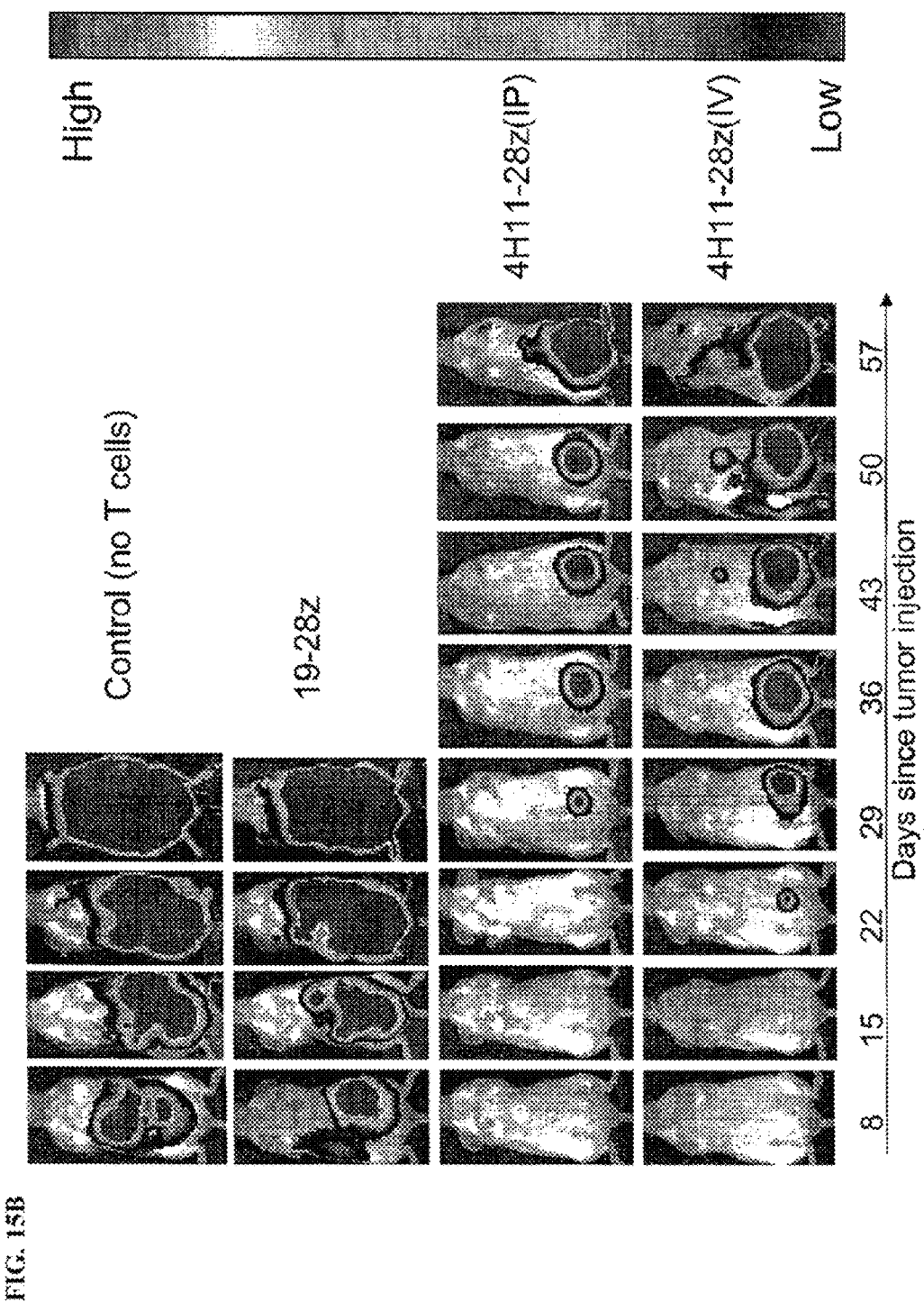
Figure 15C:
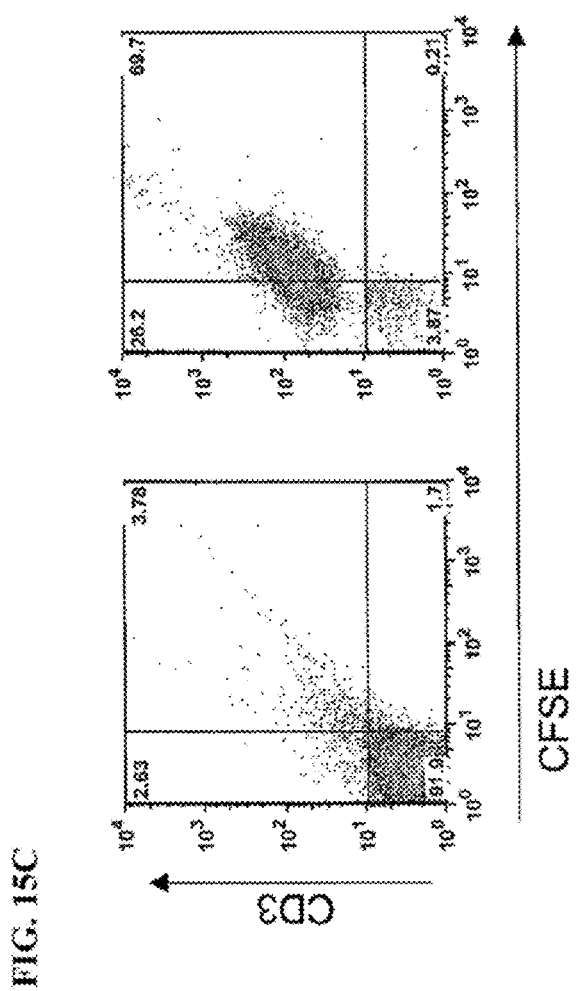

To assess whether systemically infused MUC-CD-targeted T cells successfully traffic to ip tumors, we next compared ip to iv infusion of 4H11-28z$^+$ T cells in SCID-Beige mice bearing ip OV-CAR3(MUC-CD/GFP-FFLuc) tumors. Both ip and iv 4H11-28z$^+$ T cell treated mice exhibited statistically enhanced survival when compared to untreated or 19-28z$^+$ T cell treated control cohorts as assessed by overall survival (FIG. 15A) as well as by BLI of tumor progression (FIG. 15B). Furthermore, we found overall survival between the ip and iv treated groups to be statistically equivalent by log rank analysis. These data imply successful trafficking of iv infused 4H11-28z$^+$ T cells to peritoneal tumors. We further confirmed trafficking of iv infused CFSE labeled 4H11-28z$^+$ T cells to the peritoneum by FACS analysis of single cell suspensions of macerated OV-CAR3(MUC-CD) tumors (FIG. 15C).

In Vivo Anti-Tumor Activity of MUC-CD Targeted T Cells in SCID-Beige Mice Bearing Well Established OV-CAR3(MUC-CD/GFP-FFLuc) Tumors.

Figure 16A:
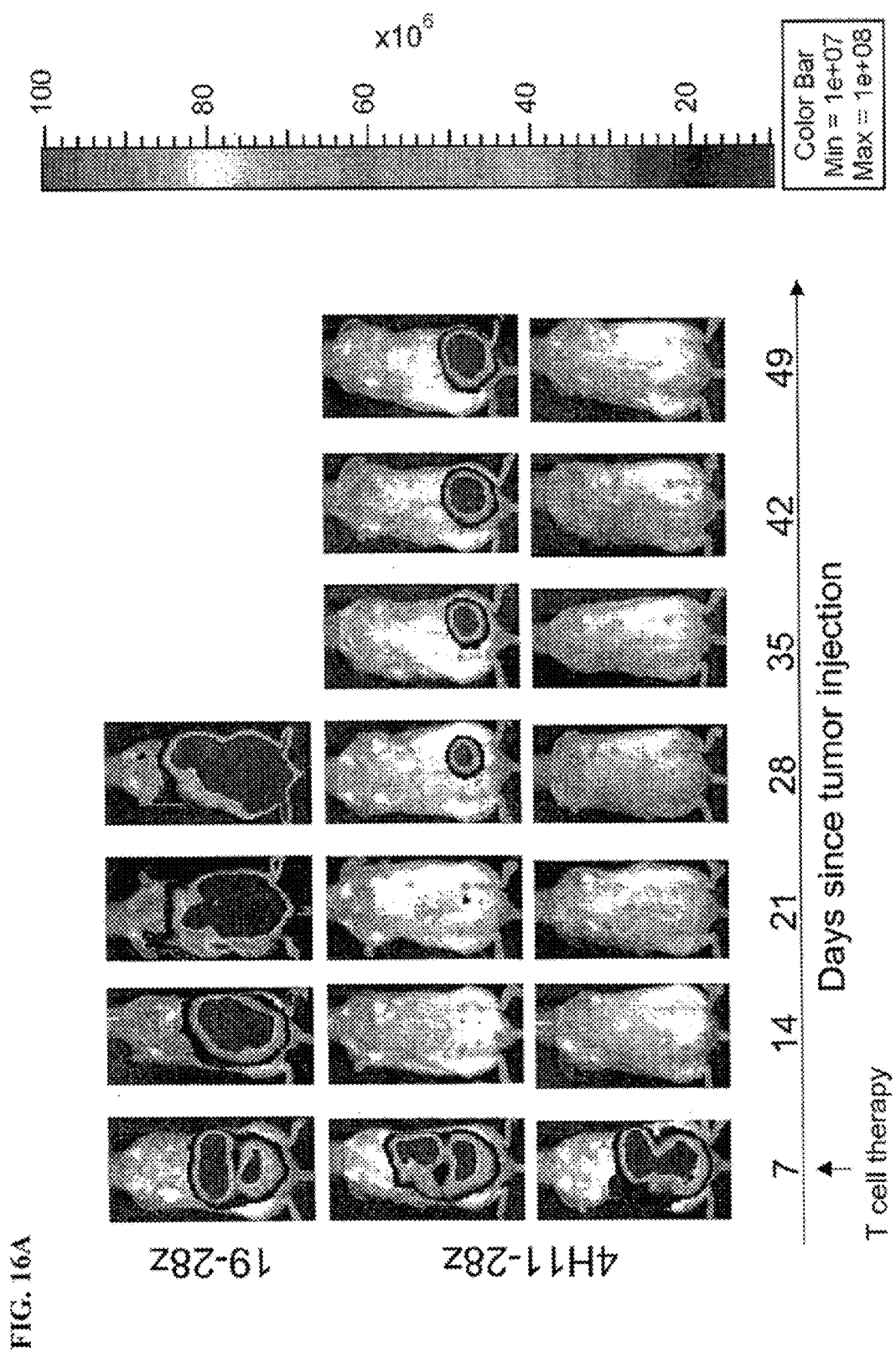
FIGS. 16A-16B. Eradication of advanced OV-CAR3 (MUC-CD) tumors in SCID-Beige mice by ip infusion of 4H11-28z+ T cells. SCID-Beige mice were injected ip with $3 \times 10^6$ OV-CAR3(MUC-CD/GFP-FFLuc) tumor cells 7 days prior to ip treatment with $3 \times 10^7$ 4H11-28z+ T cells.
Figure 16B:
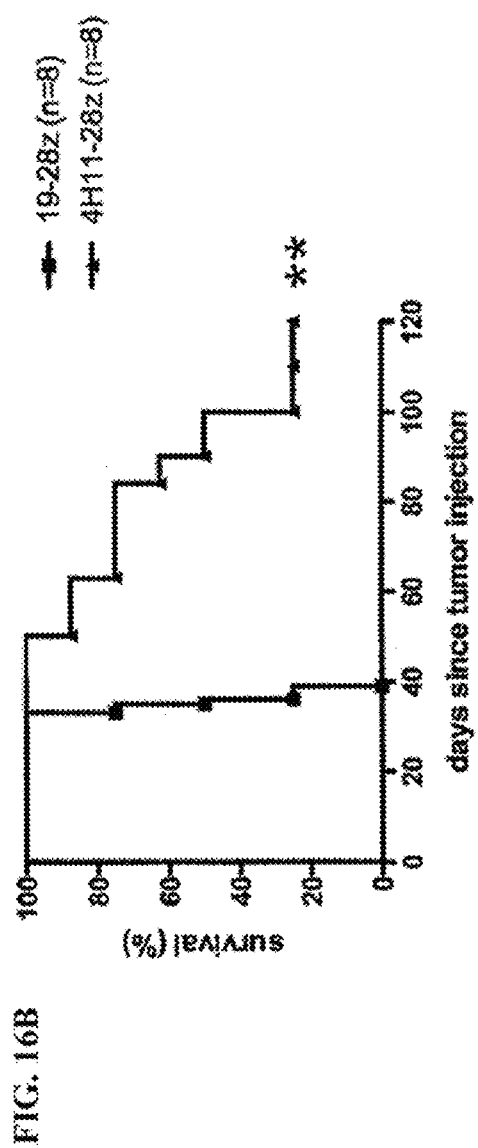

To further assess whether 4H11-28z$^+$ T cells were able to eradicate more clinically relevant tumor burdens, we next treated SCID-Beige mice bearing well established ip OV-CAR3(MUC-CD/GFP-FFLuc) tumor injected 7 days prior to adoptive T cell therapy. Once more, we found that therapy with MUC-CD targeted T cells markedly eradicated BLI evident disease in all treated mice (FIG. 16A) with 5 of 8 treated mice eventually developing relapsed progressive disease, and 3 mice remaining disease free as assessed by BLI imaging (not shown) out to 120 days post-tumor cell infusion (FIG. 16B). These data demonstrate potent in vivo anti-tumor activity mediated by MUC-CD targeted T cells even in the setting of advanced disease.

Discussion

Based on extensive analyses of patient tumor samples, ovarian carcinomas appear to be relatively immunogenic tumors. Specifically, researchers have found there to be a direct correlation between prognosis following surgery and chemotherapy and the quantity of tumor infiltrating effector T cells (TILs) in pretreatment tumor samples (25, 49, 50). Furthermore, others have described an inverse correlation between prognosis following therapy and pre-treatment levels of Tregs within the tumor, which in turn presumably inhibit the anti-tumor function of tumor specific effector TILs (26, 28, 51). Both of these findings imply a role for an endogenous effector T cell response to tumor in controlling disease progression both prior to and following initial therapy and strongly support the contention that ovarian carcinomas may be susceptible to killing by adoptive infusion of autologous T cells targeted to ovarian tumor cell antigens.

While endogenous effector TILs are one source for presumably tumor specific T cells, an alternative approach to adoptive T cell therapy is to isolate autologous peripheral blood T cells which in turn may be genetically modified ex vivo to target tumor cell antigens. One such genetic approach is to retrovirally transduce patient T cells with CARs targeted to surface exposed antigens either unique to or over-expressed by the tumor. To this end, promising preclinical studies utilizing this approach in other malignancies have recently been translated into the clinical setting (6, 16, 19, 52). Similarly, we have previously generated CARs targeted to the CD19 antigen expressed on normal B cells as well as most B cell malignancies and are currently conducting clinical trials treating patients with relapsed B cell chronic lymphocytic leukemia and acute lymphoblastic leukemias with autologous T cell modified to express a CD19 specific CAR (53).

Application of this approach to ovarian carcinomas requires the identification to suitable target antigens expressed on the tumor cell surface. Significantly, other investigators have studied this approach in both the preclinical and clinical setting (4, 11, 54-57). Specifically, several groups have demonstrated significant anti-tumor responses to subcutaneous human ovarian carcinoma cell line tumors in immune compromised mice following intratumoral and/or intravenous infusion of T cells expressing CARs specific to the mesothelin and Lewis-Y antigens overexpressed on these tumor cell lines (56, 58, 59). Furthermore, Kershaw et al recently published the results of a phase I clinical trial treating patients with relapsed ovarian carcinomas with autologous T cells modified to express a CAR specific to the alpha-folate receptor (6). The authors of this study found that therapy with targeted T cells was well tolerated, but noted a lack of anti-tumor response in these studies related to poor persistence of modified T cells over time as well as a yet undefined T cell inhibitory factor in the serum of several treated patients.

In our studies, we have chosen to target the MUC-16 glycoprotein which is over-expressed on a majority of ovarian carcinomas (1, 30, 32, 33). The utility of MUC-16 as a target antigen for adoptive T cell therapy is compromised by the fact that most of the extracellular portion of this molecule is cleaved by the tumor cell, secreted, and may be detected in the serum as the CA-125 tumor marker. However, following cleavage of this secreted fraction of MUC-16, there remains a residual extracellular fraction of the glycoprotein, termed MUC-CD, which is retained on the tumor surface and is therefore an attractive target for immune-based therapies. To this end, we utilized a series of murine hybridomas generated to the MUC-CD antigen to construct CARs specific to MUC-CD. Of these CARs, we identified a CAR generated from the 4H11 murine hybridoma termed 4H11z, which, when expressed in human T cells, following co-culture on 3T3(MUC-CD/B7.1) AAPCs, resulted in rapid destruction of AAPC monolayers as well as marked modified T cell expansion. Significantly, the antigen to the 4H11 antibody is highly expressed on a majority of pre-treatment ovarian carcinoma surgical tumor samples obtained from patients treated at our institution as assessed by immuno-histochemistry (48).

Optimal T cell activation requires both a primary T cell receptor mediated signal, "signal 1," along with a co-stimulatory "signal 2." Classically, this co-stimulatory signal may be provided by ligation of either B7.1 (CD80) or B7.2 (CD86) on the target cell with the T cell co-stimulatory receptor CD28. Alternatively, co-stimulation may be generated by ligation of 4-1BBL or OX-40L on the target cell with the respective 4-1BB or OX40 co-stimulatory receptors on the T cell (12, 60, 61). Since most tumor cells fail to express co-stimulatory ligands, we and others have previously demonstrated that second generation CARs further incorporating the cytoplasmic signaling domains the co-stimulatory receptors CD28, 4-1BB, and/or OX40 resulted in CARs capable of providing both signal 1 and signal 2 to the T cell upon binding to cognate antigen in the absence of exogenous co-stimulatory ligands (7-10, 12, 13, 15, 16, 62-65). To this end, we constructed a second generation CAR from the 4H11z CAR incorporating the transmembrane and cytoplasmic signaling domain of CD28 as described elsewhere (3, 9, 43). Consistent with previous studies, we found that T cells transduced to express the resulting 4H11-28z CAR, but not the first generation 4H11z CAR, efficiently expanded upon co-culture with 3T3(MUC-CD) fibroblasts in the absence of exogenous co-stimulation consistent with the ability of the 4H11-28z CAR to deliver both signal 1 and signal 2 to the T cell. This conclusion is further supported by the finding that 4H11-28z$^+$ T cells secreted significantly higher levels of IL-2, a cytokine indicative of T cell co-stimulation, upon co-culture on 3T3(MUC-CD) fibroblasts when compared to T cells transduced to express the first generation 4H11z CAR.

We next assessed the ability of 4H11z$^+$ and 4H11-28z$^+$ T cells to target and lyse human ovarian carcinoma tumor cells. To this end, we initially utilized the OV-CAR3 human ovarian cancer cell line. Since the OV-CAR3 tumor cell line binds the 4H11 antibody weakly, we further genetically modified the cell line to express MUC-CD (OV-CAR3 (MUC-CD)) to better mimic the clinical setting wherein a majority of clinical ovarian carcinoma tumor specimens highly express the 4H11 MUC-CD antigen (48). We demonstrated that human T cells modified to express either 4H11z or 4H11-28z eradicated OV-CAR3(MUC-CD) tumor cells in vitro, and surprisingly observed that both 4H11z$^+$ and 4H11-28z$^+$ T cells expanded following co-culture with tumor in vitro. To define the etiology of this unanticipated 4H11z$^+$ T cell expansion, we further assessed whether OV-CAR3(MUC-CD) tumor cells expressed co-stimulatory ligands, and found that this tumor cell line expressed 4-1BBL, consistent with our experimental findings as well as with previously published reports demonstrating 4-1BBL expression by a variety of carcinoma cell lines (66-68). In order to further validate the clinical relevance of these findings, we subsequently demonstrated specific in vitro lysis of primary ascites-derived tumor cells isolated from untreated ovarian carcinoma patients by both healthy donor allogeneic 4H11-28z$^+$ T cells as well as more significantly autologous 4H11-28z$^+$ patient peripheral blood T cells. These data strongly support the contention that treatment with autologous 4H11-based CAR$^+$ T cells have promise in future clinical applications.

In order to assess the in vivo relevance of our in vitro findings, we next generated a murine orthotopic OV-CAR3 (MUC-CD) tumor model in SCID-Beige mice. We injected mice i.p. with OV-CAR3(MUC-CD) tumor cells and the following day infused 4H11z$^+$, 4H11-28z$^+$, and control 19z1$^+$ T cells i.p. This treatment approach resulted in a significant but similar delay to tumor progression and long-term survival in both the 4H11z$^+$ and 4H11-28z$^+$ T cell treated cohorts when compared to untreated mice or mice treated with control T cells targeted to the irrelevant CD19 antigen. We next compared ip to iv treatment with 4H11-28z$^+$ T cells of orthotopic OV-CAR3(MUC-CD/GFP-FF-Luc) bearing mice, and found similar statistically significant survivals of mice over time with either direct ip infusion of T cells or systemic iv infusion of targeted T cells. Significantly, iv treated mice by day 1 following treatment, exhibited successful trafficking of targeted T cells to the peritoneum. These data suggests that adoptive therapy with targeted T cells may be equally efficacious following either a direct infusion into the peritoneum or through systemic iv infusion. These findings further support the future clinical potential of this approach in treating patients both with local relapse of disease as well as metastatic relapse to sites outside of the peritoneum.

Finally, we assessed the ability of 4H11-28z$^+$ T cells to eradicate more established disease by delaying modified T cell ip infusion by 7 days, when mice had greater established tumor burdens as assessed by bioluminescent imaging. This experimental setting better reflects the initial clinical setting wherein this adoptive T cell approach would be utilized. Significantly, despite the setting of markedly established disease, 4H11-28z$^+$ T cells retained the ability to lyse larger tumor burdens, delay relapse of tumor, and in a significant percentage of mice, fully eradicate disease.

In the studies presented here, we have consistently utilized mixed populations of CD4$^+$ and CD8$^+$ CAR$^+$ T cells to assess both in vitro and in vivo anti-tumor activity. To this end, ongoing studies will address the role of isolated CD4$^+$ and CD8$^+$ CAR$^+$ T cell subsets in the successful eradication of disease in this SCID-Beige OV-CAR3(MUC-CD) tumor model. The results of these studies may have implications to translating this therapeutic approach to the clinical setting. Furthermore, we acknowledge the limitations associated with the presented SCID-Beige tumor model. Namely, this is a xenotransplant model in an immune compromised mouse. To this end, ongoing studies in or laboratory are focused on generating a more clinically relevant syngeneic immune competent tumor model to better define the biology and anti-tumor efficacy of MUC-CD targeted CAR-modified T cells in the context of an intact immune system.

In conclusion, herein we present the first published data demonstrating the feasibility of targeting MUC-16, an antigen over-expressed on a majority of ovarian carcinomas, through adoptive therapy with genetically modified T cells targeted to the retained MUC-CD portion of the MUC-16 antigen. Further, this report is the first to demonstrate efficient targeting of T cells in an orthotopic, clinically relevant, murine model of ovarian cancer, demonstrating efficacy both by ip and iv infusion of modified T cells. Finally, these data support the further translation of this approach to the clinical setting in the form of a phase I clinical trial in patients with persistent or relapsed ovarian carcinomas following initial therapy with surgery and chemotherapy.

Example 5

Raising Mouse MUC16 Monoclonal Antibodies in Mice and Hamsters

We selected 3 different regions of mouse MUC16 genome for which monoclonal antibodies were generated in mouse and hamster. The selected regions of the mouse MUC16 are Peptide 1 (SEQ ID NO:21, ecto region of cytoplasmic domain), Peptide 2 (SEQ ID NO:22, first cysteine loop) and Peptide 3 (SEQ ID NO:23, second cysteine loop) (FIG. 20A) and its comparison with human MUC16 is shown in FIG. 20B. A cysteine was added to the peptide sequence at the N terminus of Peptide 1 (SEQ ID NO:21) and Peptide 3 (SEQ ID NO:23) for better conjugation with KLH. Individual peptides were conjugated to KLH using Promega kit. These 3 conjugated peptides were pooled and immunized into 5 mice and 4 hamsters. 5 immunizations with a 3 week interval for each immunization were administered. Sera from these animals were tested by ELISA for their specific reactivity with individual peptides (SEQ ID NO:21, 22 and 23). Positive selected animals were allowed to rest for a month and then i.v. boosted with pooled peptides immunogen (SEQ ID NO:21, 22 and 23) and harvested the spleens after 4 days. Splenocytes were mixed with hybridoma partners and plated into microtiter plates at various clonal densities. Plates were cultured at 37° C. 5% CO$_2$ for 10 days and then selected the clones. Supernatants from these selected clones were tested by ELISA for their specific reactivity with individual peptides (SEQ ID NO:21, 22 and 23). Positive clonal sups were tested by FACS, western blot and imaging using 2 mouse cell lines (ID8 and BR5-FVB1) and a human cell line (OVCAR-3).

Table 4 shows the summary of mouse and hamster monoclonal antibodies against mouse MUC16 peptide antigens Peptide 1 (SEQ ID NO:21), Peptide 2 (SEQ ID NO:22), and Peptide 3 (SEQ ID NO:23). A very strong antigenic response was seen with Peptide 1 (SEQ ID NO:21).

TABLE 4

| Mouse MUC16 | Mouse mAbs | Frozen Mouse mAb | |
|---|---|---|---|
| Peptide 1 | 46 | 16 (3-IgG1; 8-IgG2b; 1-IgM; 4-Unkown isotype) | |
| Peptide 2 | 0 | 0 | Animals not iv boosted with peptide 2 |
| Peptide 3 | 6 | 6 (4-IgG1; 2-IgM) | |

TABLE 4-continued

| | | |
|---|---|---|
| Peptide 1, 2, 3 | 0 | 0 |
| Peptide 1, 2 | 0 | 0 |
| Peptide 2, 3 | 0 | 0 |
| No Peptide | 0 | 0 |

| Mouse MUC16 | Hamster mAbs | Frozen Hamster mAb |
|---|---|---|
| Peptide 1 | 69 | 21 |
| Peptide 2 | 6 | 6 |

TABLE 4-continued

| | | |
|---|---|---|
| Peptide 3 | 7 | 7 |
| Peptide 1, 2, 3 | 2 | 1 |
| Peptide 1, 2 | 1 | 1 |
| Peptide 2, 3 | 1 | 0 |
| No Peptide | 10 | 2 |

Details of mouse and hamster mAbs against Peptide 1 (SEQ ID NO:21), Peptide 2 (SEQ ID NO:22), and Peptide 3 (SEQ ID NO:23 are listed in Table 5 and Table 6 respectively.

TABLE 5

| isotype | PEPTIDE | Fusion Well | Cloned | Clones | | | |
|---|---|---|---|---|---|---|---|
| — | 1 | 01D01 | | | | | |
| — | 1 | 09F07 | | | | | |
| IgG 1 | 1 | 16A09 | no success | | | | |
| — | 1 | 21A07 | | | | | |
| — | 1 | 24G10 | | | | | |
| IgG 1 | 1 | 10C04 | yes | 10C4-3H5 | 10C4-1F2 | 10C4-2H8 | 10C4-1G7 |
| IgG 1 | 1 | 17F02 | yes | 17F2-3G5 | 17F2-3F6 | 17F2-2F9 | 17F2-1E11 |
| IgG 2b | 1 | 01A08 | | | | | |
| IgG 2b | 1 | 01F08 | | | | | |
| IgG 2b | 1 | 12B10 | yes | 12B10-3F7 | 12B10-3G10 | 12B10-2F6 | 12B10-2F10 |
| IgG 2b | 1 | 17H10 | | | | | |
| IgG 2b | 1 | 18D05 | | | | | |
| IgG 2b | 1 | 23B12 | | | | | |
| IgG 2b | 1 | 25E09 | | 25E9-3 | 25E9-5 | 25E9-13 | 25E9-16 |
| IgM | 1 | 16F12 | | | | | |
| IgG 1 | 3 | 04A06 | no success | | | | |
| IgG 1 | 3 | 05D01 | no success | | | | |
| IgG 1 | 3 | 21B08 | yes | 21B8-1H11 | 21B8-3G6 | 21B8-3H9 | 21B8-1G8 |
| IgG 1 | 3 | 21E01 | yes | 21E1-1E3 | 21E1-1G9 | 21E1-2G7 | 21E1-3G12 |
| IgM | 3 | 08A02 | | | | | |
| IgM | 3 | 13E05 | | | | | |

TABLE 6

| Hamster mAb | Peptide | Cloned | | | |
|---|---|---|---|---|---|
| 01H03 | | | | | |
| 02F02 | 1 | | | | |
| 04E 4 | | | | | |
| 04G07 | 1 | | | | |
| 04H01 | 3 | 4H1-2E1 | 4H1-2E3 | 4H1-3E1 | 4H1-3H3 |
| 06A08 | 1 | | | | |
| 06F02 | 1 | | | | |
| 07F08 | 3 | | | | |
| 07H05 | 2 | | | | |
| 09A05 | | | | | |
| 09E 1 | 3 | | | | |
| 09F08 | 1 | | | | |
| 09H10 | | | | | |
| 10G06 | 1 | | | | |
| 10H11 | 1 | | | | |
| 11B10 | 1 | | | | |
| 12F09 | 2 | | | | |
| 15A08 | 1 | 15A8-2E2 | 15A8-2E10 | 15A8-2E11 | 15A8-3D2 |
| 15H08 | 3 | | | | |
| 19B05 | 1 | | | | |
| 21H04 | 3 | | | | |
| 22B05 | 2 | 22B5-1F6 | 22B5-3G9 | 22B5-2G8 | 22B5-3F11 |
| 22D11 | 3 | | | | |
| 23G12 | 1 | | | | |
| 25E 8 | 1 | | | | |
| 27H09 | 3 | | | | |
| 28B12 | 1&2&3 | | | | |
| 28C12 | 2 | | | | |
| 30H02 | 1 | | | | |
| 31A11 | 2 | | | | |
| 31C01 | 2 | | | | |

TABLE 6-continued

| Hamster mAb | Peptide | Cloned |
|---|---|---|
| 33H06 | 1&2 | |
| 34F10 | 1 | |
| 34H05 | 1 | |
| 36C01 | 1 | |
| 36C11 | | |
| 36E 4 | 1 | |
| 37E 10 | 1 | |
| 10H11 | 1 | |

Hamster antibody 22B05 recognizes mouse (SEQ ID NO:22) and also the corresponding human sequence (SEQ ID NO:15).

Figure 22:
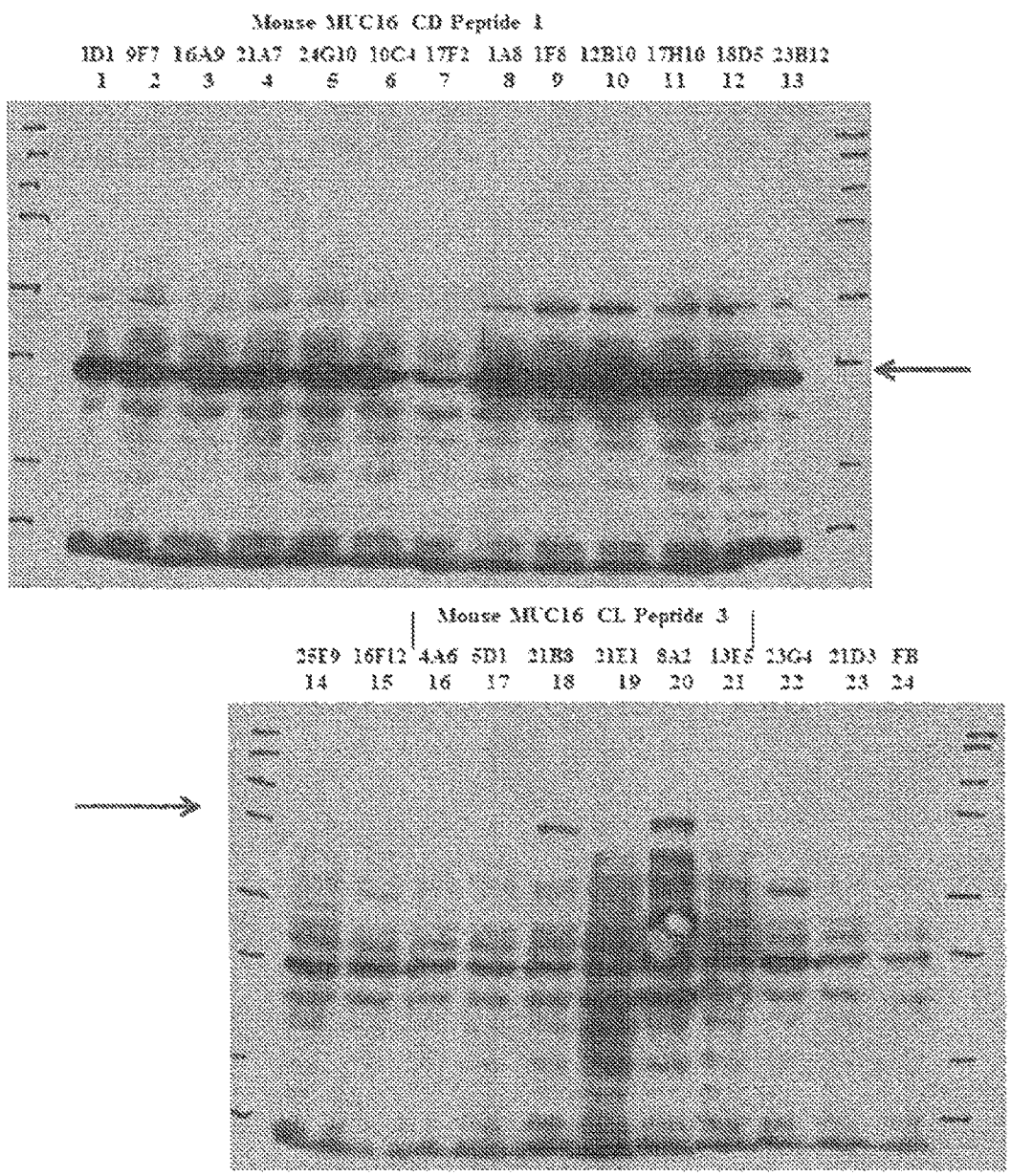
FIG. 22: BR5-FVB1 extract with 1:10 dilution of Mouse MUC16 monoclonal Primary Supernatants

Western blot analysis using mouse IDB and BR5-FVB1 cell extracts were also performed for all the selected monoclonal antibodies as shown in FIG. 21 and FIG. 22 respectively.

Among the mouse MUC16 monoclonal antibodies, we selected 12B10-3G10 subclone mouse mAb for further screening. Similarly, hamster monoclonal antibodies, 15A8-2E10, 22B5-2G8 and 4H1-2E1 subclones were selected for further screening.

Figure 23A:
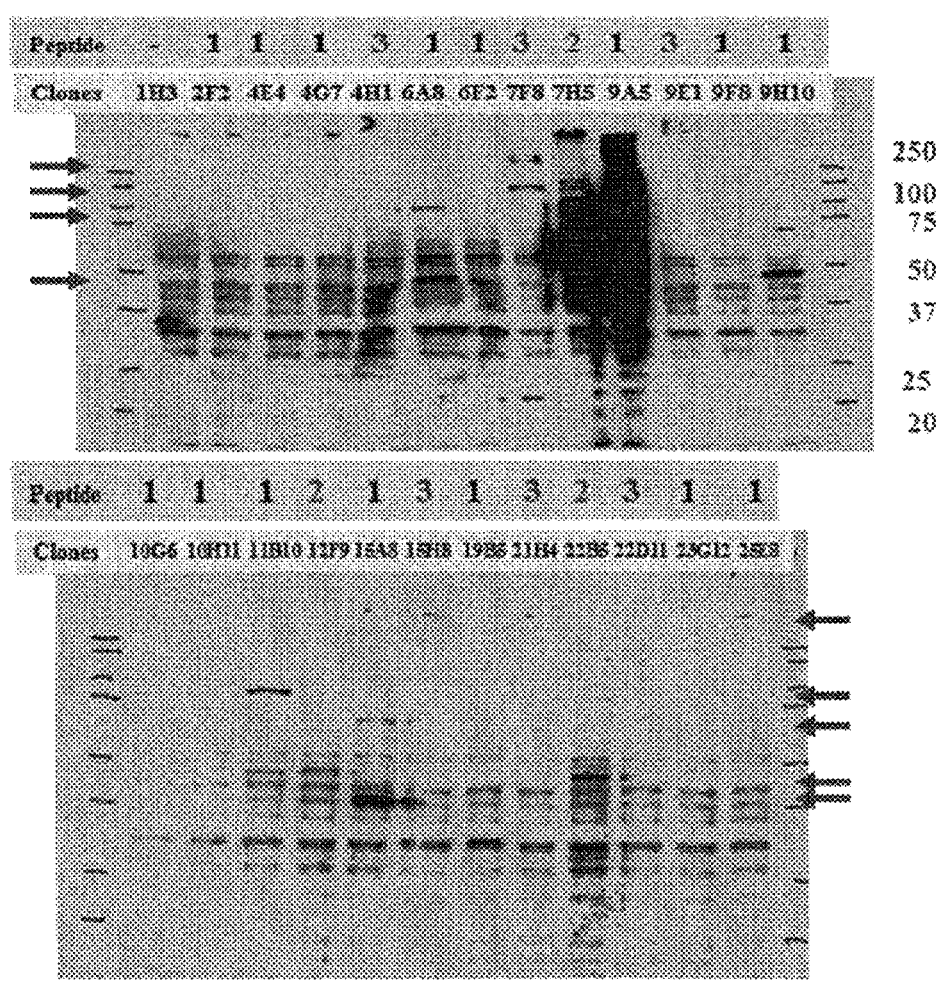
FIG. 23A and FIG. 23B: Western Blot showing 38 hamster's monoclonal antibody Supernatants on IDB cell extracts.
Figure 23B:
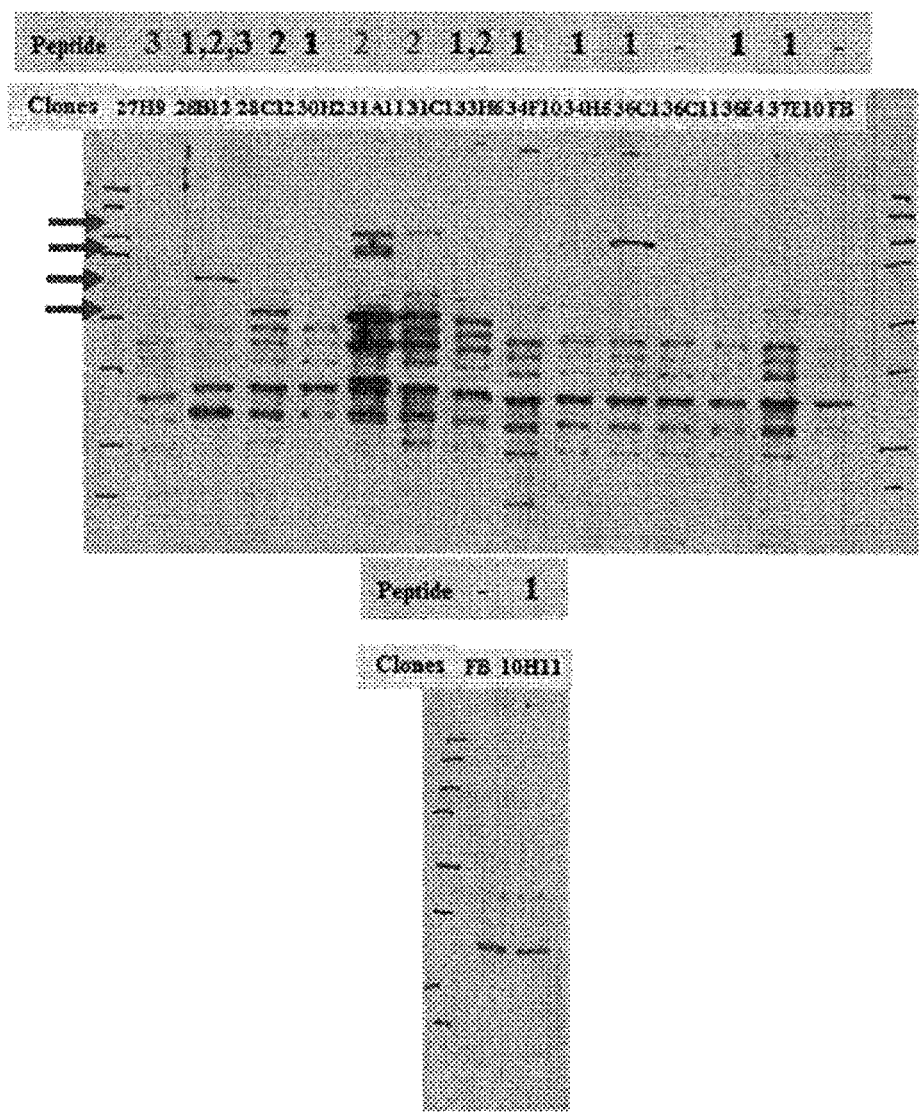

Immunohistochemical analysis was performed with paraffin and cryosections of IDB (mouse), OVCAR-3 (human), BR5-FVB1 (mouse) cell lines and 13.5 days of Embryo. Paraffin or cryosections were probed with mouse 12B10 mAb, hamster 15A8, hamster 22B5 and hamster 4E1 mAbs to see the early development of mouse MUC16 (FIGS. 23A-23B)

Figure 25:
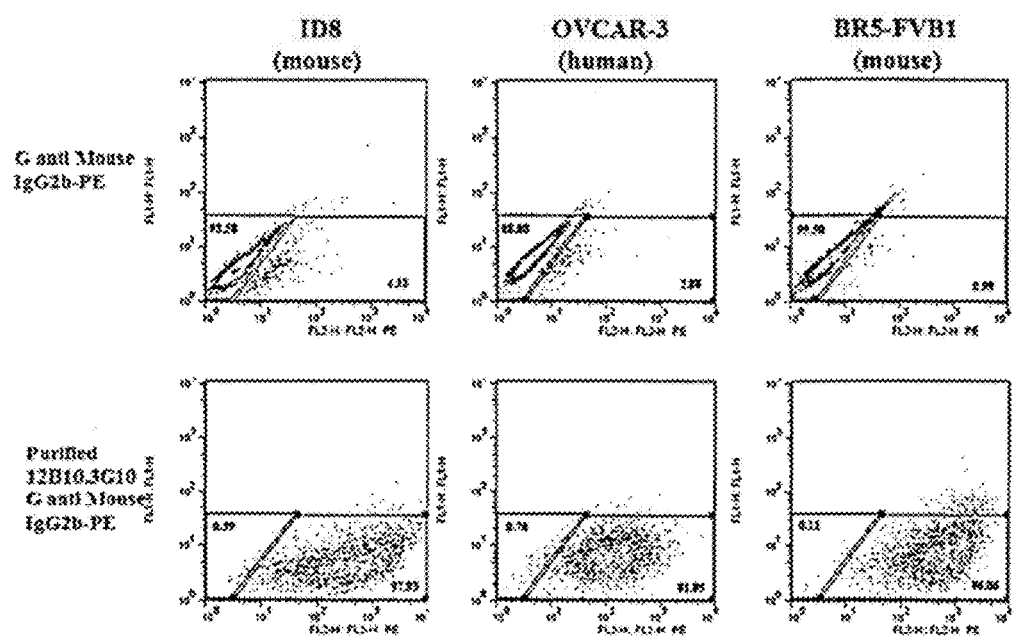
FIG. 25: FACS Analysis with Purified 12B10-3G10 mAb on IDB (mouse), OVCAR-3 (human) and BR5-FVB1 (mouse) cell lines.

12B10-3G10 sub clone were further analyzed for single chain Fv fragments. FIGS. 24A-24D show 12B10-3G10 $V_H$ and $V_L$ DNA and Amino Acids sequences. Bioreactive supernatants and purified 12B10-3G10 were generated for animal studies and other characterization studies. FACS analysis was performed with purified 12B10-3G10 on ID8, OVCAR3 and BR5-FVB1 cells showing over 90% positivity to both mouse and human MUC16 ecto-domain fragment (FIG. 25).

REFERENCES CITED IN THE SPECIFICATION AND EXAMPLES 1-3

1. Bast R C, Jr., Feeney M, Lazarus H, Nadler L M, Colvin R B, Knapp R C. Reactivity of a monoclonal antibody with human ovarian carcinoma. J Clin Invest 1981; 68(5):1331-7.
2. Bast R C, Jr., Klug T L, St John E, Jenison E, Niloff J M, Lazarus H, et al. A radioimmunoassay using a monoclonal antibody to monitor the course of epithelial ovarian cancer. N Engl J Med 1983; 309(15):883-7.
3. Rustin G J, Bast R C, Jr., Kelloff G J, Barrett J C, Carter S K, Nisen P D, et al. Use of CA-125 in clinical trial evaluation of new therapeutic drugs for ovarian cancer. Clin Cancer Res 2004; 10(11):3919-26.
4. Rosen D G, Wang L, Atkinson J N, Yu Y, Lu K H, Diamandis E P, et al. Potential markers that complement expression of CA125 in epithelial ovarian cancer. Gynecol Oncol 2005; 99(2):267-77.
5. Bast R C, Jr., Badgwell D, Lu Z, Marquez R, Rosen D, Liu J, et al. New tumor markers: CA125 and beyond. Int J Gynecol Cancer 2005; 15 Suppl 3:274-81.
6. Moore R G, Maclaughlan S, Bast R C, Jr. Current state of biomarker development for clinical application in epithelial ovarian cancer. Gynecol Oncol 2009.
7. Nustad K, Lebedin Y, Lloyd K O, Shigemasa K, de Bruijn H W, Jansson B, et al. Epitopes on CA 125 from cervical mucus and ascites fluid and characterization of six new antibodies. Third report from the ISOBM TD-1 workshop. Tumour Biol 2002; 23(5):303-14.
8. Fendrick J L, Konishi I, Geary S M, Parmley T H, Quirk J G, Jr., O'Brien T J. CA125 phosphorylation is associated with its secretion from the WISH human amnion cell line. Tumour Biol 1997; 18(5):278-89.
9. Fendrick J L, Staley K A, Gee M K, McDougald S R, Quirk J G, Jr., O'Brien T J. Characterization of CA 125 synthesized by the human epithelial amnion WISH cell line. Tumour Biol 1993; 14(5):310-8.
10. O'Brien T J, Beard J B, Underwood L J, Shigemasa K. The CA 125 gene: a newly discovered extension of the glycosylated N-terminal domain doubles the size of this extracellular superstructure. Tumour Biol 2002; 23(3):154-69.
11. Yin B W, Dnistrian A, Lloyd K O. Ovarian cancer antigen CA125 is encoded by the MUC16 mucin gene. Int J Cancer 2002; 98(5):737-40.
12. Yin B W, Lloyd K O. Molecular cloning of the CA125 ovarian cancer antigen: identification as a new mucin, MUC16. J Biol Chem 2001; 276(29):27371-5.
13. Hollingsworth M, Swanson B. Mucins in Cancer: protection and control of the cell surface. Nature Reviews: Cancer 2004; 4(1):45-60.
14. Huang L, Ren J, Chen D, Li Y, Kharbanda S, Kufe D. MUC1 cytoplasmic domain coactivates Wnt target gene transcription and confers transformation. Cancer Biol Ther 2003; 2(6):702-6.
15. Li Q, Ren J, Kufe D. Interaction of human MUC1 and beta-catenin is regulated by Lck and ZAP-70 in activated Jurkat T cells. Biochem Biophys Res Commun 2004; 315(2):471-6.
16. Ren J, Agata N, Chen D, Li Y, Yu W H, Huang L, et al. Human MUC1 carcinoma-associated protein confers resistance to genotoxic anticancer agents. Cancer Cell 2004; 5(2):163-75.
17. Ren J, Bharti A, Raina D, Chen W, Ahmad R, Kufe D. MUC1 oncoprotein is targeted to mitochondria by heregulin-induced activation of c-Src and the molecular chaperone HSP90. Oncogene 2006; 25(1):20-31.
18. Ramsauer V P, Pino V, Farooq A, Carothers Carraway C A, Salas P J, Carraway K L. Muc4-ErbB2 Complex Formation and Signaling in Polarized CACO-2 Epithelial Cells Indicate That Muc4 Acts as an Unorthodox Ligand for ErbB2. Mol Biol Cell 2006.
19. Bafna S, Singh A P, Moniaux N, Eudy J D, Meza J L, Batra S K. MUC4, a multifunctional transmembrane glycoprotein, induces oncogenic transformation of NIH3T3 mouse fibroblast cells. Cancer Res 2008; 68(22):9231-8.

20. Ponnusamy M P, Singh A P, Jain M, Chakraborty S, Moniaux N, Batra S K. MUC4 activates HER2 signalling and enhances the motility of human ovarian cancer cells. Br J Cancer 2008; 99(3):520-6.
21. Nap M, Vitali A, Nustad K, Bast R C, Jr., O'Brien T J, Nilsson O, et al. Immunohistochemical characterization of 22 monoclonal antibodies against the CA125 antigen: 2nd report from the ISOBM TD-1 Workshop. Tumour Biol 1996; 17(6):325-31.
22. Markwell M A, Fox C F. Surface—specific iodination of membrane proteins of viruses and eucarytic cells using 1,3,4,6-tetrachloro-3alpha,6alpha-diphenylglycouril. Biochemistry 1978; 17:4807-4817.
23. Kononen J, Bubendorf L, Kallioniemi A, Barlund M, Schraml P, Leighton S, et al. Tissue microarrays for high-throughput molecular profiling of tumor specimens. Nat Med 1998; 4(7):844-7.
24. Hedvat C V, Hegde A, Chaganti R S, Chen B, Qin J, Filippa D A, et al. Application of tissue microarray technology to the study of non-Hodgkin's and Hodgkin's lymphoma. Hum Pathol 2002; 33(10):968-74.
25. Soslow R A. Histologic subtypes of ovarian carcinoma: an overview. Int J Gynecol Pathol 2008; 27(2):161-74.
26. O'Brien T J, Beard J B, Underwood L J, Dennis R A, Santin A D, York L. The CA 125 gene: an extracellular superstructure dominated by repeat sequences. Tumour Biol 2001; 22(6):348-66.
27. Harris M, Howell A, Chrissohou M, Swindell R I, Hudson M, Sellwood R A. A comparison of the metastatic pattern of infiltrating lobular carcinoma and infiltrating duct carcinoma of the breast. Br J Cancer 1984; 50(1): 23-30.
28. Kaneko O, Gong L, Zhang J, Hansen J K, Hassan R, Lee B, et al. A binding domain on mesothelin for CA125/MUC16. J Biol Chem 2009; 284(6):3739-49.

REFERENCES CITED IN EXAMPLE 4

1. Singh A P, Senapati S, Ponnusamy M P, et al. Clinical potential of mucins in diagnosis, prognosis, and therapy of ovarian cancer. Lancet Oncol 2008; 9(11):1076-85.
2. Sun C C, Ramirez P T, Bodurka D C. Quality of life for patients with epithelial ovarian cancer. Nat Clin Pract Oncol 2007; 4(1):18-29.
3. Brentjens R J, Latouche J B, Santos E, et al. Eradication of systemic B-cell tumors by genetically targeted human T lymphocytes co-stimulated by CD80 and interleukin-15. Nat Med 2003; 9(3):279-86.
4. Hwu P, Yang J C, Cowherd R, et al. In vivo antitumor activity of T cells redirected with chimeric antibody/T-cell receptor genes. Cancer Res 1995; 55(15):3369-73.
5. Imai C, Mihara K, Andreansky M, et al. Chimeric receptors with 4-1BB signaling capacity provoke potent cytotoxicity against acute lymphoblastic leukemia. Leukemia 2004; 18(4):676-84.
6. Kershaw M H, Westwood J A, Parker L L, et al. A phase I study on adoptive immunotherapy using gene-modified T cells for ovarian cancer. Clin Cancer Res 2006; 12(20 Pt 1):6106-15.
7. Kochenderfer J N, Feldman S A, Zhao Y, et al. Construction and preclinical evaluation of an anti-CD19 chimeric antigen receptor. J Immunother 2009; 32(7):689-702.
8. Loskog A, Giandomenico V, Rossig C, Pule M, Dotti G, Brenner M K. Addition of the CD28 signaling domain to chimeric T-cell receptors enhances chimeric T-cell resistance to T regulatory cells. Leukemia 2006; 20(10):1819-28.
9. Maher J, Brentjens R J, Gunset G, Riviere I, Sadelain M. Human T-lymphocyte cytotoxicity and proliferation directed by a single chimeric TCRzeta/CD28 receptor. Nat Biotechnol 2002; 20(1):70-5.
10. Moeller M, Haynes N M, Trapani J A, et al. A functional role for CD28 costimulation in tumor recognition by single-chain receptor-modified T cells. Cancer Gene Ther 2004; 11(5):371-9.
11. Parker L L, Do M T, Westwood J A, et al. Expansion and characterization of T cells transduced with a chimeric receptor against ovarian cancer. Hum Gene Ther 2000; 11(17):2377-87.
12. Sadelain M, Brentjens R, Riviere I. The promise and potential pitfalls of chimeric antigen receptors. Curr Opin Immunol 2009; 21(2):215-23.
13. Stephan M T, Ponomarev V, Brentjens R J, et al. T cell-encoded CD80 and 4-1BBL induce auto- and transcostimulation, resulting in potent tumor rejection. Nat Med 2007; 13(12):1440-9.
14. Daly T, Royal R E, Kershaw M H, et al. Recognition of human colon cancer by T cells transduced with a chimeric receptor gene. Cancer Gene Ther 2000; 7(2):284-91.
15. Jensen M C, Cooper L J, Wu A M, Forman S J, Raubitschek A. Engineered CD20-specific primary human cytotoxic T lymphocytes for targeting B-cell malignancy. Cytotherapy 2003; 5(2):131-8.
16. Pule M A, Savoldo B, Myers G D, et al. Virus-specific T cells engineered to coexpress tumor-specific receptors: persistence and antitumor activity in individuals with neuroblastoma. Nat Med 2008; 14(11):1264-70.
17. Savoldo B, Rooney C M, Di Stasi A, et al. Epstein Barr virus specific cytotoxic T lymphocytes expressing the anti-CD30zeta artificial chimeric T-cell receptor for immunotherapy of Hodgkin disease. Blood 2007; 110(7): 2620-30.
18. Wang G, Chopra R K, Royal R E, Yang J C, Rosenberg S A, Hwu P. A T cell-independent antitumor response in mice with bone marrow cells retrovirally transduced with an antibody/Fc-gamma chain chimeric receptor gene recognizing a human ovarian cancer antigen. Nat Med 1998; 4(2):168-72.
19. Hollyman D, Stefanski J, Przybylowski M, et al. Manufacturing validation of biologically functional T cells targeted to CD19 antigen for autologous adoptive cell therapy. J Immunother 2009; 32(2):169-80.
20. Lamers C H, Sleijfer S, Vulto A G, et al. Treatment of metastatic renal cell carcinoma with autologous T-lymphocytes genetically retargeted against carbonic anhydrase IX: first clinical experience. J Clin Oncol 2006; 24(13):e20-2.
21. Till B G, Jensen M C, Wang J, et al. Adoptive immunotherapy for indolent non-Hodgkin lymphoma and mantle cell lymphoma using genetically modified autologous CD20-specific T cells. Blood 2008; 112(6):2261-71.
22. Hamanishi J, Mandai M, Iwasaki M, et al. Programmed cell death 1 ligand 1 and tumor-infiltrating CD8+T lymphocytes are prognostic factors of human ovarian cancer. Proc Natl Acad Sci USA 2007; 104(9):3360-5.
23. Leffers N, Gooden M J, de Jong R A, et al. Prognostic significance of tumor-infiltrating T-lymphocytes in primary and metastatic lesions of advanced stage ovarian cancer. Cancer Immunol Immunother 2009; 58(3):449-59.

24. Sato E, Olson S H, Ahn J, et al. Intraepithelial CD8+ tumor-infiltrating lymphocytes and a high CD8+/regulatory T cell ratio are associated with favorable prognosis in ovarian cancer. Proc Natl Acad Sci USA 2005; 102(51): 18538-43.
25. Zhang L, Conejo-Garcia J R, Katsaros D, et al. Intratumoral T cells, recurrence, and survival in epithelial ovarian cancer. N Engl J Med 2003; 348(3):203-13.
26. Curiel T J, Coukos G, Zou L, et al. Specific recruitment of regulatory T cells in ovarian carcinoma fosters immune privilege and predicts reduced survival. Nat Med 2004; 10(9):942-9.
27. Leffers N, Lambeck A J, de Graeff P, et al. Survival of ovarian cancer patients overexpressing the tumour antigen p53 is diminished in case of MHC class I down-regulation. Gynecol Oncol 2008; 110(3):365-73.
28. Nelson B H. The impact of T-cell immunity on ovarian cancer outcomes. Immunol Rev 2008; 222:101-16.
29. Wolf D, Wolf A M, Rumpold H, et al. The expression of the regulatory T cell-specific forkhead box transcription factor FoxP3 is associated with poor prognosis in ovarian cancer. Clin Cancer Res 2005; 11(23):8326-31.
30. Badgwell D, Bast R C, Jr. Early detection of ovarian cancer. Dis Markers 2007; 23(5-6):397-410.
31. Bast R C, Jr., Badgwell D, Lu Z, et al. New tumor markers: CA125 and beyond. Int J Gynecol Cancer 2005; 15 Suppl 3:274-81.
32. Fritsche H A, Bast R C. CA 125 in ovarian cancer: advances and controversy. Clin Chem 1998; 44(7):1379-80.
33. Krivak T C, Tian C, Rose G S, Armstrong D K, Maxwell G L. A Gynecologic Oncology Group Study of serum CA-125 levels in patients with stage III optimally debulked ovarian cancer treated with intraperitoneal compared to intravenous chemotherapy: an analysis of patients enrolled in GOG 172. Gynecol Oncol 2009; 115(1):81-5.
34. O'Brien T J, Beard J B, Underwood L J, Dennis R A, Santin A D, York L. The CA 125 gene: an extracellular superstructure dominated by repeat sequences. Tumour Biol 2001; 22(6):348-66.
35. Bellone S, Anfossi S, O'Brien T J, et al. Generation of CA125-specific cytotoxic T lymphocytes in human leukocyte antigen-A2.1-positive healthy donors and patients with advanced ovarian cancer. Am J Obstet Gynecol 2009; 200(1):75 el-10.
36. Berek J S. Immunotherapy of ovarian cancer with antibodies: a focus on oregovomab. Expert Opin Biol Ther 2004; 4(7):1159-65.
37. O'Brien T J, Tanimoto H, Konishi I, Gee M. More than 15 years of CA 125: what is known about the antigen, its structure and its function. Int J Biol Markers 1998; 13(4):188-95.
38. Rao T D, Park K J, Smith-Jones P, et al. Novel monoclonal antibodies against proximal (carboxy-terminal) portions of MUC16 (submitted to Applied Immunohistochemistry and Molecular Morphometry).
39. Wang Z, Raifu M, Howard M, et al. Universal PCR amplification of mouse immunoglobulin gene variable regions: the design of degenerate primers and an assessment of the effect of DNA polymerase 3' to 5' exonuclease activity. J Immunol Methods 2000; 233(1-2):167-77.
40. Doenecke A, Winnacker E L, Hallek M. Rapid amplification of cDNA ends (RACE) improves the PCR-based isolation of immunoglobulin variable region genes from murine and human lymphoma cells and cell lines. Leukemia 1997; 11(10):1787-92.
41. Gong M C, Latouche J B, Krause A, Heston W D, Bander N H, Sadelain M. Cancer patient T cells genetically targeted to prostate-specific membrane antigen specifically lyse prostate cancer cells and release cytokines in response to prostate-specific membrane antigen. Neoplasia 1999; 1(2):123-7.
42. Orlandi R, Gussow D H, Jones P T, Winter G. Cloning immunoglobulin variable domains for expression by the polymerase chain reaction. Proc Natl Acad Sci USA 1989; 86(10):3833-7.
43. Brentjens R J, Santos E, Nikhamin Y, et al. Genetically targeted T cells eradicate systemic acute lymphoblastic leukemia xenografts. Clin Cancer Res 2007; 13(18 Pt 1):5426-35.
44. Riviere I, Brose K, Mulligan R C. Effects of retroviral vector design on expression of human adenosine deaminase in murine bone marrow transplant recipients engrafted with genetically modified cells. Proc Natl Acad Sci USA 1995; 92(15):6733-7.
45. Quintas-Cardama A, Yeh R K, Hollyman D, et al. Multifactorial optimization of gammaretroviral gene transfer into human T lymphocytes for clinical application. Hum Gene Ther 2007; 18(12):1253-60.
46. Latouche J B, Sadelain M. Induction of human cytotoxic T lymphocytes by artificial antigen-presenting cells. Nat Biotechnol 2000; 18(4):405-9.
47. Santos E B, Yeh R, Lee J, et al. Sensitive in vivo imaging of T cells using a membrane-bound Gaussia princeps luciferase. Nat Med 2009; 15(3):338-44.
48. Park K J, Soslow R, Linkov I, Rao T D, D S. The extracellular portion of the MUC16 cytoplasmic domain is detectable in ovarian carcinomas using novel monoclonal antibody, 4H11. Mod Pathol, 2008; 21(1s):217A-218A.
49. Raspollini M R, Castiglione F, Rossi Degl'innocenti D, et al. Tumour-infiltrating gamma/delta T-lymphocytes are correlated with a brief disease-free interval in advanced ovarian serous carcinoma. Ann Oncol 2005; 16(4):590-6.
50. Tomsova M, Melichar B, Sedlakova I, Steiner I. Prognostic significance of CD3+ tumor-infiltrating lymphocytes in ovarian carcinoma. Gynecol Oncol 2008; 108(2): 415-20.
51. Woo E Y, Chu C S, Goletz T J, et al. Regulatory CD4(+)CD25(+) T cells in tumors from patients with early-stage non-small cell lung cancer and late-stage ovarian cancer. Cancer Res 2001; 61(12):4766-72.
52. Lamers C H, Langeveld S C, Groot-van Ruijven C M, Debets R, Sleijfer S, Gratama J W. Gene-modified T cells for adoptive immunotherapy of renal cell cancer maintain transgene-specific immune functions in vivo. Cancer Immunol Immunother 2007; 56(12):1875-83.
53. Brentjens R, Hollyman D, Weiss M, et al. A Phase I trial for the treatment of chemo-refractory chronic lymphocytic leukemia with CD19-targeted autologous T cells. Molecular Therapy 2008; 16:S15.
54. Barber A, Zhang T, DeMars L R, Conejo-Garcia J, Roby K F, Sentman C L. Chimeric NKG2D receptor-bearing T cells as immunotherapy for ovarian cancer. Cancer Res 2007; 67(10):5003-8.
55. Barber A, Zhang T, Sentman C L. Immunotherapy with chimeric NKG2D receptors leads to long-term tumor-free survival and development of host antitumor immunity in murine ovarian cancer. J Immunol 2008; 180(1):72-8.
56. Carpenito C, Milone M C, Hassan R, et al. Control of large, established tumor xenografts with genetically retargeted human T cells containing CD28 and CD137 domains. Proc Natl Acad Sci USA 2009; 106(9):3360-5.
57. Kershaw M H, Westwood J A, Hwu P. Dual-specific T cells combine proliferation and antitumor activity. Nat Biotechnol 2002; 20(12):1221-7.
58. Hung C F, Wu T C, Monie A, Roden R. Antigen-specific immunotherapy of cervical and ovarian cancer. Immunol Rev 2008; 222:43-69.

59. Westwood J A, Smyth M J, Teng M W, et al. Adoptive transfer of T cells modified with a humanized chimeric receptor gene inhibits growth of Lewis-Y-expressing tumors in mice. Proc Natl Acad Sci USA 2005; 102(52): 19051-6.
60. Habib-Agahi M, Jaberipour M, Searle P F. 4-1BBL costimulation retrieves CD28 expression in activated T cells. Cell Immunol 2009; 256(1-2):39-46.
61. Habib-Agahi M, Phan T T, Searle P F. Co-stimulation with 4-1BB ligand allows extended T-cell proliferation, synergizes with CD80/CD86 and can reactivate anergic T cells. Int Immunol 2007; 19(12):1383-94.
62. Brentjens R J, Sadelain M. Somatic cell engineering and the immunotherapy of leukemias and lymphomas. Adv Pharmacol 2004; 51:347-70.
63. Finney H M, Akbar A N, Lawson A D. Activation of resting human primary T cells with chimeric receptors: costimulation from CD28, inducible costimulator, CD134, and CD137 in series with signals from the TCR zeta chain. J Immunol 2004; 172(1):104-13.
64. Sadelain M, Riviere I, Brentjens R. Targeting tumours with genetically enhanced T lymphocytes. Nat Rev Cancer 2003; 3(1):35-45.
65. Wilkie S, Picco G, Foster J, et al. Retargeting of human T cells to tumor-associated MUC1: the evolution of a chimeric antigen receptor. J Immunol 2008; 180(7):4901-9.
66. Li Q, Ai J, Song Z, Liu J, Shan B. 4-1BB (CD137) ligand enhanced anti-tumor immune response against mouse forestomach carcinoma in vivo. Cell Mol Immunol 2008; 5(5):379-84.
67. Salih H R, Kosowski S G, Haluska V F, et al. Constitutive expression of functional 4-1BB (CD137) ligand on carcinoma cells. J Immunol 2000; 165(5):2903-10.
68. Wan Y L, Zheng S S, Zhao Z C, Li M W, Jia C K, Zhang H. Expression of co-stimulator 4-1BB molecule in hepatocellular carcinoma and adjacent non-tumor liver tissue, and its possible role in tumor immunity. World J Gastroenterol 2004; 10(2):195-9.

MICROORGANISM DEPOSIT

A hybridoma designated huMUC16Pep3-31A3.5, which produces the antibody designated 31A3 (also designated 31A3.5.1) in this specification, was deposited with the American Type Culture Collection (ATCC), located at 10801 University Boulevard, Manassas, Va. 20110-2209, on Mar. 25, 2011, in compliance with the Budapest Treaty on the International Recognition of the Deposit of Microorganisms for the Purposes of Patent Procedure, and was assigned ATCC Accession No. PTA-11773.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. An isolated monoclonal antibody, or an antigen-binding fragment thereof, that specifically binds to a MUC16 polypeptide or to an antigenic portion thereof, wherein the amino acid sequence of the MUC16 polypeptide is CGVLVTTRRRKKEGEYNVQQQ (SEQ ID N0:03).

2. The antibody or antigen-binding fragment of claim 1, wherein the antibody is as produced by a hybridoma cell deposited at the American Type Culture Collection (ATCC) under accession number PTA-11773.

3. The antibody or antigen-binding fragment of claim 1, wherein the antibody is a chimeric antibody.

4. The antibody or antigen-binding fragment of claim 1, wherein the antibody is a humanized antibody.

5. A chimeric monoclonal antibody comprising (a) human constant regions; and (b) the variable regions of an antibody as produced by a hybridoma cell deposited at the ATCC under accession number PTA-11773, or an antigen-binding fragment of said chimeric monoclonal antibody.

6. A humanized monoclonal antibody comprising (a) human constant regions; (b) human framework regions; and (c) the complementary determining regions of an antibody as produced by a hybridoma cell deposited at the ATCC under accession number PTA-11773, or an antigen-binding fragment of said humanized monoclonal antibody.

7. The antibody or antigen-binding fragment of claim 6, wherein substantially all of the framework region residues of the humanized antibody are those of a human immunoglobulin sequence, and wherein one or more of the framework region residues are replaced by corresponding nonhuman residues.

8. The antibody or antigen-binding fragment of claim 1, wherein the antigen-binding fragment is selected from the group consisting of a Fab fragment, a F(ab')2 fragment, and a Fv fragment.

9. The chimeric monoclonal antibody or antigen-binding fragment of claim 5 which is a chimeric monoclonal antibody comprising (a) human constant regions; and (b) the variable regions of an antibody as produced by a hybridoma cell deposited at the ATCC under accession number PTA-11773.

10. The humanized monoclonal antibody or antigen-binding fragment of claim 6 which is a humanized monoclonal antibody comprising (a) human constant regions; (b) human framework regions; and (c) the complementary determining regions of an antibody as produced by a hybridoma cell deposited at the ATCC under accession number PTA-11773.

11. A single chain variable fragment (scFv) comprising a variable heavy (VH) chain and a variable light (VL) chain, wherein the VH chain and the VL chain are of a monoclonal antibody that specifically binds to a MUC16 polypeptide or to an antigenic portion thereof, wherein the amino acid sequence of the MUC16 polypeptide is CGVLVTTRRRKKEGEYNVQQQ (SEQ ID NO:03).

12. A scFv comprising a VH chain and a VL chain, wherein the VH chain and the VL chain are of an antibody as produced by a hybridoma cell deposited at the ATCC under accession number PTA-11773.

13. A scFv comprising a VH chain and a VL chain, wherein the VH chain and the VL chain are of an antibody comprising (a) human framework regions; and (b) the complementary determining regions of an antibody as produced by a hybridoma cell deposited at the ATCC under accession number PTA-11773.

14. The antibody or antigen-binding fragment of claim 1, wherein the antibody or antigen-binding fragment is covalently linked to a cytotoxic agent or a prodrug of a cytotoxic agent.

15. The antibody or antigen-binding fragment of claim 6, wherein the antibody or antigen-binding fragment is covalently linked to a cytotoxic agent or a prodrug of a cytotoxic agent.

16. The scFv of claim 11 which is covalently linked to a cytotoxic agent or a prodrug of a cytotoxic agent.

17. The scFv of claim 12 which is covalently linked to a cytotoxic agent or a prodrug of a cytotoxic agent.

18. The antibody or antigen-binding fragment of claim 1, wherein the antibody internalizes into a cell.

19. The antibody or antigen-binding fragment of claim 6, wherein the antibody internalizes into a cell.

20. The antibody or antigen-binding fragment of claim 1, wherein the antibody lacks specific binding to a glycosylated MUC16 extracellular domain.

21. The antibody or antigen-binding fragment of claim 6, wherein the antibody lacks specific binding to a glycosylated MUC16 extracellular domain.

22. The antibody or antigen-binding fragment of claim 1, wherein the antibody is an IgG.

23. The antibody or antigen-binding fragment of claim 6, wherein the antibody is an IgG.

24. A hybridoma cell that produces an antibody that specifically binds to a MUC16 polypeptide or to an antigenic portion thereof, wherein the amino acid sequence of the MUC16 polypeptide is CGVLVTTRRRKKEGEYNVQQQ (SEQ ID NO:03).

25. The hybridoma cell of claim 24, wherein the hybridoma cell is as deposited at the ATCC under accession number PTA-11773.

26. A method for producing an antibody that specifically binds to a MUC16 polypeptide or to an antigenic portion thereof, comprising administering to a subject an immunologically effective amount of a MUC16 polypeptide, wherein the amino acid sequence of the MUC16 polypeptide is CGVLVTTRRRKKEGEYNVQQQ (SEQ ID NO:03).

27. A method for identifying a subject as having a cancer in which MUC16 is expressed, wherein said method comprises administering the antibody of claim 1 to the subject, and determining the presence and location of the antibody in the subject, wherein said antibody is labeled.

28. A method for identifying a subject as having a cancer in which MUC16 is expressed, wherein said method comprises administering the antibody of claim 6 to the subject, and determining the presence and location of the antibody in the subject, wherein said antibody is labeled.

29. The method of claim 27, wherein the cancer is selected from the group consisting of ovarian cancer and breast cancer.

30. The method of claim 28, wherein the cancer is selected from the group consisting of ovarian cancer and breast cancer.

31. An ex vivo method for identifying a subject as having a cancer in which MUC16 is expressed, wherein said method comprises:
   (a) contacting a sample obtained from the subject with the antibody of claim 1; and
   (b) determining whether the antibody has an increased level of binding to the sample as compared to binding to a sample obtained from a subject lacking the cancer in which MUC16 is expressed.

32. A method for treating a cancer in which MUC16 is expressed, comprising administering to a subject the antibody or antigen-binding fragment of claim 1.

33. A method for treating a cancer in which MUC16 is expressed, comprising administering to a subject the antibody of claim 6.

34. A method for treating a cancer in which MUC16 is expressed, comprising administering to a subject the scFv of claim 11.

35. A method for treating a cancer in which MUC16 is expressed, comprising administering to a subject the scFv of claim 13.

36. A method for treating a cancer in which MUC16 is expressed, comprising administering to a subject the antigen-binding fragment of claim 6.

37. The method of claim 32, wherein the cancer is selected from the group consisting of ovarian cancer and breast cancer.

38. The method of claim 33, wherein the cancer is selected from the group consisting of ovarian cancer and breast cancer.

39. The method of claim 34, wherein the cancer is selected from the group consisting of ovarian cancer and breast cancer.

40. The method of claim 35, wherein the cancer is selected from the group consisting of ovarian cancer and breast cancer.

41. The method of claim 36, wherein the cancer is selected from the group consisting of ovarian cancer and breast cancer.

42. The method of claim 32, which further comprises detecting a reduction in one or more symptoms of the cancer disease after the administering step.

43. A composition comprising (a) the antibody or antigen-binding fragment of claim 1 and (b) a pharmaceutically acceptable carrier.

* * * * *

SEQUENCE LISTING

```
<160> NUMBER OF SEQ ID NOS: 40

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Asn Phe Ser Pro Leu Ala Arg Arg Val Asp Arg Val Ala Ile Tyr Glu
1               5                   10                  15

Glu

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Thr Leu Asp Arg Ser Ser Val Leu Val Asp Gly Tyr Ser Pro Asn Arg
1               5                   10                  15

Asn Glu

<210> SEQ ID NO 3
<211> LENGTH: 21
<212> TYPE: PRT
<213> ORGANISM: Artificial Sequence
```

<220> FEATURE:
<223> OTHER INFORMATION: Synthetic

<400> SEQUENCE: 3

Cys Gly Val Leu Val Thr Thr Arg Arg Lys Lys Glu Gly Glu Tyr
1               5                   10                  15

Asn Val Gln Gln Gln
            20

<210> SEQ ID NO 4
<211> LENGTH: 366
<212> TYPE: DNA
<213> ORGANISM: Artificial Sequence
<220> FEATURE:
<223> OTHER INFORMATION: Synthetic

<400> SEQUENCE: 4
gtgaagctgg aggagtcagg gggaggcttc gtgaagcctg agggtccct caaaatctcc      60 tgtgcagcct ctggattcac tttcagaaac tatgccatgt cctgggttcg cctgagtccg    120
gagatgaggc tggagtgggt cgcaaccatt agcagtgctg gtggttacat cttctattct    180
gacagtgtgc agggacgatt caccatttcc agagacaatg ccaagaacac cctccacttg    240
caaatgggca gtctgaggtc tggggacacg gccatgtatt actgtgcaag gcagggattt    300
ggtaactacg gtgattacta tgctatggac tactggggcc aagggaccac ggtcaccgtc    360
tcctca                                                              366

<210> SEQ ID NO 5
<211> LENGTH: 339
<212> TYPE: DNA
<213> ORGANISM: Artificial Sequence
<220> FEATURE:
<223> OTHER INFORMATION: Synthetic

<400> SEQUENCE: 5
gacattgagc tcacccagtc tccatcctcc ctggctgtgt cagcaggaga gaaggtcact     60
atgagctgca atccagtca gagtctgctc aacagtagaa cccgaaagaa ccagttggct    120
tggtaccagc aaaaaacagg acagtctcct gaactgctga tctactgggc atccactcgg    180
caatctgggg tccctgatcg cttcacaggc agtggatctg ggacagattt cactctcacc    240
atcagcagtg tgcaggctga agacctggca gtttattact gccagcaatc ttataatcta    300
ctcacgttcg gtcctgggac caagctggag atcaaacgg                          339

<210> SEQ ID NO 6
<211> LENGTH: 366
<212> TYPE: DNA
<213> ORGANISM: Artificial Sequence
<220> FEATURE:
<223> OTHER INFORMATION: Synthetic

<400> SEQUENCE: 6
gtgaagctgc aggagtcagg gggaggcttc gtgaagcctg agggtccct caaagtctcc      60 tgtgcagcct ctggattcac tttcagtagc tatgccatgt cctgggttcg cctgagtccg    120
gagatgaggc tggagtgggt cgcaaccatt agcagtgctg gtggttacat cttctattct    180
gacagtgtgc agggacgatt caccatttcc agagacaatg ccaagaacac cctgcacctg    240
caaatgggca gtctgaggtc tggggacacg gccatgtatt actgtgcaag gcagggattt    300

```
ggtaactacg gtgattacta tgctatggac tactggggcc aagggaccac ggtcaccgtc      360
tcctca                                                                 366

<210> SEQ ID NO 7
<211> LENGTH: 339
<212> TYPE: DNA
<213> ORGANISM: Artificial Sequence
<220> FEATURE:
<223> OTHER INFORMATION: Synthetic

<400> SEQUENCE: 7
gacattgagc tcacccagtc tccatcctcc ctggctgtgt cagcaggaga gaaggtcact       60
atgagctgca atccagtca gagtctgctc aacagtagaa cccgaaagaa ccagttggct      120
tggtaccagc aaaaaccagg acagtctcct gaactgctga tctactgggc atccactagg     180
caatctggag tccctgatcg cttcacaggc agtggatctg gacagatttt cactctcacc     240
atcagcagtg tgcaggctga agacctggca gtttattact gccagcaatc ttataatcta     300
ctcacgttcg gtcctgggac caagctggag gtcaaacgg                            339

<210> SEQ ID NO 8
<211> LENGTH: 348
<212> TYPE: DNA
<213> ORGANISM: Artificial Sequence
<220> FEATURE:
<223> OTHER INFORMATION: Synthetic

<400> SEQUENCE: 8
gtgaagctgg aggagtcagg gggagacttg gtgaagcctg agggtccct gaaactctcc       60 tgtgcagtct ctggattcac tttcagtagc cattccatgt cttggattcg tcagactcca    120
gagaagaggc tagagtgggt cgcatccgtg agtagtggtg gtaggatcta ctattcggac    180
agtgtgaagg gccgattcac cgtcaccaga gaaaatgaca ggaacaccct gtatttgtta    240
atgagtagtc tgaggtctga ggacacggcc atgtattatt gtggaagagg acaggtattt    300
tatgctttgg acaattgggg ccaagggacc acggtcaccg tctcctca                 348

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacattgagc tcacccagtc tccatcctcc ctggctgtgt cagcaggaga gaaggtcact       60
atgagctgca atccagtca gagtctgctc aacagtagaa cccgaaagaa ccagttggct      120
tggtaccagc aaaaaccagg acagtctcct gaactgctga tctactgggc atccactagg     180
caatctggag tccctgatcg cttcacaggc agtggatctg gacagatttt cactctcacc     240
atcagcagtg tgcaggctga agacctggca gtttattact gccagcaatc ttataatcta     300
ctcacgttcg gtcctgggac caagctggag gtcaaacgg                            339

<210> SEQ ID NO 10
<211> LENGTH: 216
<212> TYPE: DNA
<213> ORGANISM: Artificial Sequence
<220> FEATURE:
<223> OTHER INFORMATION: Synthetic
```

<400> SEQUENCE: 10

```
gacattgagc tcacccagtc tccaaagctc ctgatctaca aggtttccaa ccgattttct    60
ggggtcccag acaggttcag tggcagtgga tcagggacag atttcacact caagatcagc   120
agagtggagg ctgaggatct gggagtttat tactgctttc aaggttcaca tgttccgtgg   180
acgttcggtg gagggaccaa gctggagatc aaacgg                             216
```

<210> SEQ ID NO 11
<211> LENGTH: 354
<212> TYPE: DNA
<213> ORGANISM: Artificial Sequence
<220> FEATURE:
<223> OTHER INFORMATION: Synthetic

<400> SEQUENCE: 11

```
gaggtgaagc tggaggagtc aggacctgaa ctggtgaagc ctggggcttc agtgaagata    60
tcctgcaagg cttctggtta ctcatttact ggctacttta tgaactgggt gaagcagacc   120
catggaaaga gccttgagtg gattggacgt attaatcctt acaatggtgc tactttctac   180
aatcagaagt tcacgggcaa ggccacaatg actgtagaca atcctctaca cagcccac     240
atggagctcc tgagcctgac atctgaggac tctgcagtct attattgtgg aaaggggaat   300
tactacggcc cctttgatta ctggggccaa gggaccacgg tcaccgtctc ctca         354
```

<210> SEQ ID NO 12
<211> LENGTH: 333
<212> TYPE: DNA
<213> ORGANISM: Artificial Sequence
<220> FEATURE:
<223> OTHER INFORMATION: Synthetic

<400> SEQUENCE: 12

```
gacattgagc tcacccagtc tccatcttat cttgctgcat ctcctgaaga aaccattact    60
attaattgca gggcaagtaa agagcattag caaatattag cctggtatca aaagaaacct   120
gggaaaacta ataagcttct tatctactct ggatccactt tgcaatctgg aattccatca   180
aggttcagtg gcagtggatc tggtacagat ttcactctca ccatcagtag cctggagcct   240
gaagattttg caatgtatta ctgtcaacag cataatgaat acccgtggac gttcggtgga   300
gggaccaagc tggagatcaa acgggcggcc gca                                333
```

<210> SEQ ID NO 13
<211> LENGTH: 14507
<212> TYPE: PRT
<213> ORGANISM: Homo sapiens

<400> SEQUENCE: 13

```
Met Leu Lys Pro Ser Gly Leu Pro Gly Ser Ser Pro Thr Arg Ser
 1               5                  10                  15

Leu Met Thr Gly Ser Arg Ser Thr Lys Ala Thr Pro Glu Met Asp Ser
                20                  25                  30

Gly Leu Thr Gly Ala Thr Leu Ser Pro Lys Thr Ser Thr Gly Ala Ile
            35                  40                  45

Val Val Thr Glu His Thr Leu Pro Phe Thr Ser Pro Asp Lys Thr Leu
        50                  55                  60

Ala Ser Pro Thr Ser Ser Val Val Gly Arg Thr Thr Gln Ser Leu Gly
    65                  70                  75                  80

Val Met Ser Ser Ala Leu Pro Glu Ser Thr Ser Arg Gly Met Thr His
                85                  90                  95
```

-continued

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Thr Glu Gly Asn Phe Thr Lys Glu Ala
    130                 135                 140

Ser Thr Tyr Thr Leu Thr Val Glu Thr Ser Gly Pro Val Thr Glu
145                 150                 155                 160

Lys Tyr Thr Val Pro Thr Glu Thr Ser Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
        195                 200                 205

Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
        275                 280                 285

Ser Val Leu Asp Asn Lys Ile Ser Glu Thr Ser Ile Phe Ser Gly Gln
    290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
        355                 360                 365

Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
        435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

```
Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
    595                 600                 605

Ile Ser Met Thr Gly Gly Ser Ser Thr Arg Gly Ser Gln Gly Thr Thr
610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
    675                 680                 685

Ala Phe Arg Glu Gly Thr Ser Leu Gly Leu Thr Pro Leu Asn Thr Arg
690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
    755                 760                 765

Val Leu Ser Ser Met Thr Leu Ser Asn Ala Ala Thr Ser Pro Glu Arg
770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
    835                 840                 845

Thr Phe Ser Ser Ser Thr Pro Ser Thr His Leu Phe Thr Ser Gly Glu
850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
    915                 920                 925

Thr Asn Ser Thr Gly Ser Ala Leu Pro Lys Ile Ser His Leu Thr Gly
```

-continued

```
              930             935             940
Thr Ala Thr Met Ser Gln Thr Asn Arg Asp Thr Phe Asn Asp Ser Ala
945             950             955             960
Ala Pro Gln Ser Thr Thr Trp Pro Glu Thr Ser Pro Arg Phe Lys Thr
            965             970             975
Gly Leu Pro Ser Ala Thr Thr Val Ser Thr Ser Ala Thr Ser Leu
        980             985             990
Ser Ala Thr Val Met Val Ser Lys Phe Thr Ser Pro Ala Thr Ser Ser
        995             1000            1005
Met Glu Ala Thr Ser Ile Arg Glu Pro Ser Thr Thr Ile Leu Thr
    1010            1015            1020
Thr Glu Thr Thr Asn Gly Pro Gly Ser Met Ala Val Ala Ser Thr
1025            1030            1035
Asn Ile Pro Ile Gly Lys Gly Tyr Ile Thr Glu Gly Arg Leu Asp
1040            1045            1050
Thr Ser His Leu Pro Ile Gly Thr Thr Ala Ser Ser Glu Thr Ser
1055            1060            1065
Met Asp Phe Thr Met Ala Lys Glu Ser Val Ser Met Ser Val Ser
1070            1075            1080
Pro Ser Gln Ser Met Asp Ala Ala Gly Ser Ser Thr Pro Gly Arg
1085            1090            1095
Thr Ser Gln Phe Val Asp Thr Phe Ser Asp Asp Val Tyr His Leu
1100            1105            1110
Thr Ser Arg Glu Ile Thr Ile Pro Arg Asp Gly Thr Ser Ser Ala
1115            1120            1125
Leu Thr Pro Gln Met Thr Ala Thr His Pro Pro Ser Pro Asp Pro
1130            1135            1140
Gly Ser Ala Arg Ser Thr Trp Leu Gly Ile Leu Ser Ser Ser Pro
1145            1150            1155
Ser Ser Pro Thr Pro Lys Val Thr Met Ser Ser Thr Phe Ser Thr
1160            1165            1170
Gln Arg Val Thr Thr Ser Met Ile Met Asp Thr Val Glu Thr Ser
1175            1180            1185
Arg Trp Asn Met Pro Asn Leu Pro Ser Thr Thr Ser Leu Thr Pro
1190            1195            1200
Ser Asn Ile Pro Thr Ser Gly Ala Ile Gly Lys Ser Thr Leu Val
1205            1210            1215
Pro Leu Asp Thr Pro Ser Pro Ala Thr Ser Leu Glu Ala Ser Glu
1220            1225            1230
Gly Gly Leu Pro Thr Leu Ser Thr Tyr Pro Glu Ser Thr Asn Thr
1235            1240            1245
Pro Ser Ile His Leu Gly Ala His Ala Ser Ser Glu Ser Pro Ser
1250            1255            1260
Thr Ile Lys Leu Thr Met Ala Ser Val Val Lys Pro Gly Ser Tyr
1265            1270            1275
Thr Pro Leu Thr Phe Pro Ser Ile Glu Thr His Ile His Val Ser
1280            1285            1290
Thr Ala Arg Met Ala Tyr Ser Gly Ser Ser Pro Glu Met Thr
1295            1300            1305
Ala Pro Gly Glu Thr Asn Thr Gly Ser Thr Trp Asp Pro Thr Thr
1310            1315            1320
Tyr Ile Thr Thr Thr Asp Pro Lys Asp Thr Ser Ser Ala Gln Val
1325            1330            1335
```

-continued

```
Ser Thr Pro His Ser Val Arg Thr Leu Arg Thr Thr Glu Asn His
1340                1345                1350

Pro Lys Thr Glu Ser Ala Thr Pro Ala Ala Tyr Ser Gly Ser Pro
1355                1360                1365

Lys Ile Ser Ser Ser Pro Asn Leu Thr Ser Pro Ala Thr Lys Ala
1370                1375                1380

Trp Thr Ile Thr Asp Thr Thr Glu His Ser Thr Gln Leu His Tyr
1385                1390                1395

Thr Lys Leu Ala Glu Lys Ser Ser Gly Phe Glu Thr Gln Ser Ala
1400                1405                1410

Pro Gly Pro Val Ser Val Val Ile Pro Thr Ser Pro Thr Ile Gly
1415                1420                1425

Ser Ser Thr Leu Glu Leu Thr Ser Asp Val Pro Gly Glu Pro Leu
1430                1435                1440

Val Leu Ala Pro Ser Glu Gln Thr Thr Ile Thr Leu Pro Met Ala
1445                1450                1455

Thr Trp Leu Ser Thr Ser Leu Thr Glu Glu Met Ala Ser Thr Asp
1460                1465                1470

Leu Asp Ile Ser Ser Pro Ser Ser Pro Met Ser Thr Phe Ala Ile
1475                1480                1485

Phe Pro Pro Met Ser Thr Pro Ser His Glu Leu Ser Lys Ser Glu
1490                1495                1500

Ala Asp Thr Ser Ala Ile Arg Asn Thr Asp Ser Thr Thr Leu Asp
1505                1510                1515

Gln His Leu Gly Ile Arg Ser Leu Gly Arg Thr Gly Asp Leu Thr
1520                1525                1530

Thr Val Pro Ile Thr Pro Leu Thr Thr Thr Trp Thr Ser Val Ile
1535                1540                1545

Glu His Ser Thr Gln Ala Gln Asp Thr Leu Ser Ala Thr Met Ser
1550                1555                1560

Pro Thr His Val Thr Gln Ser Leu Lys Asp Gln Thr Ser Ile Pro
1565                1570                1575

Ala Ser Ala Ser Pro Ser His Leu Thr Glu Val Tyr Pro Glu Leu
1580                1585                1590

Gly Thr Gln Gly Arg Ser Ser Ser Glu Ala Thr Thr Phe Trp Lys
1595                1600                1605

Pro Ser Thr Asp Thr Leu Ser Arg Glu Ile Glu Thr Gly Pro Thr
1610                1615                1620

Asn Ile Gln Ser Thr Pro Pro Met Asp Asn Thr Thr Thr Gly Ser
1625                1630                1635

Ser Ser Ser Gly Val Thr Leu Gly Ile Ala His Leu Pro Ile Gly
1640                1645                1650

Thr Ser Ser Pro Ala Glu Thr Ser Thr Asn Met Ala Leu Glu Arg
1655                1660                1665

Arg Ser Ser Thr Ala Thr Val Ser Met Ala Gly Thr Met Gly Leu
1670                1675                1680

Leu Val Thr Ser Ala Pro Gly Arg Ser Ile Ser Gln Ser Leu Gly
1685                1690                1695

Arg Val Ser Ser Val Leu Ser Glu Ser Thr Thr Glu Gly Val Thr
1700                1705                1710

Asp Ser Ser Lys Gly Ser Ser Pro Arg Leu Asn Thr Gln Gly Asn
1715                1720                1725
```

```
Thr Ala  Leu Ser Ser  Ser Leu  Glu Pro Ser  Tyr Ala  Glu Gly Ser
1730              1735                  1740

Gln Met  Ser Thr Ser  Ile Pro  Leu Thr Ser  Ser Pro  Thr Thr Pro
1745              1750                  1755

Asp Val  Glu Phe Ile  Gly Gly  Ser Thr Phe  Trp Thr  Lys Glu Val
1760              1765                  1770

Thr Thr  Val Met Thr  Ser Asp  Ile Ser Lys  Ser Ser  Ala Arg Thr
1775              1780                  1785

Glu Ser  Ser Ser Ala  Thr Leu  Met Ser Thr  Ala Leu  Gly Ser Thr
1790              1795                  1800

Glu Asn  Thr Gly Lys  Glu Lys  Leu Arg Thr  Ala Ser  Met Asp Leu
1805              1810                  1815

Pro Ser  Pro Thr Pro  Ser Met  Glu Val Thr  Pro Trp  Ile Ser Leu
1820              1825                  1830

Thr Leu  Ser Asn Ala  Pro Asn  Thr Thr Asp  Ser Leu  Asp Leu Ser
1835              1840                  1845

His Gly  Val His Thr  Ser Ser  Ala Gly Thr  Leu Ala  Thr Asp Arg
1850              1855                  1860

Ser Leu  Asn Thr Gly  Val Thr  Arg Ala Ser  Arg Leu  Glu Asn Gly
1865              1870                  1875

Ser Asp  Thr Ser Ser  Lys Ser  Leu Ser Met  Gly Asn  Ser Thr His
1880              1885                  1890

Thr Ser  Met Thr Tyr  Thr Glu  Lys Ser Glu  Val Ser  Ser Ser Ile
1895              1900                  1905

His Pro  Arg Pro Glu  Thr Ser  Ala Pro Gly  Ala Glu  Thr Thr Leu
1910              1915                  1920

Thr Ser  Thr Pro Gly  Asn Arg  Ala Ile Ser  Leu Thr  Leu Pro Phe
1925              1930                  1935

Ser Ser  Ile Pro Val  Glu Glu  Val Ile Ser  Thr Gly  Ile Thr Ser
1940              1945                  1950

Gly Pro  Asp Ile Asn  Ser Ala  Pro Met Thr  His Ser  Pro Ile Thr
1955              1960                  1965

Pro Pro  Thr Ile Val  Trp Thr  Ser Thr Gly  Thr Ile  Glu Gln Ser
1970              1975                  1980

Thr Gln  Pro Leu His  Ala Val  Ser Ser Glu  Lys Val  Ser Val Gln
1985              1990                  1995

Thr Gln  Ser Thr Pro  Tyr Val  Asn Ser Val  Ala Val  Ser Ala Ser
2000              2005                  2010

Pro Thr  His Glu Asn  Ser Val  Ser Ser Gly  Ser Ser  Thr Ser Ser
2015              2020                  2025

Pro Tyr  Ser Ser Ala  Ser Leu  Glu Ser Leu  Asp Ser  Thr Ile Ser
2030              2035                  2040

Arg Arg  Asn Ala Ile  Thr Ser  Trp Leu Trp  Asp Leu  Thr Thr Ser
2045              2050                  2055

Leu Pro  Thr Thr Thr  Trp Pro  Ser Thr Ser  Leu Ser  Glu Ala Leu
2060              2065                  2070

Ser Ser  Gly His Ser  Gly Val  Ser Asn Pro  Ser Ser  Thr Thr Thr
2075              2080                  2085

Glu Phe  Pro Leu Phe  Ser Ala  Ala Ser Thr  Ser Ala  Ala Lys Gln
2090              2095                  2100

Arg Asn  Pro Glu Thr  Glu Thr  His Gly Pro  Gln Asn  Thr Ala Ala
2105              2110                  2115

Ser Thr  Leu Asn Thr  Asp Ala  Ser Ser Val  Thr Gly  Leu Ser Glu
```

-continued

```
            2120                2125                  2130
Thr Pro Val Gly Ala Ser Ile Ser Ser Glu Val Pro Leu Pro Met
2135                2140                  2145

Ala Ile Thr Ser Arg Ser Asp Val Ser Gly Leu Thr Ser Glu Ser
2150                2155                  2160

Thr Ala Asn Pro Ser Leu Gly Thr Ala Ser Ser Ala Gly Thr Lys
2165                2170                  2175

Leu Thr Arg Thr Ile Ser Leu Pro Thr Ser Glu Ser Leu Val Ser
2180                2185                  2190

Phe Arg Met Asn Lys Asp Pro Trp Thr Val Ser Ile Pro Leu Gly
2195                2200                  2205

Ser His Pro Thr Thr Asn Thr Glu Thr Ser Ile Pro Val Asn Ser
2210                2215                  2220

Ala Gly Pro Pro Gly Leu Ser Thr Val Ala Ser Asp Val Ile Asp
2225                2230                  2235

Thr Pro Ser Asp Gly Ala Glu Ser Ile Pro Thr Val Ser Phe Ser
2240                2245                  2250

Pro Ser Pro Asp Thr Glu Val Thr Thr Ile Ser His Phe Pro Glu
2255                2260                  2265

Lys Thr Thr His Ser Phe Arg Thr Ile Ser Ser Leu Thr His Glu
2270                2275                  2280

Leu Thr Ser Arg Val Thr Pro Ile Pro Gly Asp Trp Met Ser Ser
2285                2290                  2295

Ala Met Ser Thr Lys Pro Thr Gly Ala Ser Pro Ser Ile Thr Leu
2300                2305                  2310

Gly Glu Arg Arg Thr Ile Thr Ser Ala Ala Pro Thr Thr Ser Pro
2315                2320                  2325

Ile Val Leu Thr Ala Ser Phe Thr Glu Thr Ser Thr Val Ser Leu
2330                2335                  2340

Asp Asn Glu Thr Thr Val Lys Thr Ser Asp Ile Leu Asp Ala Arg
2345                2350                  2355

Lys Thr Asn Glu Leu Pro Ser Asp Ser Ser Ser Ser Asp Leu
2360                2365                  2370

Ile Asn Thr Ser Ile Ala Ser Ser Thr Met Asp Val Thr Lys Thr
2375                2380                  2385

Ala Ser Ile Ser Pro Thr Ser Ile Ser Gly Met Thr Ala Ser Ser
2390                2395                  2400

Ser Pro Ser Leu Phe Ser Ser Asp Arg Pro Gln Val Pro Thr Ser
2405                2410                  2415

Thr Thr Glu Thr Asn Thr Ala Thr Ser Pro Ser Val Ser Ser Asn
2420                2425                  2430

Thr Tyr Ser Leu Asp Gly Gly Ser Asn Val Gly Gly Thr Pro Ser
2435                2440                  2445

Thr Leu Pro Pro Phe Thr Ile Thr His Pro Val Glu Thr Ser Ser
2450                2455                  2460

Ala Leu Leu Ala Trp Ser Arg Pro Val Arg Thr Phe Ser Thr Met
2465                2470                  2475

Val Ser Thr Asp Thr Ala Ser Gly Glu Asn Pro Thr Ser Ser Asn
2480                2485                  2490

Ser Val Val Thr Ser Val Pro Ala Pro Gly Thr Trp Thr Ser Val
2495                2500                  2505

Gly Ser Thr Thr Asp Leu Pro Ala Met Gly Phe Leu Lys Thr Ser
2510                2515                  2520
```

-continued

Pro Ala Gly Glu Ala His Ser Leu Leu Ala Ser Thr Ile Glu Pro
2525                2530                2535

Ala Thr Ala Phe Thr Pro His Leu Ser Ala Ala Val Val Thr Gly
2540                2545                2550

Ser Ser Ala Thr Ser Glu Ala Ser Leu Leu Thr Thr Ser Glu Ser
2555                2560                2565

Lys Ala Ile His Ser Ser Pro Gln Thr Pro Thr Thr Pro Thr Ser
2570                2575                2580

Gly Ala Asn Trp Glu Thr Ser Ala Thr Pro Glu Ser Leu Leu Val
2585                2590                2595

Val Thr Glu Thr Ser Asp Thr Thr Leu Thr Ser Lys Ile Leu Val
2600                2605                2610

Thr Asp Thr Ile Leu Phe Ser Thr Val Ser Thr Pro Pro Ser Lys
2615                2620                2625

Phe Pro Ser Thr Gly Thr Leu Ser Gly Ala Ser Phe Pro Thr Leu
2630                2635                2640

Leu Pro Asp Thr Pro Ala Ile Pro Leu Thr Ala Thr Glu Pro Thr
2645                2650                2655

Ser Ser Leu Ala Thr Ser Phe Asp Ser Thr Pro Leu Val Thr Ile
2660                2665                2670

Ala Ser Asp Ser Leu Gly Thr Val Pro Glu Thr Thr Leu Thr Met
2675                2680                2685

Ser Glu Thr Ser Asn Gly Asp Ala Leu Val Leu Lys Thr Val Ser
2690                2695                2700

Asn Pro Asp Arg Ser Ile Pro Gly Ile Thr Ile Gln Gly Val Thr
2705                2710                2715

Glu Ser Pro Leu His Pro Ser Ser Thr Ser Pro Ser Lys Ile Val
2720                2725                2730

Ala Pro Arg Asn Thr Thr Tyr Glu Gly Ser Ile Thr Val Ala Leu
2735                2740                2745

Ser Thr Leu Pro Ala Gly Thr Thr Gly Ser Leu Val Phe Ser Gln
2750                2755                2760

Ser Ser Glu Asn Ser Glu Thr Thr Ala Leu Val Asp Ser Ser Ala
2765                2770                2775

Gly Leu Glu Arg Ala Ser Val Met Pro Leu Thr Thr Gly Ser Gln
2780                2785                2790

Gly Met Ala Ser Ser Gly Gly Ile Arg Ser Gly Ser Thr His Ser
2795                2800                2805

Thr Gly Thr Lys Thr Phe Ser Ser Leu Pro Leu Thr Met Asn Pro
2810                2815                2820

Gly Glu Val Thr Ala Met Ser Glu Ile Thr Thr Asn Arg Leu Thr
2825                2830                2835

Ala Thr Gln Ser Thr Ala Pro Lys Gly Ile Pro Val Lys Pro Thr
2840                2845                2850

Ser Ala Glu Ser Gly Leu Leu Thr Pro Val Ser Ala Ser Ser Ser
2855                2860                2865

Pro Ser Lys Ala Phe Ala Ser Leu Thr Thr Ala Pro Pro Thr Trp
2870                2875                2880

Gly Ile Pro Gln Ser Thr Leu Thr Phe Glu Phe Ser Glu Val Pro
2885                2890                2895

Ser Leu Asp Thr Lys Ser Ala Ser Leu Pro Thr Pro Gly Gln Ser
2900                2905                2910

-continued

```
Leu Asn Thr Ile Pro Asp Ser Asp Ala Ser Thr Ala Ser Ser Ser
2915                2920                2925

Leu Ser Lys Ser Pro Glu Lys Asn Pro Arg Ala Arg Met Met Thr
2930                2935                2940

Ser Thr Lys Ala Ile Ser Ala Ser Ser Phe Gln Ser Thr Gly Phe
2945                2950                2955

Thr Glu Thr Pro Glu Gly Ser Ala Ser Pro Ser Met Ala Gly His
2960                2965                2970

Glu Pro Arg Val Pro Thr Ser Gly Thr Gly Asp Pro Arg Tyr Ala
2975                2980                2985

Ser Glu Ser Met Ser Tyr Pro Asp Pro Ser Lys Ala Ser Ser Ala
2990                2995                3000

Met Thr Ser Thr Ser Leu Ala Ser Lys Leu Thr Thr Leu Phe Ser
3005                3010                3015

Thr Gly Gln Ala Ala Arg Ser Gly Ser Ser Ser Ser Pro Ile Ser
3020                3025                3030

Leu Ser Thr Glu Lys Glu Thr Ser Phe Leu Ser Pro Thr Ala Ser
3035                3040                3045

Thr Ser Arg Lys Thr Ser Leu Phe Leu Gly Pro Ser Met Ala Arg
3050                3055                3060

Gln Pro Asn Ile Leu Val His Leu Gln Thr Ser Ala Leu Thr Leu
3065                3070                3075

Ser Pro Thr Ser Thr Leu Asn Met Ser Gln Glu Glu Pro Pro Glu
3080                3085                3090

Leu Thr Ser Ser Gln Thr Ile Ala Glu Glu Glu Gly Thr Thr Ala
3095                3100                3105

Glu Thr Gln Thr Leu Thr Phe Thr Pro Ser Glu Thr Pro Thr Ser
3110                3115                3120

Leu Leu Pro Val Ser Ser Pro Thr Glu Pro Thr Ala Arg Arg Lys
3125                3130                3135

Ser Ser Pro Glu Thr Trp Ala Ser Ser Ile Ser Val Pro Ala Lys
3140                3145                3150

Thr Ser Leu Val Glu Thr Thr Asp Gly Thr Leu Val Thr Thr Ile
3155                3160                3165

Lys Met Ser Ser Gln Ala Ala Gln Gly Asn Ser Thr Trp Pro Ala
3170                3175                3180

Pro Ala Glu Glu Thr Gly Ser Ser Pro Ala Gly Thr Ser Pro Gly
3185                3190                3195

Ser Pro Glu Met Ser Thr Thr Leu Lys Ile Met Ser Ser Lys Glu
3200                3205                3210

Pro Ser Ile Ser Pro Glu Ile Arg Ser Thr Val Arg Asn Ser Pro
3215                3220                3225

Trp Lys Thr Pro Glu Thr Thr Val Pro Met Glu Thr Thr Val Glu
3230                3235                3240

Pro Val Thr Leu Gln Ser Thr Ala Leu Gly Ser Gly Ser Thr Ser
3245                3250                3255

Ile Ser His Leu Pro Thr Gly Thr Thr Ser Pro Thr Lys Ser Pro
3260                3265                3270

Thr Glu Asn Met Leu Ala Thr Glu Arg Val Ser Leu Ser Pro Ser
3275                3280                3285

Pro Pro Glu Ala Trp Thr Asn Leu Tyr Ser Gly Thr Pro Gly Gly
3290                3295                3300

Thr Arg Gln Ser Leu Ala Thr Met Ser Ser Val Ser Leu Glu Ser
```

-continued

```
             3305                3310                 3315

Pro Thr Ala Arg Ser Ile Thr Gly Thr Gly Gln Gln Ser Ser Pro
3320                3325                3330

Glu Leu Val Ser Lys Thr Thr Gly Met Glu Phe Ser Met Trp His
3335                3340                3345

Gly Ser Thr Gly Gly Thr Thr Gly Asp Thr His Val Ser Leu Ser
3350                3355                3360

Thr Ser Ser Asn Ile Leu Glu Asp Pro Val Thr Ser Pro Asn Ser
3365                3370                3375

Val Ser Ser Leu Thr Asp Lys Ser Lys His Lys Thr Glu Thr Trp
3380                3385                3390

Val Ser Thr Thr Ala Ile Pro Ser Thr Val Leu Asn Asn Lys Ile
3395                3400                3405

Met Ala Ala Glu Gln Gln Thr Ser Arg Ser Val Asp Glu Ala Tyr
3410                3415                3420

Ser Ser Thr Ser Ser Trp Ser Asp Gln Thr Ser Gly Ser Asp Ile
3425                3430                3435

Thr Leu Gly Ala Ser Pro Asp Val Thr Asn Thr Leu Tyr Ile Thr
3440                3445                3450

Ser Thr Ala Gln Thr Thr Ser Leu Val Ser Leu Pro Ser Gly Asp
3455                3460                3465

Gln Gly Ile Thr Ser Leu Thr Asn Pro Ser Gly Gly Lys Thr Ser
3470                3475                3480

Ser Ala Ser Ser Val Thr Ser Pro Ser Ile Gly Leu Glu Thr Leu
3485                3490                3495

Arg Ala Asn Val Ser Ala Val Lys Ser Asp Ile Ala Pro Thr Ala
3500                3505                3510

Gly His Leu Ser Gln Thr Ser Ser Pro Ala Glu Val Ser Ile Leu
3515                3520                3525

Asp Val Thr Thr Ala Pro Thr Pro Gly Ile Ser Thr Thr Ile Thr
3530                3535                3540

Thr Met Gly Thr Asn Ser Ile Ser Thr Thr Thr Pro Asn Pro Glu
3545                3550                3555

Val Gly Met Ser Thr Met Asp Ser Thr Pro Ala Thr Glu Arg Arg
3560                3565                3570

Thr Thr Ser Thr Glu His Pro Ser Thr Trp Ser Ser Thr Ala Ala
3575                3580                3585

Ser Asp Ser Trp Thr Val Thr Asp Met Thr Ser Asn Leu Lys Val
3590                3595                3600

Ala Arg Ser Pro Gly Thr Ile Ser Thr Met His Thr Thr Ser Phe
3605                3610                3615

Leu Ala Ser Ser Thr Glu Leu Asp Ser Met Ser Thr Pro His Gly
3620                3625                3630

Arg Ile Thr Val Ile Gly Thr Ser Leu Val Thr Pro Ser Ser Asp
3635                3640                3645

Ala Ser Ala Val Lys Thr Glu Thr Ser Thr Ser Glu Arg Thr Leu
3650                3655                3660

Ser Pro Ser Asp Thr Thr Ala Ser Thr Pro Ile Ser Thr Phe Ser
3665                3670                3675

Arg Val Gln Arg Met Ser Ile Ser Val Pro Asp Ile Leu Ser Thr
3680                3685                3690

Ser Trp Thr Pro Ser Ser Thr Glu Ala Glu Asp Val Pro Val Ser
3695                3700                3705
```

```
Met Val Ser Thr Asp His Ala Ser Thr Lys Thr Asp Pro Asn Thr
3710            3715                3720

Pro Leu Ser Thr Phe Leu Phe Asp Ser Leu Ser Thr Leu Asp Trp
3725            3730                3735

Asp Thr Gly Arg Ser Leu Ser Ser Ala Thr Ala Thr Thr Ser Ala
3740            3745                3750

Pro Gln Gly Ala Thr Thr Pro Gln Glu Leu Thr Leu Glu Thr Met
3755            3760                3765

Ile Ser Pro Ala Thr Ser Gln Leu Pro Phe Ser Ile Gly His Ile
3770            3775                3780

Thr Ser Ala Val Thr Pro Ala Ala Met Ala Arg Ser Ser Gly Val
3785            3790                3795

Thr Phe Ser Arg Pro Asp Pro Thr Ser Lys Lys Ala Glu Gln Thr
3800            3805                3810

Ser Thr Gln Leu Pro Thr Thr Thr Ser Ala His Pro Gly Gln Val
3815            3820                3825

Pro Arg Ser Ala Ala Thr Thr Leu Asp Val Ile Pro His Thr Ala
3830            3835                3840

Lys Thr Pro Asp Ala Thr Phe Gln Arg Gln Gly Gln Thr Ala Leu
3845            3850                3855

Thr Thr Glu Ala Arg Ala Thr Ser Asp Ser Trp Asn Glu Lys Glu
3860            3865                3870

Lys Ser Thr Pro Ser Ala Pro Trp Ile Thr Glu Met Met Asn Ser
3875            3880                3885

Val Ser Glu Asp Thr Ile Lys Glu Val Thr Ser Ser Ser Ser Val
3890            3895                3900

Leu Arg Thr Leu Asn Thr Leu Asp Ile Asn Leu Glu Ser Gly Thr
3905            3910                3915

Thr Ser Ser Pro Ser Trp Lys Ser Ser Pro Tyr Glu Arg Ile Ala
3920            3925                3930

Pro Ser Glu Ser Thr Thr Asp Lys Glu Ala Ile His Pro Ser Thr
3935            3940                3945

Asn Thr Val Glu Thr Thr Gly Trp Val Thr Ser Ser Glu His Ala
3950            3955                3960

Ser His Ser Thr Ile Pro Ala His Ser Ala Ser Ser Lys Leu Thr
3965            3970                3975

Ser Pro Val Val Thr Thr Ser Thr Arg Glu Gln Ala Ile Val Ser
3980            3985                3990

Met Ser Thr Thr Thr Trp Pro Glu Ser Thr Arg Ala Arg Thr Glu
3995            4000                4005

Pro Asn Ser Phe Leu Thr Ile Glu Leu Arg Asp Val Ser Pro Tyr
4010            4015                4020

Met Asp Thr Ser Ser Thr Thr Gln Thr Ser Ile Ile Ser Ser Pro
4025            4030                4035

Gly Ser Thr Ala Ile Thr Lys Gly Pro Arg Thr Glu Ile Thr Ser
4040            4045                4050

Ser Lys Arg Ile Ser Ser Ser Phe Leu Ala Gln Ser Met Arg Ser
4055            4060                4065

Ser Asp Ser Pro Ser Glu Ala Ile Thr Arg Leu Ser Asn Phe Pro
4070            4075                4080

Ala Met Thr Glu Ser Gly Gly Met Ile Leu Ala Met Gln Thr Ser
4085            4090                4095
```

-continued

```
Pro Pro Gly Ala Thr Ser Leu Ser Ala Pro Thr Leu Asp Thr Ser
4100                4105                4110

Ala Thr Ala Ser Trp Thr Gly Thr Pro Leu Ala Thr Thr Gln Arg
4115                4120                4125

Phe Thr Tyr Ser Glu Lys Thr Thr Leu Phe Ser Lys Gly Pro Glu
4130                4135                4140

Asp Thr Ser Gln Pro Ser Pro Pro Ser Val Glu Glu Thr Ser Ser
4145                4150                4155

Ser Ser Ser Leu Val Pro Ile His Ala Thr Thr Ser Pro Ser Asn
4160                4165                4170

Ile Leu Leu Thr Ser Gln Gly His Ser Pro Ser Ser Thr Pro Pro
4175                4180                4185

Val Thr Ser Val Phe Leu Ser Glu Thr Ser Gly Leu Gly Lys Thr
4190                4195                4200

Thr Asp Met Ser Arg Ile Ser Leu Glu Pro Gly Thr Ser Leu Pro
4205                4210                4215

Pro Asn Leu Ser Ser Thr Ala Gly Glu Ala Leu Ser Thr Tyr Glu
4220                4225                4230

Ala Ser Arg Asp Thr Lys Ala Ile His His Ser Ala Asp Thr Ala
4235                4240                4245

Val Thr Asn Met Glu Ala Thr Ser Ser Glu Tyr Ser Pro Ile Pro
4250                4255                4260

Gly His Thr Lys Pro Ser Lys Ala Thr Ser Pro Leu Val Thr Ser
4265                4270                4275

His Ile Met Gly Asp Ile Thr Ser Ser Thr Ser Val Phe Gly Ser
4280                4285                4290

Ser Glu Thr Thr Glu Ile Glu Thr Val Ser Ser Val Asn Gln Gly
4295                4300                4305

Leu Gln Glu Arg Ser Thr Ser Gln Val Ala Ser Ser Ala Thr Glu
4310                4315                4320

Thr Ser Thr Val Ile Thr His Val Ser Ser Gly Asp Ala Thr Thr
4325                4330                4335

His Val Thr Lys Thr Gln Ala Thr Phe Ser Ser Gly Thr Ser Ile
4340                4345                4350

Ser Ser Pro His Gln Phe Ile Thr Ser Thr Asn Thr Phe Thr Asp
4355                4360                4365

Val Ser Thr Asn Pro Ser Thr Ser Leu Ile Met Thr Glu Ser Ser
4370                4375                4380

Gly Val Thr Ile Thr Thr Gln Thr Gly Pro Thr Gly Ala Ala Thr
4385                4390                4395

Gln Gly Pro Tyr Leu Leu Asp Thr Ser Thr Met Pro Tyr Leu Thr
4400                4405                4410

Glu Thr Pro Leu Ala Val Thr Pro Asp Phe Met Gln Ser Glu Lys
4415                4420                4425

Thr Thr Leu Ile Ser Lys Gly Pro Lys Asp Val Ser Trp Thr Ser
4430                4435                4440

Pro Pro Ser Val Ala Glu Thr Ser Tyr Pro Ser Ser Leu Thr Pro
4445                4450                4455

Phe Leu Val Thr Thr Ile Pro Pro Ala Thr Ser Thr Leu Gln Gly
4460                4465                4470

Gln His Thr Ser Ser Pro Val Ser Ala Thr Ser Val Leu Thr Ser
4475                4480                4485

Gly Leu Val Lys Thr Thr Asp Met Leu Asn Thr Ser Met Glu Pro
```

```
            4490                4495                4500
Val Thr Asn Ser Pro Gln Asn Leu Asn Asn Pro Ser Asn Glu Ile
4505                4510                4515

Leu Ala Thr Leu Ala Ala Thr Thr Asp Ile Glu Thr Ile His Pro
4520                4525                4530

Ser Ile Asn Lys Ala Val Thr Asn Met Gly Thr Ala Ser Ser Ala
4535                4540                4545

His Val Leu His Ser Thr Leu Pro Val Ser Ser Glu Pro Ser Thr
4550                4555                4560

Ala Thr Ser Pro Met Val Pro Ala Ser Ser Met Gly Asp Ala Leu
4565                4570                4575

Ala Ser Ile Ser Ile Pro Gly Ser Glu Thr Thr Asp Ile Glu Gly
4580                4585                4590

Glu Pro Thr Ser Ser Leu Thr Ala Gly Arg Lys Glu Asn Ser Thr
4595                4600                4605

Leu Gln Glu Met Asn Ser Thr Thr Glu Ser Asn Ile Ile Leu Ser
4610                4615                4620

Asn Val Ser Val Gly Ala Ile Thr Glu Ala Thr Lys Met Glu Val
4625                4630                4635

Pro Ser Phe Asp Ala Thr Phe Ile Pro Thr Pro Ala Gln Ser Thr
4640                4645                4650

Lys Phe Pro Asp Ile Phe Ser Val Ala Ser Ser Arg Leu Ser Asn
4655                4660                4665

Ser Pro Pro Met Thr Ile Ser Thr His Met Thr Thr Thr Gln Thr
4670                4675                4680

Gly Ser Ser Gly Ala Thr Ser Lys Ile Pro Leu Ala Leu Asp Thr
4685                4690                4695

Ser Thr Leu Glu Thr Ser Ala Gly Thr Pro Ser Val Val Thr Glu
4700                4705                4710

Gly Phe Ala His Ser Lys Ile Thr Thr Ala Met Asn Asn Asp Val
4715                4720                4725

Lys Asp Val Ser Gln Thr Asn Pro Pro Phe Gln Asp Glu Ala Ser
4730                4735                4740

Ser Pro Ser Ser Gln Ala Pro Val Leu Val Thr Thr Leu Pro Ser
4745                4750                4755

Ser Val Ala Phe Thr Pro Gln Trp His Ser Thr Ser Ser Pro Val
4760                4765                4770

Ser Met Ser Ser Val Leu Thr Ser Ser Leu Val Lys Thr Ala Gly
4775                4780                4785

Lys Val Asp Thr Ser Leu Glu Thr Val Thr Ser Ser Pro Gln Ser
4790                4795                4800

Met Ser Asn Thr Leu Asp Asp Ile Ser Val Thr Ser Ala Ala Thr
4805                4810                4815

Thr Asp Ile Glu Thr Thr His Pro Ser Ile Asn Thr Val Val Thr
4820                4825                4830

Asn Val Gly Thr Thr Gly Ser Ala Phe Glu Ser His Ser Thr Val
4835                4840                4845

Ser Ala Tyr Pro Glu Pro Ser Lys Val Thr Ser Pro Asn Val Thr
4850                4855                4860

Thr Ser Thr Met Glu Asp Thr Thr Ile Ser Arg Ser Ile Pro Lys
4865                4870                4875

Ser Ser Lys Thr Thr Arg Thr Glu Thr Glu Thr Thr Ser Ser Leu
4880                4885                4890
```

-continued

Thr Pro Lys Leu Arg Glu Thr Ser Ile Ser Gln Glu Ile Thr Ser
4895                4900                4905

Ser Thr Glu Thr Ser Thr Val Pro Tyr Lys Glu Leu Thr Gly Ala
4910                4915                4920

Thr Thr Glu Val Ser Arg Thr Asp Val Thr Ser Ser Ser Ser Thr
4925                4930                4935

Ser Phe Pro Gly Pro Asp Gln Ser Thr Val Ser Leu Asp Ile Ser
4940                4945                4950

Thr Glu Thr Asn Thr Arg Leu Ser Thr Ser Pro Ile Met Thr Glu
4955                4960                4965

Ser Ala Glu Ile Thr Ile Thr Thr Gln Thr Gly Pro His Gly Ala
4970                4975                4980

Thr Ser Gln Asp Thr Phe Thr Met Asp Pro Ser Asn Thr Thr Pro
4985                4990                4995

Gln Ala Gly Ile His Ser Ala Met Thr His Gly Phe Ser Gln Leu
5000                5005                5010

Asp Val Thr Thr Leu Met Ser Arg Ile Pro Gln Asp Val Ser Trp
5015                5020                5025

Thr Ser Pro Pro Ser Val Asp Lys Thr Ser Ser Pro Ser Ser Phe
5030                5035                5040

Leu Ser Ser Pro Ala Met Thr Thr Pro Ser Leu Ile Ser Ser Thr
5045                5050                5055

Leu Pro Glu Asp Lys Leu Ser Ser Pro Met Thr Ser Leu Leu Thr
5060                5065                5070

Ser Gly Leu Val Lys Ile Thr Asp Ile Leu Arg Thr Arg Leu Glu
5075                5080                5085

Pro Val Thr Ser Ser Leu Pro Asn Phe Ser Ser Thr Ser Asp Lys
5090                5095                5100

Ile Leu Ala Thr Ser Lys Asp Ser Lys Asp Thr Lys Glu Ile Phe
5105                5110                5115

Pro Ser Ile Asn Thr Glu Glu Thr Asn Val Lys Ala Asn Asn Ser
5120                5125                5130

Gly His Glu Ser His Ser Pro Ala Leu Ala Asp Ser Glu Thr Pro
5135                5140                5145

Lys Ala Thr Thr Gln Met Val Ile Thr Thr Thr Val Gly Asp Pro
5150                5155                5160

Ala Pro Ser Thr Ser Met Pro Val His Gly Ser Ser Glu Thr Thr
5165                5170                5175

Asn Ile Lys Arg Glu Pro Thr Tyr Phe Leu Thr Pro Arg Leu Arg
5180                5185                5190

Glu Thr Ser Thr Ser Gln Glu Ser Ser Phe Pro Thr Asp Thr Ser
5195                5200                5205

Phe Leu Leu Ser Lys Val Pro Thr Gly Thr Ile Thr Glu Val Ser
5210                5215                5220

Ser Thr Gly Val Asn Ser Ser Ser Lys Ile Ser Thr Pro Asp His
5225                5230                5235

Asp Lys Ser Thr Val Pro Asp Asp Thr Phe Thr Gly Glu Ile Pro
5240                5245                5250

Arg Val Phe Thr Ser Ser Ile Lys Thr Lys Ser Ala Glu Met Thr
5255                5260                5265

Ile Thr Thr Gln Ala Ser Pro Pro Glu Ser Ala Ser His Ser Thr
5270                5275                5280

```
Leu Pro  Leu Asp Thr Ser Thr  Thr Leu Ser Gln Gly  Gly Thr His
5285                5290                5295

Ser Thr  Val Thr Gln Gly Phe  Pro Tyr Ser Glu Val  Thr Thr Leu
5300                5305                5310

Met Gly  Met Gly Pro Gly Asn  Val Ser Trp Met Thr  Thr Pro Pro
5315                5320                5325

Val Glu  Glu Thr Ser Ser Val  Ser Ser Leu Met Ser  Ser Pro Ala
5330                5335                5340

Met Thr  Ser Pro Ser Pro Val  Ser Ser Thr Ser Pro  Gln Ser Ile
5345                5350                5355

Pro Ser  Ser Pro Leu Pro Val  Thr Ala Leu Pro Thr  Ser Val Leu
5360                5365                5370

Val Thr  Thr Thr Asp Val Leu  Gly Thr Thr Ser Pro  Glu Ser Val
5375                5380                5385

Thr Ser  Ser Pro Pro Asn Leu  Ser Ser Ile Thr His  Glu Arg Pro
5390                5395                5400

Ala Thr  Tyr Lys Asp Thr Ala  His Thr Glu Ala Ala  Met His His
5405                5410                5415

Ser Thr  Asn Thr Ala Val Thr  Asn Val Gly Thr Ser  Gly Ser Gly
5420                5425                5430

His Lys  Ser Gln Ser Ser Val  Leu Ala Asp Ser Glu  Thr Ser Lys
5435                5440                5445

Ala Thr  Pro Leu Met Ser Thr  Thr Ser Thr Leu Gly  Asp Thr Ser
5450                5455                5460

Val Ser  Thr Ser Thr Pro Asn  Ile Ser Gln Thr Asn  Gln Ile Gln
5465                5470                5475

Thr Glu  Pro Thr Ala Ser Leu  Ser Pro Arg Leu Arg  Glu Ser Ser
5480                5485                5490

Thr Ser  Glu Lys Thr Ser Ser  Thr Thr Glu Thr Asn  Thr Ala Phe
5495                5500                5505

Ser Tyr  Val Pro Thr Gly Ala  Ile Thr Gln Ala Ser  Arg Thr Glu
5510                5515                5520

Ile Ser  Ser Ser Arg Thr Ser  Ile Ser Asp Leu Asp  Arg Pro Thr
5525                5530                5535

Ile Ala  Pro Asp Ile Ser Thr  Gly Met Ile Thr Arg  Leu Phe Thr
5540                5545                5550

Ser Pro  Ile Met Thr Lys Ser  Ala Glu Met Thr Val  Thr Thr Gln
5555                5560                5565

Thr Thr  Thr Pro Gly Ala Thr  Ser Gln Gly Ile Leu  Pro Trp Asp
5570                5575                5580

Thr Ser  Thr Thr Leu Phe Gln  Gly Gly Thr His Ser  Thr Val Ser
5585                5590                5595

Gln Gly  Phe Pro His Ser Glu  Ile Thr Thr Leu Arg  Ser Arg Thr
5600                5605                5610

Pro Gly  Asp Val Ser Trp Met  Thr Thr Pro Pro Val  Glu Glu Thr
5615                5620                5625

Ser Ser  Gly Phe Ser Leu Met  Ser Pro Ser Met Thr  Ser Pro Ser
5630                5635                5640

Pro Val  Ser Ser Thr Ser Pro  Glu Ser Ile Pro Ser  Ser Pro Leu
5645                5650                5655

Pro Val  Thr Ala Leu Leu Thr  Ser Val Leu Val Thr  Thr Thr Asn
5660                5665                5670

Val Leu  Gly Thr Thr Ser Pro  Glu Pro Val Thr Ser  Ser Pro Pro
```

```
                        5675                    5680                    5685
Asn Leu Ser Ser Pro Thr Gln Glu Arg Leu Thr Thr Tyr Lys Asp
5690                    5695                    5700
Thr Ala His Thr Glu Ala Met His Ala Ser Met His Thr Asn Thr
5705                    5710                    5715
Ala Val Ala Asn Val Gly Thr Ser Ile Ser Gly His Glu Ser Gln
5720                    5725                    5730
Ser Ser Val Pro Ala Asp Ser His Thr Ser Lys Ala Thr Ser Pro
5735                    5740                    5745
Met Gly Ile Thr Phe Ala Met Gly Asp Thr Ser Val Ser Thr Ser
5750                    5755                    5760
Thr Pro Ala Phe Phe Glu Thr Arg Ile Gln Thr Glu Ser Thr Ser
5765                    5770                    5775
Ser Leu Ile Pro Gly Leu Arg Asp Thr Arg Thr Ser Glu Glu Ile
5780                    5785                    5790
Asn Thr Val Thr Glu Thr Ser Thr Val Leu Ser Glu Val Pro Thr
5795                    5800                    5805
Thr Thr Thr Thr Glu Val Ser Arg Thr Glu Val Ile Thr Ser Ser
5810                    5815                    5820
Arg Thr Thr Ile Ser Gly Pro Asp His Ser Lys Met Ser Pro Tyr
5825                    5830                    5835
Ile Ser Thr Glu Thr Ile Thr Arg Leu Ser Thr Phe Pro Phe Val
5840                    5845                    5850
Thr Gly Ser Thr Glu Met Ala Ile Thr Asn Gln Thr Gly Pro Ile
5855                    5860                    5865
Gly Thr Ile Ser Gln Ala Thr Leu Thr Leu Asp Thr Ser Ser Thr
5870                    5875                    5880
Ala Ser Trp Glu Gly Thr His Ser Pro Val Thr Gln Arg Phe Pro
5885                    5890                    5895
His Ser Glu Glu Thr Thr Thr Met Ser Arg Ser Thr Lys Gly Val
5900                    5905                    5910
Ser Trp Gln Ser Pro Pro Ser Val Glu Glu Thr Ser Ser Pro Ser
5915                    5920                    5925
Ser Pro Val Pro Leu Pro Ala Ile Thr Ser His Ser Ser Leu Tyr
5930                    5935                    5940
Ser Ala Val Ser Gly Ser Ser Pro Thr Ser Ala Leu Pro Val Thr
5945                    5950                    5955
Ser Leu Leu Thr Ser Gly Arg Arg Lys Thr Ile Asp Met Leu Asp
5960                    5965                    5970
Thr His Ser Glu Leu Val Thr Ser Ser Leu Pro Ser Ala Ser Ser
5975                    5980                    5985
Phe Ser Gly Glu Ile Leu Thr Ser Glu Ala Ser Thr Asn Thr Glu
5990                    5995                    6000
Thr Ile His Phe Ser Glu Asn Thr Ala Glu Thr Asn Met Gly Thr
6005                    6010                    6015
Thr Asn Ser Met His Lys Leu His Ser Ser Val Ser Ile His Ser
6020                    6025                    6030
Gln Pro Ser Gly His Thr Pro Pro Lys Val Thr Gly Ser Met Met
6035                    6040                    6045
Glu Asp Ala Ile Val Ser Thr Ser Thr Pro Gly Ser Pro Glu Thr
6050                    6055                    6060
Lys Asn Val Asp Arg Asp Ser Thr Ser Pro Leu Thr Pro Glu Leu
6065                    6070                    6075
```

```
Lys Glu Asp Ser Thr Ala Leu Val Met Asn Ser Thr Thr Glu Ser
6080            6085            6090

Asn Thr Val Phe Ser Ser Val Ser Leu Asp Ala Ala Thr Glu Val
6095            6100            6105

Ser Arg Ala Glu Val Thr Tyr Tyr Asp Pro Thr Phe Met Pro Ala
6110            6115            6120

Ser Ala Gln Ser Thr Lys Ser Pro Asp Ile Ser Pro Glu Ala Ser
6125            6130            6135

Ser Ser His Ser Asn Ser Pro Pro Leu Thr Ile Ser Thr His Lys
6140            6145            6150

Thr Ile Ala Thr Gln Thr Gly Pro Ser Gly Val Thr Ser Leu Gly
6155            6160            6165

Gln Leu Thr Leu Asp Thr Ser Thr Ile Ala Thr Ser Ala Gly Thr
6170            6175            6180

Pro Ser Ala Arg Thr Gln Asp Phe Val Asp Ser Glu Thr Thr Ser
6185            6190            6195

Val Met Asn Asn Asp Leu Asn Asp Val Leu Lys Thr Ser Pro Phe
6200            6205            6210

Ser Ala Glu Glu Ala Asn Ser Leu Ser Ser Gln Ala Pro Leu Leu
6215            6220            6225

Val Thr Thr Ser Pro Ser Pro Val Thr Ser Thr Leu Gln Glu His
6230            6235            6240

Ser Thr Ser Ser Leu Val Ser Val Thr Ser Val Pro Thr Pro Thr
6245            6250            6255

Leu Ala Lys Ile Thr Asp Met Asp Thr Asn Leu Glu Pro Val Thr
6260            6265            6270

Arg Ser Pro Gln Asn Leu Arg Asn Thr Leu Ala Thr Ser Glu Ala
6275            6280            6285

Thr Thr Asp Thr His Thr Met His Pro Ser Ile Asn Thr Ala Val
6290            6295            6300

Ala Asn Val Gly Thr Thr Ser Ser Pro Asn Glu Phe Tyr Phe Thr
6305            6310            6315

Val Ser Pro Asp Ser Asp Pro Tyr Lys Ala Thr Ser Ala Val Val
6320            6325            6330

Ile Thr Ser Thr Ser Gly Asp Ser Ile Val Ser Thr Ser Met Pro
6335            6340            6345

Arg Ser Ser Ala Met Lys Lys Ile Glu Ser Glu Thr Thr Phe Ser
6350            6355            6360

Leu Ile Phe Arg Leu Arg Glu Thr Ser Thr Ser Gln Lys Ile Gly
6365            6370            6375

Ser Ser Ser Asp Thr Ser Thr Val Phe Asp Lys Ala Phe Thr Ala
6380            6385            6390

Ala Thr Thr Glu Val Ser Arg Thr Glu Leu Thr Ser Ser Ser Arg
6395            6400            6405

Thr Ser Ile Gln Gly Thr Glu Lys Pro Thr Met Ser Pro Asp Thr
6410            6415            6420

Ser Thr Arg Ser Val Thr Met Leu Ser Thr Phe Ala Gly Leu Thr
6425            6430            6435

Lys Ser Glu Glu Arg Thr Ile Ala Thr Gln Thr Gly Pro His Arg
6440            6445            6450

Ala Thr Ser Gln Gly Thr Leu Thr Trp Asp Thr Ser Ile Thr Thr
6455            6460            6465
```

```
Ser Gln Ala Gly Thr His Ser Ala Met Thr His Gly Phe Ser Gln
6470                    6475                6480

Leu Asp Leu Ser Thr Leu Thr Ser Arg Val Pro Glu Tyr Ile Ser
6485                    6490                6495

Gly Thr Ser Pro Pro Ser Val Glu Lys Thr Ser Ser Ser Ser Ser
6500                    6505                6510

Leu Leu Ser Leu Pro Ala Ile Thr Ser Pro Ser Pro Val Pro Thr
6515                    6520                6525

Thr Leu Pro Glu Ser Arg Pro Ser Ser Pro Val His Leu Thr Ser
6530                    6535                6540

Leu Pro Thr Ser Gly Leu Val Lys Thr Thr Asp Met Leu Ala Ser
6545                    6550                6555

Val Ala Ser Leu Pro Pro Asn Leu Gly Ser Thr Ser His Lys Ile
6560                    6565                6570

Pro Thr Thr Ser Glu Asp Ile Lys Asp Thr Glu Lys Met Tyr Pro
6575                    6580                6585

Ser Thr Asn Ile Ala Val Thr Asn Val Gly Thr Thr Thr Ser Glu
6590                    6595                6600

Lys Glu Ser Tyr Ser Ser Val Pro Ala Tyr Ser Glu Pro Pro Lys
6605                    6610                6615

Val Thr Ser Pro Met Val Thr Ser Phe Asn Ile Arg Asp Thr Ile
6620                    6625                6630

Val Ser Thr Ser Met Pro Gly Ser Ser Glu Ile Thr Arg Ile Glu
6635                    6640                6645

Met Glu Ser Thr Phe Ser Leu Ala His Gly Leu Lys Gly Thr Ser
6650                    6655                6660

Thr Ser Gln Asp Pro Ile Val Ser Thr Glu Lys Ser Ala Val Leu
6665                    6670                6675

His Lys Leu Thr Thr Gly Ala Thr Glu Thr Ser Arg Thr Glu Val
6680                    6685                6690

Ala Ser Ser Arg Arg Thr Ser Ile Pro Gly Pro Asp His Ser Thr
6695                    6700                6705

Glu Ser Pro Asp Ile Ser Thr Glu Val Ile Pro Ser Leu Pro Ile
6710                    6715                6720

Ser Leu Gly Ile Thr Glu Ser Ser Asn Met Thr Ile Ile Thr Arg
6725                    6730                6735

Thr Gly Pro Pro Leu Gly Ser Thr Ser Gln Gly Thr Phe Thr Leu
6740                    6745                6750

Asp Thr Pro Thr Thr Ser Ser Arg Ala Gly Thr His Ser Met Ala
6755                    6760                6765

Thr Gln Glu Phe Pro His Ser Glu Met Thr Thr Val Met Asn Lys
6770                    6775                6780

Asp Pro Glu Ile Leu Ser Trp Thr Ile Pro Pro Ser Ile Glu Lys
6785                    6790                6795

Thr Ser Phe Ser Ser Ser Leu Met Pro Ser Pro Ala Met Thr Ser
6800                    6805                6810

Pro Pro Val Ser Ser Thr Leu Pro Lys Thr Ile His Thr Thr Pro
6815                    6820                6825

Ser Pro Met Thr Ser Leu Leu Thr Pro Ser Leu Val Met Thr Thr
6830                    6835                6840

Asp Thr Leu Gly Thr Ser Pro Glu Pro Thr Thr Ser Ser Pro Pro
6845                    6850                6855

Asn Leu Ser Ser Thr Ser His Glu Ile Leu Thr Thr Asp Glu Asp
```

-continued

```
                    6860                6865                    6870
Thr Thr Ala Ile Glu Ala Met His Pro Ser Thr Ser Thr Ala Ala
6875                6880                    6885

Thr Asn Val Glu Thr Thr Ser Ser Gly His Gly Ser Gln Ser Ser
6890                6895                    6900

Val Leu Ala Asp Ser Glu Lys Thr Lys Ala Thr Ala Pro Met Asp
6905                6910                    6915

Thr Thr Ser Thr Met Gly His Thr Thr Val Ser Thr Ser Met Ser
6920                6925                    6930

Val Ser Ser Glu Thr Thr Lys Ile Lys Arg Glu Ser Thr Tyr Ser
6935                6940                    6945

Leu Thr Pro Gly Leu Arg Glu Thr Ser Ile Ser Gln Asn Ala Ser
6950                6955                    6960

Phe Ser Thr Asp Thr Ser Ile Val Leu Ser Glu Val Pro Thr Gly
6965                6970                    6975

Thr Thr Ala Glu Val Ser Arg Thr Glu Val Thr Ser Ser Gly Arg
6980                6985                    6990

Thr Ser Ile Pro Gly Pro Ser Gln Ser Thr Val Leu Pro Glu Ile
6995                7000                    7005

Ser Thr Arg Thr Met Thr Arg Leu Phe Ala Ser Pro Thr Met Thr
7010                7015                    7020

Glu Ser Ala Glu Met Thr Ile Pro Thr Gln Thr Gly Pro Ser Gly
7025                7030                    7035

Ser Thr Ser Gln Asp Thr Leu Thr Leu Asp Thr Ser Thr Thr Lys
7040                7045                    7050

Ser Gln Ala Lys Thr His Ser Thr Leu Thr Gln Arg Phe Pro His
7055                7060                    7065

Ser Glu Met Thr Thr Leu Met Ser Arg Gly Pro Gly Asp Met Ser
7070                7075                    7080

Trp Gln Ser Ser Pro Ser Leu Glu Asn Pro Ser Ser Leu Pro Ser
7085                7090                    7095

Leu Leu Ser Leu Pro Ala Thr Thr Ser Pro Pro Pro Ile Ser Ser
7100                7105                    7110

Thr Leu Pro Val Thr Ile Ser Ser Ser Pro Leu Pro Val Thr Ser
7115                7120                    7125

Leu Leu Thr Ser Ser Pro Val Thr Thr Thr Asp Met Leu His Thr
7130                7135                    7140

Ser Pro Glu Leu Val Thr Ser Ser Pro Pro Lys Leu Ser His Thr
7145                7150                    7155

Ser Asp Glu Arg Leu Thr Thr Gly Lys Asp Thr Thr Asn Thr Glu
7160                7165                    7170

Ala Val His Pro Ser Thr Asn Thr Ala Ala Ser Asn Val Glu Ile
7175                7180                    7185

Pro Ser Ser Gly His Glu Ser Pro Ser Ser Ala Leu Ala Asp Ser
7190                7195                    7200

Glu Thr Ser Lys Ala Thr Ser Pro Met Phe Ile Thr Ser Thr Gln
7205                7210                    7215

Glu Asp Thr Thr Val Ala Ile Ser Thr Pro His Phe Leu Glu Thr
7220                7225                    7230

Ser Arg Ile Gln Lys Glu Ser Ile Ser Ser Leu Ser Pro Lys Leu
7235                7240                    7245

Arg Glu Thr Gly Ser Ser Val Glu Thr Ser Ser Ala Ile Glu Thr
7250                7255                    7260
```

-continued

Ser Ala Val Leu Ser Glu Val Ser Ile Gly Ala Thr Thr Glu Ile
7265            7270            7275

Ser Arg Thr Glu Val Thr Ser Ser Ser Arg Thr Ser Ile Ser Gly
7280            7285            7290

Ser Ala Glu Ser Thr Met Leu Pro Glu Ile Ser Thr Thr Arg Lys
7295            7300            7305

Ile Ile Lys Phe Pro Thr Ser Pro Ile Leu Ala Glu Ser Ser Glu
7310            7315            7320

Met Thr Ile Lys Thr Gln Thr Ser Pro Pro Gly Ser Thr Ser Glu
7325            7330            7335

Ser Thr Phe Thr Leu Asp Thr Ser Thr Thr Pro Ser Leu Val Ile
7340            7345            7350

Thr His Ser Thr Met Thr Gln Arg Leu Pro His Ser Glu Ile Thr
7355            7360            7365

Thr Leu Val Ser Arg Gly Ala Gly Asp Val Pro Arg Pro Ser Ser
7370            7375            7380

Leu Pro Val Glu Glu Thr Ser Pro Pro Ser Ser Gln Leu Ser Leu
7385            7390            7395

Ser Ala Met Ile Ser Pro Ser Pro Val Ser Thr Leu Pro Ala
7400            7405            7410

Ser Ser His Ser Ser Ser Ala Ser Val Thr Ser Leu Leu Thr Pro
7415            7420            7425

Gly Gln Val Lys Thr Thr Glu Val Leu Asp Ala Ser Ala Glu Pro
7430            7435            7440

Glu Thr Ser Ser Pro Pro Ser Leu Ser Ser Thr Ser Val Glu Ile
7445            7450            7455

Leu Ala Thr Ser Glu Val Thr Thr Asp Thr Glu Lys Ile His Pro
7460            7465            7470

Phe Ser Asn Thr Ala Val Thr Lys Val Gly Thr Ser Ser Ser Gly
7475            7480            7485

His Glu Ser Pro Ser Ser Val Leu Pro Asp Ser Glu Thr Thr Lys
7490            7495            7500

Ala Thr Ser Ala Met Gly Thr Ile Ser Ile Met Gly Asp Thr Ser
7505            7510            7515

Val Ser Thr Leu Thr Pro Ala Leu Ser Asn Thr Arg Lys Ile Gln
7520            7525            7530

Ser Glu Pro Ala Ser Ser Leu Thr Thr Arg Leu Arg Glu Thr Ser
7535            7540            7545

Thr Ser Glu Glu Thr Ser Leu Ala Thr Glu Ala Asn Thr Val Leu
7550            7555            7560

Ser Lys Val Ser Thr Gly Ala Thr Thr Glu Val Ser Arg Thr Glu
7565            7570            7575

Ala Ile Ser Phe Ser Arg Thr Ser Met Ser Gly Pro Glu Gln Ser
7580            7585            7590

Thr Met Ser Gln Asp Ile Ser Ile Gly Thr Ile Pro Arg Ile Ser
7595            7600            7605

Ala Ser Ser Val Leu Thr Glu Ser Ala Lys Met Thr Ile Thr Thr
7610            7615            7620

Gln Thr Gly Pro Ser Glu Ser Thr Leu Glu Ser Thr Leu Asn Leu
7625            7630            7635

Asn Thr Ala Thr Thr Pro Ser Trp Val Glu Thr His Ser Ile Val
7640            7645            7650

-continued

```
Ile Gln Gly Phe Pro His Pro Glu Met Thr Thr Ser Met Gly Arg
7655                7660                7665

Gly Pro Gly Gly Val Ser Trp Pro Ser Pro Pro Phe Val Lys Glu
7670                7675                7680

Thr Ser Pro Pro Ser Ser Pro Leu Ser Leu Pro Ala Val Thr Ser
7685                7690                7695

Pro His Pro Val Ser Thr Thr Phe Leu Ala His Ile Pro Pro Ser
7700                7705                7710

Pro Leu Pro Val Thr Ser Leu Leu Thr Ser Gly Pro Ala Thr Thr
7715                7720                7725

Thr Asp Ile Leu Gly Thr Ser Thr Glu Pro Gly Thr Ser Ser Ser
7730                7735                7740

Ser Ser Leu Ser Thr Thr Ser His Glu Arg Leu Thr Thr Tyr Lys
7745                7750                7755

Asp Thr Ala His Thr Glu Ala Val His Pro Ser Thr Asn Thr Gly
7760                7765                7770

Gly Thr Asn Val Ala Thr Thr Ser Ser Gly Tyr Lys Ser Gln Ser
7775                7780                7785

Ser Val Leu Ala Asp Ser Ser Pro Met Cys Thr Thr Ser Thr Met
7790                7795                7800

Gly Asp Thr Ser Val Leu Thr Ser Thr Pro Ala Phe Leu Glu Thr
7805                7810                7815

Arg Arg Ile Gln Thr Glu Leu Ala Ser Ser Leu Thr Pro Gly Leu
7820                7825                7830

Arg Glu Ser Ser Gly Ser Glu Gly Thr Ser Ser Gly Thr Lys Met
7835                7840                7845

Ser Thr Val Leu Ser Lys Val Pro Thr Gly Ala Thr Thr Glu Ile
7850                7855                7860

Ser Lys Glu Asp Val Thr Ser Ile Pro Gly Pro Ala Gln Ser Thr
7865                7870                7875

Ile Ser Pro Asp Ile Ser Thr Arg Thr Val Ser Trp Phe Ser Thr
7880                7885                7890

Ser Pro Val Met Thr Glu Ser Ala Glu Ile Thr Met Asn Thr His
7895                7900                7905

Thr Ser Pro Leu Gly Ala Thr Thr Gln Gly Thr Ser Thr Leu Asp
7910                7915                7920

Thr Ser Ser Thr Thr Ser Leu Thr Met Thr His Ser Thr Ile Ser
7925                7930                7935

Gln Gly Phe Ser His Ser Gln Met Ser Thr Leu Met Arg Arg Gly
7940                7945                7950

Pro Glu Asp Val Ser Trp Met Ser Pro Pro Leu Leu Glu Lys Thr
7955                7960                7965

Arg Pro Ser Phe Ser Leu Met Ser Ser Pro Ala Thr Thr Ser Pro
7970                7975                7980

Ser Pro Val Ser Ser Thr Leu Pro Glu Ser Ile Ser Ser Ser Pro
7985                7990                7995

Leu Pro Val Thr Ser Leu Leu Thr Ser Gly Leu Ala Lys Thr Thr
8000                8005                8010

Asp Met Leu His Lys Ser Ser Glu Pro Val Thr Asn Ser Pro Ala
8015                8020                8025

Asn Leu Ser Ser Thr Ser Val Glu Ile Leu Ala Thr Ser Glu Val
8030                8035                8040

Thr Thr Asp Thr Glu Lys Thr His Pro Ser Ser Asn Arg Thr Val
```

-continued

```
             8045                  8050                    8055
Thr Asp Val Gly Thr Ser Ser   Ser Gly His Glu Ser   Thr Ser Phe
8060                  8065                    8070

Val Leu Ala Asp Ser Gln Thr   Ser Lys Val Thr Ser   Pro Met Val
8075                  8080                    8085

Ile Thr Ser Thr Met Glu Asp   Thr Ser Val Ser Thr   Ser Thr Pro
8090                  8095                    8100

Gly Phe Phe Glu Thr Ser Arg   Ile Gln Thr Glu Pro   Thr Ser Ser
8105                  8110                    8115

Leu Thr Leu Gly Leu Arg Lys   Thr Ser Ser Ser Glu   Gly Thr Ser
8120                  8125                    8130

Leu Ala Thr Glu Met Ser Thr   Val Leu Ser Gly Val   Pro Thr Gly
8135                  8140                    8145

Ala Thr Ala Glu Val Ser Arg   Thr Glu Val Thr Ser   Ser Ser Arg
8150                  8155                    8160

Thr Ser Ile Ser Gly Phe Ala   Gln Leu Thr Val Ser   Pro Glu Thr
8165                  8170                    8175

Ser Thr Glu Thr Ile Thr Arg   Leu Pro Thr Ser Ser   Ile Met Thr
8180                  8185                    8190

Glu Ser Ala Glu Met Met Ile   Lys Thr Gln Thr Asp   Pro Pro Gly
8195                  8200                    8205

Ser Thr Pro Glu Ser Thr His   Thr Val Asp Ile Ser   Thr Thr Pro
8210                  8215                    8220

Asn Trp Val Glu Thr His Ser   Thr Val Thr Gln Arg   Phe Ser His
8225                  8230                    8235

Ser Glu Met Thr Thr Leu Val   Ser Arg Ser Pro Gly   Asp Met Leu
8240                  8245                    8250

Trp Pro Ser Gln Ser Ser Val   Glu Glu Thr Ser Ser   Ala Ser Ser
8255                  8260                    8265

Leu Leu Ser Leu Pro Ala Thr   Thr Ser Pro Ser Pro   Val Ser Ser
8270                  8275                    8280

Thr Leu Val Glu Asp Phe Pro   Ser Ala Ser Leu Pro   Val Thr Ser
8285                  8290                    8295

Leu Leu Asn Pro Gly Leu Val   Ile Thr Thr Asp Arg   Met Gly Ile
8300                  8305                    8310

Ser Arg Glu Pro Gly Thr Ser   Ser Thr Ser Asn Leu   Ser Ser Thr
8315                  8320                    8325

Ser His Glu Arg Leu Thr Thr   Leu Glu Asp Thr Val   Asp Thr Glu
8330                  8335                    8340

Asp Met Gln Pro Ser Thr His   Thr Ala Val Thr Asn   Val Arg Thr
8345                  8350                    8355

Ser Ile Ser Gly His Glu Ser   Gln Ser Ser Val Leu   Ser Asp Ser
8360                  8365                    8370

Glu Thr Pro Lys Ala Thr Ser   Pro Met Gly Thr Thr   Tyr Thr Met
8375                  8380                    8385

Gly Glu Thr Ser Val Ser Ile   Ser Thr Ser Asp Phe   Phe Glu Thr
8390                  8395                    8400

Ser Arg Ile Gln Ile Glu Pro   Thr Ser Ser Leu Thr   Ser Gly Leu
8405                  8410                    8415

Arg Glu Thr Ser Ser Ser Glu   Arg Ile Ser Ser Ala   Thr Glu Gly
8420                  8425                    8430

Ser Thr Val Leu Ser Glu Val   Pro Ser Gly Ala Thr   Thr Glu Val
8435                  8440                    8445
```

```
Ser Arg  Thr Glu Val Ile Ser  Ser Arg Gly Thr Ser  Met Ser Gly
8450             8455             8460

Pro Asp  Gln Phe Thr Ile Ser  Pro Asp Ile Ser Thr  Glu Ala Ile
8465             8470             8475

Thr Arg  Leu Ser Thr Ser Pro  Ile Met Thr Glu Ser  Ala Glu Ser
8480             8485             8490

Ala Ile  Thr Ile Glu Thr Gly  Ser Pro Gly Ala Thr  Ser Glu Gly
8495             8500             8505

Thr Leu  Thr Leu Asp Thr Ser  Thr Thr Thr Phe Trp  Ser Gly Thr
8510             8515             8520

His Ser  Thr Ala Ser Pro Gly  Phe Ser His Ser Glu  Met Thr Thr
8525             8530             8535

Leu Met  Ser Arg Thr Pro Gly  Asp Val Pro Trp Pro  Ser Leu Pro
8540             8545             8550

Ser Val  Glu Glu Ala Ser Ser  Val Ser Ser Ser Leu  Ser Ser Pro
8555             8560             8565

Ala Met  Thr Ser Thr Ser Phe  Phe Ser Thr Leu Pro  Glu Ser Ile
8570             8575             8580

Ser Ser  Ser Pro His Pro Val  Thr Ala Leu Leu Thr  Leu Gly Pro
8585             8590             8595

Val Lys  Thr Thr Asp Met Leu  Arg Thr Ser Ser Glu  Pro Glu Thr
8600             8605             8610

Ser Ser  Pro Pro Asn Leu Ser  Ser Thr Ser Ala Glu  Ile Leu Ala
8615             8620             8625

Thr Ser  Glu Val Thr Lys Asp  Arg Glu Lys Ile His  Pro Ser Ser
8630             8635             8640

Asn Thr  Pro Val Val Asn Val  Gly Thr Val Ile Tyr  Lys His Leu
8645             8650             8655

Ser Pro  Ser Ser Val Leu Ala  Asp Leu Val Thr Thr  Lys Pro Thr
8660             8665             8670

Ser Pro  Met Ala Thr Thr Ser  Thr Leu Gly Asn Thr  Ser Val Ser
8675             8680             8685

Thr Ser  Thr Pro Ala Phe Pro  Glu Thr Met Met Thr  Gln Pro Thr
8690             8695             8700

Ser Ser  Leu Thr Ser Gly Leu  Arg Glu Ile Ser Thr  Ser Gln Glu
8705             8710             8715

Thr Ser  Ser Ala Thr Glu Arg  Ser Ala Ser Leu Ser  Gly Met Pro
8720             8725             8730

Thr Gly  Ala Thr Thr Lys Val  Ser Arg Thr Glu Ala  Leu Ser Leu
8735             8740             8745

Gly Arg  Thr Ser Thr Pro Gly  Pro Ala Gln Ser Thr  Ile Ser Pro
8750             8755             8760

Glu Ile  Ser Thr Glu Thr Ile  Thr Arg Ile Ser Thr  Pro Leu Thr
8765             8770             8775

Thr Thr  Gly Ser Ala Glu Met  Thr Ile Thr Pro Lys  Thr Gly His
8780             8785             8790

Ser Gly  Ala Ser Ser Gln Gly  Thr Phe Thr Leu Asp  Thr Ser Ser
8795             8800             8805

Arg Ala  Ser Trp Pro Gly Thr  His Ser Ala Ala Thr  His Arg Ser
8810             8815             8820

Pro His  Ser Gly Met Thr Thr  Pro Met Ser Arg Gly  Pro Glu Asp
8825             8830             8835
```

```
Val Ser Trp Pro Ser Arg Pro Ser Val Glu Lys Thr Ser Pro Pro
8840            8845            8850

Ser Ser Leu Val Ser Leu Ser Ala Val Thr Ser Pro Ser Pro Leu
8855            8860            8865

Tyr Ser Thr Pro Ser Glu Ser Ser His Ser Ser Pro Leu Arg Val
8870            8875            8880

Thr Ser Leu Phe Thr Pro Val Met Met Lys Thr Thr Asp Met Leu
8885            8890            8895

Asp Thr Ser Leu Glu Pro Val Thr Thr Ser Pro Pro Ser Met Asn
8900            8905            8910

Ile Thr Ser Asp Glu Ser Leu Ala Thr Ser Lys Ala Thr Met Glu
8915            8920            8925

Thr Glu Ala Ile Gln Leu Ser Glu Asn Thr Ala Val Thr Gln Met
8930            8935            8940

Gly Thr Ile Ser Ala Arg Gln Glu Phe Tyr Ser Ser Tyr Pro Gly
8945            8950            8955

Leu Pro Glu Pro Ser Lys Val Thr Ser Pro Val Val Thr Ser Ser
8960            8965            8970

Thr Ile Lys Asp Ile Val Ser Thr Thr Ile Pro Ala Ser Ser Glu
8975            8980            8985

Ile Thr Arg Ile Glu Met Glu Ser Thr Ser Thr Leu Thr Pro Thr
8990            8995            9000

Pro Arg Glu Thr Ser Thr Ser Gln Glu Ile His Ser Ala Thr Lys
9005            9010            9015

Pro Ser Thr Val Pro Tyr Lys Ala Leu Thr Ser Ala Thr Ile Glu
9020            9025            9030

Asp Ser Met Thr Gln Val Met Ser Ser Ser Arg Gly Pro Ser Pro
9035            9040            9045

Asp Gln Ser Thr Met Ser Gln Asp Ile Ser Thr Glu Val Ile Thr
9050            9055            9060

Arg Leu Ser Thr Ser Pro Ile Lys Thr Glu Ser Thr Glu Met Thr
9065            9070            9075

Ile Thr Thr Gln Thr Gly Ser Pro Gly Ala Thr Ser Arg Gly Thr
9080            9085            9090

Leu Thr Leu Asp Thr Ser Thr Thr Phe Met Ser Gly Thr His Ser
9095            9100            9105

Thr Ala Ser Gln Gly Phe Ser His Ser Gln Met Thr Ala Leu Met
9110            9115            9120

Ser Arg Thr Pro Gly Asp Val Pro Trp Leu Ser His Pro Ser Val
9125            9130            9135

Glu Glu Ala Ser Ser Ala Ser Phe Ser Leu Ser Ser Pro Val Met
9140            9145            9150

Thr Ser Ser Ser Pro Val Ser Ser Thr Leu Pro Asp Ser Ile His
9155            9160            9165

Ser Ser Ser Leu Pro Val Thr Ser Leu Leu Thr Ser Gly Leu Val
9170            9175            9180

Lys Thr Thr Glu Leu Leu Gly Thr Ser Ser Glu Pro Glu Thr Ser
9185            9190            9195

Ser Pro Pro Asn Leu Ser Ser Thr Ser Ala Glu Ile Leu Ala Ile
9200            9205            9210

Thr Glu Val Thr Thr Asp Thr Glu Lys Leu Glu Met Thr Asn Val
9215            9220            9225

Val Thr Ser Gly Tyr Thr His Glu Ser Pro Ser Ser Val Leu Ala
```

-continued

```
                    9230                9235                    9240

Asp Ser Val Thr Thr Lys Ala Thr Ser Ser Met Gly Ile Thr Tyr
9245                9250                    9255

Pro Thr Gly Asp Thr Asn Val Leu Thr Ser Thr Pro Ala Phe Ser
9260                9265                    9270

Asp Thr Ser Arg Ile Gln Thr Lys Ser Lys Leu Ser Leu Thr Pro
9275                9280                    9285

Gly Leu Met Glu Thr Ser Ile Ser Glu Glu Thr Ser Ser Ala Thr
9290                9295                    9300

Glu Lys Ser Thr Val Leu Ser Ser Val Pro Thr Gly Ala Thr Thr
9305                9310                    9315

Glu Val Ser Arg Thr Glu Ala Ile Ser Ser Ser Arg Thr Ser Ile
9320                9325                    9330

Pro Gly Pro Ala Gln Ser Thr Met Ser Ser Asp Thr Ser Met Glu
9335                9340                    9345

Thr Ile Thr Arg Ile Ser Thr Pro Leu Thr Arg Lys Glu Ser Thr
9350                9355                    9360

Asp Met Ala Ile Thr Pro Lys Thr Gly Pro Ser Gly Ala Thr Ser
9365                9370                    9375

Gln Gly Thr Phe Thr Leu Asp Ser Ser Ser Thr Ala Ser Trp Pro
9380                9385                    9390

Gly Thr His Ser Ala Thr Thr Gln Arg Phe Pro Gln Ser Val Val
9395                9400                    9405

Thr Thr Pro Met Ser Arg Gly Pro Glu Asp Val Ser Trp Pro Ser
9410                9415                    9420

Pro Leu Ser Val Glu Lys Asn Ser Pro Ser Ser Leu Val Ser
9425                9430                    9435

Ser Ser Ser Val Thr Ser Pro Ser Pro Leu Tyr Ser Thr Pro Ser
9440                9445                    9450

Gly Ser Ser His Ser Ser Pro Val Pro Val Thr Ser Leu Phe Thr
9455                9460                    9465

Ser Ile Met Met Lys Ala Thr Asp Met Leu Asp Ala Ser Leu Glu
9470                9475                    9480

Pro Glu Thr Thr Ser Ala Pro Asn Met Asn Ile Thr Ser Asp Glu
9485                9490                    9495

Ser Leu Ala Ala Ser Lys Ala Thr Thr Glu Thr Glu Ala Ile His
9500                9505                    9510

Val Phe Glu Asn Thr Ala Ala Ser His Val Glu Thr Thr Ser Ala
9515                9520                    9525

Thr Glu Glu Leu Tyr Ser Ser Ser Pro Gly Phe Ser Glu Pro Thr
9530                9535                    9540

Lys Val Ile Ser Pro Val Val Thr Ser Ser Ser Ile Arg Asp Asn
9545                9550                    9555

Met Val Ser Thr Thr Met Pro Gly Ser Ser Gly Ile Thr Arg Ile
9560                9565                    9570

Glu Ile Glu Ser Met Ser Ser Leu Thr Pro Gly Leu Arg Glu Thr
9575                9580                    9585

Arg Thr Ser Gln Asp Ile Thr Ser Ser Thr Glu Thr Ser Thr Val
9590                9595                    9600

Leu Tyr Lys Met Pro Ser Gly Ala Thr Pro Glu Val Ser Arg Thr
9605                9610                    9615

Glu Val Met Pro Ser Ser Arg Thr Ser Ile Pro Gly Pro Ala Gln
9620                9625                    9630
```

-continued

Ser Thr Met Ser Leu Asp Ile Ser Asp Glu Val Val Thr Arg Leu
9635                9640            9645

Ser Thr Ser Pro Ile Met Thr Glu Ser Ala Glu Ile Thr Ile Thr
9650                9655            9660

Thr Gln Thr Gly Tyr Ser Leu Ala Thr Ser Gln Val Thr Leu Pro
9665                9670            9675

Leu Gly Thr Ser Met Thr Phe Leu Ser Gly Thr His Ser Thr Met
9680                9685            9690

Ser Gln Gly Leu Ser His Ser Glu Met Thr Asn Leu Met Ser Arg
9695                9700            9705

Gly Pro Glu Ser Leu Ser Trp Thr Ser Pro Arg Phe Val Glu Thr
9710                9715            9720

Thr Arg Ser Ser Ser Ser Leu Thr Ser Leu Pro Leu Thr Thr Ser
9725                9730            9735

Leu Ser Pro Val Ser Ser Thr Leu Leu Asp Ser Ser Pro Ser Ser
9740                9745            9750

Pro Leu Pro Val Thr Ser Leu Ile Leu Pro Gly Leu Val Lys Thr
9755                9760            9765

Thr Glu Val Leu Asp Thr Ser Ser Glu Pro Lys Thr Ser Ser Ser
9770                9775            9780

Pro Asn Leu Ser Ser Thr Ser Val Glu Ile Pro Ala Thr Ser Glu
9785                9790            9795

Ile Met Thr Asp Thr Glu Lys Ile His Pro Ser Ser Asn Thr Ala
9800                9805            9810

Val Ala Lys Val Arg Thr Ser Ser Ser Val His Glu Ser His Ser
9815                9820            9825

Ser Val Leu Ala Asp Ser Glu Thr Thr Ile Thr Ile Pro Ser Met
9830                9835            9840

Gly Ile Thr Ser Ala Val Asp Asp Thr Thr Val Phe Thr Ser Asn
9845                9850            9855

Pro Ala Phe Ser Glu Thr Arg Arg Ile Pro Thr Glu Pro Thr Phe
9860                9865            9870

Ser Leu Thr Pro Gly Phe Arg Glu Thr Ser Thr Ser Glu Glu Thr
9875                9880            9885

Thr Ser Ile Thr Glu Thr Ser Ala Val Leu Tyr Gly Val Pro Thr
9890                9895            9900

Ser Ala Thr Thr Glu Val Ser Met Thr Glu Ile Met Ser Ser Asn
9905                9910            9915

Arg Ile His Ile Pro Asp Ser Asp Gln Ser Thr Met Ser Pro Asp
9920                9925            9930

Ile Ile Thr Glu Val Ile Thr Arg Leu Ser Ser Ser Ser Met Met
9935                9940            9945

Ser Glu Ser Thr Gln Met Thr Ile Thr Thr Gln Lys Ser Ser Pro
9950                9955            9960

Gly Ala Thr Ala Gln Ser Thr Leu Thr Leu Ala Thr Thr Thr Ala
9965                9970            9975

Pro Leu Ala Arg Thr His Ser Thr Val Pro Pro Arg Phe Leu His
9980                9985            9990

Ser Glu Met Thr Thr Leu Met Ser Arg Ser Pro Glu Asn Pro Ser
9995                10000           10005

Trp Lys Ser Ser Leu Phe Val Glu Lys Thr Ser Ser Ser Ser Ser
10010               10015           10020

| | | | | | |
|---|---|---|---|---|---|
| Leu Leu 10025 | Ser Leu Pro | Val Thr 10030 | Thr Ser Pro | Ser Val 10035 | Ser Ser Thr |
| Leu Pro 10040 | Gln Ser Ile | Pro Ser 10045 | Ser Ser Phe | Ser Val 10050 | Thr Ser Leu |
| Leu Thr 10055 | Pro Gly Met | Val Lys 10060 | Thr Thr Asp | Thr Ser 10065 | Thr Glu Pro |
| Gly Thr 10070 | Ser Leu Ser | Pro Asn 10075 | Leu Ser Gly | Thr Ser 10080 | Val Glu Ile |
| Leu Ala 10085 | Ala Ser Glu | Val Thr 10090 | Thr Asp Thr | Glu Lys 10095 | Ile His Pro |
| Ser Ser 10100 | Ser Met Ala | Val Thr 10105 | Asn Val Gly | Thr Thr 10110 | Ser Ser Gly |
| His Glu 10115 | Leu Tyr Ser | Ser Val 10120 | Ser Ile His | Ser Glu 10125 | Pro Ser Lys |
| Ala Thr 10130 | Tyr Pro Val | Gly Thr 10135 | Pro Ser Ser | Met Ala 10140 | Glu Thr Ser |
| Ile Ser 10145 | Thr Ser Met | Pro Ala 10150 | Asn Phe Glu | Thr Thr 10155 | Gly Phe Glu |
| Ala Glu 10160 | Pro Phe Ser | His Leu 10165 | Thr Ser Gly | Phe Arg 10170 | Lys Thr Asn |
| Met Ser 10175 | Leu Asp Thr | Ser Ser 10180 | Val Thr Pro | Thr Asn 10185 | Thr Pro Ser |
| Ser Pro 10190 | Gly Ser Thr | His Leu 10195 | Leu Gln Ser | Ser Lys 10200 | Thr Asp Phe |
| Thr Ser 10205 | Ser Ala Lys | Thr Ser 10210 | Ser Pro Asp | Trp Pro 10215 | Pro Ala Ser |
| Gln Tyr 10220 | Thr Glu Ile | Pro Val 10225 | Asp Ile Ile | Thr Pro 10230 | Phe Asn Ala |
| Ser Pro 10235 | Ser Ile Thr | Glu Ser 10240 | Thr Gly Ile | Thr Ser 10245 | Phe Pro Glu |
| Ser Arg 10250 | Phe Thr Met | Ser Val 10255 | Thr Glu Ser | Thr His 10260 | His Leu Ser |
| Thr Asp 10265 | Leu Leu Pro | Ser Ala 10270 | Glu Thr Ile | Ser Thr 10275 | Gly Thr Val |
| Met Pro 10280 | Ser Leu Ser | Glu Ala 10285 | Met Thr Ser | Phe Ala 10290 | Thr Thr Gly |
| Val Pro 10295 | Arg Ala Ile | Ser Gly 10300 | Ser Gly Ser | Pro Phe 10305 | Ser Arg Thr |
| Glu Ser 10310 | Gly Pro Gly | Asp Ala 10315 | Thr Leu Ser | Thr Ile 10320 | Ala Glu Ser |
| Leu Pro 10325 | Ser Ser Thr | Pro Val 10330 | Pro Phe Ser | Ser Ser 10335 | Thr Phe Thr |
| Thr Thr 10340 | Asp Ser Ser | Thr Ile 10345 | Pro Ala Leu | His Glu 10350 | Ile Thr Ser |
| Ser Ser 10355 | Ala Thr Pro | Tyr Arg 10360 | Val Asp Thr | Ser Leu 10365 | Gly Thr Glu |
| Ser Ser 10370 | Thr Thr Glu | Gly Arg 10375 | Leu Val Met | Val Ser 10380 | Thr Leu Asp |
| Thr Ser 10385 | Ser Gln Pro | Gly Arg 10390 | Thr Ser Ser | Ser Pro 10395 | Ile Leu Asp |
| Thr Arg 10400 | Met Thr Glu | Ser Val 10405 | Glu Leu Gly | Thr Val 10410 | Thr Ser Ala |
| Tyr Gln | Val Pro Ser | Leu Ser | Thr Arg Leu | Thr Arg | Thr Asp Gly |

-continued

|  |  |  |  |
|---|---|---|---|
| 10415 | 10420 | 10425 | |
| Ile Met 10430 | Glu His Ile Thr Lys 10435 | Ile Pro Asn Glu Ala 10440 | Ala His Arg |
| Gly Thr 10445 | Ile Arg Pro Val Lys 10450 | Gly Pro Gln Thr Ser 10455 | Thr Ser Pro |
| Ala Ser 10460 | Pro Lys Gly Leu His 10465 | Thr Gly Gly Thr Lys 10470 | Arg Met Glu |
| Thr Thr 10475 | Thr Thr Ala Leu Lys 10480 | Thr Thr Thr Thr Ala 10485 | Leu Lys Thr |
| Thr Ser 10490 | Arg Ala Thr Leu Thr 10495 | Thr Ser Val Tyr Thr 10500 | Pro Thr Leu |
| Gly Thr 10505 | Leu Thr Pro Leu Asn 10510 | Ala Ser Met Gln Met 10515 | Ala Ser Thr |
| Ile Pro 10520 | Thr Glu Met Met Ile 10525 | Thr Thr Pro Tyr Val 10530 | Phe Pro Asp |
| Val Pro 10535 | Glu Thr Thr Ser Ser 10540 | Leu Ala Thr Ser Leu 10545 | Gly Ala Glu |
| Thr Ser 10550 | Thr Ala Leu Pro Arg 10555 | Thr Thr Pro Ser Val 10560 | Phe Asn Arg |
| Glu Ser 10565 | Glu Thr Thr Ala Ser 10570 | Leu Val Ser Arg Ser 10575 | Gly Ala Glu |
| Arg Ser 10580 | Pro Val Ile Gln Thr 10585 | Leu Asp Val Ser Ser 10590 | Ser Glu Pro |
| Asp Thr 10595 | Thr Ala Ser Trp Val 10600 | Ile His Pro Ala Glu 10605 | Thr Ile Pro |
| Thr Val 10610 | Ser Lys Thr Thr Pro 10615 | Asn Phe Phe His Ser 10620 | Glu Leu Asp |
| Thr Val 10625 | Ser Ser Thr Ala Thr 10630 | Ser His Gly Ala Asp 10635 | Val Ser Ser |
| Ala Ile 10640 | Pro Thr Asn Ile Ser 10645 | Pro Ser Glu Leu Asp 10650 | Ala Leu Thr |
| Pro Leu 10655 | Val Thr Ile Ser Gly 10660 | Thr Asp Thr Ser Thr 10665 | Thr Phe Pro |
| Thr Leu 10670 | Thr Lys Ser Pro His 10675 | Glu Thr Glu Thr Arg 10680 | Thr Thr Trp |
| Leu Thr 10685 | His Pro Ala Glu Thr 10690 | Ser Ser Thr Ile Pro 10695 | Arg Thr Ile |
| Pro Asn 10700 | Phe Ser His His Glu 10705 | Ser Asp Ala Thr Pro 10710 | Ser Ile Ala |
| Thr Ser 10715 | Pro Gly Ala Glu Thr 10720 | Ser Ser Ala Ile Pro 10725 | Ile Met Thr |
| Val Ser 10730 | Pro Gly Ala Glu Asp 10735 | Leu Val Thr Ser Gln 10740 | Val Thr Ser |
| Ser Gly 10745 | Thr Asp Arg Asn Met 10750 | Thr Ile Pro Thr Leu 10755 | Thr Leu Ser |
| Pro Gly 10760 | Glu Pro Lys Thr Ile 10765 | Ala Ser Leu Val Thr 10770 | His Pro Glu |
| Ala Gln 10775 | Thr Ser Ser Ala Ile 10780 | Pro Thr Ser Thr Ile 10785 | Ser Pro Ala |
| Val Ser 10790 | Arg Leu Val Thr Ser 10795 | Met Val Thr Ser Leu 10800 | Ala Ala Lys |
| Thr Ser 10805 | Thr Thr Asn Arg Ala 10810 | Leu Thr Asn Ser Pro 10815 | Gly Glu Pro |

| | | | | | | | | | |
|---|---|---|---|---|---|---|---|---|---|
| Ala | Thr | Thr | Val | Ser | Leu | Val | Thr | His | Pro | Ala | Gln | Thr | Ser | Pro |
| 10820 | | | | 10825 | | | | 10830 | | | | | | |
| Thr | Val | Pro | Trp | Thr | Thr | Ser | Ile | Phe | Phe | His | Ser | Lys | Ser | Asp |
| 10835 | | | | 10840 | | | | 10845 | | | | | | |
| Thr | Thr | Pro | Ser | Met | Thr | Thr | Ser | His | Gly | Ala | Glu | Ser | Ser | Ser |
| 10850 | | | | 10855 | | | | 10860 | | | | | | |
| Ala | Val | Pro | Thr | Pro | Thr | Val | Ser | Thr | Glu | Val | Pro | Gly | Val | Val |
| 10865 | | | | 10870 | | | | 10875 | | | | | | |
| Thr | Pro | Leu | Val | Thr | Ser | Ser | Arg | Ala | Val | Ile | Ser | Thr | Thr | Ile |
| 10880 | | | | 10885 | | | | 10890 | | | | | | |
| Pro | Ile | Leu | Thr | Leu | Ser | Pro | Gly | Glu | Pro | Glu | Thr | Thr | Pro | Ser |
| 10895 | | | | 10900 | | | | 10905 | | | | | | |
| Met | Ala | Thr | Ser | His | Gly | Glu | Glu | Ala | Ser | Ser | Ala | Ile | Pro | Thr |
| 10910 | | | | 10915 | | | | 10920 | | | | | | |
| Pro | Thr | Val | Ser | Pro | Gly | Val | Pro | Gly | Val | Val | Thr | Ser | Leu | Val |
| 10925 | | | | 10930 | | | | 10935 | | | | | | |
| Thr | Ser | Ser | Arg | Ala | Val | Thr | Ser | Thr | Thr | Ile | Pro | Ile | Leu | Thr |
| 10940 | | | | 10945 | | | | 10950 | | | | | | |
| Phe | Ser | Leu | Gly | Glu | Pro | Glu | Thr | Thr | Pro | Ser | Met | Ala | Thr | Ser |
| 10955 | | | | 10960 | | | | 10965 | | | | | | |
| His | Gly | Thr | Glu | Ala | Gly | Ser | Ala | Val | Pro | Thr | Val | Leu | Pro | Glu |
| 10970 | | | | 10975 | | | | 10980 | | | | | | |
| Val | Pro | Gly | Met | Val | Thr | Ser | Leu | Val | Ala | Ser | Ser | Arg | Ala | Val |
| 10985 | | | | 10990 | | | | 10995 | | | | | | |
| Thr | Ser | Thr | Thr | Leu | Pro | Thr | Leu | Thr | Leu | Ser | Pro | Gly | Glu | Pro |
| 11000 | | | | 11005 | | | | 11010 | | | | | | |
| Glu | Thr | Thr | Pro | Ser | Met | Ala | Thr | Ser | His | Gly | Ala | Glu | Ala | Ser |
| 11015 | | | | 11020 | | | | 11025 | | | | | | |
| Ser | Thr | Val | Pro | Thr | Val | Ser | Pro | Glu | Val | Pro | Gly | Val | Val | Thr |
| 11030 | | | | 11035 | | | | 11040 | | | | | | |
| Ser | Leu | Val | Thr | Ser | Ser | Ser | Gly | Val | Asn | Ser | Thr | Ser | Ile | Pro |
| 11045 | | | | 11050 | | | | 11055 | | | | | | |
| Thr | Leu | Ile | Leu | Ser | Pro | Gly | Glu | Leu | Glu | Thr | Thr | Pro | Ser | Met |
| 11060 | | | | 11065 | | | | 11070 | | | | | | |
| Ala | Thr | Ser | His | Gly | Ala | Glu | Ala | Ser | Ser | Ala | Val | Pro | Thr | Pro |
| 11075 | | | | 11080 | | | | 11085 | | | | | | |
| Thr | Val | Ser | Pro | Gly | Val | Ser | Gly | Val | Val | Thr | Pro | Leu | Val | Thr |
| 11090 | | | | 11095 | | | | 11100 | | | | | | |
| Ser | Ser | Arg | Ala | Val | Thr | Ser | Thr | Thr | Ile | Pro | Ile | Leu | Thr | Leu |
| 11105 | | | | 11110 | | | | 11115 | | | | | | |
| Ser | Ser | Ser | Glu | Pro | Glu | Thr | Thr | Pro | Ser | Met | Ala | Thr | Ser | His |
| 11120 | | | | 11125 | | | | 11130 | | | | | | |
| Gly | Val | Glu | Ala | Ser | Ser | Ala | Val | Leu | Thr | Val | Ser | Pro | Glu | Val |
| 11135 | | | | 11140 | | | | 11145 | | | | | | |
| Pro | Gly | Met | Val | Thr | Ser | Leu | Val | Thr | Ser | Ser | Arg | Ala | Val | Thr |
| 11150 | | | | 11155 | | | | 11160 | | | | | | |
| Ser | Thr | Thr | Ile | Pro | Thr | Leu | Thr | Ile | Ser | Ser | Asp | Glu | Pro | Glu |
| 11165 | | | | 11170 | | | | 11175 | | | | | | |
| Thr | Thr | Thr | Ser | Leu | Val | Thr | His | Ser | Glu | Ala | Lys | Met | Ile | Ser |
| 11180 | | | | 11185 | | | | 11190 | | | | | | |
| Ala | Ile | Pro | Thr | Leu | Ala | Val | Ser | Pro | Thr | Val | Gln | Gly | Leu | Val |
| 11195 | | | | 11200 | | | | 11205 | | | | | | |

-continued

| | | | |
|---|---|---|---|
| Thr Ser Leu Val Thr Ser Ser 11210 11215 | | Gly Ser Glu Thr Ser 11220 | Ala Phe Ser |
| Asn Leu Thr Val Ala Ser Ser 11225 11230 | | Gln Pro Glu Thr Ile 11235 | Asp Ser Trp |
| Val Ala His Pro Gly Thr Glu 11240 11245 | | Ala Ser Ser Val Val 11250 | Pro Thr Leu |
| Thr Val Ser Thr Gly Glu Pro 11255 11260 | | Phe Thr Asn Ile Ser 11265 | Leu Val Thr |
| His Pro Ala Glu Ser Ser Ser 11270 11275 | | Thr Leu Pro Arg Thr 11280 | Thr Ser Arg |
| Phe Ser His Ser Glu Leu Asp 11285 11290 | | Thr Met Pro Ser Thr 11295 | Val Thr Ser |
| Pro Glu Ala Glu Ser Ser Ser 11300 11305 | | Ala Ile Ser Thr Thr 11310 | Ile Ser Pro |
| Gly Ile Pro Gly Val Leu Thr 11315 11320 | | Ser Leu Val Thr Ser 11325 | Ser Gly Arg |
| Asp Ile Ser Ala Thr Phe Pro 11330 11335 | | Thr Val Pro Glu Ser 11340 | Pro His Glu |
| Ser Glu Ala Thr Ala Ser Trp 11345 11350 | | Val Thr His Pro Ala 11355 | Val Thr Ser |
| Thr Thr Val Pro Arg Thr Thr 11360 11365 | | Pro Asn Tyr Ser His 11370 | Ser Glu Pro |
| Asp Thr Thr Pro Ser Ile Ala 11375 11380 | | Thr Ser Pro Gly Ala 11385 | Glu Ala Thr |
| Ser Asp Phe Pro Thr Ile Thr 11390 11395 | | Val Ser Pro Asp Val 11400 | Pro Asp Met |
| Val Thr Ser Gln Val Thr Ser 11405 11410 | | Ser Gly Thr Asp Thr 11415 | Ser Ile Thr |
| Ile Pro Thr Leu Thr Leu Ser 11420 11425 | | Ser Gly Glu Pro Glu 11430 | Thr Thr Thr |
| Ser Phe Ile Thr Tyr Ser Glu 11435 11440 | | Thr His Thr Ser Ser 11445 | Ala Ile Pro |
| Thr Leu Pro Val Ser Pro Gly 11450 11455 | | Ala Ser Lys Met Leu 11460 | Thr Ser Leu |
| Val Ile Ser Ser Gly Thr Asp 11465 11470 | | Ser Thr Thr Thr Phe 11475 | Pro Thr Leu |
| Thr Glu Thr Pro Tyr Glu Pro 11480 11485 | | Glu Thr Thr Ala Ile 11490 | Gln Leu Ile |
| His Pro Ala Glu Thr Asn Thr 11495 11500 | | Met Val Pro Arg Thr 11505 | Thr Pro Lys |
| Phe Ser His Ser Lys Ser Asp 11510 11515 | | Thr Thr Leu Pro Val 11520 | Ala Ile Thr |
| Ser Pro Gly Pro Glu Ala Ser 11525 11530 | | Ser Ala Val Ser Thr 11535 | Thr Thr Ile |
| Ser Pro Asp Met Ser Asp Leu 11540 11545 | | Val Thr Ser Leu Val 11550 | Pro Ser Ser |
| Gly Thr Asp Thr Ser Thr Thr 11555 11560 | | Phe Pro Thr Leu Ser 11565 | Glu Thr Pro |
| Tyr Glu Pro Glu Thr Thr Ala 11570 11575 | | Thr Trp Leu Thr His 11580 | Pro Ala Glu |
| Thr Ser Thr Thr Val Ser Gly 11585 11590 | | Thr Ile Pro Asn Phe 11595 | Ser His Arg |
| Gly Ser Asp Thr Ala Pro Ser | | Met Val Thr Ser Pro | Gly Val Asp |

-continued

| | | | |
|---|---|---|---|
| 11600 | 11605 | 11610 | |
| Thr Arg 11615 | Ser Gly Val Pro Thr 11620 | Thr Thr Ile Pro Pro 11625 | Ser Ile Pro |
| Gly Val 11630 | Val Thr Ser Gln Val 11635 | Thr Ser Ser Ala Thr 11640 | Asp Thr Ser |
| Thr Ala 11645 | Ile Pro Thr Leu Thr 11650 | Pro Ser Pro Gly Glu 11655 | Pro Glu Thr |
| Thr Ala 11660 | Ser Ser Ala Thr His 11665 | Pro Gly Thr Gln Thr 11670 | Gly Phe Thr |
| Val Pro 11675 | Ile Arg Thr Val Pro 11680 | Ser Ser Glu Pro Asp 11685 | Thr Met Ala |
| Ser Trp 11690 | Val Thr His Pro Pro 11695 | Gln Thr Ser Thr Pro 11700 | Val Ser Arg |
| Thr Thr 11705 | Ser Ser Phe Ser His 11710 | Ser Ser Pro Asp Ala 11715 | Thr Pro Val |
| Met Ala 11720 | Thr Ser Pro Arg Thr 11725 | Glu Ala Ser Ser Ala 11730 | Val Leu Thr |
| Thr Ile 11735 | Ser Pro Gly Ala Pro 11740 | Glu Met Val Thr Ser 11745 | Gln Ile Thr |
| Ser Ser 11750 | Gly Ala Ala Thr Ser 11755 | Thr Thr Val Pro Thr 11760 | Leu Thr His |
| Ser Pro 11765 | Gly Met Pro Glu Thr 11770 | Thr Ala Leu Leu Ser 11775 | Thr His Pro |
| Arg Thr 11780 | Glu Thr Ser Lys Thr 11785 | Phe Pro Ala Ser Thr 11790 | Val Phe Pro |
| Gln Val 11795 | Ser Glu Thr Thr Ala 11800 | Ser Leu Thr Ile Arg 11805 | Pro Gly Ala |
| Glu Thr 11810 | Ser Thr Ala Leu Pro 11815 | Thr Gln Thr Thr Ser 11820 | Ser Leu Phe |
| Thr Leu 11825 | Leu Val Thr Gly Thr 11830 | Ser Arg Val Asp Leu 11835 | Ser Pro Thr |
| Ala Ser 11840 | Pro Gly Val Ser Ala 11845 | Lys Thr Ala Pro Leu 11850 | Ser Thr His |
| Pro Gly 11855 | Thr Glu Thr Ser Thr 11860 | Met Ile Pro Thr Ser 11865 | Thr Leu Ser |
| Leu Gly 11870 | Leu Leu Glu Thr Thr 11875 | Gly Leu Leu Ala Thr 11880 | Ser Ser Ser |
| Ala Glu 11885 | Thr Ser Thr Ser Thr 11890 | Leu Thr Leu Thr Val 11895 | Ser Pro Ala |
| Val Ser 11900 | Gly Leu Ser Ser Ala 11905 | Ser Ile Thr Thr Asp 11910 | Lys Pro Gln |
| Thr Val 11915 | Thr Ser Trp Asn Thr 11920 | Glu Thr Ser Pro Ser 11925 | Val Thr Ser |
| Val Gly 11930 | Pro Pro Glu Phe Ser 11935 | Arg Thr Val Thr Gly 11940 | Thr Thr Met |
| Thr Leu 11945 | Ile Pro Ser Glu Met 11950 | Pro Thr Pro Pro Lys 11955 | Thr Ser His |
| Gly Glu 11960 | Gly Val Ser Pro Thr 11965 | Thr Ile Leu Arg Thr 11970 | Thr Met Val |
| Glu Ala 11975 | Thr Asn Leu Ala Thr 11980 | Thr Gly Ser Ser Pro 11985 | Thr Val Ala |
| Lys Thr 11990 | Thr Thr Thr Phe Asn 11995 | Thr Leu Ala Gly Ser 12000 | Leu Phe Thr |

-continued

| | | | | |
|---|---|---|---|---|
| Pro Leu 12005 | Thr Thr Pro Gly Met 12010 | Ser Thr Leu Ala Ser 12015 | Glu Ser Val | |
| Thr Ser 12020 | Arg Thr Ser Tyr Asn 12025 | His Arg Ser Trp Ile 12030 | Ser Thr Thr | |
| Ser Ser 12035 | Tyr Asn Arg Arg Tyr 12040 | Trp Thr Pro Ala Thr 12045 | Ser Thr Pro | |
| Val Thr 12050 | Ser Thr Phe Ser Pro 12055 | Gly Ile Ser Thr Ser 12060 | Ser Ile Pro | |
| Ser Ser 12065 | Thr Ala Ala Thr Val 12070 | Pro Phe Met Val Pro 12075 | Phe Thr Leu | |
| Asn Phe 12080 | Thr Ile Thr Asn Leu 12085 | Gln Tyr Glu Glu Asp 12090 | Met Arg His | |
| Pro Gly 12095 | Ser Arg Lys Phe Asn 12100 | Ala Thr Glu Arg Glu 12105 | Leu Gln Gly | |
| Leu Leu 12110 | Lys Pro Leu Phe Arg 12115 | Asn Ser Ser Leu Glu 12120 | Tyr Leu Tyr | |
| Ser Gly 12125 | Cys Arg Leu Ala Ser 12130 | Leu Arg Pro Glu Lys 12135 | Asp Ser Ser | |
| Ala Thr 12140 | Ala Val Asp Ala Ile 12145 | Cys Thr His Arg Pro 12150 | Asp Pro Glu | |
| Asp Leu 12155 | Gly Leu Asp Arg Glu 12160 | Arg Leu Tyr Trp Glu 12165 | Leu Ser Asn | |
| Leu Thr 12170 | Asn Gly Ile Gln Glu 12175 | Leu Gly Pro Tyr Thr 12180 | Leu Asp Arg | |
| Asn Ser 12185 | Leu Tyr Val Asn Gly 12190 | Phe Thr His Arg Ser 12195 | Ser Met Pro | |
| Thr Thr 12200 | Ser Thr Pro Gly Thr 12205 | Ser Thr Val Asp Val 12210 | Gly Thr Ser | |
| Gly Thr 12215 | Pro Ser Ser Ser Pro 12220 | Ser Pro Thr Thr Ala 12225 | Gly Pro Leu | |
| Leu Met 12230 | Pro Phe Thr Leu Asn 12235 | Phe Thr Ile Thr Asn 12240 | Leu Gln Tyr | |
| Glu Glu 12245 | Asp Met Arg Arg Thr 12250 | Gly Ser Arg Lys Phe 12255 | Asn Thr Met | |
| Glu Ser 12260 | Val Leu Gln Gly Leu 12265 | Leu Lys Pro Leu Phe 12270 | Lys Asn Thr | |
| Ser Val 12275 | Gly Pro Leu Tyr Ser 12280 | Gly Cys Arg Leu Thr 12285 | Leu Leu Arg | |
| Pro Glu 12290 | Lys Asp Gly Ala Ala 12295 | Thr Gly Val Asp Ala 12300 | Ile Cys Thr | |
| His Arg 12305 | Leu Asp Pro Lys Ser 12310 | Pro Gly Leu Asn Arg 12315 | Glu Gln Leu | |
| Tyr Trp 12320 | Glu Leu Ser Lys Leu 12325 | Thr Asn Asp Ile Glu 12330 | Glu Leu Gly | |
| Pro Tyr 12335 | Thr Leu Asp Arg Asn 12340 | Ser Leu Tyr Val Asn 12345 | Gly Phe Thr | |
| His Gln 12350 | Ser Ser Val Ser Thr 12355 | Thr Ser Thr Pro Gly 12360 | Thr Ser Thr | |
| Val Asp 12365 | Leu Arg Thr Ser Gly 12370 | Thr Pro Ser Ser Leu 12375 | Ser Ser Pro | |
| Thr Ile 12380 | Met Ala Ala Gly Pro 12385 | Leu Leu Val Pro Phe 12390 | Thr Leu Asn | |

-continued

| | | | | | |
|---|---|---|---|---|---|
| Phe Thr 12395 | Ile Thr Asn Leu Gln 12400 | Tyr Gly Glu Asp Met 12405 | Gly His Pro | | |
| Gly Ser 12410 | Arg Lys Phe Asn Thr 12415 | Thr Glu Arg Val Leu 12420 | Gln Gly Leu | | |
| Leu Gly 12425 | Pro Ile Phe Lys Asn 12430 | Thr Ser Val Gly Pro 12435 | Leu Tyr Ser | | |
| Gly Cys 12440 | Arg Leu Thr Ser Leu 12445 | Arg Ser Glu Lys Asp 12450 | Gly Ala Ala | | |
| Thr Gly 12455 | Val Asp Ala Ile Cys 12460 | Ile His His Leu Asp 12465 | Pro Lys Ser | | |
| Pro Gly 12470 | Leu Asn Arg Glu Arg 12475 | Leu Tyr Trp Glu Leu 12480 | Ser Gln Leu | | |
| Thr Asn 12485 | Gly Ile Lys Glu Leu 12490 | Gly Pro Tyr Thr Leu 12495 | Asp Arg Asn | | |
| Ser Leu 12500 | Tyr Val Asn Gly Phe 12505 | Thr His Arg Thr Ser 12510 | Val Pro Thr | | |
| Ser Ser 12515 | Thr Pro Gly Thr Ser 12520 | Thr Val Asp Leu Gly 12525 | Thr Ser Gly | | |
| Thr Pro 12530 | Phe Ser Leu Pro Ser 12535 | Pro Ala Thr Ala Gly 12540 | Pro Leu Leu | | |
| Val Leu 12545 | Phe Thr Leu Asn Phe 12550 | Thr Ile Thr Asn Leu 12555 | Lys Tyr Glu | | |
| Glu Asp 12560 | Met His Arg Pro Gly 12565 | Ser Arg Lys Phe Asn 12570 | Thr Thr Glu | | |
| Arg Val 12575 | Leu Gln Thr Leu Leu 12580 | Gly Pro Met Phe Lys 12585 | Asn Thr Ser | | |
| Val Gly 12590 | Leu Leu Tyr Ser Gly 12595 | Cys Arg Leu Thr Leu 12600 | Leu Arg Ser | | |
| Glu Lys 12605 | Asp Gly Ala Ala Thr 12610 | Gly Val Asp Ala Ile 12615 | Cys Thr His | | |
| Arg Leu 12620 | Asp Pro Lys Ser Pro 12625 | Gly Val Asp Arg Glu 12630 | Gln Leu Tyr | | |
| Trp Glu 12635 | Leu Ser Gln Leu Thr 12640 | Asn Gly Ile Lys Glu 12645 | Leu Gly Pro | | |
| Tyr Thr 12650 | Leu Asp Arg Asn Ser 12655 | Leu Tyr Val Asn Gly 12660 | Phe Thr His | | |
| Trp Ile 12665 | Pro Val Pro Thr Ser 12670 | Ser Thr Pro Gly Thr 12675 | Ser Thr Val | | |
| Asp Leu 12680 | Gly Ser Gly Thr Pro 12685 | Ser Ser Leu Pro Ser 12690 | Pro Thr Thr | | |
| Ala Gly 12695 | Pro Leu Leu Val Pro 12700 | Phe Thr Leu Asn Phe 12705 | Thr Ile Thr | | |
| Asn Leu 12710 | Lys Tyr Glu Glu Asp 12715 | Met His Cys Pro Gly 12720 | Ser Arg Lys | | |
| Phe Asn 12725 | Thr Thr Glu Arg Val 12730 | Leu Gln Ser Leu Leu 12735 | Gly Pro Met | | |
| Phe Lys 12740 | Asn Thr Ser Val Gly 12745 | Pro Leu Tyr Ser Gly 12750 | Cys Arg Leu | | |
| Thr Leu 12755 | Leu Arg Ser Glu Lys 12760 | Asp Gly Ala Ala Thr 12765 | Gly Val Asp | | |
| Ala Ile 12770 | Cys Thr His Arg Leu 12775 | Asp Pro Lys Ser Pro 12780 | Gly Val Asp | | |
| Arg Glu | Gln Leu Tyr Trp Glu | Leu Ser Gln Leu Thr | Asn Gly Ile | | |

-continued

| | | | |
|---|---|---|---|
| 12785 | | 12790 | 12795 |
| Lys Glu 12800 | Leu Gly Pro | Tyr Thr 12805 | Leu Asp Arg Asn Ser 12810 | Leu Tyr Val |
| Asn Gly 12815 | Phe Thr His | Gln Thr 12820 | Ser Ala Pro Asn Thr 12825 | Ser Thr Pro |
| Gly Thr 12830 | Ser Thr Val | Asp Leu 12835 | Gly Thr Ser Gly Thr 12840 | Pro Ser Ser |
| Leu Pro 12845 | Ser Pro Thr | Ser Ala 12850 | Gly Pro Leu Leu Val 12855 | Pro Phe Thr |
| Leu Asn 12860 | Phe Thr Ile | Thr Asn 12865 | Leu Gln Tyr Glu Glu 12870 | Asp Met His |
| His Pro 12875 | Gly Ser Arg | Lys Phe 12880 | Asn Thr Thr Glu Arg 12885 | Val Leu Gln |
| Gly Leu 12890 | Leu Gly Pro | Met Phe 12895 | Lys Asn Thr Ser Val 12900 | Gly Leu Leu |
| Tyr Ser 12905 | Gly Cys Arg | Leu Thr 12910 | Leu Leu Arg Pro Glu 12915 | Lys Asn Gly |
| Ala Ala 12920 | Thr Gly Met | Asp Ala 12925 | Ile Cys Ser His Arg 12930 | Leu Asp Pro |
| Lys Ser 12935 | Pro Gly Leu | Asn Arg 12940 | Glu Gln Leu Tyr Trp 12945 | Glu Leu Ser |
| Gln Leu 12950 | Thr His Gly | Ile Lys 12955 | Glu Leu Gly Pro Tyr 12960 | Thr Leu Asp |
| Arg Asn 12965 | Ser Leu Tyr | Val Asn 12970 | Gly Phe Thr His Arg 12975 | Ser Ser Val |
| Ala Pro 12980 | Thr Ser Thr | Pro Gly 12985 | Thr Ser Thr Val Asp 12990 | Leu Gly Thr |
| Ser Gly 12995 | Thr Pro Ser | Ser Leu 13000 | Pro Ser Pro Thr Thr 13005 | Ala Val Pro |
| Leu Leu 13010 | Val Pro Phe | Thr Leu 13015 | Asn Phe Thr Ile Thr 13020 | Asn Leu Gln |
| Tyr Gly 13025 | Glu Asp Met | Arg His 13030 | Pro Gly Ser Arg Lys 13035 | Phe Asn Thr |
| Thr Glu 13040 | Arg Val Leu | Gln Gly 13045 | Leu Leu Gly Pro Leu 13050 | Phe Lys Asn |
| Ser Ser 13055 | Val Gly Pro | Leu Tyr 13060 | Ser Gly Cys Arg Leu 13065 | Ile Ser Leu |
| Arg Ser 13070 | Glu Lys Asp | Gly Ala 13075 | Ala Thr Gly Val Asp 13080 | Ala Ile Cys |
| Thr His 13085 | His Leu Asn | Pro Gln 13090 | Ser Pro Gly Leu Asp 13095 | Arg Glu Gln |
| Leu Tyr 13100 | Trp Gln Leu | Ser Gln 13105 | Met Thr Asn Gly Ile 13110 | Lys Glu Leu |
| Gly Pro 13115 | Tyr Thr Leu | Asp Arg 13120 | Asn Ser Leu Tyr Val 13125 | Asn Gly Phe |
| Thr His 13130 | Arg Ser Ser | Gly Leu 13135 | Thr Thr Ser Thr Pro 13140 | Trp Thr Ser |
| Thr Val 13145 | Asp Leu Gly | Thr Ser 13150 | Gly Thr Pro Ser Pro 13155 | Val Pro Ser |
| Pro Thr 13160 | Thr Thr Gly | Pro Leu 13165 | Leu Val Pro Phe Thr 13170 | Leu Asn Phe |
| Thr Ile 13175 | Thr Asn Leu | Gln Tyr 13180 | Glu Glu Asn Met Gly 13185 | His Pro Gly |

-continued

| | | | |
|---|---|---|---|
| Ser Arg 13190 | Lys Phe Asn Ile Thr 13195 | Glu Ser Val Leu Gln 13200 | Gly Leu Leu |
| Lys Pro 13205 | Leu Phe Lys Ser Thr 13210 | Ser Val Gly Pro Leu 13215 | Tyr Ser Gly |
| Cys Arg 13220 | Leu Thr Leu Leu Arg 13225 | Pro Glu Lys Asp Gly 13230 | Val Ala Thr |
| Arg Val 13235 | Asp Ala Ile Cys Thr 13240 | His Arg Pro Asp Pro 13245 | Lys Ile Pro |
| Gly Leu 13250 | Asp Arg Gln Gln Leu 13255 | Tyr Trp Glu Leu Ser 13260 | Gln Leu Thr |
| His Ser 13265 | Ile Thr Glu Leu Gly 13270 | Pro Tyr Thr Leu Asp 13275 | Arg Asp Ser |
| Leu Tyr 13280 | Val Asn Gly Phe Thr 13285 | Gln Arg Ser Ser Val 13290 | Pro Thr Thr |
| Ser Thr 13295 | Pro Gly Thr Phe Thr 13300 | Val Gln Pro Glu Thr 13305 | Ser Glu Thr |
| Pro Ser 13310 | Ser Leu Pro Gly Pro 13315 | Thr Ala Thr Gly Pro 13320 | Val Leu Leu |
| Pro Phe 13325 | Thr Leu Asn Phe Thr 13330 | Ile Thr Asn Leu Gln 13335 | Tyr Glu Glu |
| Asp Met 13340 | Arg Arg Pro Gly Ser 13345 | Arg Lys Phe Asn Thr 13350 | Thr Glu Arg |
| Val Leu 13355 | Gln Gly Leu Leu Met 13360 | Pro Leu Phe Lys Asn 13365 | Thr Ser Val |
| Ser Ser 13370 | Leu Tyr Ser Gly Cys 13375 | Arg Leu Thr Leu Leu 13380 | Arg Pro Glu |
| Lys Asp 13385 | Gly Ala Ala Thr Arg 13390 | Val Asp Ala Val Cys 13395 | Thr His Arg |
| Pro Asp 13400 | Pro Lys Ser Pro Gly 13405 | Leu Asp Arg Glu Arg 13410 | Leu Tyr Trp |
| Lys Leu 13415 | Ser Gln Leu Thr His 13420 | Gly Ile Thr Glu Leu 13425 | Gly Pro Tyr |
| Thr Leu 13430 | Asp Arg His Ser Leu 13435 | Tyr Val Asn Gly Phe 13440 | Thr His Gln |
| Ser Ser 13445 | Met Thr Thr Thr Arg 13450 | Thr Pro Asp Thr Ser 13455 | Thr Met His |
| Leu Ala 13460 | Thr Ser Arg Thr Pro 13465 | Ala Ser Leu Ser Gly 13470 | Pro Met Thr |
| Ala Ser 13475 | Pro Leu Leu Val Leu 13480 | Phe Thr Ile Asn Phe 13485 | Thr Ile Thr |
| Asn Leu 13490 | Arg Tyr Glu Glu Asn 13495 | Met His His Pro Gly 13500 | Ser Arg Lys |
| Phe Asn 13505 | Thr Thr Glu Arg Val 13510 | Leu Gln Gly Leu Leu 13515 | Arg Pro Val |
| Phe Lys 13520 | Asn Thr Ser Val Gly 13525 | Pro Leu Tyr Ser Gly 13530 | Cys Arg Leu |
| Thr Leu 13535 | Leu Arg Pro Lys Lys 13540 | Asp Gly Ala Ala Thr 13545 | Lys Val Asp |
| Ala Ile 13550 | Cys Thr Tyr Arg Pro 13555 | Asp Pro Lys Ser Pro 13560 | Gly Leu Asp |
| Arg Glu 13565 | Gln Leu Tyr Trp Glu 13570 | Leu Ser Gln Leu Thr 13575 | His Ser Ile |

| | | | | | | | | |
|---|---|---|---|---|---|---|---|---|
| Thr Glu 13580 | Leu Gly Pro | Tyr Thr 13585 | Leu Asp Arg | Asp Ser 13590 | Leu Tyr Val | | | |
| Asn Gly 13595 | Phe Thr Gln | Arg Ser 13600 | Ser Val Pro | Thr Thr 13605 | Ser Ile Pro | | | |
| Gly Thr 13610 | Pro Thr Val | Asp Leu 13615 | Gly Thr Ser | Gly Thr 13620 | Pro Val Ser | | | |
| Lys Pro 13625 | Gly Pro Ser | Ala Ala 13630 | Ser Pro Leu | Leu Val 13635 | Leu Phe Thr | | | |
| Leu Asn 13640 | Phe Thr Ile | Thr Asn 13645 | Leu Arg Tyr | Glu Glu 13650 | Asn Met Gln | | | |
| His Pro 13655 | Gly Ser Arg | Lys Phe 13660 | Asn Thr Thr | Glu Arg 13665 | Val Leu Gln | | | |
| Gly Leu 13670 | Leu Arg Ser | Leu Phe 13675 | Lys Ser Thr | Ser Val 13680 | Gly Pro Leu | | | |
| Tyr Ser 13685 | Gly Cys Arg | Leu Thr 13690 | Leu Leu Arg | Pro Glu 13695 | Lys Asp Gly | | | |
| Thr Ala 13700 | Thr Gly Val | Asp Ala 13705 | Ile Cys Thr | His His 13710 | Pro Asp Pro | | | |
| Lys Ser 13715 | Pro Arg Leu | Asp Arg 13720 | Glu Gln Leu | Tyr Trp 13725 | Glu Leu Ser | | | |
| Gln Leu 13730 | Thr His Asn | Ile Thr 13735 | Glu Leu Gly | Pro Tyr 13740 | Ala Leu Asp | | | |
| Asn Asp 13745 | Ser Leu Phe | Val Asn 13750 | Gly Phe Thr | His Arg 13755 | Ser Ser Val | | | |
| Ser Thr 13760 | Thr Ser Thr | Pro Gly 13765 | Thr Pro Thr | Val Tyr 13770 | Leu Gly Ala | | | |
| Ser Lys 13775 | Thr Pro Ala | Ser Ile 13780 | Phe Gly Pro | Ser Ala 13785 | Ala Ser His | | | |
| Leu Leu 13790 | Ile Leu Phe | Thr Leu 13795 | Asn Phe Thr | Ile Thr 13800 | Asn Leu Arg | | | |
| Tyr Glu 13805 | Glu Asn Met | Trp Pro 13810 | Gly Ser Arg | Lys Phe 13815 | Asn Thr Thr | | | |
| Glu Arg 13820 | Val Leu Gln | Gly Leu 13825 | Leu Arg Pro | Leu Phe 13830 | Lys Asn Thr | | | |
| Ser Val 13835 | Gly Pro Leu | Tyr Ser 13840 | Gly Cys Arg | Leu Thr 13845 | Leu Leu Arg | | | |
| Pro Glu 13850 | Lys Asp Gly | Glu Ala 13855 | Thr Gly Val | Asp Ala 13860 | Ile Cys Thr | | | |
| His Arg 13865 | Pro Asp Pro | Thr Gly 13870 | Pro Gly Leu | Asp Arg 13875 | Glu Gln Leu | | | |
| Tyr Leu 13880 | Glu Leu Ser | Gln Leu 13885 | Thr His Ser | Ile Thr 13890 | Glu Leu Gly | | | |
| Pro Tyr 13895 | Thr Leu Asp | Arg Asp 13900 | Ser Leu Tyr | Val Asn 13905 | Gly Phe Thr | | | |
| His Arg 13910 | Ser Ser Val | Pro Thr 13915 | Thr Ser Thr | Gly Val 13920 | Val Ser Glu | | | |
| Glu Pro 13925 | Phe Thr Leu | Asn Phe 13930 | Thr Ile Asn | Asn Leu 13935 | Arg Tyr Met | | | |
| Ala Asp 13940 | Met Gly Gln | Pro Gly 13945 | Ser Leu Lys | Phe Asn 13950 | Ile Thr Asp | | | |
| Asn Val 13955 | Met Gln His | Leu Leu 13960 | Ser Pro Leu | Phe Gln 13965 | Arg Ser Ser | | | |
| Leu Gly | Ala Arg Tyr | Thr Gly | Cys Arg Val | Ile Ala | Leu Arg Ser | | | |

-continued

| | | | |
|---|---|---|---|
| 13970 | 13975 | 13980 | |
| Val Lys 13985 | Asn Gly Ala Glu Thr 13990 | Arg Val Asp Leu Leu 13995 | Cys Thr Tyr |
| Leu Gln 14000 | Pro Leu Ser Gly Pro 14005 | Gly Leu Pro Ile Lys 14010 | Gln Val Phe |
| His Glu 14015 | Leu Ser Gln Gln Thr 14020 | His Gly Ile Thr Arg 14025 | Leu Gly Pro |
| Tyr Ser 14030 | Leu Asp Lys Asp Ser 14035 | Leu Tyr Leu Asn Gly 14040 | Tyr Asn Glu |
| Pro Gly 14045 | Pro Asp Glu Pro Pro 14050 | Thr Thr Pro Lys Pro 14055 | Ala Thr Thr |
| Phe Leu 14060 | Pro Pro Leu Ser Glu 14065 | Ala Thr Thr Ala Met 14070 | Gly Tyr His |
| Leu Lys 14075 | Thr Leu Thr Leu Asn 14080 | Phe Thr Ile Ser Asn 14085 | Leu Gln Tyr |
| Ser Pro 14090 | Asp Met Gly Lys Gly 14095 | Ser Ala Thr Phe Asn 14100 | Ser Thr Glu |
| Gly Val 14105 | Leu Gln His Leu Leu 14110 | Arg Pro Leu Phe Gln 14115 | Lys Ser Ser |
| Met Gly 14120 | Pro Phe Tyr Leu Gly 14125 | Cys Gln Leu Ile Ser 14130 | Leu Arg Pro |
| Glu Lys 14135 | Asp Gly Ala Ala Thr 14140 | Gly Val Asp Thr Thr 14145 | Cys Thr Tyr |
| His Pro 14150 | Asp Pro Val Gly Pro 14155 | Gly Leu Asp Ile Gln 14160 | Gln Leu Tyr |
| Trp Glu 14165 | Leu Ser Gln Leu Thr 14170 | His Gly Val Thr Gln 14175 | Leu Gly Phe |
| Tyr Val 14180 | Leu Asp Arg Asp Ser 14185 | Leu Phe Ile Asn Gly 14190 | Tyr Ala Pro |
| Gln Asn 14195 | Leu Ser Ile Arg Gly 14200 | Glu Tyr Gln Ile Asn 14205 | Phe His Ile |
| Val Asn 14210 | Trp Asn Leu Ser Asn 14215 | Pro Asp Pro Thr Ser 14220 | Ser Glu Tyr |
| Ile Thr 14225 | Leu Leu Arg Asp Ile 14230 | Gln Asp Lys Val Thr 14235 | Thr Leu Tyr |
| Lys Gly 14240 | Ser Gln Leu His Asp 14245 | Thr Phe Arg Phe Cys 14250 | Leu Val Thr |
| Asn Leu 14255 | Thr Met Asp Ser Val 14260 | Leu Val Thr Val Lys 14265 | Ala Leu Phe |
| Ser Ser 14270 | Asn Leu Asp Pro Ser 14275 | Leu Val Glu Gln Val 14280 | Phe Leu Asp |
| Lys Thr 14285 | Leu Asn Ala Ser Phe 14290 | His Trp Leu Gly Ser 14295 | Thr Tyr Gln |
| Leu Val 14300 | Asp Ile His Val Thr 14305 | Glu Met Glu Ser Ser 14310 | Val Tyr Gln |
| Pro Thr 14315 | Ser Ser Ser Ser Thr 14320 | Gln His Phe Tyr Leu 14325 | Asn Phe Thr |
| Ile Thr 14330 | Asn Leu Pro Tyr Ser 14335 | Gln Asp Lys Ala Gln 14340 | Pro Gly Thr |
| Thr Asn 14345 | Tyr Gln Arg Asn Lys 14350 | Arg Asn Ile Glu Asp 14355 | Ala Leu Asn |
| Gln Leu 14360 | Phe Arg Asn Ser Ser 14365 | Ile Lys Ser Tyr Phe 14370 | Ser Asp Cys |

```
Gln Val     Ser Thr Phe Arg Ser     Val Pro Asn Arg His     His Thr Gly
14375                   14380                   14385

Val Asp     Ser Leu Cys Asn Phe     Ser Pro Leu Ala Arg     Arg Val Asp
14390                   14395                   14400

Arg Val     Ala Ile Tyr Glu Glu     Phe Leu Arg Met Thr     Arg Asn Gly
14405                   14410                   14415

Thr Gln     Leu Gln Asn Phe Thr     Leu Asp Arg Ser Ser     Val Leu Val
14420                   14425                   14430

Asp Gly     Tyr Ser Pro Asn Arg     Asn Glu Pro Leu Thr     Gly Asn Ser
14435                   14440                   14445

Asp Leu     Pro Phe Trp Ala Val     Ile Leu Ile Gly Leu     Ala Gly Leu
14450                   14455                   14460

Leu Gly     Val Ile Thr Cys Leu     Ile Cys Gly Val Leu     Val Thr Thr
14465                   14470                   14475

Arg Arg     Arg Lys Lys Glu Gly     Glu Tyr Asn Val Gln     Gln Gln Cys
14480                   14485                   14490

Pro Gly     Tyr Tyr Gln Ser His     Leu Asp Leu Glu Asp     Leu Gln
14495                   14500                   14505

<210> SEQ ID NO 14
<211> LENGTH: 24
<212> TYPE: PRT
<213> ORGANISM: Artificial Sequence
<220> FEATURE:
<223> OTHER INFORMATION: Synthetic

<400> SEQUENCE: 14

Phe Trp Ala Val Ile Leu Ile Gly Leu Ala Gly Leu Leu Gly Leu Ile
1               5                   10                  15

Thr Cys Leu Ile Cys Gly Val Leu
            20

<210> SEQ ID NO 15
<211> LENGTH: 32
<212> TYPE: PRT
<213> ORGANISM: Artificial Sequence
<220> FEATURE:
<223> OTHER INFORMATION: Synthetic

<400> SEQUENCE: 15

Lys Ser Tyr Phe Ser Asp Cys Gln Val Ser Thr Phe Arg Ser Val Pro
1               5                   10                  15

Asn Arg His His Thr Gly Val Asp Ser Leu Cys Asn Phe Ser Pro Leu
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic

<400> SEQUENCE: 16

Val Thr Thr Arg Arg Arg Lys Lys Glu Gly Glu Tyr Asn Val Gln Gln
1               5                   10                  15

Gln Cys Pro Gly Tyr Tyr Gln Ser His Leu Asp Leu Glu Asp Leu Gln
            20                  25                  30

<210> SEQ ID NO 17
<211> LENGTH: 58
```

```
<212> TYPE: PRT
<213> ORGANISM: Artificial Sequence
<220> FEATURE:
<223> OTHER INFORMATION: Synthetic

<400> SEQUENCE: 17

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro
    50                  55

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Val Thr Thr Arg Arg Arg Lys Lys Glu Gly Glu Tyr Asn Val Gln Gln
1               5                   10                  15

Gln

<210> SEQ ID NO 19
<211> LENGTH: 21
<212> TYPE: PRT
<213> ORGANISM: Artificial Sequence
<220> FEATURE:
<223> OTHER INFORMATION: Synthetic

<400> SEQUENCE: 19

Cys Gln Val Ser Thr Phe Arg Ser Val Pro Asn Arg His His Thr Gly
1               5                   10                  15

Val Asp Ser Leu Cys
            20

<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

Leu Val Thr Thr Arg Arg Arg Lys Lys Glu Gly Glu Tyr Asn Val Gln
1               5                   10                  15

Gln Gln

<210> SEQ ID NO 21
<211> LENGTH: 18
<212> TYPE: PRT
<213> ORGANISM: Mus musculus

<400> SEQUENCE: 21

Thr Leu Asp Arg Lys Ser Val Phe Val Asp Gly Tyr Ser Gln Asn Arg
1               5                   10                  15

Asp Asp
```

```
<210> SEQ ID NO 22
<211> LENGTH: 33
<212> TYPE: PRT
<213> ORGANISM: Mus musculus

<400> SEQUENCE: 22

Lys Ser Tyr Phe Ser Asp Cys Gln Val Leu Ala Phe Arg Ser Val Ser
1               5                   10                  15

Asn Asn Asn Asn His Thr Gly Val Asp Ser Leu Cys Asn Phe Ser Pro
            20                  25                  30

Leu

<210> SEQ ID NO 23
<211> LENGTH: 31
<212> TYPE: PRT
<213> ORGANISM: Mus musculus

<400> SEQUENCE: 23

Ser Leu Tyr Ser Asn Cys Arg Leu Ala Ser Leu Arg Pro Lys Lys Asn
1               5                   10                  15

Gly Thr Ala Thr Gly Val Asn Ala Ile Cys Ser Tyr His Gln Asn
            20                  25                  30

<210> SEQ ID NO 24
<211> LENGTH: 402
<212> TYPE: PRT
<213> ORGANISM: Mus musculus

<400> SEQUENCE: 24

His Leu Ile Arg Pro Leu Val Gln Asn Glu Ser Leu Tyr Ser Asn Cys
1               5                   10                  15

Arg Leu Ala Ser Leu Arg Pro Lys Lys Asn Gly Thr Ala Thr Gly Val
            20                  25                  30

Asn Ala Ile Cys Ser Tyr His Gln Asn Pro Asp His Pro Glu Leu Asp
        35                  40                  45

Thr Gln Glu Leu Tyr Thr Lys Leu Thr Gln Leu Thr Gln Gly Val Thr
    50                  55                  60

Gln Leu Gly Ser Tyr Met Leu Asp Gln Asn Ser Ile Tyr Val Asn Gly
65                  70                  75                  80

Tyr Val Pro Leu Asn Ile Thr Ile Gln Gly Lys Tyr Gln Leu Asn Phe
                85                  90                  95

Cys Ile Ile Asn Trp Asn Leu Asn Asn Thr Asp Pro Thr Ser Ser Glu
            100                 105                 110

Tyr Ile Thr Leu Glu Arg Asp Ile Glu Asp Lys Val Thr Thr Leu Tyr
        115                 120                 125

Thr Gly Ser Gln Leu Lys Glu Val Phe Gln Ser Cys Leu Val Thr Asn
    130                 135                 140

Met Thr Ser Gly Ser Thr Val Val Thr Leu Glu Ala Leu Phe Ser Ser
145                 150                 155                 160

His Leu Asp Pro Asn Leu Val Lys Gln Val Phe Leu Asn Lys Thr Leu
                165                 170                 175

Asn Ala Ser Ser His Trp Leu Gly Ala Thr Tyr Gln Leu Lys Asp Leu
            180                 185                 190

His Val Ile Asp Met Lys Thr Ser Ile Leu Pro Ala Glu Ile Pro
        195                 200                 205

Thr Thr Ser Ser Ser Ser Gln His Phe Asn Leu Asn Phe Thr Ile Thr
    210                 215                 220
```

```
Asn Leu Pro Tyr Ser Gln Asp Ile Ala Gln Pro Ser Thr Thr Lys Tyr
225                 230                 235                 240

Gln Gln Thr Lys Arg Ser Ile Glu Asn Ala Leu Asn Gln Leu Phe Arg
                245                 250                 255

Asn Ser Ser Ile Lys Ser Tyr Phe Ser Asp Cys Gln Val Leu Ala Phe
            260                 265                 270

Arg Ser Val Ser Asn Asn Asn His Thr Gly Val Asp Ser Leu Cys
        275                 280                 285

Asn Phe Ser Pro Leu Ala Arg Arg Val Asp Arg Val Ala Ile Tyr Glu
    290                 295                 300

Glu Phe Leu Arg Met Thr His Asn Gly Thr Gln Leu Leu Asn Phe Thr
305                 310                 315                 320

Leu Asp Arg Lys Ser Val Phe Val Asp Gly Tyr Ser Gln Asn Arg Asp
                325                 330                 335

Asp Asp Val Met Lys Asn Ser Gly Leu Pro Phe Trp Ala Ile Ile Leu
            340                 345                 350

Ile Cys Leu Ala Val Leu Leu Val Leu Ile Thr Cys Leu Met Cys Cys
        355                 360                 365

Phe Leu Val Thr Val Cys Arg Arg Lys Lys Glu Gly Asp Tyr Gln Val
    370                 375                 380

Gln Arg His Arg Leu Ala Tyr Tyr Leu Ser His Leu Asp Leu Arg Lys
385                 390                 395                 400

Leu Gln

<210> SEQ ID NO 25
<211> LENGTH: 400
<212> TYPE: PRT
<213> ORGANISM: Homo sapiens

<400> SEQUENCE: 25

His Leu Leu Arg Pro Leu Phe Gln Lys Ser Met Gly Pro Phe Tyr
1               5                   10                  15

Leu Gly Cys Gln Leu Ile Ser Leu Arg Pro Glu Lys Asp Gly Ala Ala
            20                  25                  30

Thr Gly Val Asp Thr Thr Cys Thr Tyr His Pro Asp Pro Val Gly Pro
        35                  40                  45

Gly Leu Asp Ile Gln Gln Leu Tyr Trp Glu Leu Ser Gln Leu Thr His
    50                  55                  60

Gly Val Thr Gln Leu Gly Phe Tyr Val Leu Asp Arg Asp Ser Leu Phe
65                  70                  75                  80

Ile Asn Gly Tyr Ala Pro Gln Asn Leu Ser Ile Arg Gly Glu Tyr Gln
                85                  90                  95

Ile Asn Phe His Ile Val Asn Trp Asn Leu Ser Asn Pro Asp Pro Thr
            100                 105                 110

Ser Ser Glu Tyr Ile Thr Leu Leu Arg Asp Ile Gln Asp Lys Val Thr
        115                 120                 125

Thr Leu Tyr Lys Gly Ser Gln Leu His Asp Thr Phe Arg Phe Cys Leu
    130                 135                 140

Val Thr Asn Leu Thr Met Asp Ser Val Leu Val Thr Val Lys Ala Leu
145                 150                 155                 160

Phe Ser Ser Asn Leu Asp Pro Ser Leu Val Glu Gln Val Phe Leu Asp
                165                 170                 175

Lys Thr Leu Asn Ala Ser Phe His Trp Leu Gly Ser Thr Tyr Gln Leu
            180                 185                 190
```

```
Val Asp Ile His Val Thr Glu Met Glu Ser Ser Val Tyr Gln Pro Thr
        195                 200                 205

Ser Ser Ser Ser Thr Gln His Phe Tyr Leu Asn Phe Thr Ile Thr Asn
    210                 215                 220

Leu Pro Tyr Ser Gln Asp Lys Ala Gln Pro Gly Thr Thr Asn Tyr Gln
225                 230                 235                 240

Arg Asn Lys Arg Asn Ile Glu Asp Ala Leu Asn Gln Leu Phe Arg Asn
                245                 250                 255

Ser Ser Ile Lys Ser Tyr Phe Ser Asp Cys Gln Val Ser Thr Phe Arg
            260                 265                 270

Ser Val Pro Asn Arg His His Thr Gly Val Asp Ser Leu Cys Asn Phe
        275                 280                 285

Ser Pro Leu Ala Arg Arg Val Asp Arg Val Ala Ile Tyr Glu Glu Phe
    290                 295                 300

Leu Arg Met Thr Arg Asn Gly Thr Gln Leu Gln Asn Phe Thr Leu Asp
305                 310                 315                 320

Arg Ser Ser Val Leu Val Asp Gly Tyr Ser Pro Asn Arg Asn Glu Pro
                325                 330                 335

Leu Thr Gly Asn Ser Asp Leu Pro Phe Trp Ala Val Ile Leu Ile Gly
            340                 345                 350

Leu Ala Gly Leu Leu Gly Val Ile Thr Cys Leu Ile Cys Gly Val Leu
        355                 360                 365

Val Thr Thr Arg Arg Arg Lys Lys Glu Gly Glu Tyr Asn Val Gln Gln
    370                 375                 380

Gln Cys Pro Gly Tyr Tyr Gln Ser His Leu Asp Leu Glu Asp Leu Gln
385                 390                 395                 400

<210> SEQ ID NO 26
<211> LENGTH: 360
<212> TYPE: DNA
<213> ORGANISM: Artificial Sequence
<220> FEATURE:
<223> OTHER INFORMATION: Synthetic

<400> SEQUENCE: 26
gaggtgaagc tggaggagtc aggtggagga ttggtgcagc ctaaaggatc attgaaactc      60
tcatgtgccg cctctggttt caccttcaat acctatgccg tgcactgggt ccgccaggct     120
ccaggaaagg gtatggaatg ggttgctcgc ataagaagta aagtggaaa ttatgcaaca      180 tattatgccg attcagtgaa agacagattc accatctcca gaatgattc acagagcatg     240 ctctatctgc aaatgaacaa cctgaaaact gaggacacag ccatatatta ctgtgtgaga     300
gcgggtaaca acgggccctt tccttactgg ggccaaggga ccacggtcac cgtctcctca     360

<210> SEQ ID NO 27
<211> LENGTH: 120
<212> TYPE: PRT
<213> ORGANISM: Artificial Sequence
<220> FEATURE:
<223> OTHER INFORMATION: Synthetic

<400> SEQUENCE: 27

Glu Val Lys Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Val His Trp Val Arg Gln Ala Pro Gly Lys Gly Met Glu Trp Val
        35                  40                  45
```

```
Ala Arg Ile Arg Ser Lys Ser Gly Asn Tyr Ala Thr Tyr Tyr Ala Asp
        50                  55                  60

Ser Val Lys Asp Arg Phe Thr Ile Ser Arg Asn Asp Ser Gln Ser Met
 65                  70                  75                  80

Leu Tyr Leu Gln Met Asn Asn Leu Lys Thr Glu Asp Thr Ala Ile Tyr
                 85                  90                  95

Tyr Cys Val Arg Ala Gly Asn Asn Gly Ala Phe Pro Tyr Trp Gly Gln
            100                 105                 110

Gly Thr Thr Val Thr Val Ser Ser
            115                 120
```

<210> SEQ ID NO 28
<211> LENGTH: 330
<212> TYPE: DNA
<213> ORGANISM: Artificial Sequence
<220> FEATURE:
<223> OTHER INFORMATION: Synthetic

<400> SEQUENCE: 28

```
gacattgagc tcacccagtc tccatcctca ctgtctgcat ctctgggagg cagagtcacc   60
atcacttgca aggctagcca agatattaag aagtatatag cttggtacca acacaagcct  120
ggaaaaactc ctcgactact catacatttc acatctacat tacagacagg catcccatca  180
aggttcagtg gacgtgggtc tgggagagac tattccttca gcatcagcaa cctggagtct  240
gaagatattg caacttatta ttgtctacag tatgatagtc tgtacacgtt cggaggggggg  300
accaagctgg agatcaaacg ggcggccgca                                   330
```

<210> SEQ ID NO 29
<211> LENGTH: 110
<212> TYPE: PRT
<213> ORGANISM: Artificial Sequence
<220> FEATURE:
<223> OTHER INFORMATION: Synthetic

<400> SEQUENCE: 29

```
Asp Ile Glu Leu Thr Gln Ser Pro Ser Ser Leu Ser Ala Ser Leu Gly
  1               5                  10                  15

Gly Arg Val Thr Ile Thr Cys Lys Ala Ser Gln Asp Ile Lys Lys Tyr
             20                  25                  30

Ile Ala Trp Tyr Gln His Lys Pro Gly Lys Thr Pro Arg Leu Leu Ile
         35                  40                  45

His Phe Thr Ser Thr Leu Gln Thr Gly Ile Pro Ser Arg Phe Ser Gly
     50                  55                  60

Arg Gly Ser Gly Arg Asp Tyr Ser Phe Ser Ile Ser Asn Leu Glu Ser
 65                  70                  75                  80

Glu Asp Ile Ala Thr Tyr Tyr Cys Leu Gln Tyr Asp Ser Leu Tyr Thr
                 85                  90                  95

Phe Gly Gly Gly Thr Lys Leu Glu Ile Lys Arg Ala Ala Ala
            100                 105                 110
```

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

```
Lys Ser Tyr Phe Ser Asp Cys Gln Val Asn Asn Phe Arg Ser
1               5                   10
```

<210> SEQ ID NO 31
<211> LENGTH: 18
<212> TYPE: PRT
<213> ORGANISM: Artificial Sequence
<220> FEATURE:
<223> OTHER INFORMATION: Synthetic

<400> SEQUENCE: 31

```
Thr Leu Asp Arg Ser Ser Val Leu Val Asp Gly Tyr Ser Gln Asn Arg
1               5                   10                  15

Asp Asp
```

<210> SEQ ID NO 32
<211> LENGTH: 57
<212> TYPE: DNA
<213> ORGANISM: Artificial Sequence
<220> FEATURE:
<223> OTHER INFORMATION: CD8 leader sequence

<400> SEQUENCE: 32
atggctctcc cagtgactgc cctactgctt cccctagcgc ttctcctgca tgcagag       57

<210> SEQ ID NO 33
<211> LENGTH: 335
<212> TYPE: DNA
<213> ORGANISM: Artificial Sequence
<220> FEATURE:
<223> OTHER INFORMATION: CD3 zeta chain intracellular domain

<400> SEQUENCE: 33
agagtgaagt tcagcaggag cgcagagccc cccgcgtacc agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcg                              335

<210> SEQ ID NO 34
<211> LENGTH: 45
<212> TYPE: DNA
<213> ORGANISM: Artificial Sequence
<220> FEATURE:
<223> OTHER INFORMATION: (G4S)3 serine-glycine linker

<400> SEQUENCE: 34
ggtggaggtg gatcaggtgg aggtggatct ggtggaggtg gatct                    45

<210> SEQ ID NO 35
<211> LENGTH: 225
<212> TYPE: DNA
<213> ORGANISM: Artificial Sequence
<220> FEATURE:
<223> OTHER INFORMATION: CD8 transmembrane domain

<400> SEQUENCE: 35
gcggccgcac ccaccacgac gccagcgccg cgaccaccaa ccccggcgcc cacgatcgcg     60
tcgcagcccc tgtccctgcg cccagaggcg tgccggccag cggcgggggg cgcagtgcac    120 acgaggggc tggacttcgc ctgtgatatc tacatctggg cgcccttggc cgggacttgt    180

```
ggggtccttc tcctgtcact ggttatcacc ctttactgca accac          225
```

<210> SEQ ID NO 36
<211> LENGTH: 223
<212> TYPE: DNA
<213> ORGANISM: Artificial Sequence
<220> FEATURE:
<223> OTHER INFORMATION: CD28 transmembrane + intracellular domains
      (-STOP)

<400> SEQUENCE: 36

```
caattgaagt tatgtatcct cctccttacc tagacaatga aagagcaat ggaaccatta    60 tccatgtgaa agggaaacac ctttgtccaa gtcccctatt tcccggacct tctaagccct   120
tttgggtgct ggtggtggtt ggtggagtcc tggcttgcta tagcttgcta gtaacagtgg   180
cctttattat tttctgggtg aggagtaaga ggagcaggct cct                    223
```

<210> SEQ ID NO 37
<211> LENGTH: 7726
<212> TYPE: DNA
<213> ORGANISM: Artificial Sequence
<220> FEATURE:
<223> OTHER INFORMATION: SFG_4H11z forward sequence

<400> SEQUENCE: 37

```
ggatccggat tagtccaatt tgttaaagac aggatatcag tggtccaggc tctagttttg    60
actcaacaat atcaccagct gaagcctata gagtacgagc catagataaa ataaaagatt   120
ttatttagtc tccagaaaaa gggggggaatg aaagacccca cctgtaggtt tggcaagcta   180
gcttaagtaa cgccattttg caaggcatgg aaaaatacat aactgagaat agagaagttc   240
agatcaaggt caggaacaga tggaacagct gaatatgggc caaacaggat atctgtggta   300
agcagttcct gccccggctc agggccaaga acagatggaa cagctgaata tgggccaaac   360
aggatatctg tggtaagcag ttcctgcccc ggctcagggc caagaacaga tggtccccag   420
atgcggtcca gccctcagca gtttctagag aaccatcaga tgtttccagg gtgccccaag   480
gacctgaaat gaccctgtgc cttatttgaa ctaaccaatc agttcgcttc tcgcttctgt   540
tcgcgcgctt ctgctccccg agctcaataa aagagcccac aaccctcac tcggggcgcc   600 agtcctccga ttgactgagt cgcccgggta cccgtgtatc caataaaccc tcttgcagtt   660
gcatccgact tgtggtctcg ctgttccttg ggagggtctc ctctgagtga ttgactaccc   720
gtcagcgggg gtcttttcaca catgcagcat gtatcaaaat taatttggtt ttttttctta   780
agtatttaca ttaaatggcc atagtactta aagttacatt ggcttccttg aaataaacat   840
ggagtattca gaatgtgtca taaatatttc taattttaag atagtatctc cattggcttt   900
ctactttttc tttttatttt ttttgtcctc tgtcttccat tgttgttgt tgttgtttgt   960 ttgtttgttt gttggttggt tggttaattt tttttaaag atcctacact atagttcaag  1020
ctagactatt agctactctg taacccaggg tgaccttgaa gtcatgggta gcctgctgtt  1080
ttagccttcc cacatctaag attacaggta tgagctatca tttttggtat attgattgat  1140
tgattgattg atgtgtgtgt gtgtgattgt gtttgtgtgt gtgactgtga aaatgtgtgt  1200
atgggtgtgt gtgaatgtgt gtatgtatgt gtgtgtgtga gtgtgtgtgt gtgtgtgtgc  1260
atgtgtgtgt gtgtgactgt gtctatgtgt atgactgtgt gtgtgtgtgt gtgtgtgtgt  1320
gtgtgtgtgt gtgtgtgtgt gttgtgaaaa aatattctat ggtagtgaga gccaacgctc  1380
cggctcaggt gtcaggttgg ttttgagac agagtctttc acttagcttg gaattcactg  1440
```

-continued

```
gccgtcgttt tacaacgtcg tgactgggaa accctggcg ttacccaact taatcgcctt    1500
gcagcacatc cccctttcgc cagctggcgt aatagcgaag aggcccgcac cgatcgccct    1560
tcccaacagt tgcgcagcct gaatggcgaa tggcgcctga tgcggtattt tctccttacg    1620
catctgtgcg gtatttcaca ccgcatatgg tgcactctca gtacaatctg ctctgatgcc    1680
gcatagttaa gccagccccg acacccgcca cacccgctg acgcgccctg acgggcttgt    1740
ctgctcccgg catccgctta cagacaagct gtgaccgtct ccgggagctg catgtgtcag    1800
aggttttcac cgtcatcacc gaaacgcgcg atgacgaaag gcctcgtga tacgcctatt    1860 tttataggtt aatgtcatga taataatggt ttcttagacg tcaggtggca cttttcgggg    1920
aaatgtgcgc ggaacccta tttgtttatt ttctaaata cattcaaata tgtatccgct    1980
catgagacaa taaccctgat aaatgcttca ataatattga aaaggaaga gtatgagtat    2040 tcaacatttc cgtgtcgccc ttattcccctt ttttgcggca ttttgccttc ctgttttttgc    2100 tcacccagaa acgctggtga agtaaaaga tgctgaagat cagttgggtg cacgagtggg    2160
ttacatcgaa ctggatctca acagcggtaa gatccttgag agttttcgcc ccgaagaacg    2220
ttttccaatg atgagcactt ttaaagttct gctatgtggc gcggtattat cccgtattga    2280
cgccgggcaa gagcaactcg gtcgccgcat acactattct cagaatgact tggttgagta    2340
ctcaccagtc acagaaaagc atcttacgga tggcatgaca gtaagagaat tatgcagtgc    2400
tgccataacc atgagtgata acactgcggc caacttactt ctgacaacga tcggaggacc    2460
gaaggagcta accgctttt tgcacaacat gggggatcat gtaactcgcc ttgatcgttg    2520
ggaaccggag ctgaatgaag ccataccaaa cgacgagcgt gacaccacga tgcctgtagc    2580
aatggcaaca acgttgcgca aactattaac tggcgaacta cttactctag cttcccggca    2640
acaattaata gactggatgg aggcggataa agttgcagga ccacttctgc gctcggccct    2700
tccggctggc tggtttattg ctgataaatc tggagccggt gagcgtgggt ctcgcggtat    2760
cattgcagca ctggggccag atggtaagcc ctcccgtatc gtagttatct acacgacggg    2820
gagtcaggca actatggatg aacgaaatag acagatcgct gagataggtg cctcactgat    2880
taagcattgg taactgtcag accaagttta ctcatatata ctttagattg atttaaaact    2940
tcatttttaa tttaaaagga tctaggtgaa gatcctttt gataatctca tgaccaaaat    3000
cccttaacgt gagttttcgt tccactgagc gtcagacccc gtagaaaaga tcaaaggatc    3060
ttcttgagat ccttttttc tgcgcgtaat ctgctgcttg caaacaaaaa aaccaccgct    3120
accagcggtg gtttgtttgc cggatcaaga gctaccaact ctttttccga aggtaactgg    3180
cttcagcaga gcgcagatac caaatactgt ccttctagtg tagccgtagt taggccacca    3240
cttcaagaac tctgtagcac cgcctacata cctcgctctg ctaatcctgt taccagtggc    3300
tgctgccagt ggcgataagt cgtgtcttac cgggttggac tcaagacgat agttaccgga    3360
taaggcgcag cggtcgggct gaacggggg ttcgtgcaca cagcccagct tggagcgaac    3420
gacctacacc gaactgagat acctacagcg tgagcattga gaaagcgcca cgcttcccga    3480
agggagaaag gcggacaggt atccggtaag cggcagggtc ggaacaggag agcgcacgag    3540
ggagcttcca ggggaaacg cctggtatct ttatagtcct gtcgggtttc gccacctctg    3600
acttgagcgt cgatttttgt gatgctcgtc aggggggcgg agcctatgga aaaacgccag    3660
caacgcggcc tttttacggt tcctggcctt ttgctggcct tttgctcaca tgttctttcc    3720
tgcgttatcc cctgattctg tggataaccg tattaccgcc tttgagtgag ctgataccgc    3780
```

```
tcgccgcagc cgaacgaccg agcgcagcga gtcagtgagc gaggaagcgg aagagcgccc    3840
aatacgcaaa ccgcctctcc ccgcgcgttg gccgattcat taatgcagct ggcacgacag    3900
gtttcccgac tggaaagcgg gcagtgagcg caacgcaatt aatgtgagtt agctcactca    3960
ttaggcaccc caggctttac actttatgct tccggctcgt atgttgtgtg gaattgtgag    4020
cggataacaa tttcacacag gaaacagcta tgaccatgat tacgccaagc tttgctctta    4080
ggagtttcct aatacatccc aaactcaaat atataaagca tttgacttgt tctatgccct    4140
agggggcggg gggaagctaa gccagctttt tttaacattt aaaatgttaa ttccatttta    4200
aatgcacaga tgtttttatt tcataagggt ttcaatgtgc atgaatgctg caatattcct    4260
gttaccaaag ctagtataaa taaaaataga taaacgtgga aattacttag agtttctgtc    4320
attaacgttt ccttcctcag ttgacaacat aaatgcgctg ctgagcaagc cagtttgcat    4380
ctgtcaggat caatttccca ttatgccagt catattaatt actagtcaat tagttgattt    4440 ttattttga catatacatg tgaatgaaag accccacctg taggtttggc aagctagctt    4500
aagtaacgcc attttgcaag gcatggaaaa atacataact gagaatagaa aagttcagat    4560
caaggtcagg aacagatgga acagctgaat atgggccaaa caggatatct gtggtaagca    4620
gttcctgccc cggctcaggg ccaagaacag atggaacagc tgaatatggg ccaaacagga    4680
tatctgtggt aagcagttcc tgccccggct cagggccaag aacagatggt ccccagatgc    4740
ggtccagccc tcagcagttt ctagagaacc atcagatgtt tccagggtgc cccaaggacc    4800
tgaaatgacc ctgtgcctta tttgaactaa ccaatcagtt cgcttctcgc ttctgttcgc    4860
gcgcttatgc tccccgagct caataaaaga gcccacaacc cctcactcgg ggcgccagtc    4920
ctccgattga ctgagtcgcc cgggtacccg tgtatccaat aaaccctctt gcagttgcat    4980
ccgacttgtg gtctcgctgt tccttgggag ggtctcctct gagtgattga ctacccgtca    5040 gcggggggtct ttcatttggg ggctcgtccg ggatcgggag acccctgccc agggaccacc    5100
gacccaccac cggaggtaa gctggccagc aacttatctg tgtctgtccg attgtctagt    5160
gtctatgact gattttatgc gcctgcgtcg gtactagtta gctaactagc tctgtatctg    5220
gcggacccgt ggtggaactg acgagttcgg aacacccggc cgcaaccctg ggagacgtcc    5280
cagggacttc gggggccgtt tttgtggccc gacctgagtc ctaaaatccc gatcgtttag    5340
gactctttgg tgcaccccc ttagaggagg gatatgtggt tctggtagga acgagaacc    5400 taaaacagtt cccgcctccg tctgaatttt tgctttcggt ttgggaccga agccgcgccg    5460
cgcgtcttgt ctgctgcagc atcgttctgt gttgtctctg tctgactgtg tttctgtatt    5520
tgtctgaaaa tatgggcccg ggctagactg ttaccactcc cttaagtttg accttaggtc    5580
actggaaaga tgtcgagcgg atcgctcaca accagtcggt agatgtcaag aagagacgtt    5640
gggttacctt ctgctctgca gaatggccaa cctttaacgt cggatggccg cgagacggca    5700
cctttaaccg agacctcatc acccaggtta agatcaaggt cttttcacct ggcccgcatg    5760
gacacccaga ccaggtcccc tacatcgtga cctgggaagc cttggctttt gacccccctc    5820
cctgggtcaa gccctttgta caccctaagc ctccgcctcc tcttcctcca tccgccccgt    5880
ctctccccct tgaacctcct cgttcgaccc cgcctcgatc ctcccttat ccagccctca    5940 ctccttctct aggcgccccc atatggccat atgagatctt atgtgggca ccccgcccc    6000 ttgtaaactt ccctgaccct gacatgacaa gagttactaa cagcccctct ctccaagctc    6060
acttacaggc tctctactta gtccagcacg aagtctggag acctctggcg gcagcctacc    6120
aagaacaact ggaccgaccg gtggtacctc acccttaccg agtcggcgac acagtgtggg    6180
```

```
tccgccgaca ccagactaag aacctagaac ctcgctggaa aggaccttac acagtcctgc   6240
tgaccacccc caccgccctc aaagtagacg gcatcgcagc ttggatacac gccgcccacg   6300
tgaaggctgc cgaccccggg ggtggaccat cctctagact gccatggctc tcccagtgac   6360
tgccctactg cttcccctag cgcttctcct gcatgcagag gtgaagctgc aggagtcagg   6420
gggaggcttc gtgaagcctg agggtccct caaagtctcc tgtgcagcct ctggattcac    6480
tttcagtagc tatgccatgt cctgggttcg cctgagtccg gagatgaggc tggagtgggt   6540
cgcaaccatt agcagtgctg gtggttacat cttctattct gacagtgtgc agggacgatt   6600
caccatttcc agagacaatg ccaagaacac cctgcacctg caaatgggca gtctgaggtc   6660
tggggacacg gccatgtatt actgtgcaag gcagggattt ggtaactacg gtgattacta   6720
tgctatggac tactggggcc aagggaccac ggtcaccgtc tcctcaggtg gaggtggatc   6780
aggtggaggt ggatctggtg gaggtggatc tgacattgag ctcacccagt ctccatcctc   6840
cctggctgtg tcagcaggag agaaggtcac tatgagctgc aaatccagtc agagtctgct   6900
caacagtaga acccgaaaga accagttggc ttggtaccag caaaaaccag acagtctcc    6960 tgaactgctg atctactggg catccactag gcaatctgga gtccctgatc gcttcacagg   7020
cagtggatct gggacagatt tcactctcac catcagcagt gtgcaggctg aagacctggc   7080
agtttattac tgccagcaat cttataatct actcacgttc ggtcctggga ccaagctgga   7140
gatcaaacgg gcggccgcac ccaccacgac gccagcgccg cgaccaccaa cccggcgcc    7200 cacgatcgcg tcgcagcccc tgtccctgcg cccagaggcg tgccggccag cggcggggg    7260 cgcagtgcac acgagggggc tggacttcgc ctgtgatatc tacatctggg cgcccttggc   7320
cgggacttgt ggggtccttc tcctgtcact ggttatcacc ctttactgca accacagagt   7380
gaagttcagc aggagcgcag agccccccgc gtaccagcag ggccagaacc agctctataa   7440
cgagctcaat ctaggacgaa gagaggagta cgatgttttg gacaagagac gtggccggga   7500
ccctgagatg gggggaaagc cgagaaggaa gaaccctcag gaaggcctgt acaatgaact   7560
gcagaaagat aagatggcgg aggcctacag tgagattggg atgaaaggcg agcgccggag   7620
gggcaagggg cacgatggcc tttaccaggg tctcagtaca gccaccaagg acacctacga   7680
cgcccttcac atgcaggccc tgccccctcg ctaacagcca ctcgag            7726
```

<210> SEQ ID NO 38
<211> LENGTH: 7726
<212> TYPE: DNA
<213> ORGANISM: Artificial Sequence
<220> FEATURE:
<223> OTHER INFORMATION: SFG_4H11z reverse sequence

<400> SEQUENCE: 38

```
cctaggccta atcaggttaa acaatttctg tcctatagtc accaggtccg agatcaaaac    60
tgagttgtta tagtggtcga cttcggatat ctcatgctcg gtatctattt tatttttctaa  120 aataaatcag aggtctttt ccccccttac tttctggggt ggacatccaa accgttcgat    180
cgaattcatt gcgtaaaac gttccgtacc tttttatgta ttgactctta tctcttcaag    240
tctagttcca gtccttgtct accttgtcga cttatacccg gtttgtccta tagacaccat   300
tcgtcaagga cggggccgag tcccggttct tgtctacctt gtcgacttat acccggtttg   360
tcctatagac accattcgtc aaggacgggg ccgagtcccg gttcttgtct accagggggtc  420 tacgccaggt cgggagtcgt caaagatctc ttggtagtct acaaaggtcc cacggggttc   480
```

-continued

```
ctggacttta ctgggacacg gaataaactt gattggttag tcaagcgaag agcgaagaca    540
agcgcgcgaa gacgaggggc tcgagttatt ttctcgggtg ttggggagtg agccccgcgg    600
tcaggaggct aactgactca gcgggcccat gggcacatag gttatttggg agaacgtcaa    660
cgtaggctga acaccagagc gacaaggaac cctcccagag gagactcact aactgatggg    720
cagtcgcccc cagaaagtgt gtacgtcgta catagtttta attaaaccaa aaaaaagaat    780
tcataaatgt aatttaccgg tatcatgaat ttcaatgtaa ccgaaggaac tttatttgta    840
cctcataagt cttacacagt atttataaag attaaaattc tatcatagag gtaaccgaaa    900
gatgaaaaag aaaataaaaa aaaacaggag acagaaggta aacaacaaca acaacaaaca    960
aacaaacaaa caaccaacca accaattaaa aaaaatttc taggatgtga tatcaagttc    1020
gatctgataa tcgatgagac attgggtccc actggaactt cagtacccat cggacgacaa    1080
aatcggaagg gtgtagattc taatgtccat actcgatagt aaaaaccata taactaacta    1140
actaactaac tacacacaca cactaacaa caaacacaca cactgacact tttacacaca    1200
tacccacaca cacttacaca catacataca cacacacact cacacacaca cacacacacg    1260
tacacacaca cacactgaca cagatacaca tactgacaca cacacacaca cacacacaca    1320
cacacacaca cacacacaca caacactttt ttataagata ccatcactct cggttgcgag    1380
gccgagtcca cagtccaacc aaaaactctg tctcagaaag tgaatcgaac cttaagtgac    1440
cggcagcaaa atgttgcagc actgacccct ttgggaccgc aatgggttga attagcggaa    1500
cgtcgtgtag ggggaaagcg gtcgaccgca ttatcgcttc tccgggcgtg gctagcggga    1560
agggttgtca acgcgtcgga cttaccgctt accgcggact acgccataaa agaggaatgc    1620
gtagacacgc cataaagtgt ggcgtatacc acgtgagagt catgttagac gagactacgg    1680
cgtatcaatt cggtcgggc tgtgggcggt tgtgggcgac tgcgcgggac tgcccgaaca    1740
gacgagggcc gtaggcgaat gtctgttcga cactggcaga ggccctcgac gtacacagtc    1800
tccaaaagtg gcagtagtgg cttttgcgcg ctactgcttt ccggagcact atgcggataa    1860
aaatatccaa ttacagtact attattacca aagaatctgc agtccaccgt gaaaagcccc    1920
tttacacgcg ccttggggat aaacaaataa aaagatttat gtaagtttat acataggcga    1980
gtactctgtt attgggacta tttacgaagt tattataact ttttccttct catactcata    2040
agttgtaaag gcacagcggg aataagggaa aaaacgccgt aaaacggaag gacaaaaacg    2100
agtgggtctt tgcgaccact ttcatttcct acgacttcta gtcaacccac gtgctcaccc    2160
aatgtagctt gacctagagt tgtcgccatt ctaggaactc tcaaaagcgg ggcttcttgc    2220
aaaaggttac tactcgtgaa aatttcaaga cgatacaccg cgccataata gggcataact    2280
gcggcccgtt ctcgttgagc cagcggcgta tgtgataaga gtcttactga accaactcat    2340
gagtggtcag tgtcttttcg tagaatgcct accgtactgt cattctctta atacgtcacg    2400
acggtattgg tactcactat tgtgacgccg gttgaatgaa gactgttgct agcctcctgg    2460
cttcctcgat tggcgaaaaa acgtgttgta ccccctagta cattgagcgg aactagcaac    2520
ccttggcctc gacttacttc ggtatggttt gctgctcgca ctgtggtgct acggacatcg    2580
ttaccgttgt tgcaacgcgt ttgataattg accgcttgat gaatgagatc gaagggccgt    2640
tgttaattat ctgacctacc tccgcctatt tcaacgtcct ggtgaagacg cgagccggga    2700
aggccgaccg accaaataac gactatttag acctcggcca ctcgcaccca gagcgccata    2760
gtaacgtcgt gaccccggtc taccattcgg gagggcatag catcaataga tgtgctgccc    2820
ctcagtccgt tgatacctac ttgctttatc tgtctagcga ctctatccac ggagtgacta    2880
```

```
attcgtaacc attgacagtc tggttcaaat gagtatatat gaaatctaac taaattttga    2940
agtaaaaatt aaattttcct agatccactt ctaggaaaaa ctattagagt actggtttta    3000
gggaattgca ctcaaaagca aggtgactcg cagtctgggg catcttttct agtttcctag    3060
aagaactcta ggaaaaaaag acgcgcatta gacgacgaac gtttgttttt ttggtggcga    3120
tggtcgccac caaacaaacg gcctagttct cgatggttga gaaaaaggct tccattgacc    3180
gaagtcgtct cgcgtctatg gtttatgaca ggaagatcac atcggcatca atccggtggt    3240
gaagttcttg agacatcgtg gcggatgtat ggagcgagac gattaggaca atggtcaccg    3300
acgacggtca ccgctattca gcacagaatg gcccaacctg agttctgcta tcaatggcct    3360
attccgcgtc gccagcccga cttgcccccc aagcacgtgt gtcgggtcga acctcgcttg    3420
ctggatgtgg cttgactcta tggatgtcgc actcgtaact ctttcgcggt gcgaagggct    3480
tccctctttc cgcctgtcca taggccattc gccgtccagc cttgtcctc tcgcgtgctc    3540 cctcgaaggt ccccctttgc ggaccataga aatatcagga cagcccaaag cggtggagac    3600
tgaactcgca gctaaaaaca ctacgagcag tccccccgcc tcggatacct ttttgcggtc    3660
gttgcgccgg aaaaatgcca aggaccggaa acgaccggaa aacgagtgt acaagaaagg    3720 acgcaatagg ggactaagac acctattggc ataatggcgg aaactcactc gactatggcg    3780
agcggcgtcg gcttgctggc tcgcgtcgct cagtcactcg ctccttcgcc ttctcgcggg    3840
ttatgcgttt ggcggagagg ggcgcgcaac cggctaagta attacgtcga ccgtgctgtc    3900
caaagggctg acctttcgcc cgtcactcgc gttgcgttaa ttacactcaa tcgagtgagt    3960
aatccgtggg gtccgaaatg tgaaatacga aggccgagca tacaacacac cttaacactc    4020
gcctattgtt aaagtgtgtc ctttgtcgat actggtacta atgcggttcg aaacgagaat    4080
cctcaaagga ttatgtaggg tttgagttta tatatttcgt aaactgaaca agatacggga    4140
tcccccgccc cccttcgatt cggtcgaaaa aaattgtaaa ttttacaatt aaggtaaaat    4200
ttacgtgtct acaaaaataa agtattccca aagttacacg tacttacgac gttataagga    4260
caatggtttc gatcatattt attttatct atttgcacct ttaatgaatc tcaaagacag    4320
taattgcaaa ggaaggagtc aactgttgta tttacgcgac gactcgttcg gtcaaacgta    4380
gacagtccta gttaaagggt aatacggtca gtataattaa tgatcagtta atcaactaaa    4440
aataaaaact gtatatgtac acttactttc tggggtggac atccaaaccg ttcgatcgaa    4500
ttcattgcgg taaaacgttc cgtacctttt tatgtattga ctcttatctt ttcaagtcta    4560
gttccagtcc ttgtctacct tgtcgactta tacccggttt gtcctataga caccattcgt    4620
caaggacggg gccgagtccc ggttcttgtc taccttgtcg acttataccc ggtttgtcct    4680
atagacacca ttcgtcaagg acggggccga gtcccggttc ttgtctacca ggggtctacg    4740
ccaggtcggg agtcgtcaaa gatctcttgg tagtctacaa aggtcccacg gggttcctgg    4800
actttactgg gacacggaat aaacttgatt ggttagtcaa gcgaagagcg aagacaagcg    4860
cgcgaatacg aggggctcga gttattttct cgggtgttgg ggagtgagcc ccgcggtcag    4920
gaggctaact gactcagcgg gcccatgggc acataggtta tttgggagaa cgtcaacgta    4980
ggctgaacac cagagcgaca aggaaccctc ccagaggaga ctcactaact gatgggcagt    5040
cgcccccaga aagtaaaccc ccgagcaggc cctagccctc tggggacggg tccctggtgg    5100
ctgggtggtg gccctccatt cgaccggtcg ttgaatagac acagacaggc taacagatca    5160
cagatactga ctaaaatacg cggacgcagc catgatcaat cgattgatcg agacatagac    5220
```

```
cgcctgggca ccaccttgac tgctcaagcc ttgtgggccg gcgttgggac cctctgcagg   5280
gtccctgaag cccccggcaa aaacaccggg ctggactcag gattttaggg ctagcaaatc   5340
ctgagaaacc acgtgggggg aatctcctcc ctatacacca agaccatcct ctgctcttgg   5400
attttgtcaa gggcggaggc agacttaaaa acgaaagcca aaccctggct tcggcgcggc   5460
gcgcagaaca gacgacgtcg tagcaagaca caacagagac agactgacac aaagacataa   5520
acagactttt atacccgggc ccgatctgac aatggtgagg gaattcaaac tggaatccag   5580
tgaccttcct acagctcgcc tagcgagtgt tggtcagcca tctacagttc ttctctgcaa   5640
cccaatggaa gacgagacgt cttaccggtt ggaaattgca gcctaccggc gctctgccgt   5700
ggaaattggc tctggagtag tgggtccaat tctagttcca gaaaagtgga ccgggcgtac   5760
ctgtgggtct ggtccagggg atgtagcact ggacccttcg gaaccgaaaa ctgggggggag   5820 ggacccagtt cgggaaacat gtgggattcg gaggcggagg agaaggaggt aggcggggca   5880 gagagggggga acttggagga gcaagctggg gcggagctag gagggaaata ggtcgggagt   5940
gaggaagaga tccgcggggg tataccggta tactctagaa tataccccgt gggggcgggg   6000
aacatttgaa gggactggga ctgtactgtt ctcaatgatt gtcggggaga gaggttcgag   6060
tgaatgtccg agagatgaat caggtcgtgc ttcagacctc tggagaccgc cgtcggatgg   6120
ttcttgttga cctggctggc caccatggag tgggaatggc tcagccgctg tgtcacaccc   6180
aggcggctgt ggtctgattc ttggatcttg agcgaccttt cctgaaatg tgtcaggacg   6240 actggtgggg gtggcgggag tttcatctgc cgtagcgtcg aacctatgtg cggcgggtgc   6300
acttccgacg gctgggggccc ccacctggta ggagatctga cggtaccgag agggtcactg   6360
acgggatgac gaaggggatc gcgaagagga cgtacgtctc cacttcgacg tcctcagtcc   6420
ccctccgaag cacttcggac ctcccaggga gtttcagagg acacgtcgga gacctaagtg   6480
aaagtcatcg atacggtaca ggacccaagc ggactcaggc ctctactccg acctcaccca   6540
gcgttggtaa tcgtcacgac caccaatgta gaagataaga ctgtcacacg tccctgctaa   6600
gtggtaaagg tctctgttac ggttcttgtg ggacgtggac gtttacccgt cagactccag   6660
acccctgtgc cggtacataa tgacacgttc cgtccctaaa ccattgatgc cactaatgat   6720
acgatacctg atgaccccgg ttccctggtg ccagtggcag aggagtccac ctccacctag   6780
tccacctcca cctagaccac ctccacctag actgtaactc gagtgggtca gaggtaggag   6840
ggaccgacac agtcgtcctc tcttccagtg atactcgacg tttaggtcag tctcagacga   6900
gttgtcatct tgggctttct tggtcaaccg aaccatggtc gttttttggtc ctgtcagagg   6960 acttgacgac tagatgaccc gtaggtgatc cgttagacct cagggactag cgaagtgtcc   7020
gtcacctaga ccctgtctaa agtgagagtg gtagtcgtca cacgtccgac ttctggaccg   7080
tcaaataatg acggtcgtta gaatattaga tgagtgcaag ccaggaccct ggttcgacct   7140
ctagtttgcc cgccggcgtg ggtggtgctg cggtcgcggc gctggtggtt ggggccgcgg   7200
gtgctagcgc agcgtcgggg acaggacgcg gggtctccgc acggccggtc gccgccccc   7260 gcgtcacgtg tgctccccg acctgaagcg gacactatag atgtagaccc gcgggaaccg   7320
gccctgaaca ccccaggaag aggacagtga ccaatagtgg gaaatgacgt tggtgtctca   7380
cttcaagtcg tcctcgcgtc tcgggggggcg catggtcgtc ccggtcttgg tcgagatatt   7440
gctcgagtta gatcctgctt ctctcctcat gctacaaaac ctgttctctg caccggccct   7500
gggactctac ccccctttcg gctcttcctt cttgggagtc cttccggaca tgttacttga   7560 cgtcttttcta ttctaccgcc tccggatgtc actctaaccc tactttccgc tcgcggcctc   7620
```

-continued

```
cccgttcccc gtgctaccgg aaatggtccc agagtcatgt cggtggttcc tgtggatgct    7680
gcgggaagtg tacgtccggg acgggggagc gattgtcggt gagctc                  7726

<210> SEQ ID NO 39
<211> LENGTH: 7831
<212> TYPE: DNA
<213> ORGANISM: Artificial Sequence
<220> FEATURE:
<223> OTHER INFORMATION: SFG_4H11-28z forward sequence

<400> SEQUENCE: 39
ggatccggat tagtccaatt tgttaaagac aggatatcag tggtccaggc tctagttttg      60
actcaacaat atcaccagct gaagcctata gagtacgagc catagataaa ataaaagatt     120
ttatttagtc tccagaaaaa ggggggaatg aaagacccca cctgtaggtt tggcaagcta     180
gcttaagtaa cgccattttg caaggcatgg aaaaatacat aactgagaat agagaagttc     240
agatcaaggt caggaacaga tggaacagct gaatatgggc caaacaggat atctgtggta     300
agcagttcct gccccggctc agggccaaga acagatggaa cagctgaata tgggccaaac     360
aggatatctg tggtaagcag ttcctgcccc ggctcagggc caagaacaga tggtccccag     420
atgcggtcca gccctcagca gtttctagag aaccatcaga tgtttccagg gtgccccaag     480
gacctgaaat gaccctgtgc cttatttgaa ctaaccaatc agttcgcttc tcgcttctgt     540
tcgcgcgctt ctgctccccg agctcaataa aagagcccac aaccctcac tcggggcgcc     600 agtcctccga ttgactgagt cgcccgggta cccgtgtatc caataaaccc tcttgcagtt     660
gcatccgact tgtggtctcg ctgttccttg ggagggtctc ctctgagtga ttgactaccc     720
gtcagcgggg gtcttccaca catgcagcat gtatcaaaat taatttggtt ttttttctta     780
agtatttaca ttaaatggcc atagtactta aagttacatt ggcttccttg aaataaacat     840
ggagtattca gaatgtgtca taaatatttc taattttaag atagtatctc cattggcttt     900
ctactttttc ttttatttt ttttgtcctc tgtcttccat ttgttgttgt tgttgtttgt     960
ttgtttgttt gttggttggt tggttaattt tttttttaaag atcctacact atagttcaag    1020
ctagactatt agctactctg taacccaggg tgaccttgaa gtcatgggta gcctgctgtt    1080
ttagccttcc cacatctaag attacaggta tgagctatca ttttggtat attgattgat    1140 tgattgattg atgtgtgtgt gtgtgattgt gtttgtgtgt gtgactgtga aaatgtgtgt    1200
atgggtgtgt gtgaatgtgt gtatgtatgt gtgtgtgtga gtgtgtgtgt gtgtgtgtgc    1260
atgtgtgtgt gtgtgactgt gtctatgtgt atgactgtgt gtgtgtgtgt gtgtgtgtgt    1320
gtgtgtgtgt gtgtgtgtgt gttgtgaaaa atattctat ggtagtgaga gccaacgctc    1380
cggctcaggt gtcaggttgg tttttgagac agagtctttc acttagcttg gaattcactg    1440
gccgtcgttt tacaacgtcg tgactgggaa accctggcg ttacccaact aatcgccttt    1500
gcagcacatc cccctttcgc cagctggcgt aatagcgaag aggcccgcac cgatcgccct    1560
tcccaacagt tgcgcagcct gaatggcgaa tggcgcctga tgcggtattt tctccttacg    1620
catctgtgcg gtatttcaca ccgcatatgg tgcactctca gtacaatctg ctctgatgcc    1680
gcatagttaa gccagccccg acacccgcca acacccgctg acgcgccctg acgggcttgt    1740
ctgctcccgg catccgctta cagacaagct gtgaccgtct ccgggagctg catgtgtcag    1800
aggttttcac cgtcatcacc gaaacgcgcg atgacgaaag gcctcgtga tacgcctatt    1860 tttataggtt aatgtcatga taataatggt ttcttagacg tcaggtggca cttttcgggg    1920
```

```
aaatgtgcgc ggaaccccta tttgtttatt tttctaaata cattcaaata tgtatccgct   1980
catgagacaa taaccctgat aaatgcttca ataatattga aaaggaaga gtatgagtat    2040 tcaacatttc cgtgtcgccc ttattccctt ttttgcggca ttttgccttc ctgttttgc    2100 tcacccagaa acgctggtga aagtaaaaga tgctgaagat cagttgggtg cacgagtggg   2160
ttacatcgaa ctggatctca acagcggtaa gatccttgag agttttcgcc ccgaagaacg   2220
ttttccaatg atgagcactt ttaaagttct gctatgtggc gcggtattat cccgtattga   2280
cgccgggcaa gagcaactcg gtcgccgcat acactattct cagaatgact tggttgagta   2340
ctcaccagtc acagaaaagc atcttacgga tggcatgaca gtaagagaat tatgcagtgc   2400
tgccataacc atgagtgata acactgcggc caacttactt ctgacaacga tcggaggacc   2460
gaaggagcta accgcttttt tgcacaacat gggggatcat gtaactcgcc ttgatcgttg   2520
ggaaccggag ctgaatgaag ccataccaaa cgacgagcgt gacaccacga tgcctgtagc   2580
aatggcaaca acgttgcgca aactattaac tggcgaacta cttactctag cttcccggca   2640
acaattaata gactggatgg aggcggataa agttgcagga ccacttctgc gctcggccct   2700
tccggctggc tggtttattg ctgataaatc tggagccggt gagcgtgggt ctcgcggtat   2760
cattgcagca ctggggccag atggtaagcc ctcccgtatc gtagttatct acacgacggg   2820
gagtcaggca actatggatg aacgaaatag acagatcgct gagataggtg cctcactgat   2880
taagcattgg taactgtcag accaagttta ctcatatata ctttagattg atttaaaact   2940
tcatttttaa tttaaaagga tctaggtgaa gatcctttt gataatctca tgaccaaaat    3000
cccttaacgt gagttttcgt tccactgagc gtcagacccc gtagaaaaga tcaaaggatc   3060
ttcttgagat ccttttttc tgcgcgtaat ctgctgcttg caaacaaaaa aaccaccgct    3120
accagcggtg gtttgtttgc cggatcaaga ctaccaact cttttccga aggtaactgg     3180 cttcagcaga gcgcagatac caaatactgt ccttctagtg tagccgtagt taggccacca   3240
cttcaagaac tctgtagcac cgcctacata cctcgctctg ctaatcctgt taccagtggc   3300
tgctgccagt ggcgataagt cgtgtcttac cgggttggac tcaagacgat agttaccgga   3360
taaggcgcag cggtcgggct gaacggggg ttcgtgcaca cagcccagct tggagcgaac    3420
gacctacacc gaactgagat acctacagcg tgagcattga aaagcgcca cgcttcccga    3480 agggagaaag gcggacaggt atccggtaag cggcagggtc ggaacaggag agcgcacgag   3540
ggagcttcca gggggaaacg cctggtatct ttatagtcct gtcgggtttc gccacctctg   3600
acttgagcgt cgatttttgt gatgctcgtc agggggggcgg agcctatgga aaaacgccag   3660
caacgcggcc ttttacggt tcctggcctt ttgctggcct tttgctcaca tgttctttcc     3720
tgcgttatcc cctgattctg tggataaccg tattaccgcc tttgagtgag ctgataccgc   3780
tcgccgcagc cgaacgaccg agcgcagcga gtcagtgagc gaggaagcgg aagagcgccc   3840
aatacgcaaa ccgcctctcc ccgcgcgttg gccgattcat taatgcagct ggcacgacag   3900
gtttcccgac tggaaagcgg gcagtgagcg caacgcaatt aatgtgagtt agctcactca   3960
ttaggcaccc caggctttac actttatgct tccggctcgt atgttgtgtg gaattgtgag   4020
cggataacaa tttcacacag gaaacagcta tgaccatgat tacgccaagc tttgctctta   4080
ggagtttcct aatacatccc aaactcaaat atataaagca tttgacttgt tctatgccct   4140
agggggcggg gggaagctaa gccagctttt tttaacattt aaaatgttaa ttccatttta   4200
aatgcacaga tgttttatt tcataagggt ttcaatgtgc atgaatgctg caatattcct    4260
gttaccaaag ctagtataaa taaaaataga taaacgtgga aattacttag agtttctgtc   4320
```

-continued

```
attaacgttt ccttcctcag ttgacaacat aaatgcgctg ctgagcaagc cagtttgcat    4380
ctgtcaggat caatttccca ttatgccagt catattaatt actagtcaat tagttgattt    4440
ttatttttga catatacatg tgaatgaaag accccacctg taggtttggc aagctagctt    4500
aagtaacgcc attttgcaag gcatggaaaa atacataact gagaatagaa aagttcagat    4560
caaggtcagg aacagatgga acagctgaat atgggccaaa caggatatct gtggtaagca    4620
gttcctgccc cggctcaggg ccaagaacag atggaacagc tgaatatggg ccaaacagga    4680
tatctgtggt aagcagttcc tgccccggct cagggccaag aacagatggt ccccagatgc    4740
ggtccagccc tcagcagttt ctagagaacc atcagatgtt tccagggtgc cccaaggacc    4800
tgaaatgacc ctgtgcctta tttgaactaa ccaatcagtt cgcttctcgc ttctgttcgc    4860
gcgcttatgc tccccgagct caataaaaga gcccacaacc cctcactcgg ggcgccagtc    4920
ctccgattga ctgagtcgcc cgggtacccg tgtatccaat aaaccctctt gcagttgcat    4980
ccgacttgtg gtctcgctgt tccttgggag ggtctcctct gagtgattga ctacccgtca    5040
gcggggtct ttcatttggg ggctcgtccg ggatcgggag accctgccc agggaccacc     5100
gacccaccac cgggaggtaa gctggccagc aacttatctg tgtctgtccg attgtctagt    5160
gtctatgact gattttatgc gcctgcgtcg gtactagtta gctaactagc tctgtatctg    5220
gcggacccgt ggtggaactg acgagttcgg aacacccggc cgcaaccctg ggagacgtcc    5280
cagggacttc gggggccgtt tttgtggccc gacctgagtc ctaaaatccc gatcgtttag    5340
gactcttggg tgcaccccc ttagaggagg atatgtggt tctggtagga dacgagaacc      5400
taaaacagtt cccgcctccg tctgaatttt tgctttcggt ttgggaccga agccgcgccg    5460
cgcgtcttgt ctgctgcagc atcgttctgt gttgtctctg tctgactgtg tttctgtatt    5520
tgtctgaaaa tatgggcccg ggctagactg ttaccactcc cttaagtttg accttaggtc    5580
actggaaaga tgtcgagcgg atcgctcaca accagtcggt agatgtcaag aagagacgtt    5640
gggttacctt ctgctctgca gaatggccaa cctttaacgt cggatggccg cgagacggca    5700
cctttaaccg agacctcatc acccaggtta agatcaaggt cttttcacct ggcccgcatg    5760
gacacccaga ccaggtcccc tacatcgtga cctgggaagc cttggctttt gacccccctc    5820
cctgggtcaa gccctttgta caccctaagc ctccgcctcc tcttcctcca tccgccccgt    5880
ctctccccct tgaacctcct cgttcgaccc cgcctcgatc ctcccttat ccagccctca     5940
ctccttctct aggcgccccc atatggccat atgagatctt atatgggca ccccgcccc      6000
ttgtaaactt ccctgaccct gacatgacaa gagttactaa cagcccctct ctccaagctc    6060
acttacaggc tctctactta gtccagcacg aagtctggag acctctggcg gcagcctacc    6120
aagaacaact ggaccgaccg gtggtacctc acccttaccg agtcggcgac acagtgtggg    6180
tccgccgaca ccagactaag aacctagaac ctcgctggaa aggaccttac acagtcctgc    6240
tgaccacccc caccgccctc aaagtagacg gcatcgcagc ttggatacac gccgcccacg    6300
tgaaggctgc cgaccccggg ggtggaccat cctctagact gccatggctc tcccagtgac    6360
tgccctactg cttcccctag cgcttctcct gcatgcagag gtgaagctgc aggagtcagg    6420
gggaggcttc gtgaagcctg gagggtccct caaagtctcc tgtgcagcct ctggattcac    6480
tttcagtagc tatgccatgt cctgggttcg cctgagtccg gagatgaggc tggagtgggt    6540
cgcaaccatt agcagtgctg gtggttacat cttctattct gacagtgtgc agggacgatt    6600
caccatttcc agagacaatg ccaagaacac cctgcacctg caaatgggca gtctgaggtc    6660
```

```
tggggacacg gccatgtatt actgtgcaag gcagggattt ggtaactacg gtgattacta    6720
tgctatggac tactgggcc aagggaccac ggtcaccgtc tcctcaggtg gaggtggatc    6780
aggtggaggt ggatctggtg gaggtggatc tgacattgag ctcacccagt ctccatcctc    6840
cctggctgtg tcagcaggag agaaggtcac tatgagctgc aaatccagtc agagtctgct    6900
caacagtaga acccgaaaga accagttggc ttggtaccag caaaaaccag acagtctcc    6960 tgaactgctg atctactggg catccactag gcaatctgga gtccctgatc gcttcacagg    7020
cagtggatct gggacagatt tcactctcac catcagcagt gtgcaggctg aagacctggc    7080
agtttattac tgccagcaat cttataatct actcacgttc ggtcctggga ccaagctgga    7140
gatcaaacgg gcggccgcaa ttgaagttat gtatcctcct ccttacctag acaatgagaa    7200
gagcaatgga accattatcc atgtgaaagg gaaacacctt tgtccaagtc cctatttcc    7260 cggaccttct aagccctttt gggtgctggt ggtggttggt ggagtcctgg cttgctatag    7320
cttgctagta acagtggcct ttattatttt ctgggtgagg agtaagagga gcaggctcct    7380
gcacagtgac tacatgaaca tgactccccg ccgccccggg cccacccgca agcattacca    7440
gccctatgcc ccaccacgcg acttcgcagc ctatcgctcc agagtgaagt tcagcaggag    7500
cgcagagccc cccgcgtacc agcagggcca gaaccagctc tataacgagc tcaatctagg    7560
acgaagagag gagtacgatg tttggacaa gagacgtggc cgggaccctg agatgggggg    7620
aaagccgaga aggaagaacc ctcaggaagg cctgtacaat gaactgcaga agataagat    7680 ggcggaggcc tacagtgaga ttgggatgaa aggcgagcgc cggaggggca aggggcacga    7740
tggcctttac cagggtctca gtacagccac caaggacacc tacgacgccc ttcacatgca    7800
ggccctgccc cctcgctaac agccactcga g                                  7831
```

<210> SEQ ID NO 40
<211> LENGTH: 7831
<212> TYPE: DNA
<213> ORGANISM: Artificial Sequence
<220> FEATURE:
<223> OTHER INFORMATION: SFG_4H11-28z reverse sequence

<400> SEQUENCE: 40

```
cctaggccta atcaggttaa acaatttctg tcctatagtc accaggtccg agatcaaaac      60
tgagttgtta tagtggtcga cttcggatat ctcatgctcg gtatctattt tattttctaa    120
aataaatcag aggtcttttt cccccttac tttctggggt ggacatccaa accgttcgat    180
cgaattcatt gcggtaaaac gttccgtacc tttttatgta ttgactctta tctcttcaag    240
tctagttcca gtccttgtct accttgtcga cttataccg gtttgtccta tagacaccat    300
tcgtcaagga cggggccgag tcccggttct tgtctacctt gtcgacttat acccggtttg    360
tcctatagac accattcgtc aaggacgggg ccgagtcccg gttcttgtct accagggggtc    420 tacgccaggt cgggagtcgt caaagatctc ttggtagtct acaaaggtcc cacggggttc    480
ctggacttta ctgggacacg gaataaactt gattggttag tcaagcgaag agcgaagaca    540
agcgcgcgaa gacgagggc tcgagttatt ttctcgggtg ttggggagtg agccccgcgg    600
tcaggaggct aactgactca gcgggcccat gggcacatag gttatttggg agaacgtcaa    660
cgtaggctga acaccagagc gacaaggaac cctcccagag gagactcact aactgatggg    720
cagtcgcccc cagaaagtgt gtacgtcgta catagtttta attaaaccaa aaaaaagaat    780
tcataaatgt aatttaccgg tatcatgaat ttcaatgtaa ccgaaggaac tttatttgta    840
cctcataagt cttacacagt atttataaag attaaaattc tatcatagag gtaaccgaaa    900
```

```
gatgaaaaag aaaataaaaa aaaacaggag acagaaggta aacaacaaca acaacaaaca       960
aacaaacaaa caaccaacca accaattaaa aaaaaatttc taggatgtga tatcaagttc      1020
gatctgataa tcgatgagac attgggtccc actggaactt cagtacccat cggacgacaa      1080
aatcggaagg gtgtagattc taatgtccat actcgatagt aaaaaccata taactaacta      1140
actaactaac tacacacaca cacactaaca caaacacaca cactgacact tttacacaca      1200
tacccacaca cacttacaca catacataca cacacacact cacacacaca cacacacacg      1260
tacacacaca cacactgaca cagatacaca tactgacaca cacacacaca cacacacaca      1320
cacacacaca cacacacaca caacactttt ttataagata ccatcactct cggttgcgag      1380
gccgagtcca cagtccaacc aaaaactctg tctcagaaag tgaatcgaac cttaagtgac      1440
cggcagcaaa atgttgcagc actgacccTT ttgggaccgc aatgggttga attagcggaa      1500
cgtcgtgtag ggggaaagcg gtcgaccgca ttatcgcttc tccgggcgtg gctagcggga      1560
agggttgtca acgcgtcgga cttaccgctt accgcggact acgccataaa agaggaatgc      1620
gtagacacgc cataaagtgt ggcgtatacc acgtgagagt catgttagac gagactacgg      1680
cgtatcaatt cggtcgggc tgtgggcggt tgtgggcgac tgcgcgggac tgcccgaaca      1740
gacgagggcc gtaggcgaat gtctgttcga cactggcaga ggccctcgac gtacacagtc      1800
tccaaaagtg gcagtagtgg cttttgcgcg tactgctttc ccggagcact atgcggataa      1860
aaatatccaa ttacagtact attattacca aagaatctgc agtccaccgt gaaaagcccc      1920
tttacacgcg ccttggggat aaacaaataa aaagatttat gtaagtttat acataggcga      1980
gtactctgtt attgggacta tttacgaagt tattataact ttttccttct catactcata      2040
agttgtaaag gcacagcggg aataagggaa aaaacgccgt aaaacggaag acaaaaaacg      2100
agtgggtctt tgcgaccact ttcatttttct acgacttcta gtcaacccac gtgctcaccc      2160
aatgtagctt gacctagagt tgtcgccatt ctaggaactc tcaaaagcgg gcttcttgc      2220 aaaaggttac tactcgtgaa aatttcaaga cgatacaccg cgccataata gggcataact      2280
gcggcccgtt ctcgttgagc cagcggcgta tgtgataaga gtcttactga accaactcat      2340
gagtggtcag tgtcttttcg tagaatgcct accgtactgt cattctctta atacgtcacg      2400
acggtattgg tactcactat tgtgacgccg gttgaatgaa gactgttgct agcctcctgg      2460
cttcctcgat tggcgaaaaa acgtgttgta ccccctagta cattgagcgg aactagcaac      2520
ccttggcctc gacttacttc ggtatggttt gctgctcgca ctgtggtgct acggacatcg      2580
ttaccgttgt tgcaacgcgt ttgataattg accgcttgat gaatgagatc gaagggccgt      2640
tgttaattat ctgacctacc tccgcctatt tcaacgtcct ggtgaagacg cgagccggga      2700
aggccgaccg accaaataac gactatttag acctcggcca ctcgcaccca gagcgccata      2760
gtaacgtcgt gacccccggtc taccattcgg gagggcatag catcaataga tgtgctgccc      2820
ctcagtccgt tgatacctac ttgctttatc tgtctagcga ctctatccac ggagtgacta      2880
attcgtaacc attgacagtc tggttcaaat gagtatatat gaaatctaac taaattttga      2940
agtaaaaatt aaattttcct agatccactt ctaggaaaaa ctattagagt actggtttta      3000
gggaattgca ctcaaaagca aggtgactcg cagtctgggg catcttttct agtttcctag      3060
aagaactcta ggaaaaaaag acgcgcatta gacgacgaac gtttgttttt tggtggcga      3120 tggtcgccac caaacaaacg gcctagttct cgatggttga gaaaaaggct tccattgacc      3180
gaagtcgtct cgcgtctatg gtttatgaca ggaagatcac atcggcatca atccggtggt      3240
```

-continued

```
gaagttcttg agacatcgtg gcggatgtat ggagcgagac gattaggaca atggtcaccg    3300
acgacggtca ccgctattca gcacagaatg gcccaacctg agttctgcta tcaatggcct    3360
attccgcgtc gccagcccga cttgcccccc aagcacgtgt gtcgggtcga acctcgcttg    3420
ctggatgtgg cttgactcta tggatgtcgc actcgtaact ctttcgcggt gcgaagggct    3480
tccctctttc cgcctgtcca taggccattc gccgtcccag ccttgtcctc tcgcgtgctc    3540
cctcgaaggt ccccctttgc ggaccataga aatatcagga cagcccaaag cggtggagac    3600
tgaactcgca gctaaaaaca ctacgagcag tccccccgcc tcggatacct ttttgcggtc    3660
gttgcgccgg aaaaatgcca aggaccggaa acgaccggaa aacgagtgt acaagaaagg     3720 acgcaatagg ggactaagac acctattggc ataatggcgg aaactcactc gactatggcg    3780
agcggcgtcg gcttgctggc tcgcgtcgct cagtcactcg ctccttcgcc ttctcgcggg    3840
ttatgcgttt ggcggagagg ggcgcgcaac cggctaagta attacgtcga ccgtgctgtc    3900
caaagggctg acctttcgcc cgtcactcgc gttgcgttaa ttacactcaa tcgagtgagt    3960
aatccgtggg gtccgaaatg tgaaatacga aggccgagca tacaacacac cttaacactc    4020
gcctattgtt aaagtgtgtc ctttgtcgat actggtacta atgcggttcg aaacgagaat    4080
cctcaaagga ttatgtaggg tttgagttta tatatttcgt aaactgaaca agatacggga    4140
tcccccgccc cccttcgatt cggtcgaaaa aaattgtaaa ttttacaatt aaggtaaaat    4200
ttacgtgtct acaaaaataa agtattccca agttacacg tacttacgac gttataagga    4260
caatggtttc gatcatattt attttatct atttgcacct ttaatgaatc tcaaagacag     4320
taattgcaaa ggaaggagtc aactgttgta tttacgcgac gactcgttcg gtcaaacgta    4380
gacagtccta gttaaagggt aatacggtca gtataattaa tgatcagtta atcaactaaa    4440
aataaaaact gtatatgtac acttactttc tggggtggac atccaaaccg ttcgatcgaa    4500
ttcattgcgg taaaacgttc cgtaccttt tatgtattga ctcttatctt ttcaagtcta     4560
gttccagtcc ttgtctacct tgtcgactta tacccggttt gtcctataga caccattcgt    4620
caaggacggg gccgagtccc ggttcttgtc taccttgtcg acttataccc ggtttgtcct    4680
atagacacca ttcgtcaagg acggggccga gtccgttc ttgtctacca ggggtctacg      4740
ccaggtcggg agtcgtcaaa gatctcttgg tagtctacaa aggtcccacg gggttcctgg    4800
actttactgg gacacggaat aaacttgatt ggttagtcaa gcgaagagcg aagacaagcg    4860
cgcgaatacg aggggctcga gttatttct cgggtgttgg ggagtgagcc ccgcggtcag     4920
gaggctaact gactcagcgg gcccatgggc acataggtta tttgggagaa cgtcaacgta    4980
ggctgaacac cagagcgaca aggaaccctc ccagaggaga ctcactaact gatgggcagt    5040 cgccccaga aagtaaaccc ccgagcaggc cctagccctc tggggacggg tccctggtgg     5100
ctgggtggtg gccctccatt cgaccggtcg ttgaatagac acagacaggc taacagatca    5160
cagatactga ctaaaatacg cggacgcagc catgatcaat cgattgatcg agacatagac    5220
cgcctgggca ccaccttgac tgctcaagcc ttgtgggccg gcgttgggac cctctgcagg    5280
gtccctgaag cccccggcaa aaacaccggg ctggactcag gattttaggg ctagcaaatc    5340
ctgagaaacc acgtgggggg aatctcctcc ctatacacca agaccatcct ctgctcttgg    5400
attttgtcaa gggcggaggc agacttaaaa acgaaagcca acccctggct tcggcgcggc    5460
gcgcagaaca gacgacgtcg tagcaagaca caacagagac agactgacac aaagacataa    5520
acagactttt ataccgggc ccgatctgac aatggtgagg gaattcaaac tggaatccag     5580
```

```
tgacctttct acagctcgcc tagcgagtgt tggtcagcca tctacagttc ttctctgcaa   5640
cccaatggaa gacgagacgt cttaccggtt ggaaattgca gcctaccggc gctctgccgt   5700
ggaaattggc tctggagtag tgggtccaat tctagttcca gaaaagtgga ccgggcgtac   5760
ctgtgggtct ggtccagggg atgtagcact ggacccttcg gaaccgaaaa ctgggggggag  5820 ggacccagtt cgggaaacat gtgggattcg gaggcggagg agaaggaggt aggcggggca   5880
gagaggggga acttggagga gcaagctggg gcggagctag gagggaaata ggtcgggagt   5940
gaggaagaga tccgcggggg tataccggta tactctagaa tataccccgt gggggcgggg   6000
aacatttgaa gggactggga ctgtactgtt ctcaatgatt gtcggggaga gaggttcgag   6060
tgaatgtccg agagatgaat caggtcgtgc ttcagacctc tggagaccgc cgtcggatgg   6120
ttcttgttga cctggctggc caccatggag tgggaatggc tcagccgctg tgtcacaccc   6180
aggcggctgt ggtctgattc ttggatcttg gagcgacctt tcctggaatg tgtcaggacg   6240
actggtgggg gtggcgggag tttcatctgc cgtagcgtcg aacctatgtg cggcgggtgc   6300
acttccgacg gctgggcccc ccacctggta ggagatctga cggtaccgag agggtcactg   6360
acgggatgac gaaggggatc gcgaagagga cgtacgtctc cacttcgacg tcctcagtcc   6420
ccctccgaag cacttcggac ctcccaggga gtttcagagg acacgtcgga gacctaagtg   6480
aaagtcatcg atacggtaca ggacccaagc ggactcaggc ctctactccg acctcaccca   6540
gcgttggtaa tcgtcacgac caccaatgta aagataaga ctgtcacacg tccctgctaa    6600
gtggtaaagg tctctgttac ggttcttgtg ggacgtggac gtttacccgt cagactccag   6660
acccctgtgc cggtacataa tgacacgttc cgtccctaaa ccattgatgc cactaatgat   6720
acgatacctg atgaccccgg ttccctggtg ccagtggcag aggagtccac ctccacctag   6780
tccacctcca cctagaccac ctccacctag actgtaactc gagtgggtca gaggtaggag   6840
ggaccgacac agtcgtcctc tcttccagtg atactcgacg tttaggtcag tctcagacga   6900
gttgtcatct tgggctttct tggtcaaccg aaccatggtc gttttggtc ctgtcagagg     6960 acttgacgac tagatgaccc gtaggtgatc cgttagacct cagggactag cgaagtgtcc   7020
gtcacctaga ccctgtctaa agtgagagtg gtagtcgtca cacgtccgac ttctggaccg   7080
tcaaataatg acggtcgtta gaatattaga tgagtgcaag ccaggaccct ggttcgacct   7140
ctagtttgcc cgccggcgtt aacttcaata cataggagga ggaatggatc tgttactctt   7200
ctcgttacct tggtaatagg tacactttcc ctttgtggaa acaggttcag gggataaagg   7260
gcctggaaga ttcgggaaaa cccacgacca ccaccaacca cctcaggacc gaacgatatc   7320
gaacgatcat tgtcaccgga aataataaaa gacccactcc tcattctcct cgtccgagga   7380
cgtgtcactg atgtacttgt actgaggggc ggcggggccc gggtgggcgt tcgtaatggt   7440
cgggatacgg ggtggtgcgc tgaagcgtcg gatagcgagg tctcacttca agtcgtcctc   7500
gcgtctcggg gggcgcatgg tcgtcccggt cttggtcgag atattgctcg agttagatcc   7560
tgcttctctc ctcatgctac aaaacctgtt ctctgcaccg gccctgggac tctaccccccc  7620 tttcggctct tccttcttgg gagtccttcc ggacatgtta cttgacgtct ttctattcta   7680
ccgcctccgg atgtcactct aaccctactt tccgctcgcg gcctcccgt tccccgtgct    7740 accggaaatg gtcccagagt catgtcggtg gttcctgtgg atgctgcggg aagtgtacgt   7800
ccgggacggg ggagcgattg tcggtgagct c                                  7831
```